US009981076B2

(12) United States Patent
Callaway et al.

(10) Patent No.: US 9,981,076 B2
(45) Date of Patent: May 29, 2018

(54) VENTRICULAR CUFF

(71) Applicant: Thoratec Corporation, Pleasanton, CA (US)

(72) Inventors: Justin Aron Callaway, Goffstown, NH (US); Cori G. Pierce, Wakefield, MA (US); Julien Duhamel, Billerica, MA (US); Kevin Bourque, Reading, MA (US); J. Donald Hill, San Francisco, CA (US); Terry Barnes, Pleasanton, CA (US); Dustin Seth West, Pleasanton, CA (US); Peter Gazzara, III, Pleasant, CA (US)

(73) Assignee: TC1 LLC, St. Paul, MN (US)

( * ) Notice: Subject to any disclaimer, the term of this patent is extended or adjusted under 35 U.S.C. 154(b) by 503 days.

(21) Appl. No.: 14/641,164

(22) Filed: Mar. 6, 2015

(65) Prior Publication Data

US 2015/0273124 A1 Oct. 1, 2015

Related U.S. Application Data

(63) Continuation-in-part of application No. 13/842,578, filed on Mar. 15, 2013, now Pat. No. 9,199,019.

(Continued)

(51) Int. Cl.
*A61M 1/10* (2006.01)
*A61M 1/12* (2006.01)

(52) U.S. Cl.
CPC ............ *A61M 1/1008* (2014.02); *A61M 1/12* (2013.01); *A61M 1/1001* (2014.02); *A61M 1/122* (2014.02)

(58) Field of Classification Search
CPC .... A61M 1/10; A61M 1/1008; A61M 1/1001; A61M 1/122; A61M 1/12
See application file for complete search history.

(56) References Cited

U.S. PATENT DOCUMENTS

| 3,766,567 A | 10/1973 | Kahn et al. |
| 4,099,759 A | 7/1978 | Kornhauser |

(Continued)

FOREIGN PATENT DOCUMENTS

| CA | 2526920 | 2/2009 |
| CN | 1842354 A | 10/2006 |

(Continued)

OTHER PUBLICATIONS

Barletta et al., Design of a Bearingless Blood Pump, in Proceedings Third International Symposium of Magnetic Suspension Technology, Tallahassee, FL, 1995, pp. 265-274.

(Continued)

*Primary Examiner* — Christopher D Prone
*Assistant Examiner* — Rokhaya Diop
(74) *Attorney, Agent, or Firm* — Kilpatrick, Townsend & Stockton LLP

(57) ABSTRACT

In one general aspect, a cuff for attachment to a heart includes an attachment component configured to engage a blood pump to attach the cuff to the blood pump and a sewing ring for attachment to the heart. The sewing ring is coupled to the attachment component, and the attachment component and the sewing ring each define a central opening configured to admit an inflow cannula of a blood pump. The sewing ring comprises a member that provides rigidity to flatten a portion of a myocardium of the heart when the cuff is attached to the heart.

29 Claims, 78 Drawing Sheets

Related U.S. Application Data

(60) Provisional application No. 61/949,113, filed on Mar. 6, 2014, provisional application No. 62/127,262, filed on Mar. 2, 2015, provisional application No. 61/695,925, filed on Aug. 31, 2012.

(56) References Cited

U.S. PATENT DOCUMENTS

| | | |
|---|---|---|
| 4,458,366 A | 7/1984 | MacGregor |
| 4,688,998 A | 8/1987 | Olsen et al. |
| 4,769,031 A | 9/1988 | McGough et al. |
| 5,055,005 A | 10/1991 | Kletschka |
| 5,098,369 A | 3/1992 | Heilman et al. |
| 5,139,517 A | 8/1992 | Corral |
| 5,195,877 A | 3/1993 | Kletschka |
| 5,222,980 A | 6/1993 | Gealow |
| 5,275,580 A | 1/1994 | Yamazaki |
| 5,456,714 A | 10/1995 | Owen |
| 5,470,208 A | 11/1995 | Kletschka |
| 5,613,935 A | 3/1997 | Jarvik |
| 5,708,346 A | 1/1998 | Schob |
| 5,814,005 A | 9/1998 | Barra et al. |
| 5,827,316 A | 10/1998 | Young et al. |
| 5,843,088 A | 12/1998 | Barra et al. |
| 5,984,956 A | 11/1999 | Tweden et al. |
| 6,001,056 A | 12/1999 | Jassawalla et al. |
| 6,050,975 A | 4/2000 | Poirier |
| 6,066,085 A | 5/2000 | Heilman et al. |
| 6,146,325 A | 11/2000 | Lewis et al. |
| 6,238,334 B1 | 5/2001 | Easterbrook, III et al. |
| 6,254,564 B1 | 7/2001 | Wilk et al. |
| 6,346,071 B1 | 2/2002 | Mussivand |
| 6,390,976 B1 | 5/2002 | Spence et al. |
| 6,669,708 B1 | 12/2003 | Nissenbaum et al. |
| 6,673,043 B1 | 1/2004 | Landesberg |
| 6,689,147 B1 | 2/2004 | Koster |
| 6,705,988 B2 | 3/2004 | Spence et al. |
| 6,726,648 B2 | 4/2004 | Kaplon et al. |
| 6,732,501 B2 | 5/2004 | Yu et al. |
| 6,802,806 B2 | 10/2004 | McCarthy et al. |
| 6,808,498 B2 | 10/2004 | Laroya et al. |
| 6,863,677 B2 | 3/2005 | Breznock |
| 6,942,672 B2 | 9/2005 | Heilman et al. |
| 6,994,666 B2 | 2/2006 | Shannon et al. |
| 7,018,384 B2 | 3/2006 | Skakoon |
| 7,048,681 B2 | 5/2006 | Tsubouchi et al. |
| 7,056,286 B2 | 6/2006 | Ravenscroft et al. |
| 7,077,801 B2 | 7/2006 | Haverich |
| 7,214,234 B2 | 5/2007 | Rapacki et al. |
| 7,303,553 B2 | 12/2007 | Ott |
| 7,404,792 B2 | 7/2008 | Spence et al. |
| 7,462,019 B1 | 12/2008 | Allarie et al. |
| 7,824,358 B2 | 11/2010 | Cotter et al. |
| 8,152,845 B2 | 4/2012 | Bourque |
| 8,343,028 B2 | 1/2013 | Gregoric et al. |
| 8,500,759 B2 | 8/2013 | Koyfman et al. |
| 8,579,790 B2 | 11/2013 | Jeffery et al. |
| 9,144,637 B2 | 9/2015 | Callaway et al. |
| 2002/0045846 A1 | 4/2002 | Kaplon et al. |
| 2002/0095210 A1 | 7/2002 | Finnegan et al. |
| 2003/0023255 A1 | 1/2003 | Miles et al. |
| 2003/0040765 A1 | 2/2003 | Breznock |
| 2003/0130668 A1 | 7/2003 | Nieman et al. |
| 2004/0002624 A1 | 1/2004 | Yu et al. |
| 2004/0054251 A1 | 3/2004 | Liotta |
| 2004/0153112 A1 | 8/2004 | Nissenbaum et al. |
| 2004/0171905 A1 | 9/2004 | Yu et al. |
| 2004/0193004 A1* | 9/2004 | Tsubouchi ......... A61M 1/3653 600/16 |
| 2004/0236170 A1 | 11/2004 | Kim |
| 2005/0033107 A1 | 2/2005 | Tsubouchi |
| 2005/0101982 A1 | 5/2005 | Ravenscroft et al. |
| 2005/0131451 A1 | 6/2005 | Kleshinski et al. |
| 2005/0149093 A1 | 7/2005 | Pokorney |
| 2005/0154411 A1 | 7/2005 | Breznock et al. |
| 2005/0209502 A1 | 9/2005 | Schmid et al. |
| 2005/0251187 A1 | 11/2005 | Beane et al. |
| 2006/0036313 A1 | 2/2006 | Vassiliades |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0134993 A1* | 6/2007 | Tamez ................ A61M 1/10 439/752 |
| 2007/0167968 A1 | 7/2007 | Pandey |
| 2007/0167969 A1 | 7/2007 | Pandey |
| 2007/0173879 A1 | 7/2007 | Pandey |
| 2007/0197855 A1 | 8/2007 | Richardson et al. |
| 2007/0265643 A1 | 11/2007 | Beane et al. |
| 2008/0009668 A1 | 1/2008 | Cohn |
| 2008/0009887 A1 | 1/2008 | Cohn |
| 2008/0009891 A1 | 1/2008 | Cohn |
| 2008/0076959 A1 | 3/2008 | Farnan et al. |
| 2009/0012552 A1 | 1/2009 | Pandey et al. |
| 2009/0082792 A1 | 3/2009 | Koyfman et al. |
| 2009/0143638 A1 | 6/2009 | Keogh et al. |
| 2009/0171136 A1* | 7/2009 | Shambaugh, Jr. ...... A61M 1/10 600/16 |
| 2010/0305692 A1 | 12/2010 | Thomas et al. |
| 2011/0118766 A1 | 5/2011 | Reichenbach |
| 2011/0118829 A1 | 5/2011 | Hoarau et al. |
| 2011/0118833 A1 | 5/2011 | Reichenbach et al. |
| 2011/0144680 A1 | 6/2011 | Nguyen et al. |
| 2011/0160850 A1* | 6/2011 | Bourque ............... A61M 1/101 623/3.1 |
| 2011/0245582 A1 | 10/2011 | Zafirelis et al. |
| 2012/0010455 A1 | 1/2012 | Reichenbach et al. |
| 2012/0035411 A1 | 2/2012 | LaRose et al. |
| 2012/0046514 A1 | 2/2012 | Bourque |
| 2012/0059212 A1 | 3/2012 | Larose et al. |
| 2012/0165931 A1 | 7/2012 | Bourque |
| 2012/0226096 A1 | 9/2012 | Callaway et al. |
| 2013/0060267 A1 | 3/2013 | Farnan et al. |
| 2015/0335802 A1 | 11/2015 | Callaway et al. |

FOREIGN PATENT DOCUMENTS

| | | |
|---|---|---|
| DE | 20202883 | 7/2002 |
| DE | 10108809 A1 | 9/2002 |
| EP | 1706168 | 10/2006 |
| JP | 2006528304 | 12/2006 |
| JP | 2007-510522 A | 4/2007 |
| JP | 2009018192 | 1/2009 |
| JP | 2011/060386 A2 | 5/2011 |
| JP | 2013-510691 A | 3/2013 |
| WO | 2000/074747 A1 | 12/2000 |
| WO | 2003/001980 A2 | 1/2003 |
| WO | 2004/014456 A2 | 2/2004 |
| WO | 2005/046783 A1 | 5/2005 |
| WO | 2005051838 | 6/2005 |
| WO | 2007/038109 A2 | 4/2007 |
| WO | 2008/131453 A1 | 10/2008 |
| WO | 2009/085243 A1 | 7/2009 |
| WO | 2011081629 | 7/2011 |
| WO | 2012051454 | 4/2012 |
| WO | 2012119073 | 9/2012 |
| WO | 2013056131 | 4/2013 |
| WO | 2013064529 | 10/2013 |

OTHER PUBLICATIONS

Nickel titanium, Wikipedia[onlin] Mar. 10, 2013 [retrieved on Mar. 12, 2013], Retrieved from the Internet: http://en.wikipedia.org/wiki/Nickel_titanium, 8 pages.
Thompson, An overview of nickel-titanium allows used in dentistry, International Endodontic Journal, 2000, vol. 33, pp. 297-310.
Notification of Transmittal of The International Search Report and The Written Opinion of The International Searching Authority, or The Declaration; International Search Report and Written Opinion

(56) References Cited

OTHER PUBLICATIONS of The International Searching Authority for corresponding International Application No. PCT/US2009/069836 dated Sep. 20, 2010, 12 pages.
Notification of Transmittal of The International Search Report and The Written Opinion of The International Searching Authority, or The Declaration; Internantional Search Report and Written Opinion of The International Searching Authority for corresponding International Application No. PCT/US2012/027481 dated Jun. 6, 2012, 15 pages.
International Preliminary Report on Patentability for corresponding International Application No. PCT/US2009/069836 dated Jul. 4, 2012, 8 pages.
International Preliminary Report on Patentability for corresponding International Application No. PCT/US2012/027481 dated Sep. 3, 2013, 10 pages.
Notification of Transmittal of The International Search Report and The Written Opinion of The International Searching Authority, or The Declaration; International Search Report and Written Opinion of The International Searching Authority for corresponding International Application No. PCT/US2013/056952 dated Nov. 19, 2013, 16 pages.
Notification of Transmittal of The International Search Report and The Written Opinion of The International Searching Authority, or The Declaration; International Search Report and Written Opinion of The International Searching Authority for corresponding International Application No. PCT/US2014/021389 dated Jun. 24, 2014, 12 pages.
U.S. Appl. No. 13/832,657, filed Mar. 15, 2013, first named inventor: Justin Aron Callaway.
Non-Final Office Action for U.S. Appl. No. 12/650,017 dated Jun. 27, 2011, 9 pages.
Notice of Allowance for U.S. Appl. No. 12/650,017 dated Jan. 4, 2012, 7 pages.
Non-Final Office Action for U.S. Appl. No. 13/414,041 dated Apr. 9, 2013, 4 pages.
Non-Final Office Action for U.S. Appl. No. 13/842,578, dated May 21, 2014, 21 pages.
Final Office Action for U.S. Appl. No. 13/842,578, dated Jan. 12, 2015, 21 pages.
Notification of Transmittal of The International Search Report and The Written Opinion of The International Searching Authority, or The Declaration; Internantional Search Report and Written Opinion of The International Searching Authority for corresponding International Application No. PCT/US2015/019308 dated Jul. 14, 2015, 15 pages.

\* cited by examiner

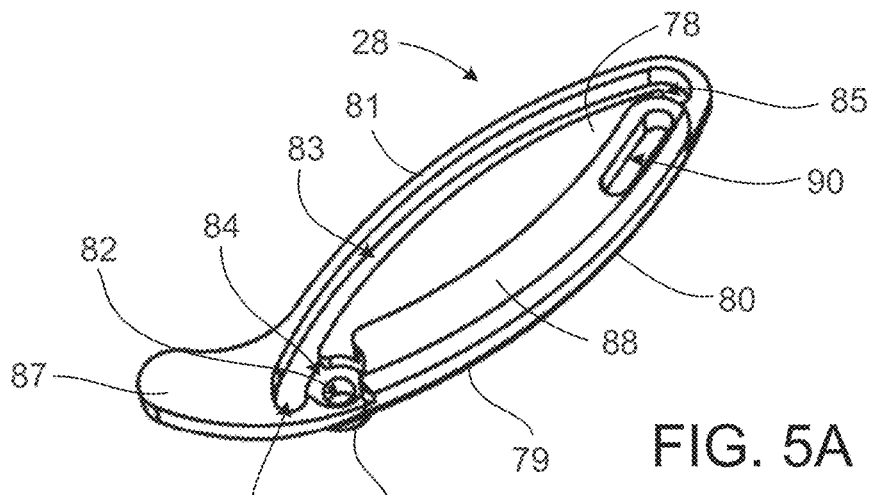
FIG. 5A
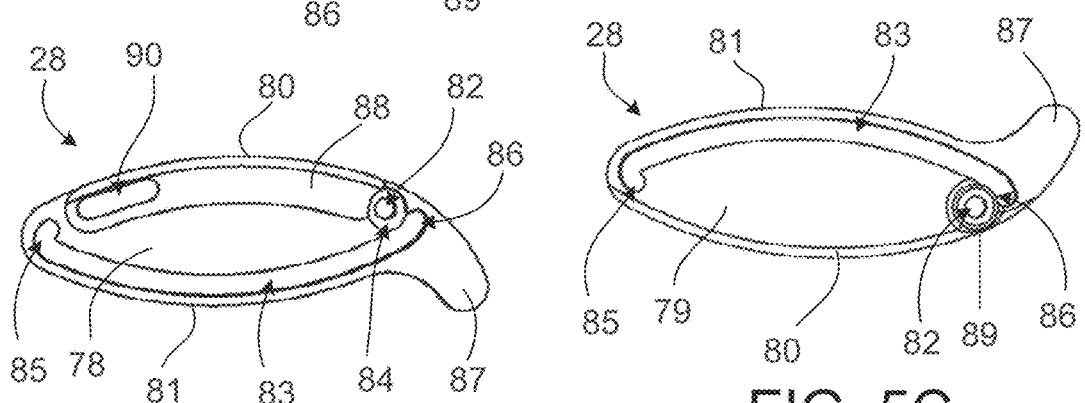
FIG. 5B
FIG. 5C
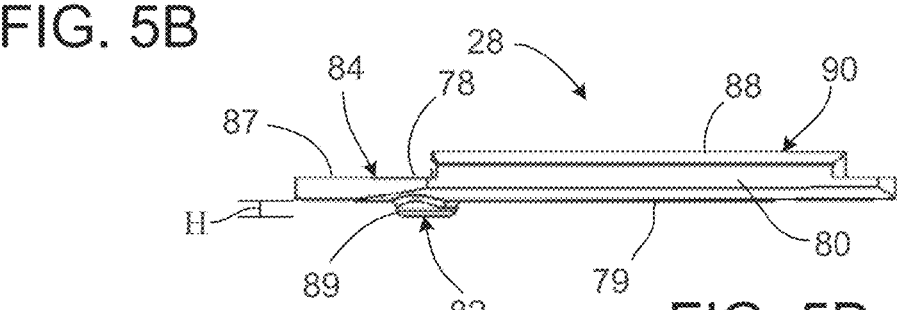
FIG. 5D
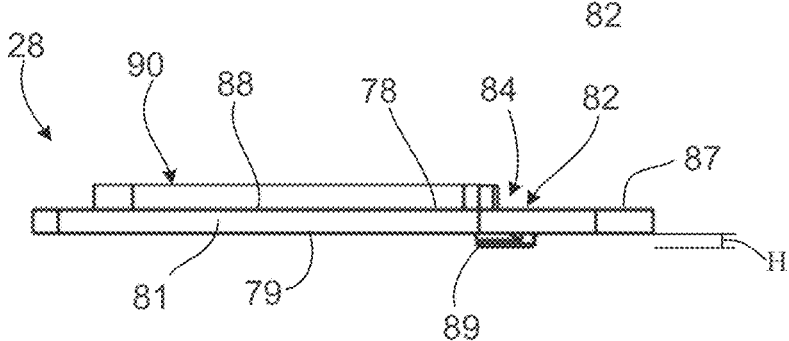
FIG. 5E

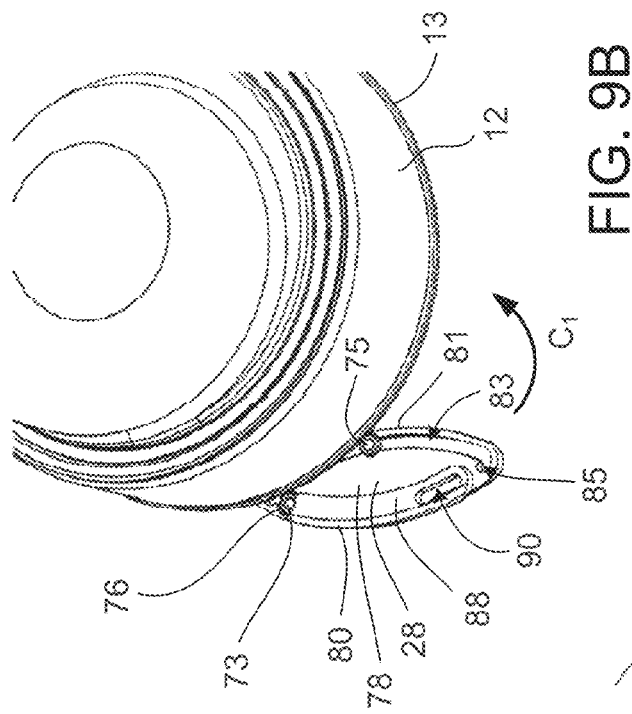
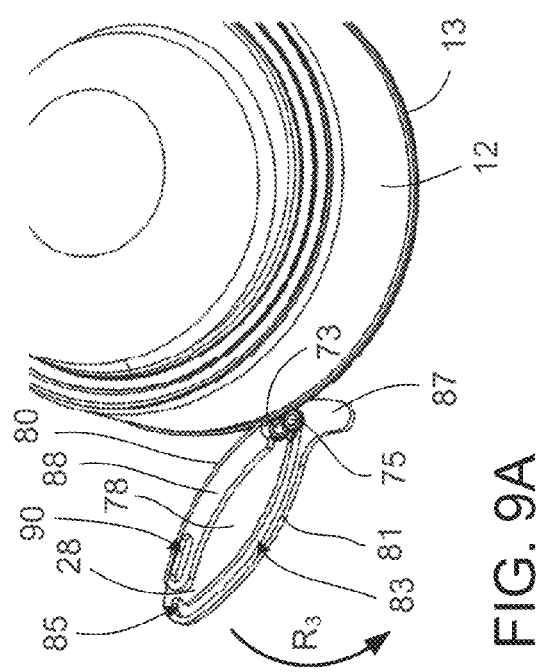
FIG. 9A
FIG. 9B
FIG. 9C

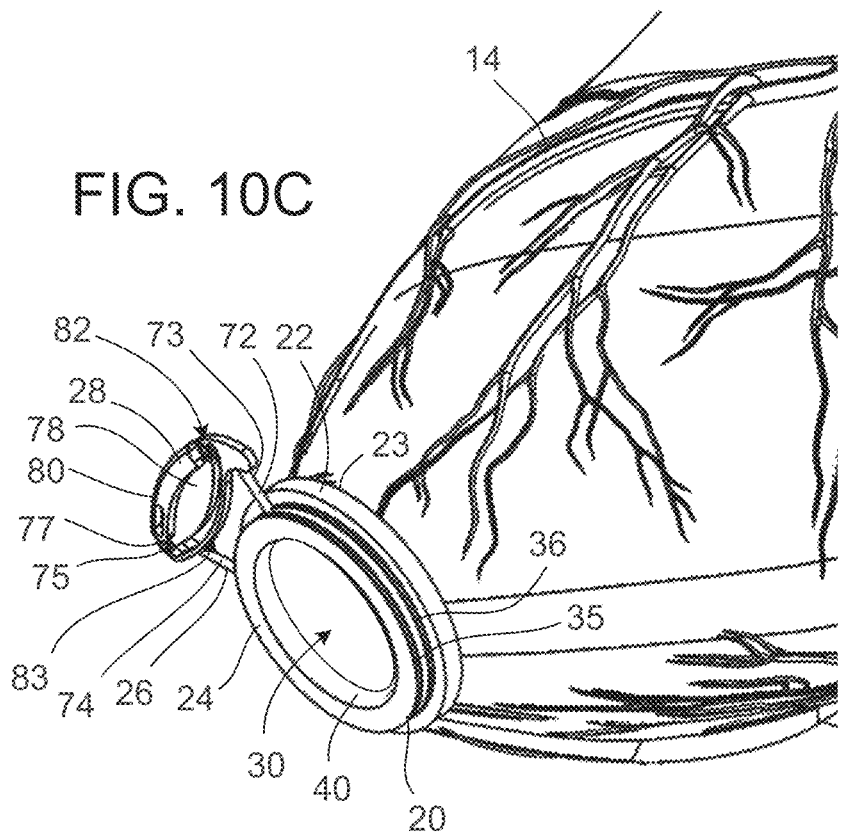
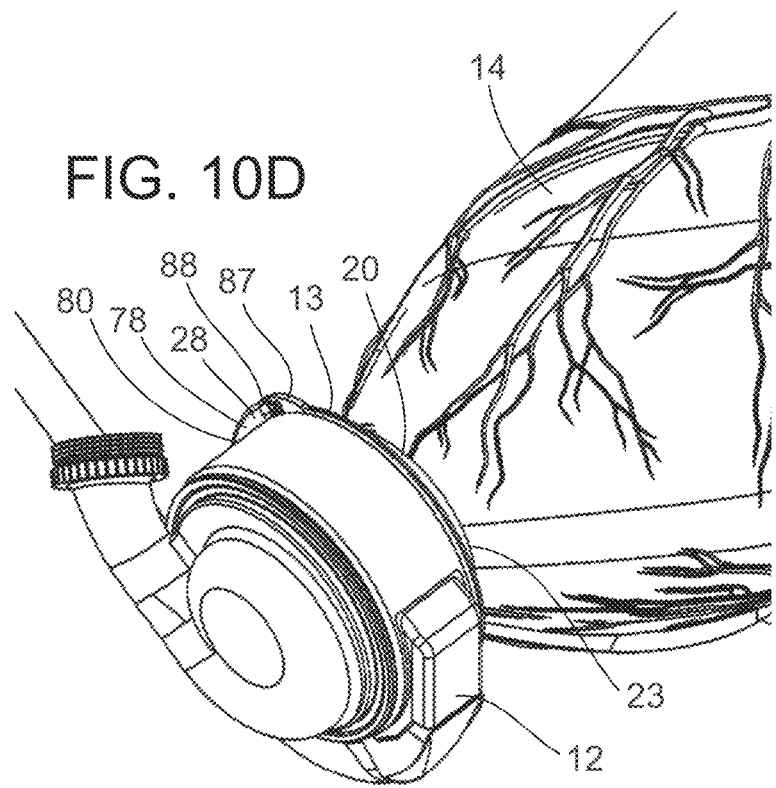

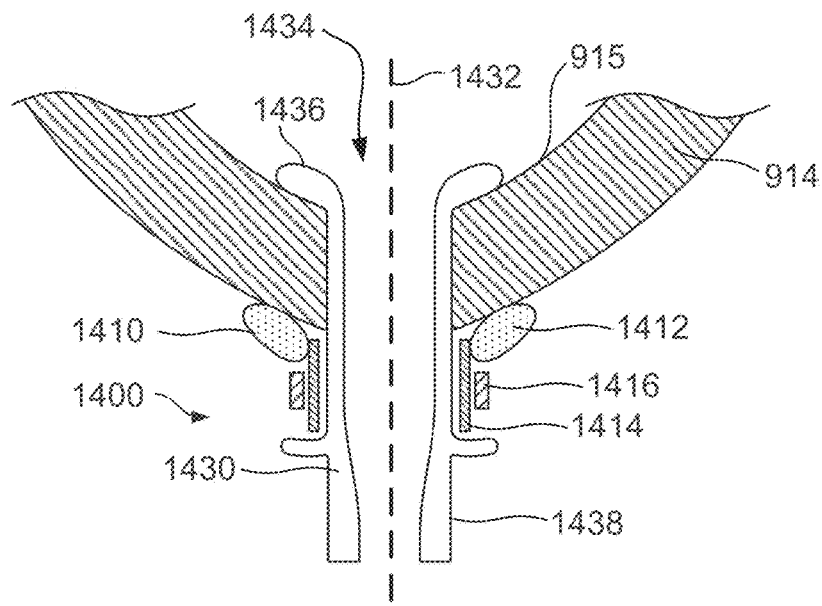
FIG. 41
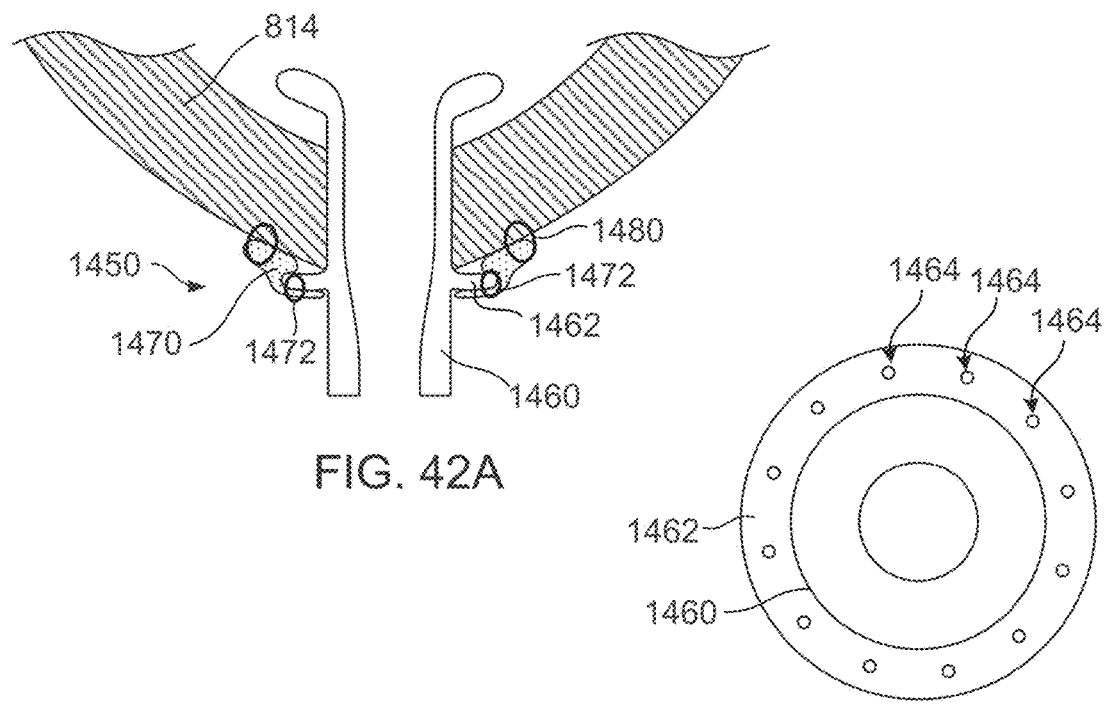
FIG. 42A
FIG. 42B

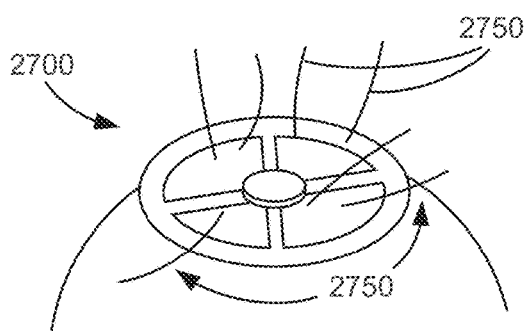
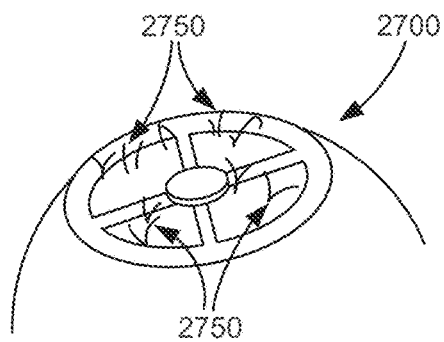
FIG. 59A   FIG. 59B
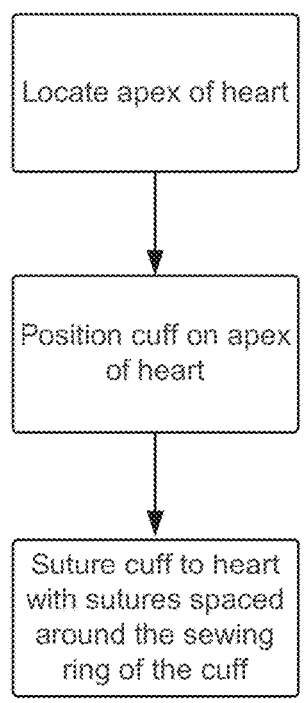
FIG. 59C

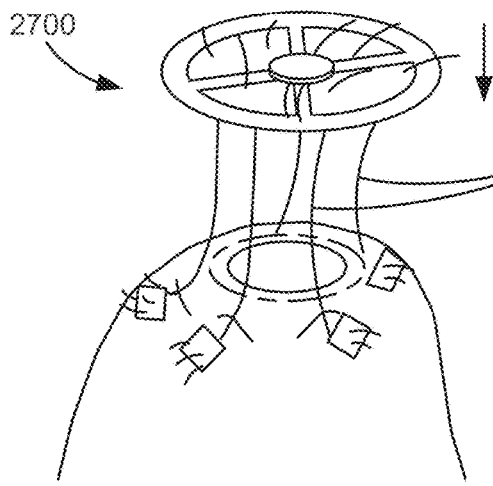
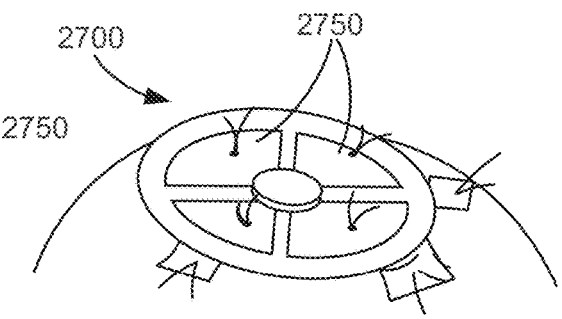
FIG. 60A
FIG. 60B
Locate apex of heart
↓
Secure ends of a plurality of sutures to heart tissue with pledgets or anchors
↓
Feed sutures through sewing ring of cuff
↓
Slide cuff along anchored sutures and push cuff against apex
↓
Align cuff as desired
↓
Tighten and fasten sutures
FIG. 60C

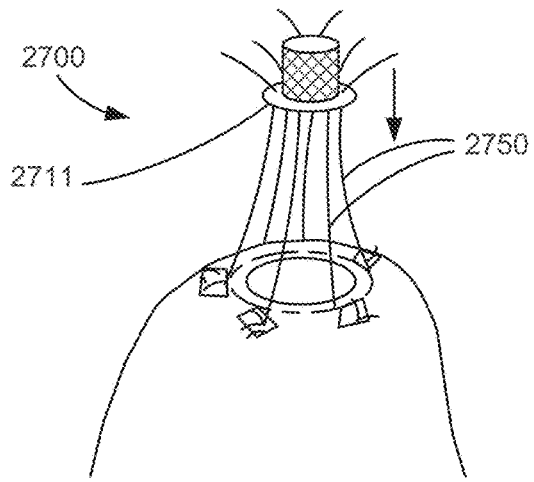
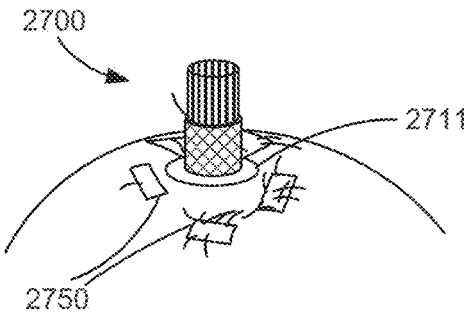
FIG. 61A    FIG. 61B
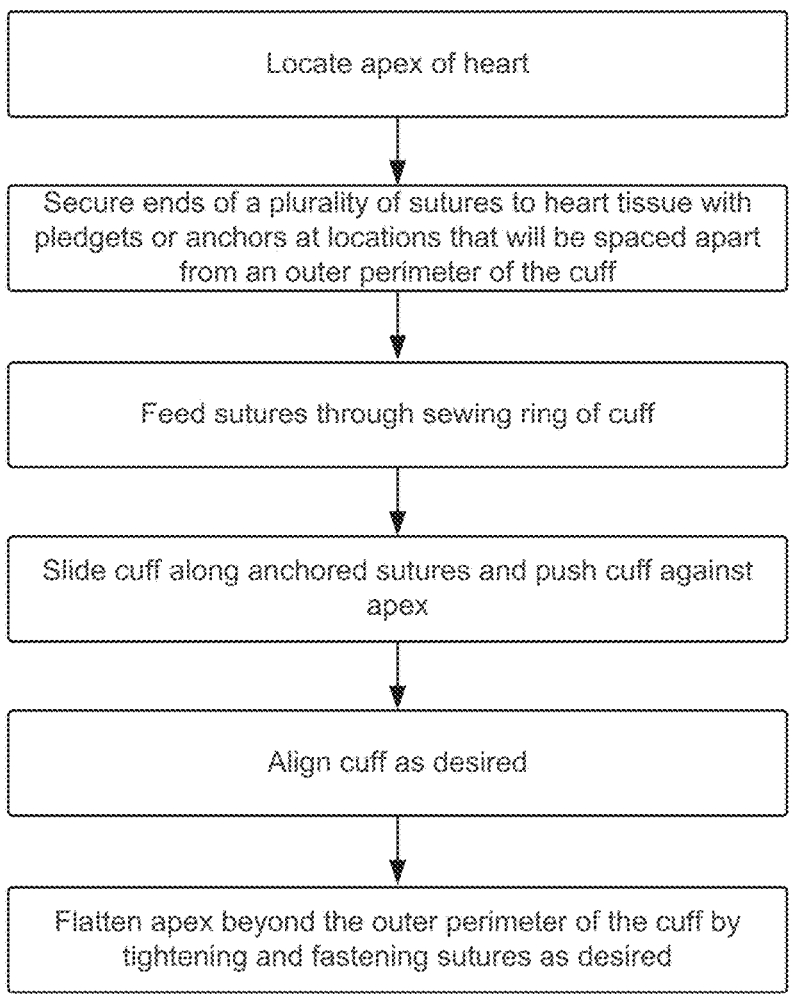
FIG. 61C

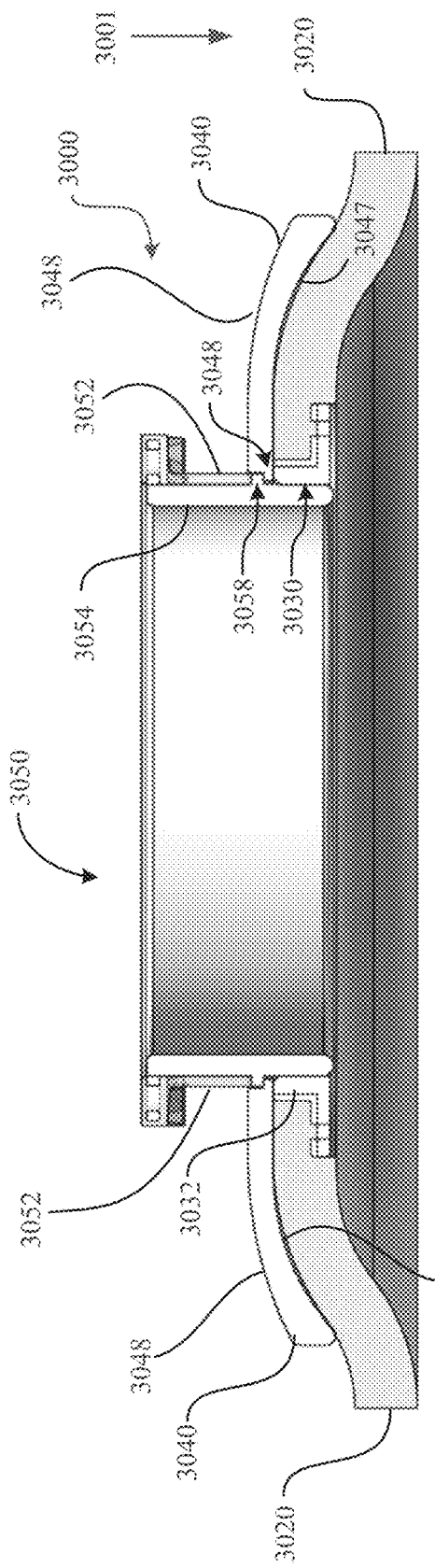
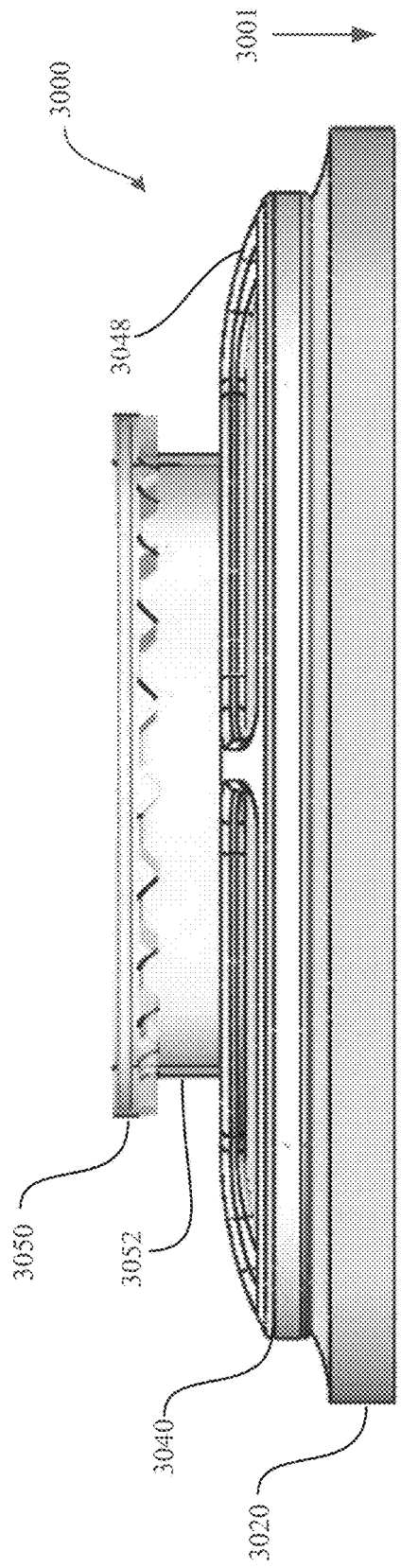
Figure 63A
Figure 63B

VENTRICULAR CUFF

CROSS-REFERENCE TO RELATED APPLICATION

This application claims priority to U.S. Provisional Patent Application No. 61/949,113 filed Mar. 6, 2014; and U.S. Provisional Patent Application No. 62/127,262 filed Mar. 2, 2015; and is also a continuation-in-part of U.S. patent application Ser. No. 13/842,578 filed Mar. 15, 2013; which claims priority to U.S. Provisional Patent Application No. 61/695,925 filed Aug. 31, 2012, the disclosures of which are incorporated herein by reference.

This application is also related to U.S. patent application Ser. No. 13/832,657 filed Mar. 15, 2013; PCT Application No. PCT/US2013/029208 filed Feb. 14, 2014; and U.S. patent application Ser. No. 13/410,670 filed Mar. 2, 2012, the disclosures of which are also incorporated herein by reference.

TECHNICAL FIELD

This disclosure relates to ventricular cuffs.

BACKGROUND

Heart assist devices or pumps can be inserted in the circulatory system to pump blood from either ventricle or atrium of a heart to the vasculature. A pump supplementing a ventricle is known as a ventricular assist device, or VAD. A VAD is useful when the ventricle alone is incapable of providing adequate blood flow.

SUMMARY

In a general aspect, a cuff for attachment to a heart defines an opening to admit a cannula of a heart pump. The cuff can be sufficiently rigid to promote flattening of the myocardium in a region where the cuff is attached.

In some implementations, the cuff includes two or more layers of, for example, felt, fabric, mesh, or another material. The two or more layers may be joined by sutures or an adhesive, such as a silicone adhesive. In some implementations, the cuff includes a wire insert, which may be covered in silicone and positioned between two layers of felt.

In another general aspect, a housing of a heart pump includes one or more anchors. The anchors admit fasteners, such as sutures, that can secure the implanted heart pump.

In some implementations, multiple anchors are located at the perimeter of the heart pump, for example, spaced apart around an outer edge of the housing. Each anchor may be a suture anchor, for example, an eyelet or other opening through which a suture can be passed to capture a portion of the housing.

In another general aspect, fabric cover is implanted around a blood pump to reduce tissue adhesion and facilitate later removal of the blood pump.

In another general aspect, a blood pump includes a housing disposed about a pump mechanism. The housing has a proximal side configured to face toward a heart and an inflow cannula extending from the proximal side. The housing has an outer perimeter, and the housing includes a plurality of suture anchors disposed along the outer perimeter of the housing.

Implementations may include one or more of the following features. For example, the suture anchors are eyelets defined through the housing. The housing has a peripheral side oriented generally perpendicular to the proximal side, and one or more of the eyelets defines a passage from the peripheral side to the proximal side. The passage extends from the peripheral side inward toward the inflow cannula. The passage has a central axis, and the central axis is oriented at an angle of between 20 degrees and 50 degrees of the peripheral side. The housing is configured to receive a ventricular cuff about the inflow cannula with the ventricular cuff adjacent the proximal side, and each of the plurality of suture anchors defines a passage oriented to direct a needle through the ventricular cuff when the ventricular cuff is positioned about the inflow cannula with the ventricular cuff adjacent the proximal side. The outer perimeter of the housing is generally circular and the housing has a circumference, and the suture anchors are spaced apart along at least a portion of the circumference. The suture anchors are disposed around more than half of the circumference. The suture anchors are spaced apart at an angular distance of between 10 and 50 degrees. The inflow cannula defines a central longitudinal axis, and the suture anchors each have an opening disposed in a plane, the plane being generally perpendicular to the central longitudinal axis of the inflow cannula.

In another general aspect, a cuff for attachment to a heart includes an attachment component configured to engage a blood pump to attach the cuff to the blood pump. The cuff also includes a sewing ring for attachment to the heart. The sewing ring is coupled to the attachment component, and the attachment component and the sewing ring each define a central opening configured to admit an inflow cannula of a blood pump. The sewing ring includes a member that provides rigidity to flatten a portion of a myocardium of the heart when the cuff is attached to the heart.

Implementations may include one or more of the following features. For example, the sewing ring includes two or more disc-shaped layers of fabric. The two or more disc-shaped layers are formed of a felt, a mesh, or a woven material. The two or more disc-shaped layers are formed of polytetrafluoroethylene, polyester, or polyethylene terephthalate. The two or more disc-shaped layers are formed of polytetrafluoroethylene felt. The two or more disc-shaped layers are attached to each other by sutures or an adhesive. Each of the two or more disc-shaped layers has a thickness between approximately 1.3 millimeters and 2.3 millimeters, and a maximum water permeability of between approximately 450 ml/cm2/min and 650 ml/cm2/min. The sewing ring includes an insert disposed between the disc-shaped layers, the insert being more rigid than the disc-shaped layers. The insert is formed of polyether ether ketone, titanium, a titanium alloy, a cobalt chromium alloy, or a shape-memory polymer. The insert is covered in silicone. The insert is a lattice or web that defines a central opening that admits the inflow cannula of the blood pump. The insert has an inner perimeter, an outer perimeter, and a plurality of extensions that extend radially inward between the outer perimeter and the inner perimeter. The insert is formed of a resilient material. The insert is formed of a nickel-titanium alloy. The sewing ring has a flexural modulus of greater than 50 psi. The sewing ring has a flexural modulus of at least 60 psi. The sewing ring has a flexural modulus of at least 75 psi. The sewing ring has a flexural modulus of at least 100 psi. The sewing ring has a flexural modulus of at least 125 psi. The sewing ring has a flexural modulus of at least 150 psi. The sewing ring has a flexural modulus of less than 1500 psi. The sewing ring has a flexural modulus of less than 1000 psi. The sewing ring has a flexural modulus of less than 750 psi.

In another general aspect, a method includes attaching a cuff to a heart, the cuff being sufficiently rigid such that at least a portion of a myocardium of the heart is flattened by the attaching. The method also includes forming an opening in the myocardium, positioning an inflow cannula of a blood pump through a central opening in the cuff and into the opening in the myocardium, and attaching the blood pump to the cuff.

Implementations may include one or more of the following features. For example, the method includes attaching one or more sutures to one or more suture anchors disposed on an exterior of the blood pump. Attaching the one or more sutures to one or more suture anchors includes passing a suture through an eyelet disposed along an outer perimeter of the blood pump and through a portion of the cuff. Attaching the one or more sutures to one or more suture anchors includes passing a suture through an eyelet disposed along an outer perimeter of the blood pump and through a portion of the myocardium. Attaching the one or more sutures to one or more suture anchors includes attaching sutures at multiple suture anchors disposed around an outer perimeter of the blood pump, the sutures extending through a sewing ring of the cuff and maintaining the position of the sewing ring generally along a plane perpendicular to the inflow cannula. Attaching the blood pump to the cuff includes engaging a coupling mechanism configured to prevent translation of the inflow cannula through the central opening of the cuff. Engaging the coupling mechanism includes holding the cuff at an outer edge of the cuff and applying a counterforce with the cuff against the blood pump. Attaching the blood pump to the cuff includes engaging a locking mechanism after engaging the coupling mechanism. Forming the opening in the myocardium includes cutting the opening in the myocardium through the cuff after the cuff is attached to the heart. Attaching the cuff to the heart includes attaching the cuff to the heart after forming the opening in the myocardium, the central opening of the cuff being positioned over the opening in the myocardium. Attaching the cuff to the heart includes attaching to the heart a cuff that includes a sewing ring that includes two or more layers of fabric. Attaching the cuff to the heart includes attaching to the heart a cuff that includes a generally planar insert disposed between two or more layers of fabric, the generally planar insert being more rigid than the two or more layers of fabric. The method includes surrounding the blood pump within an implantable fabric cover defining a pocket around the blood pump. The forming is performed before the attaching. The forming and the positioning of the inflow cannula are performed substantially in one step.

In another general aspect, a method includes: attaching a cuff to a heart, the cuff having a central opening; forming an opening in the heart; positioning an inflow cannula of a blood pump through the central opening in the cuff and into the opening in the heart; and attaching the blood pump to the cuff with a suture anchored to a suture anchor on the exterior of the blood pump.

In another general aspect, a method includes: attaching a cuff to a heart, the cuff having a central opening; forming an opening in the heart; positioning an inflow cannula of a blood pump through the central opening in the cuff and into the opening in the heart; attaching the blood pump to the cuff; and enclosing the implanted blood pump within an implantable fabric cover.

In another general aspect, a system includes a blood pump having an inflow cannula defining a lumen and a central axis and a cuff for attachment to a heart. The cuff includes a fabric disc defining a central opening. The cuff or the inflow cannula includes a portion extending radially outward from the central axis. The portion is configured to contact an endocardium of the heart when the blood pump is implanted with the inflow cannula extending into the heart through the central opening of the cuff.

Implementations may include one or more of the following features. For example, the inflow cannula includes a proximal end that flares outward. The cuff includes a flexible portion that is configured to deflect inward to enter a hole in the heart, and is configured to expand outward within the heart to rest against the endocardium. The cuff has a proximal portion and a distal portion that each extend radially outward from the central axis, and a distance between the proximal portion and the distal portion is adjustable to capture a portion of a myocardium of the heart between the proximal portion and the distal portion. The cuff includes a proximal portion and a distal portion and a length between the proximal portion and distal portion, wherein the length is adjustable. The cuff includes a member configured to exert a force on heart tissue located between the proximal portion and the distal portion. The cuff includes a frame that is resilient or has a shape memory. The frame is configured to expand a proximal portion of the cuff radially outward from the central axis within the heart to capture a portion of the heart located about the cuff. The frame is configured to contract along the central axis when deployed in a hole in the heart.

In another general aspect, a cuff for attachment to a heart defines an opening to admit a cannula of a heart pump. A coupling mechanism couples the cuff about the cannula, and a locking mechanism secures the position of the cuff set by the coupling mechanism.

In another general aspect, an implantable system includes a cuff, a surface defining channels, and a clip having arms that extend into the channels. The arms travel along the channels during movement of the clip between an unlocked position of the clip and a locked position of the clip. The clip permits the cuff to be coupled about a cannula when the clip is in the unlocked position, and the clip is configured to secure the cuff relative to the cannula when the clip is in the locked position.

Implementations can include one or more of the following features. For example, the implantable system includes a cover, and the clip is captured between the cover and the surface. The cannula has a longitudinal axis, and the clip moves between the unlocked position and the locked position in a plane perpendicular to the longitudinal axis. The cover and the surface define a slot, and the clip travels along a linear direction through the slot to enter the locked position. The channels define detents, and when the cuff is not coupled to the cannula, movement of the clip from the unlocked position toward the locked position engages the arms into the detents to impede the clip from entering the locked position. Each of the arms can engage a detent independent of whether another arm engages a detent, and engagement of any of the arms with a detent impedes the clip from entering the locked position. When the clip moves toward the locked position and the cuff is coupled about the cannula, the arms engage the cuff to avoid the detents. The arms include teeth configured to limit rotation of the cuff about the cannula when the clip is in the locked position. A sealing ring is disposed about the cannula, and the sealing ring is engageable to an inner surface of the cuff to couple the cuff to the cannula. The clip includes a visual indicator disposed such that the visual indicator is exposed when the clip is not in the locked position and the visual indicator is obscured when the clip is in the locked position. The clip includes a latch that impedes the clip from exiting the locked position.

In another general aspect, an implant includes a cuff defining an opening configured to receive a cannula coupled to a heart pump and a coupling mechanism having a first position and a second position. The cuff is uncoupled from the cannula in the first position and the coupling mechanism couples the cuff to the cannula in the second position. The implant includes a locking mechanism configured to secure the coupling mechanism in the second position, and the locking mechanism is configured to be moved to a locked position after the coupling mechanism is in the second position.

Implementations can include one or more of the following features. For example, a first action positions the coupling mechanism in the second position, and a second action activates the locking mechanism to secure the coupling mechanism in the second position, and the second action occurs subsequent to and separate from the first action. The cannula includes a flange and a circumferential ridge, and the coupling mechanism is configured to capture the cuff about the cannula between the flange and the circumferential ridge. The cannula includes (i) an attachment portion between the flange and the circumferential ridge and (ii) an inflow portion, and the attachment portion has an outer diameter greater than an outer diameter of the inflow portion. The cuff includes an inner portion, an outer portion, and a member each disposed concentrically about the opening, the member being disposed between the inner portion and the outer portion, and the outer portion extending in a direction generally perpendicular to the member. The coupling mechanism includes a clamp coupled to the cuff and disposed about the opening.

Implementations can include one or more of the following features. The clamp has a first end and a second end, the clamp configured such that bringing the first end near the second end opens the clamp and moving the two ends apart closes the clamp. The locking mechanism includes a cam that defines a channel, the cam being coupled to the first end of the clamp and being configured to rotate about the first end, the second end of the clamp being disposed in the channel and being configured to travel within the channel. The channel includes a curved portion, the curved portion being configured to limit the motion of the second end of the clamp in the channel when the clamp is closed. The coupling mechanism includes an attachment member coupled about the opening of the cuff, the attachment member having one or more flanged portions that extend outward from the opening, and the locking mechanism includes a clip configured engage the flanged portions to limit movement of the cuff relative to the cannula. The clip is configured to enter a slot in the pump to secure the cuff to the pump. The attachment member includes one or more extensions each including a contact portion that extends toward the opening, the cannula includes a tapered circumferential ridge, and the second position of the coupling mechanism, the contact portions are disposed between the pump and the circumferential ridge along the length of the cannula.

In another general aspect, a cuff for attachment to a heart includes a member defining an opening, a seal coupled to the member and disposed about the opening, and a clamp coupled to the seal and disposed about the opening. The clamp has a first end and a second end, and the clamp is configured such that (i) bringing the first end near the second end opens the clamp and (ii) moving the first end and the second end apart closes the clamp.

Implementations can include one or more of the following features. For example, a cam defining a channel, the cam being coupled to the first end of the clamp and being configured to rotate about the first end, the second end of the clamp being disposed in the channel and being configured to travel within the channel.

In another general aspect, a cuff for attachment to a heart includes a member defining an opening, a linking member coupled to the member and disposed about the opening, and an attachment member coupled to the linking member and disposed about the opening. The linking member extends about an outer surface of the attachment member. The attachment member is configured to attach the cuff to a cannula disposed through the opening. The attachment member has at least one flanged portion extending outward from the opening in a plane generally perpendicular to a circular portion of the attachment member.

Implementations can include one or more of the following features. For example, the linking member is molded over a portion of the attachment member, and the attachment member is coupled to the member through the linking member. The attachment member includes at least one extension disposed generally perpendicular to the member, the extension having a tapered portion disposed on a surface of the extension facing toward the opening. The attachment member defines circumferential groove configured to admit a sealing ring. The linking member includes an elastomer. The linking member is configured to form a seal.

In another general aspect, a method of attaching a ventricular assist device to a patient, includes: attaching a cuff to a heart, the cuff defining an opening; removing tissue of the heart through the opening of the cuff; inserting a cannula through the opening of the cuff; engaging a coupling mechanism to set a position of the cuff relative to the cannula; and engaging a locking mechanism to secure the position of the cuff relative to the cannula.

Implementations can include one or more of the following features. For example, selecting a location near the apex of the heart to attach the cuff. Engaging a cardiac bypass system so that blood is not circulating through the heart. Engaging the coupling mechanism includes inserting a tapered portion of the cannula into the cuff so that one or more extensions of the cuff engage a groove defined adjacent to the tapered portion. Engaging the locking mechanism includes inserting a clip that engages the cuff and a pump coupled to the cannula. Engaging the coupling mechanism includes closing a clamp coupled to the cuff so that the clamp engages a groove defined in the cannula. Engaging the locking mechanism includes capturing an end of a clamp to secure the clamp in a locked position. Engaging the coupling mechanism to set a position of the cuff relative to the cannula includes positioning the cuff such that an inner surface of the cuff engages a sealing ring disposed about the cannula and a bottom surface of the cuff engages a surface of the cannula or a surface of a pump that is coupled to the cannula. Engaging the locking mechanism includes moving a clip in a plane perpendicular to the cannula. Engaging the locking mechanism includes moving a clip into a locked position about the cuff, the clip limiting travel of the cannula out of the cuff. Engaging the locking mechanism includes engaging a latch that secures the clip in the locked position.

In another general aspect, a system includes a cuff having an annular member defining an opening and an attachment member disposed about the opening. The attachment member includes a flanged portion oriented generally parallel to the annular member, and the flanged portion extends outward from the opening. A clip is configured to be coupled about the attachment member between the annular member and the flanged portion.

Implementations can include one or more of the following features. For example, the system includes a pump assembly that includes a cannula, and the clip is configured to travel relative to the pump assembly from an unlocked position to a locked position in which the clip secures the cuff about the cannula. The clip is configured to travel along a substantially linear path from the unlocked position to the locked position. When the cuff is coupled to the pump assembly and the clip is in the locked position, the clip impedes rotation of the cuff about the cannula. The cuff includes ridges disposed on the attachment member, and the clip is configured to engage the ridges to impede rotation of the cuff. The clip is configured to engage the pump assembly such that the travel of clip to the locked position is impeded when the cuff is improperly seated about the cannula. The clip is configured to engage the pump assembly such that travel of clip to the locked position is impeded when the cuff is not coupled to the pump assembly. The system includes a visual indicator that is visible when the clip is not in the locked position and is obscured when the clip is in the locked position. When the clip is in the locked position, engagement of the clip and the pump assembly impedes travel of the clip out of the locked position. The clip has arms that are configured to extend about the cuff in the locked position, the arms being configured such that any of the arms can engage the pump assembly to impede travel of the clip into the locking position.

In another general aspect, a system includes a cuff having a member defining an opening and an attachment member disposed about the opening. The attachment member includes (i) a clamp having a first end and a second end, and (ii) a cam defining a channel. The cam is coupled to the first end of the clamp and is configured to rotate about the first end. The second end of the clamp is disposed in the channel and is configured to travel within the channel.

In further embodiments, a ventricular assist system for coupling with a heart of a patient is provided. The ventricular assist system may include a pump comprising a pump housing and an inflow cannula coupled thereto. The pump housing may further comprise a lip, outer ridge, notch or groove along at least an outer portion of the pump housing. The system may further include a ventricular cuff comprising a disc. The disc may have a central opening for receiving the inflow cannula of the pump. Further, the disc may be moveable between an open configuration for receiving the inflow cannula of the pump and a closed configuration for coupling the disc to the pump thereby securing the ventricular cuff to the pump. The ventricular cuff may further comprises one or more hooks or teeth extending from the disc and configured to couple with the lip, outer ridge, notch or groove of the pump housing.

Optionally, the disc may comprise an annular segment with a wedge opening between ends of the annular segment in the open configuration. The ends of the annular segment may be joined such that the disc has a circular or ring shape in the closed configuration. In some embodiments, the ends of the annular segment may comprise corresponding engagement features for locking the disc with the inflow cannula of the blood pump in the closed configuration. In some embodiments, the engagement features comprise snap-fit engagement features. In some embodiments, the engagement features comprise an ear clamp. Optionally, the engagement features comprise a screw/band clamp. In some embodiments, the screw/band clamp comprises a lockout feature. The lockout feature may be configured to allow operator actuation of the screw/band clamp only when the lockout feature is coupled with a corresponding key. The lockout feature may prevent inadvertent turning of the screw/band clamp when the key is not coupled with the lockout feature.

In some embodiments, the one or more hooks or teeth extend from an outer perimeter of the disc. In some embodiments, the one or more hooks or teeth extend along the entire outer perimeter of the disc. Optionally, the lip, outer ridge, notch or groove of the pump may extend along a top housing portion of the pump.

In further embodiments, a ventricular cuff for use with a ventricular assist device is provided. The ventricular cuff may include a disc comprising a generally circular shape and a central opening configured to receive an inflow cannula of a blood pump. The disc may have a diameter being greater than 3 cm such that the disc has a size sufficient to substantially flatten the apex of the heart of the patient when the disc is coupled thereto. The larger disc diameter may flatten the apex to create more space between the central opening of the disc and walls of the left ventricle of the heart.

Optionally, the diameter of the disc may be greater than 4 cm or greater than 5 cm. In some embodiments, an accommodation opening may be provided along an outer perimeter of the disc. The accommodation opening may be configured to be orientated toward the right ventricle of the heart so that the disc does not overlap with and flatten the right ventricle when attached to the heart. A portion of the disc may comprise a felt material. Optionally, the disc may comprise at least two layers of felt coupled together. An insert may disposed between the at least two layers of felt with the insert comprising a material more rigid than the felt layers.

In further embodiments, a ventricular cuff for use with a ventricular assist device may be provided. The ventricular cuff may comprise a disc comprising a generally circular or ring shape and a central opening configured to receive an inflow cannula of a blood pump. The disc may further have an open configuration for receiving the inflow cannula of the blood pump and a closed configuration for locking the blood pump with the disc. The disc may comprise an annular segment with a wedge opening between ends of the annular segment in the open configuration. The ends of the annular segment may be joined such that the disc has a circular or ring shape in the closed configuration.

Optionally, the ends of the annular segment comprise corresponding engagement features for locking the disc with the inflow cannula of the blood pump in the closed configuration. The engagement features may comprise snap-fit engagement features. The engagement features may comprise an ear clamp. The engagement features may comprise a screw/band clamp. Optionally, the screw/band clamp may comprise a lockout feature, the lockout feature configured to allow operator actuation of the screw/band clamp only when the lockout feature is coupled with a corresponding key. The lockout feature may prevent inadvertent turning of the screw/band clamp when the key is not coupled with the lockout feature.

In some embodiments the ventricular cuff may comprise one or more hooks or teeth extending from the disc. The one or more hooks or teeth may be configured to cooperate with a lip, outer ridge, notch or groove of an attached pump. The one or more hooks may extend from an outer perimeter of the disc. Optionally, the one or more hooks extend along the entire outer perimeter of the disc. The lip, outer ridge, notch or groove of the pump may extend along a top housing portion of the attached pump.

In further embodiments, a method of securing a ventricular cuff to an apex of a heart of a patient may be provided. The method may comprise securing one or more pledgets or anchors to tissue of the heart and then securing ends of one or more sutures to the heart via the one or more pledgets or anchors. The one or more sutures may be fed through the ventricular cuff. The ventricular cuff may be positioned against the apex of the heart and the cuff may be fastened to the heart with the one or more sutures.

In some embodiments, one or more anchors may be secured to tissue of the heart. The one or more anchors may comprise a tissue penetrating end with one or more barbs for securing the one or more anchors in the tissue. Optionally, the anchors may further comprise a suture engagement feature at an end opposite the tissue penetrating end for securing ends of the one or more sutures to the heart.

In some embodiments, a plurality of pledgets or anchors are secured to the heart to form a perimeter which is greater than an outer perimeter of the disc of the ventricular cuff. The method may further include flattening the apex of the heart beyond the outer perimeter of the disc by tightening the sutures.

Optionally, a plurality of pledgets or anchors may be secured to the heart to form a perimeter which corresponds in shape and/or size to an outer perimeter of the disc of the ventricular cuff. The method may further include flattening the apex of the heart by tightening the sutures to the cuff such that the anchors or pledgets are positioned under the disc.

In some embodiments a ventricular cuff for coupling a heart of a patient with a heart pump is provided. The ventricular cuff may include an apical ring defining an opening for receiving an inlet cannula of a heart pump, the apical ring may have a heart pump engaging perimeter and a sewing ring engaging perimeter opposite the heart pump engaging perimeter. The ventricular cuff may further include a sewing ring coupled with the sewing ring engaging perimeter of the apical ring, the sewing ring including a heart tissue engaging surface and a top surface opposite the heart tissue engaging surface. A rigid frame may be provided for backing the sewing ring along the top surface of the sewing ring, the rigid frame may include a plurality of struts extending outwardly from the opening defined by the apical ring and toward an outer perimeter of the sewing ring. The plurality of struts of the rigid frame may be configured to maintain a space between the top surface of the sewing ring and the heart pump engaging perimeter of the apical ring during implantation of the ventricular cuff and the heart pump to the heart of the patient.

Optionally, the plurality of struts extend outwardly and in an attachment direction from the opening defined by the apical ring. The struts may have a generally concave configuration. The rigid frame may include an outer ring and peripheral ends of the plurality of struts may be coupled with the outer ring. The rigid frame may include an inner ring. The plurality of struts may extend from the inner ring toward the outer ring, and the plurality of struts may be visible to a physician during implantation. The outer ring may have a diameter less than a diameter of the sewing ring. The outer ring diameter may be at least 2 mm less than the sewing ring diameter. The outer ring diameter may be at least 4 mm less than the sewing ring diameter.

The ventricular cuff may also include a insert ring for coupling the sewing ring to the apical ring. The insert ring may define an opening for receiving and engaging with the apical ring. An outer surface of the apical ring may be configured to engage with an inner surface of the insert ring in a friction fit engagement. The rigid frame may be clamped between the apical ring and the insert ring during engagement of the apical cuff and the insert ring to secure the rigid frame against the sewing ring. The apical ring may include an alignment feature for engaging with a corresponding alignment feature of the rigid frame. Engagement of the alignment feature of the apical ring with the corresponding alignment feature of the rigid frame may align the rigid frame about the opening defined by the apical ring. The insert ring may be manufactured from a metal material. The sewing ring may be constructed of a fabric material. The insert ring and sewing ring may be coupled together to provide a fluid tight seal between the insert ring and the sewing ring.

The insert ring may include an lip that overlaps with the heart tissue engaging surface of the sewing ring. The lip may have a plurality of holes therethrough. The insert ring and sewing ring may be coupled together at the overlap by an elastomer. The elastomer may impregnates the fabric material of the sewing ring and may form mechanical links through the holes in the lip of the insert ring. An adhesion of the elastomer to the metal material of the insert ring may be increased by application of an adhesion promoter to the metal of the insert ring. The rigid frame may urge the top surface of the sewing ring to a concave configuration.

In some embodiments, a method for attaching a heart pump to a heart of a patient is provided. The method may include attaching a ventricular cuff to a heart of the patient—the ventricular cuff may include a fabric material supported by a rigid member and defining a central opening for receiving an inflow cannula of the heart pump. The rigid member may have a flexural modulus of greater than 50 psi and may increase a rigidity of the cuff such that at least a portion of the myocardium of the heart conforms to the shape of the cuff by the attachment of the cuff to the myocardium. The method may further include inserting the inlet cannula of the heart pump through the opening defined by the apical ring and coupling the heart pump to the ventricular cuff.

In some embodiments, the rigid member includes a plurality of struts that extend outwardly and in an attachment direction from the central opening defined by the fabric material. The rigid member may include an outer ring and peripheral ends of the plurality of struts may be coupled with the outer ring. The rigid frame may include an inner ring and the plurality of struts may extend from the inner ring toward the outer ring. The plurality of struts may be visible to a physician during implantation. The outer ring may have a diameter less than a diameter of the sewing ring. The outer ring diameter may be at least 2 mm less than the sewing ring diameter. The outer ring diameter may be at least 4 mm less than the sewing ring diameter. The ventricular cuff may further include a insert ring coupling the fabric material to an apical ring. The insert ring may define an opening for receiving and engaging with the apical ring. An outer surface of the apical ring may be configured to engage with an inner surface of the insert ring in a friction fit engagement. The rigid member may be clamped between the apical ring and the insert ring during engagement of the apical cuff and the insert ring. This may secure the rigid member against the fabric material. The apical ring may include an alignment feature for engaging with a corresponding alignment feature of the rigid member—engagement of the alignment feature of the apical ring with the corresponding alignment feature of the rigid member may align the rigid member about the opening defined by the apical ring.

The insert ring may be constructed of a metal material, and the insert ring and fabric material may be coupled together to provide a fluid tight seal between the insert ring and the fabric material.

The insert ring may include a lip that overlaps with the heart tissue engaging surface of the fabric material. The lip may have a plurality of holes therethrough. The insert ring and fabric material may be coupled together at the overlap by an elastomer. The elastomer may impregnate the fabric material and may form mechanical links through the holes in the lip of the insert ring. An adhesion of the elastomer to the metal material of the insert ring may be increased by application of an adhesion promoter to the metal of the insert ring. Optionally, the rigid member urges the top surface of the sewing ring to a concave configuration.

In further aspects, a ventricular cuff for coupling with a heart of a patient may be provided. The ventricular cuff may include a insert ring comprising metal material having cylindrical portion defining a central opening. A single sewing ring comprising a felt material may be disposed about the insert ring. The sewing ring may include a heart tissue engaging surface and a top surface opposite the heart tissue engaging surface. An elastomer may couple the sewing ring to the insert ring at an interface between the insert ring and the sewing ring and may form a fluid tight engagement between the sewing ring and the insert ring. A concave rigid frame may be secured to the insert ring and may include a plurality of struts extending outwardly from the central opening. The rigid frame may be secured to the insert ring such that the struts of the rigid frame are urged against the sewing ring and extend toward an outer perimeter of the sewing ring. The struts may support the sewing ring so as to resist deformation of the sewing ring in a direction opposite an attachment direction during attachment of the ventricular cuff to a heart of a patient.

The insert ring may include a lip extending outwardly of the central opening of the insert ring from an end of the cylindrical portion. The lip may include a plurality of holes therethrough. The lip of the insert ring may overlap with sewing ring so as to form the interface between the insert ring and the sewing ring. The elastomer may impregnate the felt material of the sewing ring so as to form a mechanical engagement with the sewing ring and may form mechanical links through the holes of the lip of the insert ring so as to form a mechanical engagement with the insert ring. The elastomer may chemically adhere to the insert ring through the use of an adhesion promoter.

Optionally, the struts of the rigid material are visible to a surgeon during attachment of the cuff to the heart. The struts may extend outwardly and in an attachment direction toward the perimeter of the sewing ring. The struts may extend in the attachment direction at least 0.05 inches as the struts extend outwardly. The rigid frame may urge the sewing ring into a domed configuration where the top surface of the sewing ring is convex and the heart tissue engaging surface of the sewing ring is concave. The rigid frame may include an outer ring, and the struts of the rigid frame may extend outwardly and couple to the outer ring to support the outer ring against the perimeter of the sewing ring.

The ventricular cuff may further include an apical ring including a heart pump engaging end and a sewing ring engaging end. The sewing ring engaging end may be configured to engage with the insert ring. The sewing ring engaging end of the apical ring may engage with the insert ring in a press-fit engagement. The apical ring may include an alignment feature for engaging a corresponding alignment feature on the rigid frame so as to align the apical ring with the rigid frame. The rigid frame may be urged against the sewing ring by the engagement of the apical ring to the insert ring.

In further aspects, a method of manufacturing a ventricular cuff may be provided. The method may include providing a sewing ring coupled with a insert ring where the sewing ring comprises a felt material and the insert ring comprises a metal material. An apical ring may be provided. The method may include aligning a rigid frame with the apical ring or the insert ring. Thereafter, the apical ring may be engaged with the insert ring in a press-fit engagement. The engagement of the apical ring with the insert ring may secure the rigid frame against the sewing ring.

Optionally, providing the sewing ring coupled with the insert ring may include injecting elastomer at an interface between the sewing ring and the insert ring. The elastomer may impregnate voids in the felt material of the sewing ring and may mechanically and/or chemically attach with the insert ring, thereby providing a fluid tight seal between the insert ring and the sewing ring. The rigid frame may include a plurality of struts extending outwardly toward a perimeter of the sewing ring. The plurality of struts may not be obstructed from view after engagement of the apical ring with the insert ring. The rigid frame may include a plurality of struts extending outwardly toward a perimeter of the sewing ring. The plurality of struts may extend in the attachment direction as the struts extend outwardly. The struts of the rigid frame may urge the sewing ring into a dome configuration where a top surface of the sewing ring is convex and a heart tissue engaging surface of the sewing ring is concave.

The apical ring may include a cylinder having a sewing ring engaging end for engaging with the insert ring. The insert ring may define a central opening for receiving the apical ring. Engaging the apical ring with the insert ring may include engaging an outer surface of the sewing ring engaging end of the apical ring cylinder with an inner surface of the insert ring central opening.

In further aspects of the invention, stabilization tools are provided for coupling with cuff during attachment of a heart pump to the cuff and/or suturing a cuff to a heart of a patient. The stabilization tool may include a handle for grasping by a hand of a surgeon. The handle may be coupled with a tool head configured to engage with a portion of a cuff.

In some embodiments, the tool head may include a first prong and a second prong that generally define an opening for receiving a portion of the cuff. The opening may be a U-shaped opening. The opening may have a width corresponding to a diameter of an apical ring of the cuff or a cannula of the cuff. The first prong and second prong may have a generally flat bottom surface. In some embodiments, the first prong and second prong may have a bottom surface that generally defines a concave shape. Optionally, the first and second prongs have a width configured so that the first and second prongs cover a majority of the sewing ring underlying the first and second prongs. In some embodiments, the width of the first and second prongs is greater than a width of the sewing ring (i.e., the distance from the inner perimeter to the outer perimeter of the sewing ring) such that the first and second prong overhangs from the sewing ring with the tool head is engaged with the cuff.

Optionally, the tool head may include a stand-off feature that projects from a top surface of the prongs and is positioned about the opening defined by the first and second prongs. The stand-off feature may have a top edge configured to engage with a bottom surface of a lip of the cuff. In some embodiments, engagement of the stand-off feature with the bottom surface of the lip urges the first and second prongs against the sewing ring of the cuff. In some embodiments, the stand-off feature may have a C-configuration that is positioned about a U-shaped opening defined by the prongs. The ends of the stand-off feature may be ramps.

In some embodiments, tips of the first and second prong may be angled to facilitate engagement of the stabilization tool to the apical cuff. In further embodiments, rotational stabilization engagement features may project inwardly from the opening defined by the prongs. The rotational stabilization engagement features may be configured to engage with corresponding engagement features on the cuff (e.g., on the apical ring, cannula, or the like). Engagement of the rotational stabilization engagement features with the corresponding engagement features may rotationally couple the cuff to the tool to provide rotation stabilization when the stabilization tool is coupled with the cuff.

In further embodiments, the stabilization tool may further include a clip projecting within the opening defined by the first and second prongs. The clip may have first and second ends configured for releaseable snap fit engagement with a portion of the cuff (e.g., apical ring, cannula, or the like).

The features described can be used in any appropriate combination and subcombination, including combinations across multiple aspects described above. Features described with respect to one aspect can additionally or alternatively be included in implementations of any of the other aspects. The details of one or more implementations are set forth in the accompanying drawings and the description below. Other features, objects, and advantages will be apparent from the description and drawings, and from the claims.

DESCRIPTION OF DRAWINGS

FIG. 5A is a perspective view of a cam of the ventricular cuff.
FIGS. 5B to 5E are respectively top, bottom, lateral side, and opposite lateral side views of the ventricular cuff.
FIGS. 8A to 8D and 9A to 9C are perspective views illustrating the coupling of the ventricular cuff to the pump.
FIGS. 10A to 10D are perspective views illustrating a process for implanting the ventricular cuff and the pump.

FIG. 41 is a cross-sectional view of an assembly of a cuff and an inflow cannula.

FIGS. 42A and 42B are cross-sectional views of another assembly of a cuff and an inflow cannula.

FIG. 56 shows an exemplary cross-sectional view of a cuff with a pump engagement feature according to embodiments of the present invention.

FIG. 57 shows an exemplary pump for coupling with the engagement features of the cuff illustrated in FIG. 56 according to embodiments of the present invention.

FIG. 58 shows a cross-sectional view of an exemplary coupling between a pump, a cuff, and a heart according to embodiments of the present invention.

FIGS. 59A to 59C illustrate an exemplary method of attaching a cuff to the apex of the heart according to embodiments of the present invention.

FIG. 60A to 60C illustrate an alternative method of attaching a cuff to the apex of the heart according to embodiments of the present invention.

FIGS. 61A to 61C illustrate yet another method of attaching a cuff to the apex of the heart according to embodiments of the present invention.

FIGS. 63A to 63C illustrate yet another exemplary cuff according to embodiments of the present invention.

DETAILED DESCRIPTION

Figure 1:
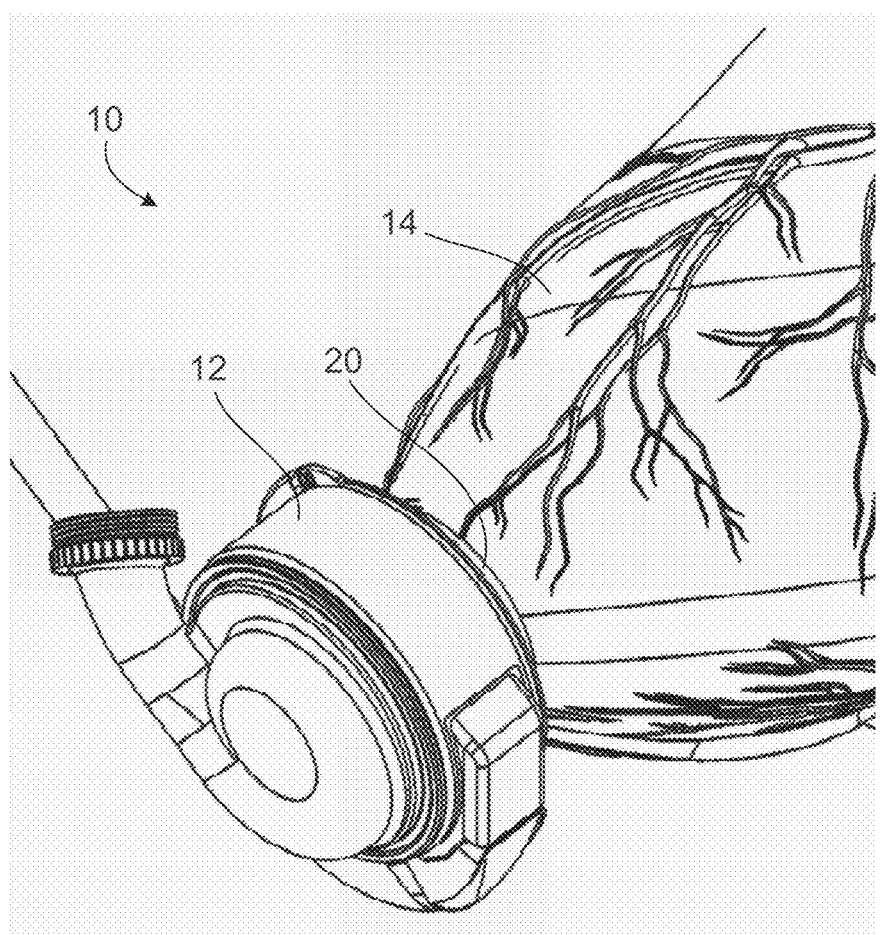
FIG. 1 is a perspective view of a pump installed at a heart.

Referring to FIG. 1, a ventricular assist system 10 for treating, for example, a patient with a weakened left ventricle, includes a blood pump 12 that receives blood from a patient's heart 14. The pump 12 is coupled to a cuff 20, which in turn is attached to the heart 14. The cuff 20 is attached to the heart by, for example, sutures that attach a portion of the cuff 20 to the apex of the left ventricle of the heart 14. The pump 12 receives blood from the heart through an inflow cannula 50 (FIG. 2B) of the pump 12 disposed through an opening in the cuff 20.

Figure 2A:
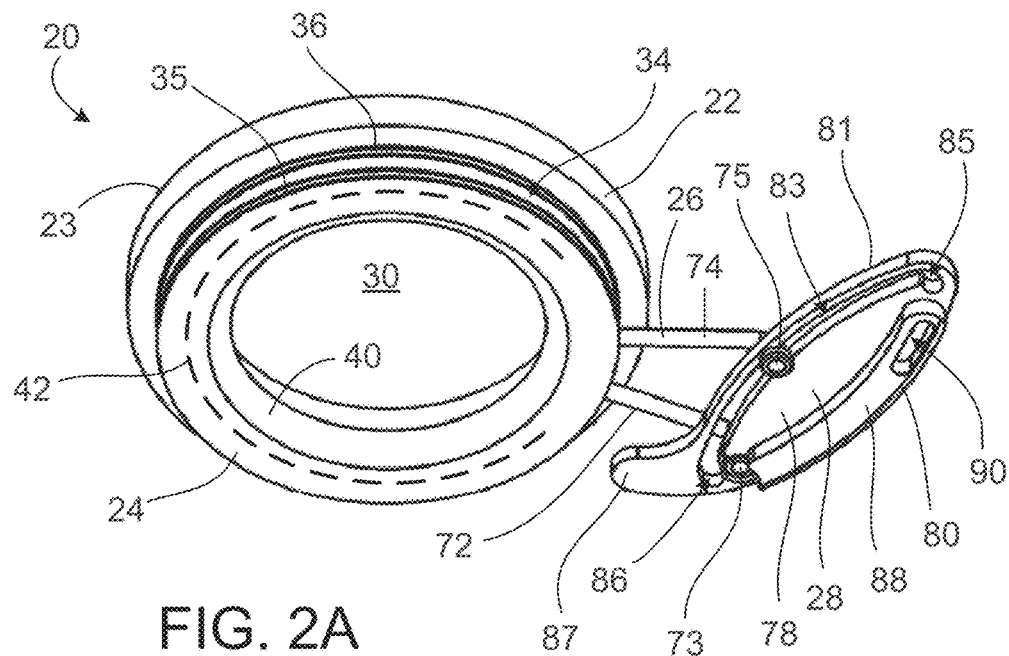
FIG. 2A is a perspective view of a ventricular cuff.
Figure 2B:
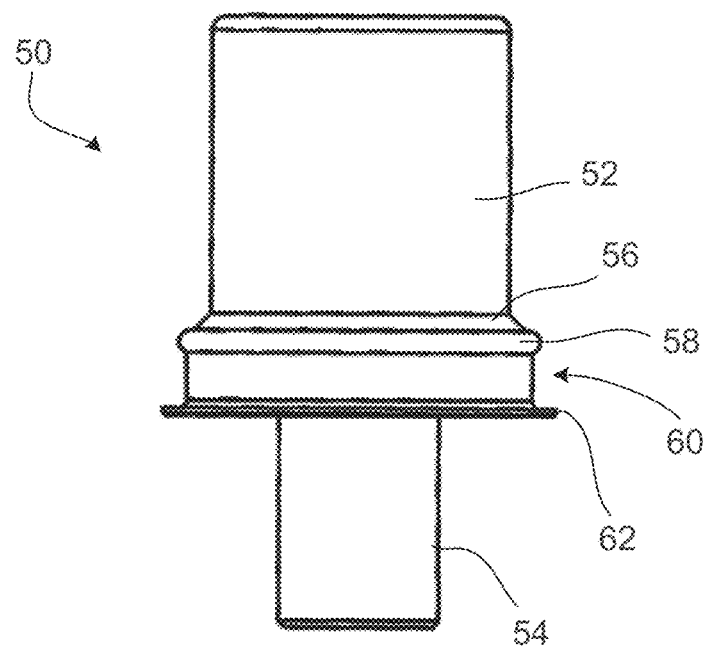
FIG. 2B is a side view of a cannula for coupling to the ventricular cuff.

Referring to FIGS. 2A and 2B, the cuff 20 defines an opening 30 that admits the inflow cannula 50. The cuff 20 includes a coupling mechanism, for example, a clamp 26 that couples the cuff 20 to the cannula 50. The cuff 20 also includes a locking mechanism in the form of a cam 28 that secures the clamp 26 in a closed position. The locking mechanism, by maintaining the position of the coupling mechanism, limits the possibility of the cuff 20 accidentally becoming uncoupled from the cannula 50. The locking mechanism can secure the cuff 20 to the cannula 50 such that, for example, removal of the cuff 20 from the cannula 50 requires more than one action, or the cannula 50 is no longer free to rotate or translate with respect to the cannula 50 without significant outside influence, such as by a clinician.

Figure 3:
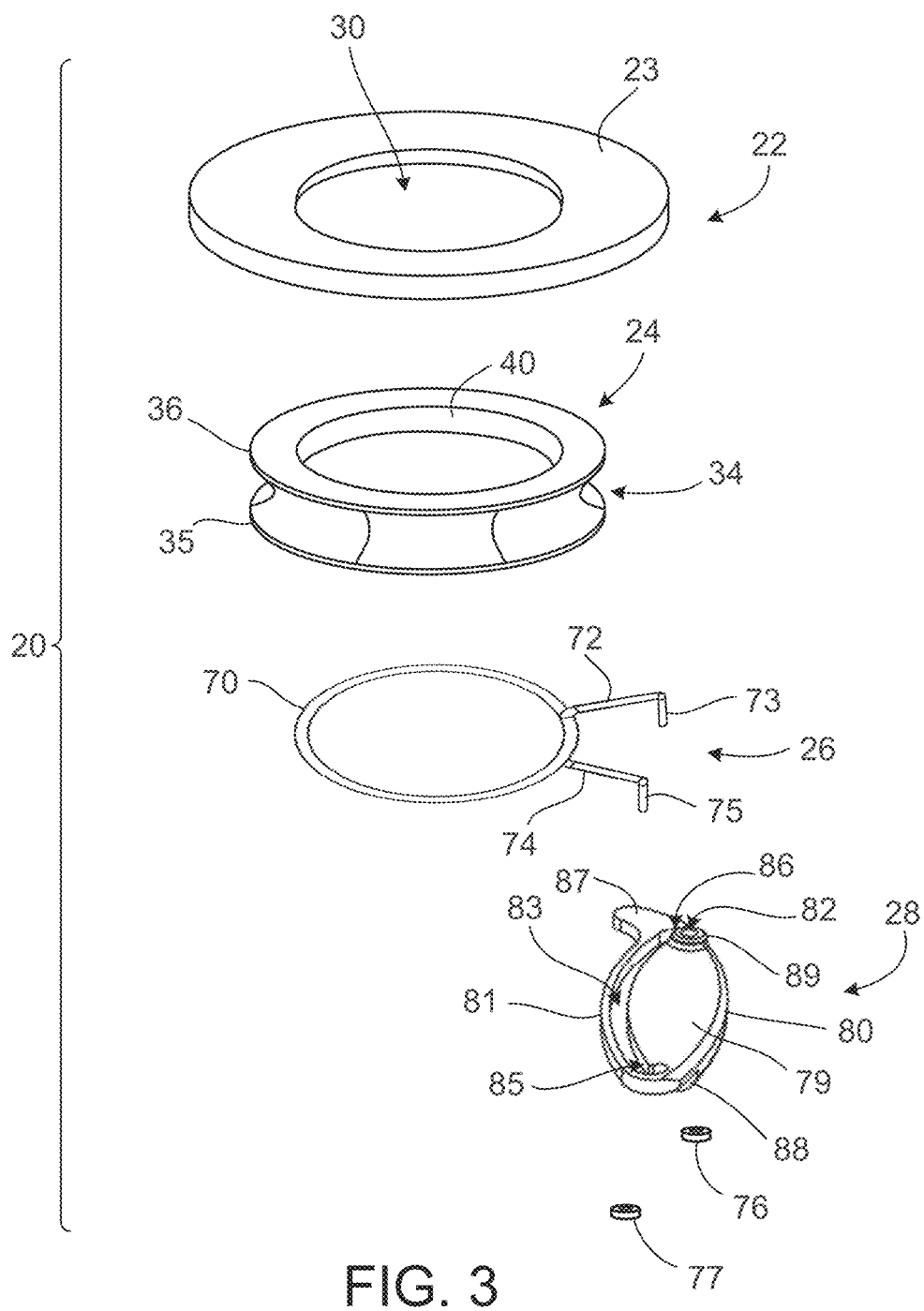
FIG. 3 is an exploded view of the ventricular cuff.

Referring to FIG. 3, the cuff 20 is illustrated in a view illustrating individual disassembled parts, including a fastening member 22, a linking member 24, the clamp 26, and the cam 28. The components illustrated can be preassembled and delivered to a clinician as a single unit. The fastening member 22 is generally ring-shaped and includes a contact surface 23 to contact heart tissue. The fastening member 22 is composed of a material through which sutures can be placed, for example a fabric such as polytetrafluoroethylene (PTFE) felt. In an implanted state, sutures or staples bind the fastening member 22 to heart tissue to couple the cuff 20 to the heart 14. In one embodiment, the fastening member 22 and the linking member 24 are pre-assembled together as one unit.

Figure 4A:
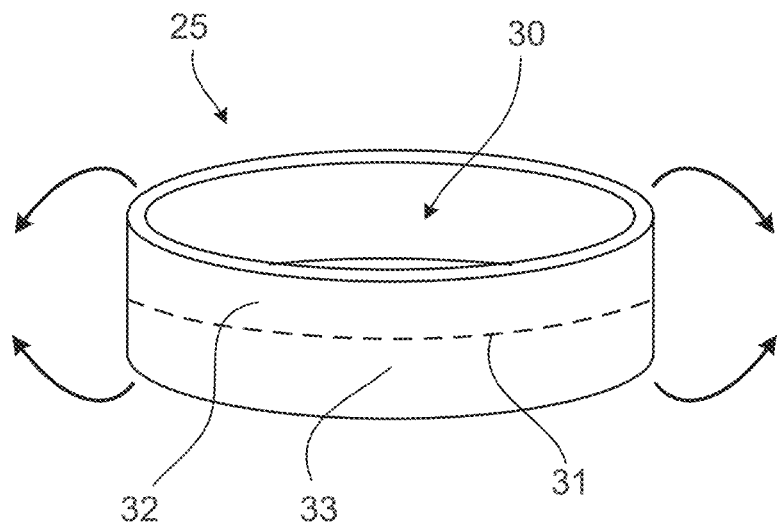
FIG. 4A is a perspective view of a tube from which a seal member of the ventricular cuff can be fabricated.
Figure 4B:
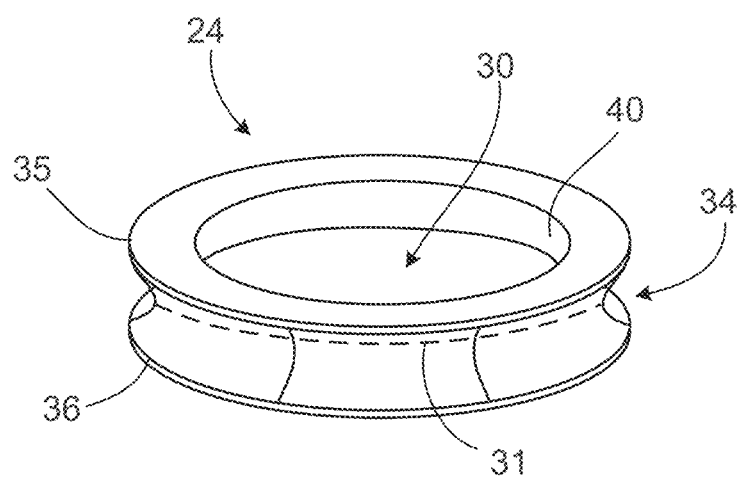
FIG. 4B is a perspective view of a seal member of the ventricular cuff.

Referring to FIGS. 4A and 4B, the linking member 24 can be fabricated by reshaping a tube 25 formed of, for example, an elastomer such as silicone. The linking member 24 is formed, for example, by folding an upper portion 32 of the tube 25 and a lower portion 33 of the tube 25 about an outer circumference 31 of the tube 25. The resulting linking member 24 defines a circumferential groove 34 between generally parallel ring-shaped portions 35, 36. The linking member 24 also includes a circumferential inner surface 40 that forms a seal with the cannula 50.

The linking member 24 can also be fabricated to include ring-shaped reinforcement members 37, 38 (FIG. 6) that includes, for example, a mesh material or a knitted fabric formed of a material such as polyester. A knitted fabric or mesh material is embedded into a silicone sheet. The silicone sheet is die-cut into ring-shaped portions 35, 36 that respectively include the ring-shaped reinforcement members 38, 37. The ring-shaped portions 35, 36 are then placed in a silicone mold and overmolded with additional silicone. The molded silicone binds the ring-shaped portions 35, 36 together and creates a flexible connection between the ring-shaped portions 35, 36, which include the reinforcement members 38, 37.

Referring to FIG. 2A and FIG. 3, the clamp 26 includes a circular portion 70 formed of a resilient material, such as metal wire. For example, the circular portion 70 can be formed of stainless steel or a cobalt chromium alloy, each of which can provide implantability, long term stability, and resiliency. In the assembled cuff 20, the circular portion 70 is disposed in the circumferential groove 34 of the linking member 24. The linking member 24 is thus couples the clamp 26 to the fastening member 22. Sutures 42 pass through the fastening member 22 and the ring-shaped portions 35, 36 of the linking member 24, capturing the circular portion 70 in the linking member 24 and coupling the linking member 24 to the fastening member 22. The reinforcement members 37, 38 limit tearing of the linking member 24 by the sutures 42. In addition to, or instead of, sutures 42, the linking member 24 can be coupled to the fastening member 22 by an adhesive or by overmolding the linking member 24 over a portion of the fastening member 22.

The clamp 26 has a relaxed position toward which it wants to return after a load is applied to open or close the clamp 26. The circular portion 70 is expanded by moving the arms 72, 74 closer together. The circular portion 70 is contracted by increasing the distance between the arms 72, 74. Expansion of the circular portion 70 beyond the relaxed position loads the circular portion 70, causing the circular portion 70 to exert a force that tends to contract the circular portion 70 (e.g., an inward radial force). Conversely, compression of the circular portion 70 beyond the relaxed position loads the circular portion 70 such that the circular portion 70 exerts a force to expand the circular portion 70 (e.g., an outward radial force).

The clamp 26 includes a pivot arm 72 and a travelling arm 74 that extend from the circular portion 70. The pivot arm 72 and the travelling arm 74 provide leverage to expand and contract the circular portion 70, thus opening and closing the clamp 26. The pivot arm 72 includes a pivot end 73, and the travelling arm 74 includes a travelling end 75. The ends 73, 75 extend generally perpendicular to their respective arms 72, 74. The ends 73, 75 each pass through the cam 28 and are captured in the cam 28 by a cap 76, 77.

Referring to FIGS. 5A to 5E, the cam 28 includes a top side 78, a bottom side 79, and opposite lateral sides 80, 81. The cam 28 can be formed of, for example, polyether ether ketone (PEEK) or stainless steel. The cam 28 defines a pivot hole 82 that admits the pivot end 73, and defines a channel 83 that admits the travelling end 75. About the pivot hole 82, in the top side 78, the cam 28 defines a recess 84 that receives the cap 76. Opposite the recess 84, the cam 28 includes a boss 89 that extends from the bottom side 79. The height, H, of the boss 89 maintains a space between the pivot arm 72 and the bottom side 79. By contrast, the travelling arm 74 can contact the bottom side 79. The two arms 72, 74 travel in different planes separated by the distance H. Because the boss 89 maintains the pivot arm 72 at a distance from the bottom side 79, the travelling arm 74 can move relative to the pivot arm 72 without contacting the pivot arm 72. The cap 77 is disposed adjacent to the top side 78 and the cap 76 is disposed in the recess 84 such that the caps 76, 77 do not contact each other during operation of the clamp 26.

The channel 83 defines a path, such as a curve, between a detent 85 and an end 86 located near the pivot hole 82. The detent 85 includes a hooked portion of the channel 83 that captures the travelling end 75 to secure the clamp 26 in the closed position.

The cam 28 includes an extension 87 that indicates proper placement of the cuff 20 relative to the pump 12. As the cuff 20 becomes coupled to the cannula 50, the extension 87 engages the surface 13 of the pump 12 to indicate proper placement of the cuff 20 relative to the pump 12. In addition, the extension 87 aligns the cam 28 in a plane generally parallel to the surface 13. Alignment of the cam 28 with respect to the surface 13 reduces the likelihood that the cam 28 may engage a portion of the pump 12 and improperly impede the clamp 26 from closing completely. The cam 28 also includes a raised portion 88 extending from the top side 78, which facilitates manipulation of the cam 28. The raised portion 88 is rounded to rest against the outer circumference of the pump 12 when the cam 28 is locked (see FIG. 9C). The raised portion 88 defines a slot 90 in which a tool or surgical instrument can be inserted to unlock the cam 28. The slot 90 can be used to pry open the clamp 26, for example, if tissue in-growth makes manual manipulation of the cam 28 difficult.

Manipulation of the cam 28 moves the clamp 26 between open and closed positions. In the open position, the clamp 26 permits a proximal portion 52 of the cannula 50 to pass through the opening 30. In the closed position, the clamp 26 presses inward to couple the cuff 20 to the cannula 50. In the closed position, the clamp 26 presses the linking member 24 into engagement with the cannula 50, and the circumferential inner surface 40 of the linking member 24 forms a seal with the cannula 50.

Referring to FIG. 2B, the cannula 50 is shown by itself here but is generally an integrated component of the pump 12. In some implementations, the pump 12 can receive different interchangeable cannulas to achieve an appropriate fit in a particular anatomy. The cannula 50 includes the proximal portion 52 that passes through the opening 30 into the heart 14 and a distal portion 54 housed within the pump 12. Along the length of the cannula 50, between the proximal portion 52 and the distal portion 54, the cannula 50 includes a circumferential tapered portion 56, a circumferential ridge 58, and a circumferential flange 62. The cannula 50 defines a circumferential groove 60 in which the clamp 26 and the linking member 24 are received.

To couple the cannula 50 to the cuff 20, the proximal portion 52 is passed through the opening 30, such that the circumferential tapered portion 56 engages the circumferential inner surface 40 of the linking member 24, guiding the cannula 50 into alignment with the cuff 20. Further advancement of the cannula 50 causes the circumferential ridge 58 to travel past the circular portion 70 of the clamp 26. The action of the circumferential ridge 58 passing the circular portion 70 provides a clinician tactile feedback about the proper location of the components. The circumferential flange 62 limits further travel of the cannula 50 relative to the cuff 20, positioning the circular portion 70 of the clamp 26 about the circumferential groove 60. The fastening member 22 is disposed about the cannula 50, generally about the circumferential ridge 58.

The cuff 20 is sized so that the inner diameter of the cuff 20 is greater than the outer diameter of the proximal portion 52, which facilitates insertion of the proximal portion 52. With the clamp 26 in its open position, the size of the inner diameter of the cuff 20 approximates that of the outer diameter of the circumferential ridge 58. The circumferential ridge 58 is rounded, permitting the linking member 24 to slide over the circumferential ridge 58 and into the circumferential groove 60. Thus a clinician can determine that the cuff 20 is properly positioned relative to the cannula 50 by experiencing the tactile sensation of the linking member 24 entering the circumferential groove 60.

Figure 6:
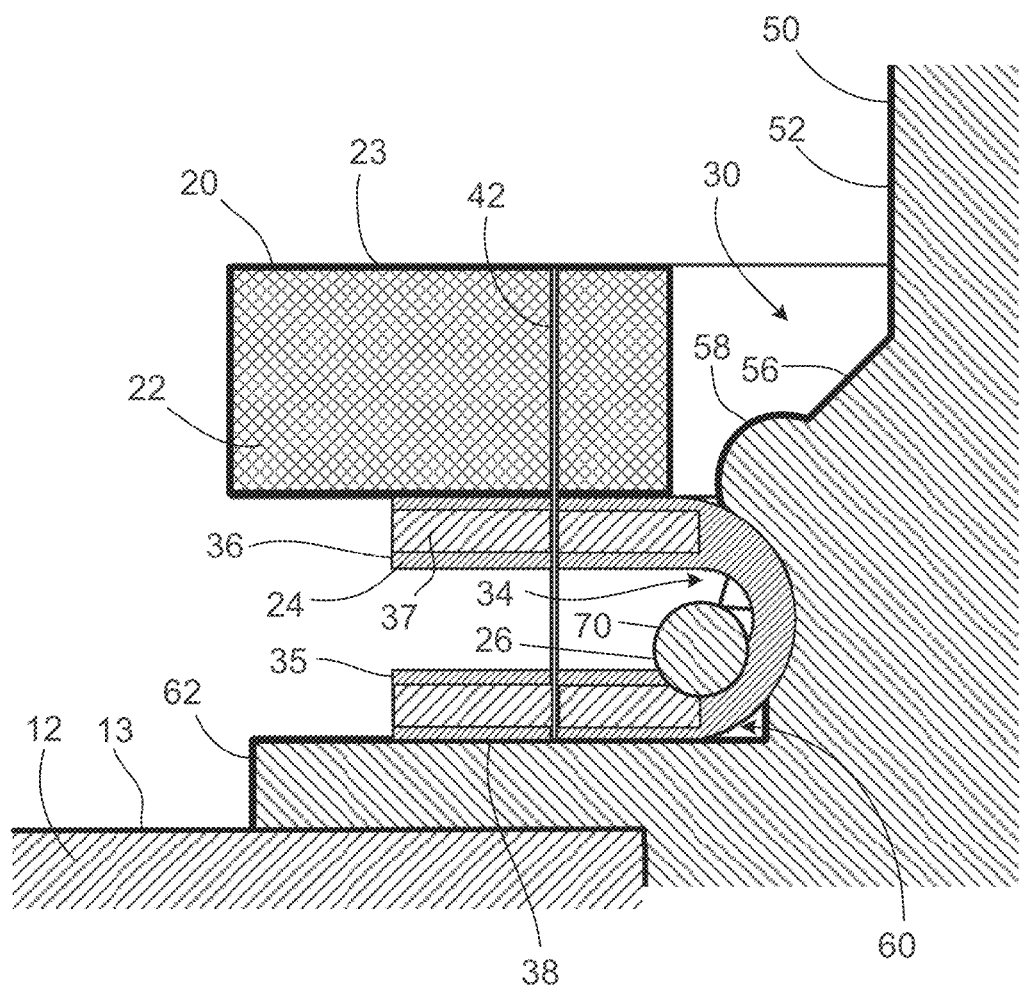
FIG. 6 is a side cross-sectional view of the ventricular cuff coupled to the cannula across line 6-6 of FIG. 8D.

Referring to FIG. 6, the cuff 20 is coupled to the cannula 50 by moving the clamp 26 to its closed position. In the closed position, the inner diameter of the clamp 26 is smaller than the outer diameter of the circumferential ridge 58. The clamp 26 presses the linking member 24 into the circumferential groove 60, forming a seal and capturing the cannula 50 in the cuff 20. The outer diameter of the cannula 50 at the circumferential groove 60 is larger than the outer diameter of the proximal portion 52. The differential in diameter allows passage of a coring tool through the cuff 20. In some instances, the coring tool can be slightly larger than the proximal portion 52 of the cannula 50. In addition, the differential in diameter can allow the clinician to further confirm proper placement of the cuff 20 relative to the cannula 50. A clinician can confirm proper placement by applying a small axial load that would tend to separate the cannula 50 from the cuff 20. If the cannula 50 and the cuff 20 separate easily, then the cuff 20 is improperly seated. If cannula 50 and the cuff 20 remain coupled, however, the cuff 20 is properly seated.

Figure 7A:
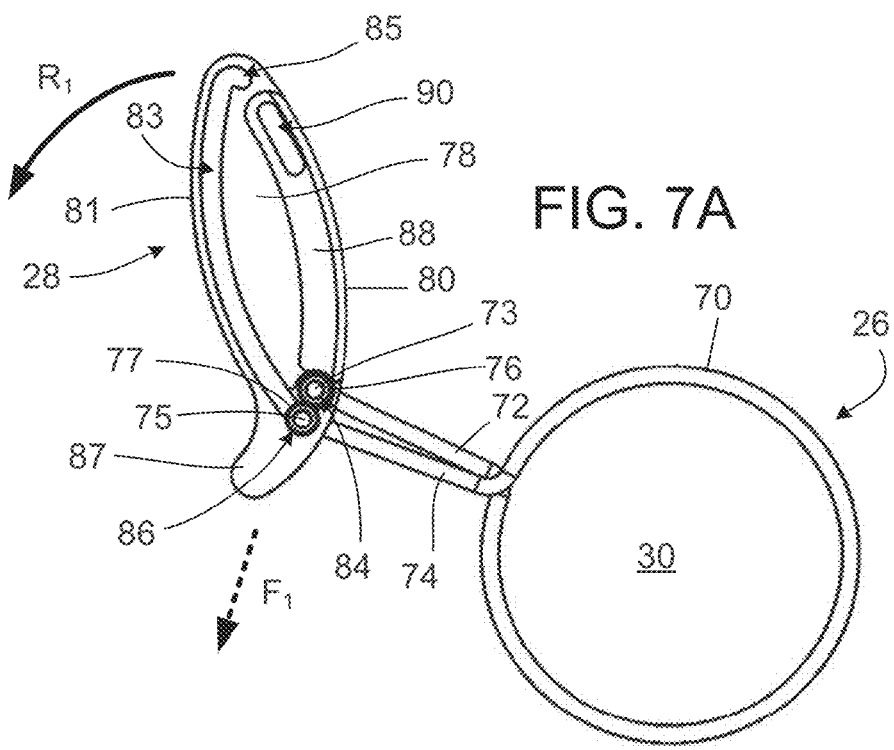
FIGS. 7A to 7D are top views illustrating the closing of a clamp of the ventricular cuff.
Figure 7B:
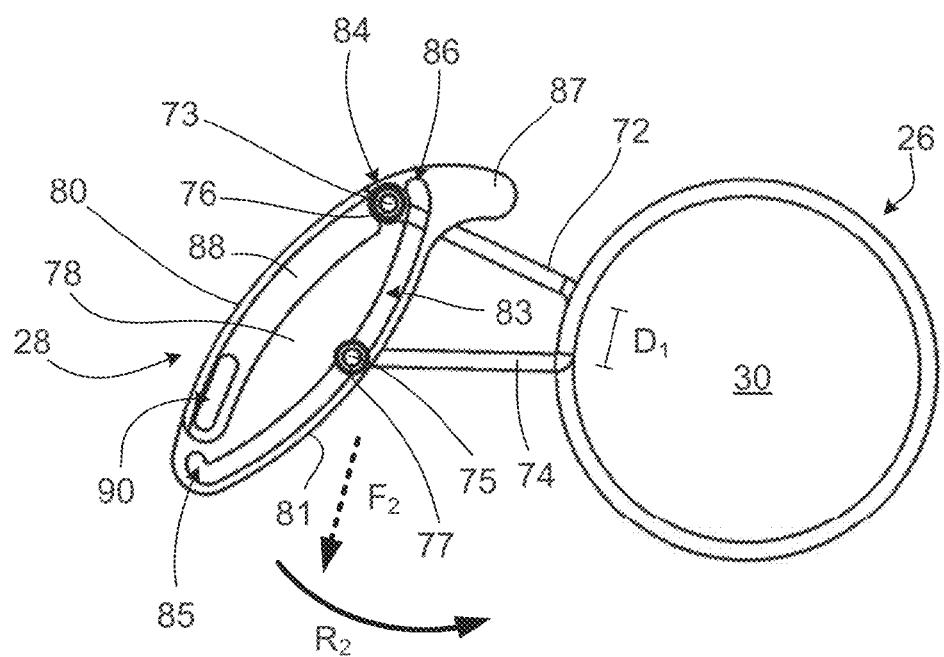
Figure 7C:
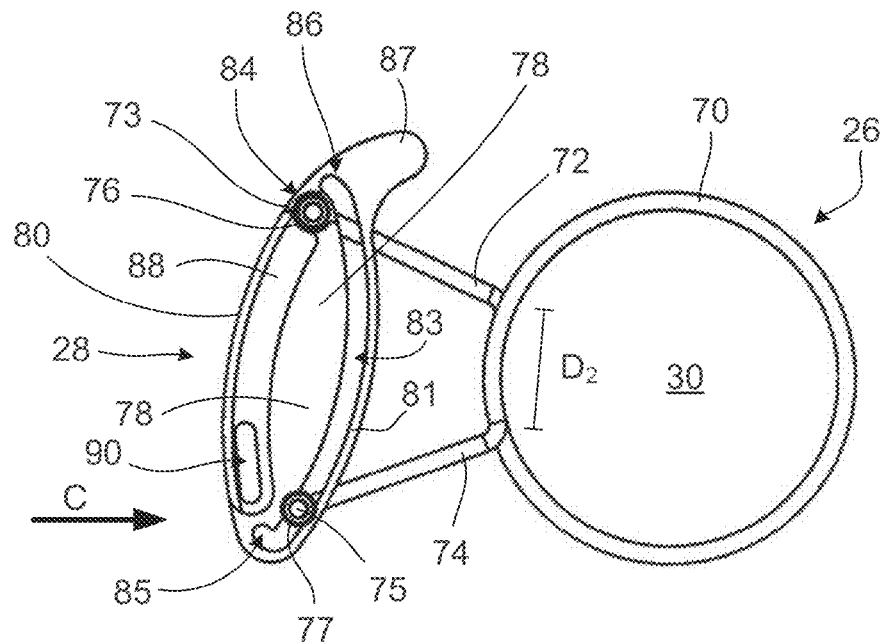

Referring to FIG. 7A, as the clamp 26 moves from the open position of FIG. 7A to the closed position of FIG. 7C, the cam 28 rotates about the pivot end 73 in a plane. As the cam 28 rotates, the travelling end 75 travels through the channel 83. In the open position, the pivot arm 72 and the travelling arm 74 are located near each other, and the circular portion 70 is expanded beyond its relaxed position. In this position, the clamp 26 can admit the circumferential ridge 58 of the cannula 50 through the opening 30. The travelling end 75 is located at the end 86 of the channel 83 nearest the pivot end 73.

Because the circular portion 70 is loaded, the circular portion 70 exerts a force on the end 75 in the direction of arrow $F_1$ to separate the pivot arm 72 and the travelling arm 74. Nevertheless, the open position is stable because the force acts away from the length of the channel 83 and instead presses the travelling end 75 into the end 86 of the channel 83. As a result, the open position can be maintained while the cannula 50 is placed relative to the clamp 26.

From the open position, a clinician closes the clamp 26 by exerting a force on the side 80 of the cam 28, causing the cam 28 to rotate in a plane about the pivot end 73. A small rotation of the cam 28 in the direction of arrow $R_1$ brings the length of the channel 83 into closer alignment with the direction of force, $F_1$, exerted by the circular portion 70 on the travelling end 75. The force exerted by the circular portion 70 continues the rotation of the cam 28 about the pivot end 73 as the clamp 26 continues to close.

Referring to FIG. 7B, the clamp 26 is in an unstable position between the open position and the closed position. Force exerted by the loaded circular portion 70 continues to rotate the cam 28 in the plane and close the clamp 26. The distance between the pivot arm 72 and the travelling arm 74 increases, and the circular portion 70 contracts, resulting in an overlap of the circular portion 70 of a distance, $D_1$. The clinician is not required to apply additional force on the cam 28 to move the clamp 26 to the closed position. The clamp 26 exerts a force in the direction of arrow $F_2$, moving the end 75 through the channel 83. As the travelling end 75 proceeds through the channel 83, the cam 28 continues to rotate about the pivot end 73, as indicated by arrow $R_2$.

Referring to FIG. 7C, with the clamp 26 in the closed position, the cannula 50 is captured within the clamp 26. The size of the circular portion 70 in the closed position can be selected to permit rotation of the cannula 50 relative to the cuff 20 or to limit such rotation.

The closed position is stable. The circular portion 70 is in its unloaded, relaxed position. As a result, the clamp 26 does not exert a force on the travelling end 75 in either direction along the channel 83. The travelling end 75 is located in the channel 83 near the detent 85 but not in the detent 85.

To lock the clamp 26, the clinician applies a force to the side 80 of the cam 28, in the direction of arrow C, which rotates the cam 28 further in the plane. As the cam 28 rotates, the cam 28 exerts a force on the travelling end 75 that is generally aligned with the channel 83, causing the arms 72, 74 to separate further. Rotation of the cam 28 moves the travelling end 75 into the detent 85 and loads the circular portion 70. This action closes the circular portion 70 beyond its relaxed position, reducing the diameter of the circular portion 70 to lock the clamp 26 about the circumferential groove 60 of the cannula 50. Locking the clamp 26 also causes the circular portion 70 to exert an inward radial force to compress the linking member 24 and press the circumferential inner surface 40 into the circumferential groove 60, forming a hemostatic seal.

Figure 7D:
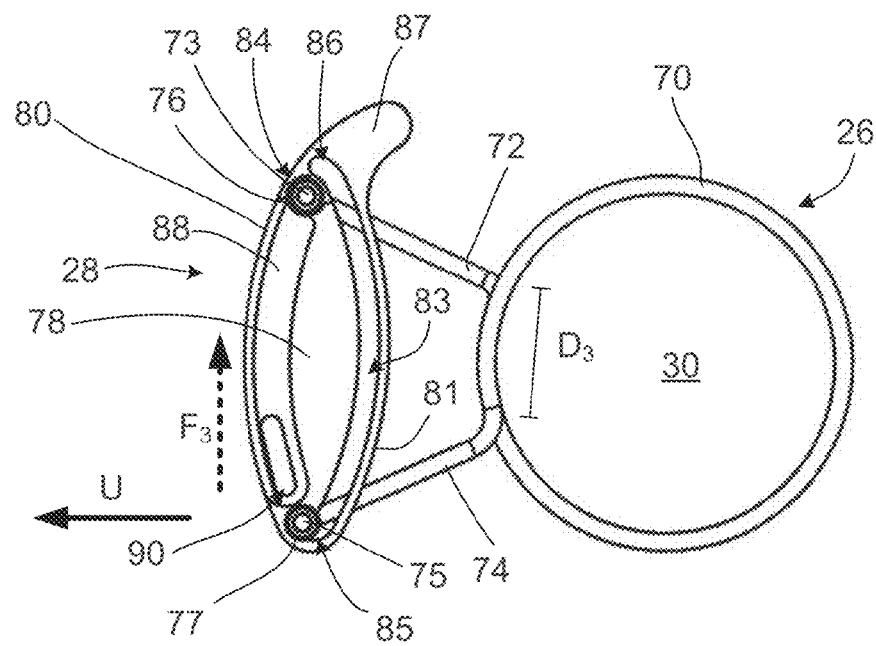

Referring to FIG. 7D, in the locked position of the clamp 26, the cam 28 impedes the clamp 26 from opening. The circular portion 70 is slightly compressed beyond its relaxed position, such that the overlap distance $D_3$ is larger than $D_2$. The loaded circular portion 70 exerts a force on the travelling end 75 in the direction of arrow $F_3$, which presses the travelling end 75 into the detent 85. Because the circular portion 70 forces the travelling end 75 into the detent 85, the travelling end 75 is impeded from traveling through the channel 83 and moving the clamp 26 into the open position.

To open the clamp 26 from the locked position, the travelling end 75 must be dislodged from the detent 85. The clinician applies a force, for example, in the direction of arrow U, to overcome the force of the loaded circular portion 70. The force rotates the cam 28 in the plane such that the travelling end 75 slides out of the detent 85.

From the closed position (FIG. 7C), the clamp 26 can be opened by exerting a force on the side 81 away from the circular portion 70, which rotates the cam 28 opposite the direction of arrows $R_1$ and $R_2$ until the open position is reached. The cannula 50 can then be removed or repositioned relative to the clamp 26 before the clamp 26 is closed again.

Figure 8A:
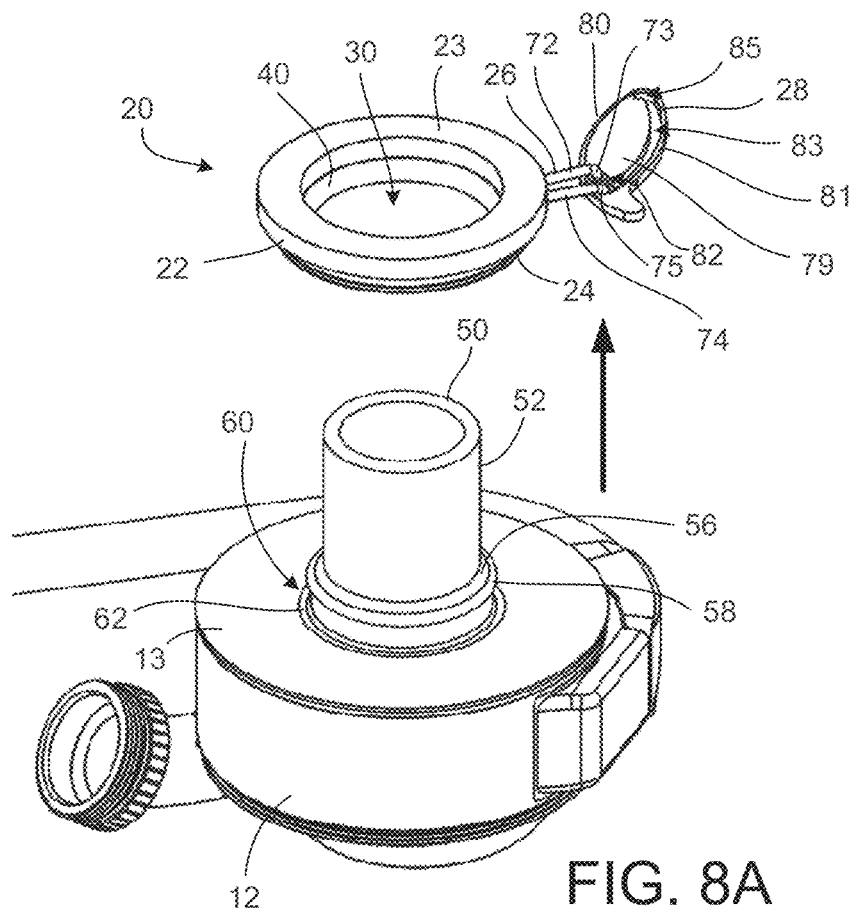

Referring to FIG. 8A, the cuff 20 is in the open position before being coupled to the cannula 50 of the pump 12. Generally, during the implantation process, the cuff 20 will first be attached to the heart 14 and then heart tissue will be removed to admit the proximal portion 52 of the cannula 50. In addition, or alternatively, heart tissue can also be removed before the cuff 20 is attached to the heart 14.

The cannula 50 is fixedly coupled to the pump 12, for example, the cannula 50 can be sealed and welded to the pump 12. Alternatively, the cannula 50 can be removably coupled to the pump 12, for example, by a threaded connection or by a mechanism that permits the cannula 50 to snap into place. A clinician can select a cannula 50 that best fits the anatomy of the patient, and can couple the cannula 50 to the pump 12 prior to or during a procedure. When the cannula 50 is coupled to the pump 12, the distal portion 54 is housed within the pump 12 and the proximal portion 52 extends from a top surface 13 of the pump 12. A clinician may select a cannula 50 that extends an appropriate distance into the heart 14. For example, a clinician may a cannula 50 with a first length for a left VAD so that the cannula 50 extends the proper distance into the heart 14. For implantation of a right VAD, however, the clinician may use a cannula with a different length so that the cannula extends a different distance into a heart.

To couple the cannula 50 to the cuff 20, the pump 12 and the cannula 50 are advanced toward the cuff 20 so that the proximal portion 52 of the cannula 50 enters the opening 30. As the cannula 50 travels relative to the cuff 20, the circumferential ridge 58 engages the circumferential inner surface 40 of the linking member 24. Further travel of the cannula 50 relative to the cuff 20 advances the circumferential ridge 58 through the linking member 24, so that the clamp 26 and the linking member 24 are disposed about the circumferential groove 60.

Advancing the circumferential ridge 58 through the linking member 24 produces tactile feedback for the clinician, such as a snap-like sensation. The tactile feedback indicates that the cuff 20 is properly seated against the circumferential flange 62 and that the circular portion 70 is disposed about the circumferential groove 60. In some implementations, as the circumferential ridge 58 engages the linking member 24 disposed over the circular portion 70, the circumferential ridge 58 slightly expands the circular portion 70. When the circumferential ridge 58 passes through the clamp 26, the clamp 26 contracts to its open position, contributing to the tactile feedback experienced by the clinician.

Figure 8B:
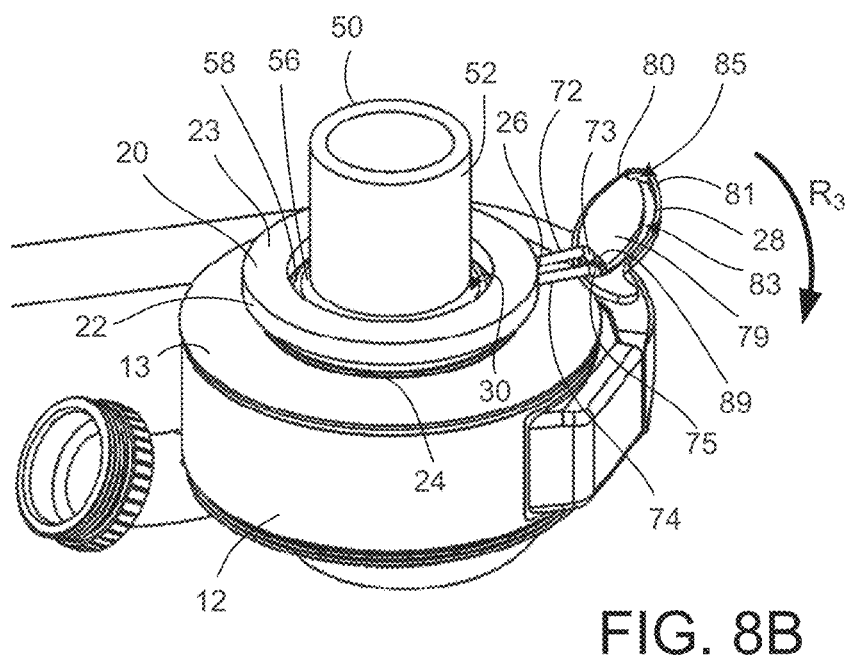

Referring to FIGS. 8B and 9A, the cuff 20 is disposed about the cannula 50, with the linking member 24 partially disposed in the circumferential groove 60. In this position, the clamp 26 can be closed to capture the cannula 50 in the cuff 20. To close the clamp 26, the clinician manipulates the cam 28 to begin rotating the cam 28 about the pivot end 73, in the direction of arrow $R_3$.

Figure 8C:
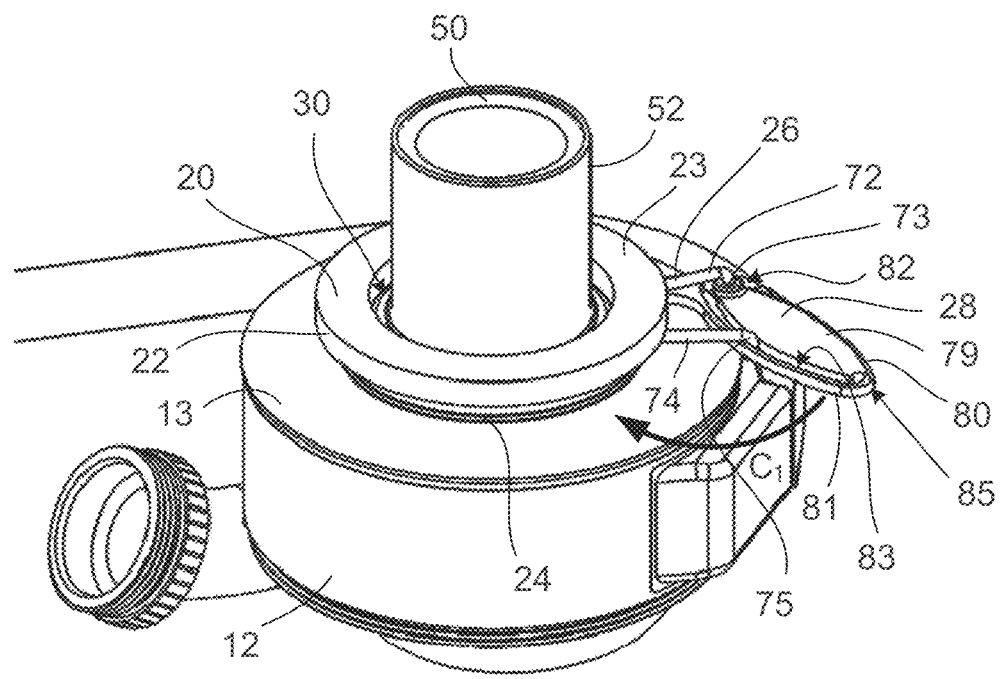

Referring to FIGS. 8C and 9B, the resilient force of the clamp 26 moves the travelling end 75 through the channel 83 defined in the cam 28, continuing the rotation of the cam 28 about the pivot end 73, in the direction of arrow $C_1$. The circular portion 70 of the clamp 26 contracts and presses the linking member 24 into the circumferential groove 60. The contraction of the circular portion 70 captures the cannula 50 within the cuff 20 because the circumferential ridge 58 cannot pass through the circular portion 70.

Figure 8D:
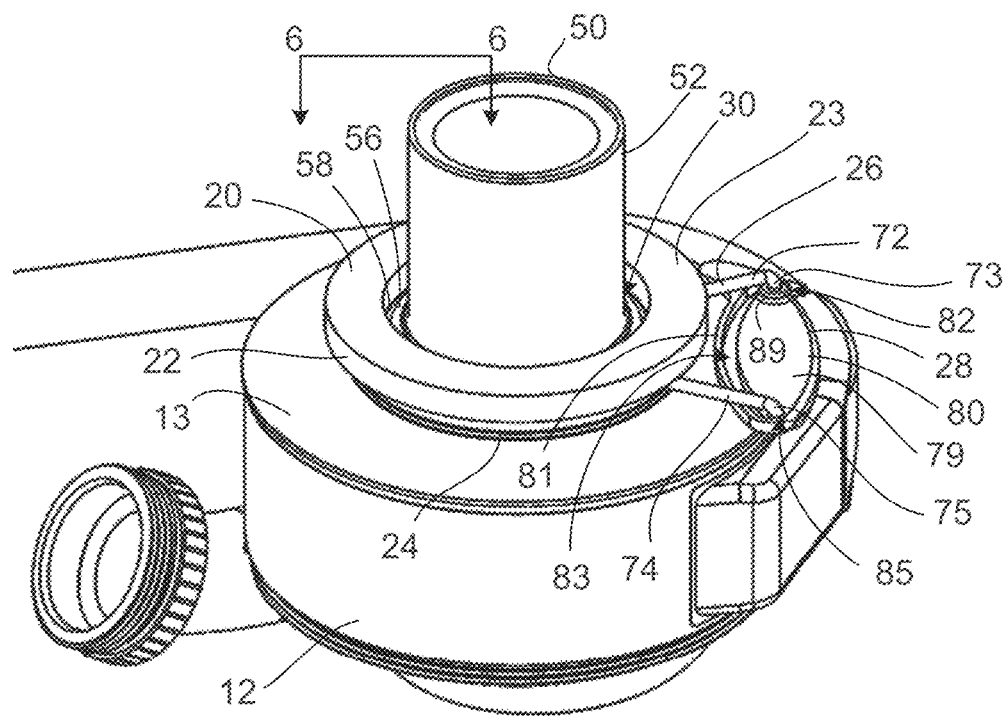

Referring to FIGS. 8D and 9C, the clamp 26 is in a closed position and the cam 28 is in a locked position, maintaining the clamp 26 in the closed position. The travelling end 75 of the clamp 26 is located in the detent 85 defined in the cam 28. From this position, the clamp 26 is unlikely to be opened accidentally, because significant force is required to remove the travelling end 75 from the detent 85. The top side 78 of the cam 28 is disposed against the top surface 13 of the pump 12, and the raised portion 88 of the cam 28 rests against the outer circumference of the pump 12.

Figure 10A:
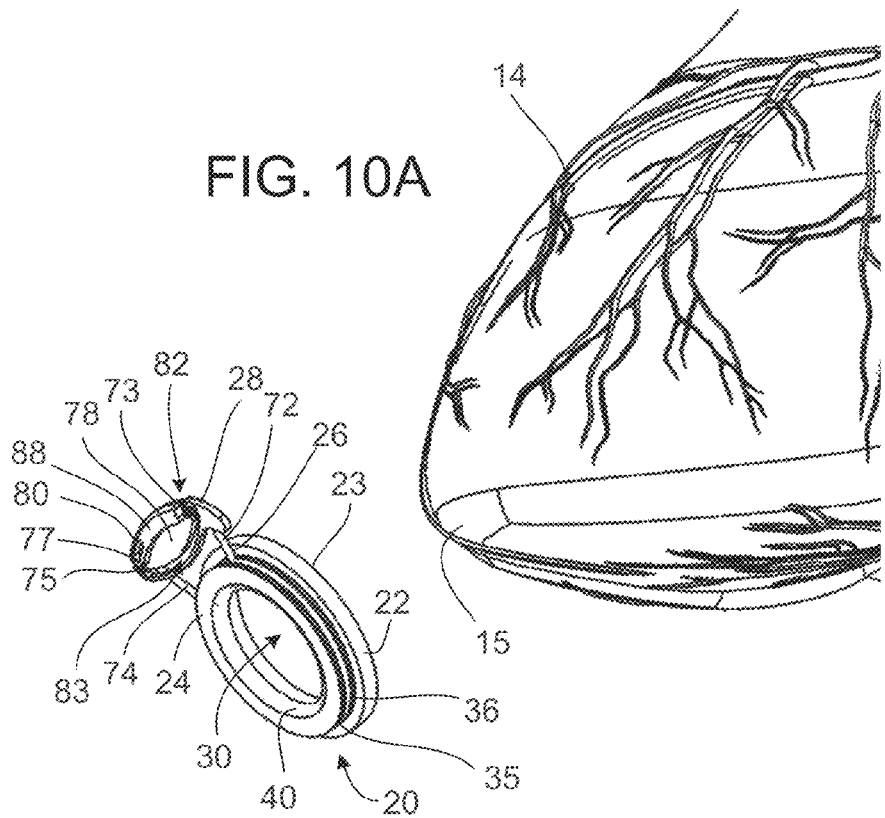

Referring to FIG. 10A, implantation of pump 12 to the heart 14 can include selecting a location to attach the cuff 20. For example, the apex 15 of the left ventricle can be selected as an operation site.

Figure 10B:
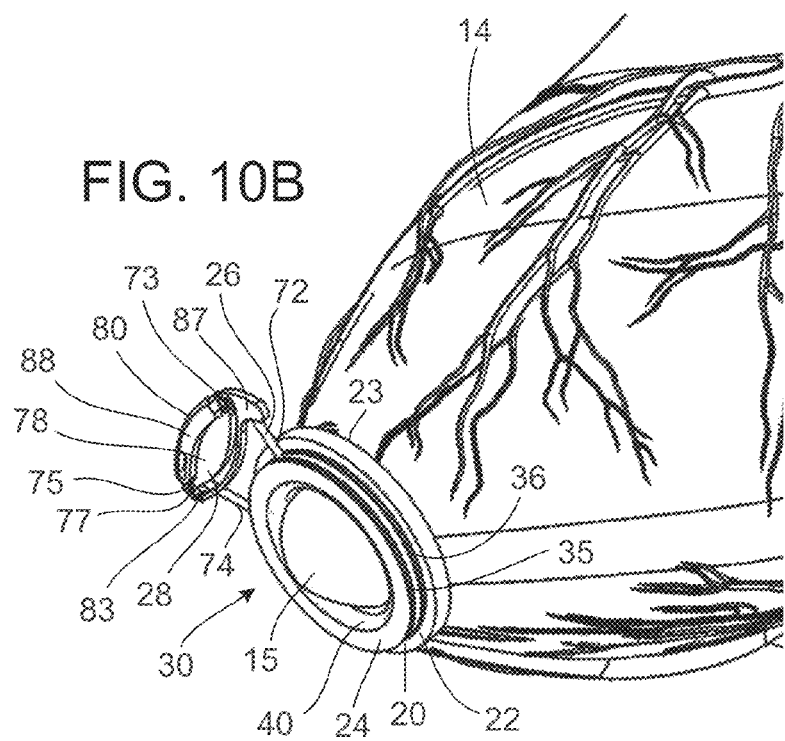

Referring to FIG. 10B, the cuff 20 is placed in contact with the heart 14 at the selected operation site. The cuff 20 is attached to the heart 14, for example, with sutures. In some embodiments, a cardiac bypass system is activated so that blood does not circulate through the heart 14. A core section of heart tissue is removed through the opening 30 of the cuff 20. Alternatively, in some embodiments, the cuff 20 can be attached to the heart 14 and a core section of heart tissue can be removed in the absence of a cardiac bypass. As another alternative, in some implementations, the core section of heart tissue can be removed before attaching the cuff 20 to the heart 14.

Referring to FIG. 10C, heart tissue has been removed so that the proximal portion 52 can be admitted through the opening 30 of the cuff 20. The clamp 26 of the cuff 20 is moved to its open position (not shown) and the proximal portion 52 of the cannula 50 is received through the opening 30.

Referring to FIG. 10D, the proximal portion 52 advances through the opening 30 until the circular portion 70 of the clamp 26 is disposed about the circumferential groove 60. The clinician determines that the circular portion 70 is located about the circumferential groove 60 based on (i) snap-like tactile feedback of the circumferential ridge 58 passing through the linking member 24 and (ii) engagement of the linking member 24 to the circumferential flange 62. The clinician couples the cuff 20 to the cannula 50 by rotating the cam 28 in a plane generally parallel to the top surface 13 of the pump 12. Rotation of the cam 28 moves the clamp 26 to its closed position, in which the cannula 50 is captured within the cuff 20. The clinician rotates the cam 28 further in the plane to engage the locking mechanism of the cam 28, impeding the clamp 26 from leaving the closed position. By engaging the locking mechanism of the cam 28, orientation of the cuff 20 to the cannula 50 can be secured such that axial movement of the cannula 50 relative to the cuff 20 and rotation of the cannula 50 relative to the cuff 20 are both impeded.

The size of the cuff 20 can be selected such that, when the pump 12 is coupled to the cuff 20, the distance between the heart 14 and the top surface 13 of the pump 12 is small. For example, the total height of the cuff 20 may be, for example, between approximately 2 mm and approximately 10 mm. Because the cam 28 can be moved to a locked position by planar movement, the locking mechanism does not require clearance between the cuff 20 and the top surface 13.

In addition, the inflow cannula 50 can define two or more circumferential grooves between two or more circumferential ridges. Multiple circumferential grooves can provide different locations along the length of the cannula 50 at which the cuff 20 can be coupled. A clinician couple the cuff 20 at a particular circumferential groove to select the distance that the cannula 50 will extend into the heart 14.

The thickness of the fastening member 22 can be selected to adjust the length that the cannula 50 extends into the heart 14. The use of a thicker fastening member 22 can result in the cannula 50 extending a shorter depth into the heart 14 than the use of a thinner fastening member 22. A clinician may select a cuff 20 that includes a fastening member 22 of an appropriate thickness to set the distance that the cannula 50 extends into the heart 14.

A clinician may also adjust the distance that the cannula 50 extends into the heart by adding one or more spacers, such as a ring-shaped fabric washer, between the cuff 20 and the heart 14. For example, a clinician may place a spacer between the surface of the heart 14 and the contact surface 23 of the fastening member 22. Sutures can be placed through the fastening member 22 and through the spacer to attach the cuff 20 at an appropriate distance from the heart 14.

In some implementations, the length of the proximal portion 52 of the cannula 50 can be varied to achieve a desired length of extension of the proximal portion 52 into the heart 14. For example, several inflow cannulas having proximal portions of different lengths can be fabricated. A clinician can select an inflow cannula that has a proximal portion corresponding to the desired length of extension into the heart of a particular patient, and can couple the selected inflow cannula to a pump before or during a procedure.

As an alternative to the clamp 26, the cuff 20 may include a resilient metal split ring. A break or gap in the split ring permits the diameter of the split ring to expand as it travels over the circumferential groove 58 of the cannula 50. Once the split ring is located about the circumferential groove 60, the split ring contracts into the circumferential groove 60 to couple the cuff 20 to the cannula 50. The split ring may thus be operated without arms extending from the split ring and without a cam.

Figure 11A:
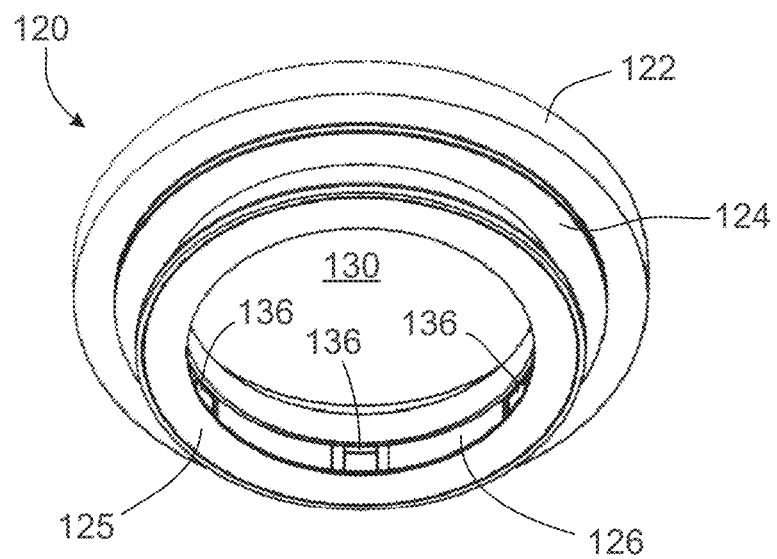
FIG. 11A is a perspective view of a ventricular cuff.
Figure 11B:
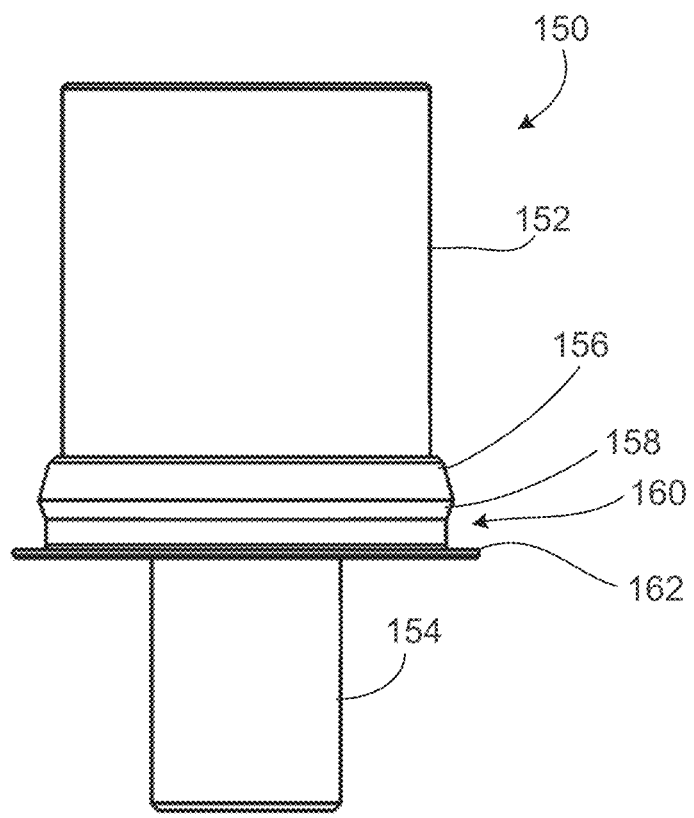
FIG. 11B is a side view of a cannula for coupling to the ventricular cuff of FIG. 11A.

Referring to FIGS. 11A and 11B, an alternative cuff 120 and an alternative cannula 150 can be used to couple a pump 250 (FIG. 14A) to heart tissue. A coupling mechanism, for example, an attachment member 126, couples the cuff 120 to the cannula 150. A locking mechanism in the form of a clip 200 (FIG. 13A) impedes the cuff 120 from becoming uncoupled from the cannula 150.

The cuff 120 defines an opening 130 that admits a proximal portion 152 of the cannula 150. The cuff 120 includes an annular fastening member 122, a linking member 124, and the attachment member 126. The fastening member 122 can be sutured to heart tissue, and can include, for example, a fabric such as PTFE felt.

The linking member 124 is formed of, for example, an elastomer such as silicone, and includes a reinforcement member 128 (FIG. 16) such as a mesh ring. The linking member 124 is disposed about an outer circumference of the attachment member 126 and serves as a linking member to couple the attachment member 126 to the fastening member 122, as discussed further below. The linking member 124 is coupled to the fastening member 122 by, for example, sutures. The linking member 124 can also be molded directly to the fastening member 122. The linking member 124 includes a bottom surface 125 configured to engage a generally flat circumferential flange 162 of the cannula 150, forming a face seal with the circumferential flange 162.

The cannula 150 includes the proximal portion 152 that enters the opening 130 of the cuff 120 and a distal portion 154 that is housed in the pump 250. The cannula 150 includes a first circumferential taper 156 that engages extensions 136 of the attachment member 126 and deflects them away from the cannula 150 as the cannula 150 advances through the opening 130. The cannula 150 includes a second circumferential taper 158 and defines a circumferential groove 160 between the second circumferential taper 158 and the circumferential flange 162.

Figure 12A:
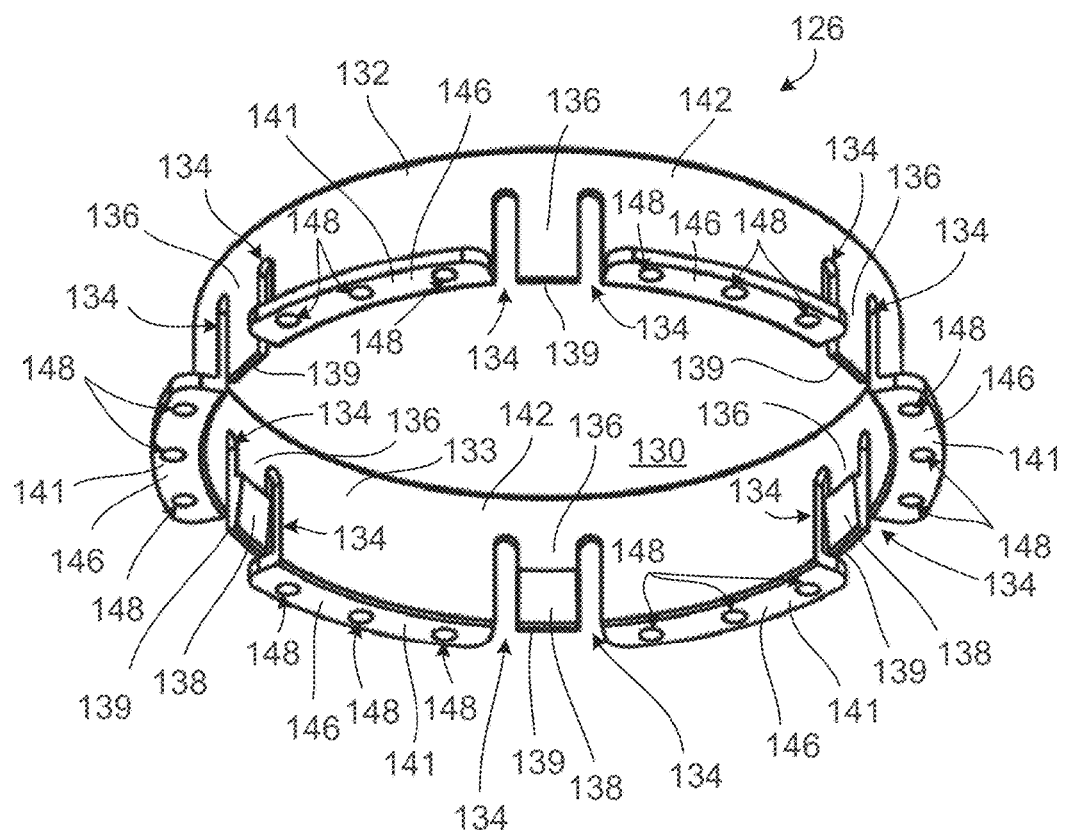
FIG. 12A is a perspective view of an attachment member of the ventricular cuff of FIG. 11A.
Figure 12B:
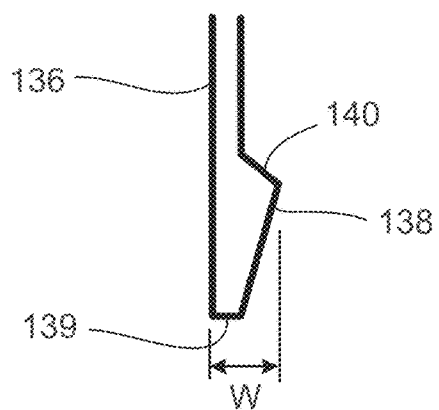
FIG. 12B is a side cutaway view of an extension of the attachment member.

Referring to FIGS. 12A and 12B, the attachment member 126 is formed of, for example, a rigid material such as metal. The attachment member 126 includes a ring portion 132 having a wall 133 with cutouts 134 that define flexible extensions 136. Each extension 136 includes a lower tapered portion 138 (FIG. 12B) disposed on a free end 139 of the extension 136, facing inward toward the opening 130. As the first circumferential taper 156 of the cannula 150 is inserted through the opening 130, the lower tapered portions 138 engage the first circumferential taper 156, causing the extensions 136 to flex outward from the opening 130 and permit the first circumferential taper 156 to pass through the opening 130. When the lower tapered portions 138 are disposed in the circumferential groove 160, the lower tapered portions 138 engage the second circumferential taper 158 of the cannula 150 to impede the cannula 150 from easily exiting the cuff 120. Each lower tapered portion 138 includes upper tapered portion 140, and the width of each lower tapered portion 138, W, decreases along the length of each lower tapered portion 138, between the upper tapered portion 140 and the free end 139.

The extensions 136 can have equal sizes or can be selected to have differing sizes. For example, asymmetrical lengths of the extensions 136 can cause the extensions 136 to engage the circumferential tapers 156, 158 sequentially rather than consecutively during travel of the cannula 150 relative to the cuff 120, reducing the force required to couple the cannula 150 to the cuff 120 or to uncouple the cannula 150 from the cuff 120.

The amount of force required to deflect the extensions is correlated with the angle of the taper of the circumferential tapers 156, 158 and the tapered portions 138, 140. The steepness of the taper angles can be selected such that different amounts of force along the length of the cannula 150 are required to couple the cuff 120 to the cannula 150 can remove the cuff 120 from the cannula 150. The engagement of tapers with a steep angle results in a lower percentage of axial force being transmitted radially outward than the engagement of shallower tapers. Thus to allow the cuff 120 to be coupled to the cannula 150 with a smaller force than the force required to remove the cuff 120 from the cannula 150, the tapers of the lower tapered portions 138 and the circumferential taper 156 are less steep than the tapers of the upper tapered portions 140 and the circumferential taper 158. Accordingly, more force is required to decouple the cuff 120 than to couple the cuff 120 to the cannula 150. The amount of force required to couple the cuff 120 to and decouple the cuff 120 from the cannula 150 can be adjusted by the materials selected for the attachment member 126, the thickness of the extensions 136, the length and width of the extensions 136, and the geometry of the cutouts 134.

The attachment member 126 includes flanged portions 146, disposed between the extensions 136 along the outer circumference of the attachment member 126, at the bottom 141 of the attachment member 126. The flanged portions 146 extend generally perpendicular to the wall 133. When the cuff 20 is coupled to the cannula 150, the flanged portions 146 are disposed in a plane generally parallel to the circumferential flange 162 of the cannula 150. When the cuff 20 is locked to the cannula 150, the flanged portions 146 are captured between the clip 200 and the circumferential flange 162, impeding the cuff 120 from becoming uncoupled from the cannula 150.

Figure 16:
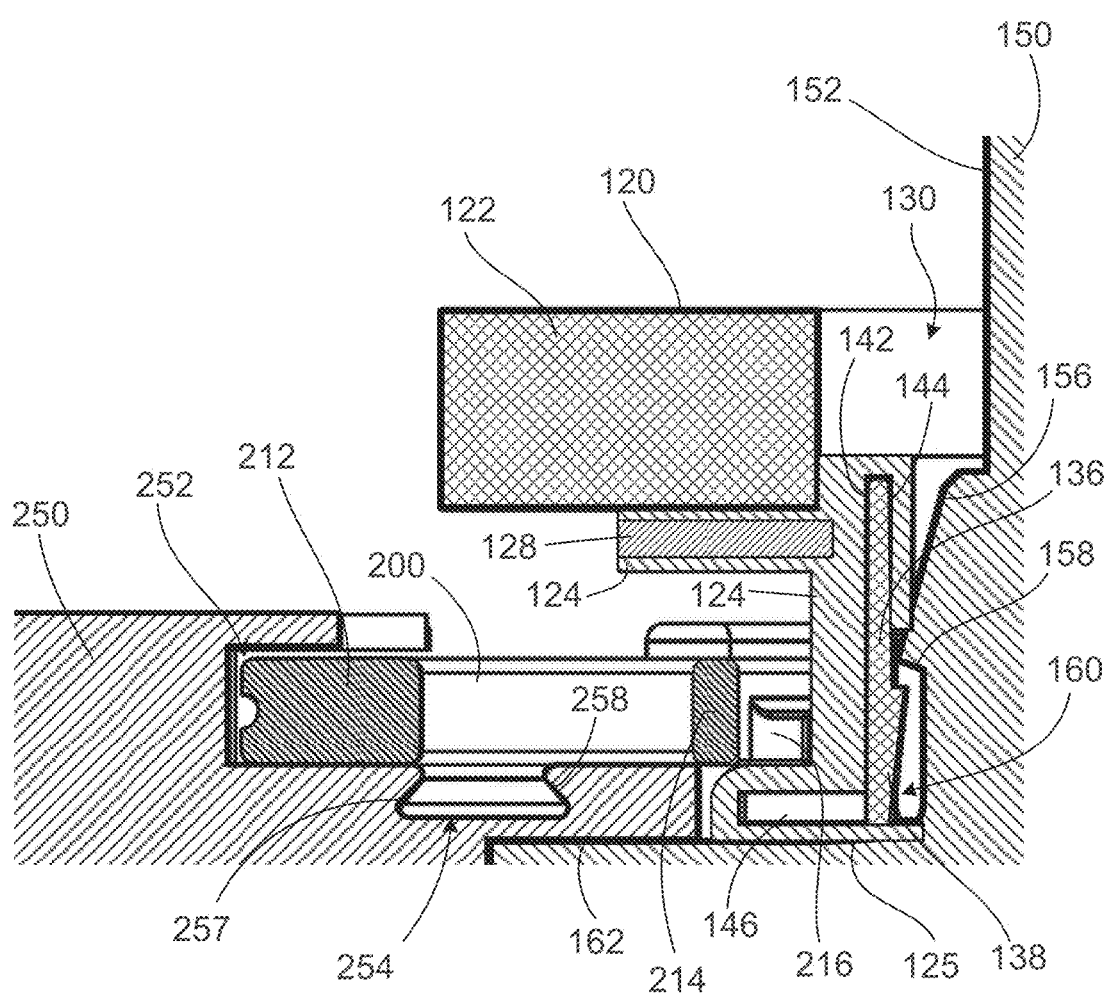
FIG. 16 is a side cross-sectional view of the ventricular cuff of FIG. 11A coupled to the cannula of FIG. 11B across line 16-16 of FIG. 15C.

The flanged portions 146 define holes 148 through which material of the linking member 124 is molded or adhesive is applied to form mechanical locks that secure the linking member 124 to the attachment member 126. Material of the linking member 124 is also molded or adhesively bonded through the cutouts 134 and over the ring portion 132. For example, silicone can be molded over the attachment member 126 and can be molded over a portion of the fastening member 122. The linking member 124 can also be coupled to the attachment member 126 with adhesive or sutures. The linking member 124 covers the flanged portions 146, an outer surface 142 of the wall 133, and a portion of an inner surface 144 of the wall 133 (FIG. 16).

The flanged portions 146 and extensions 136 are disposed symmetrically along the circumference of the attachment member 126, permitting the extensions 136 to engage the circumferential tapers 156, 158 evenly about the cannula 150, and permitting the flanged portions 146 to evenly press the bottom surface 125 of the linking member 124 into engagement with the circumferential flange 162. The attachment member 126 can include more or fewer flanged portions 146 and extensions 136 than those illustrated.

To couple the cannula 150 to the cuff 120, a clinician inserts the proximal portion 152 of the cannula 150 through the opening 130. As the cannula 150 advances through the opening 130, the first circumferential taper 156 passes the upper tapered portion 140 of the lower tapered portions 138. The engagement of the lower tapered portions 138 with the first circumferential taper 156 (which resists advancement of the cannula 150 by deflecting the extensions 136) ends abruptly, permitting the extensions 136 to straighten so that the lower tapered portions 138 reside in the circumferential groove 160. The sudden decrease in resistance to advancement of the cannula 150 produces a tactile snap-like sensation, indicating to the clinician that the cannula 150 is coupled to the cuff 120. The upper tapered portion 140 of the lower tapered portions 138 engage the second circumferential taper 158, impeding the cannula 150 from separating from the cuff 120. The bottom surface 125 of the linking member 124 engages the circumferential flange 162, limiting further advancement of the cannula 150 relative to the cuff 120.

After the cannula 150 and cuff 120 are coupled, the cannula 150 can be separated from the cuff 120 by a force sufficient to deflect the extensions 136. Engagement of the upper tapered portions 140 with the second circumferential taper 158 deflects the extensions 136, allowing the cannula 150 to be removed from the cuff 120.

Figure 13A:
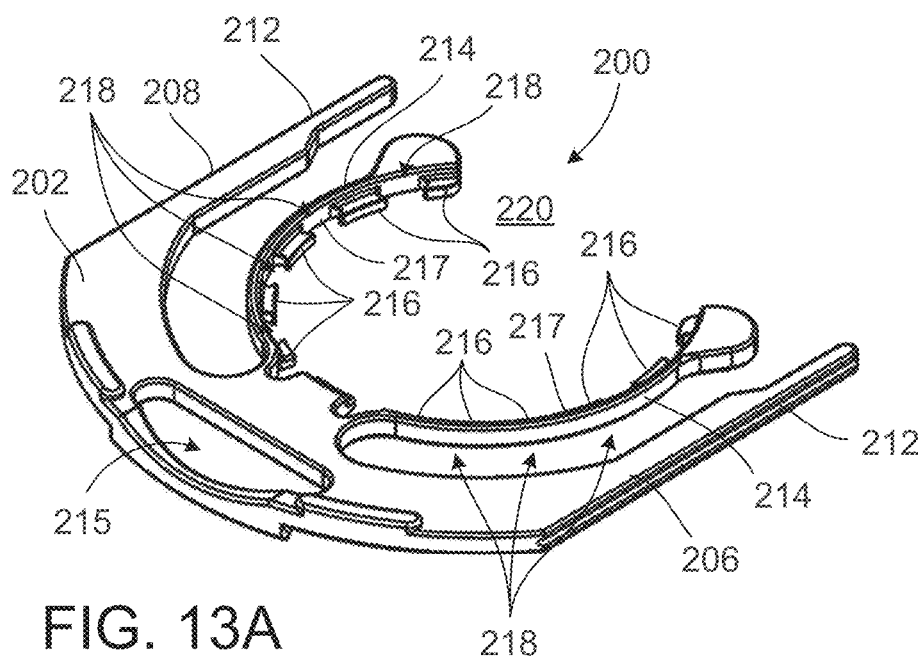
FIG. 13A is a perspective view illustrating the top of a clip.
Figure 13C:
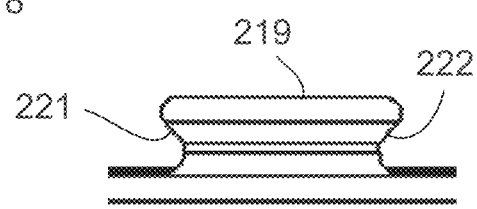
FIG. 13C is a side view of a post of the clip.
Figure 13B:
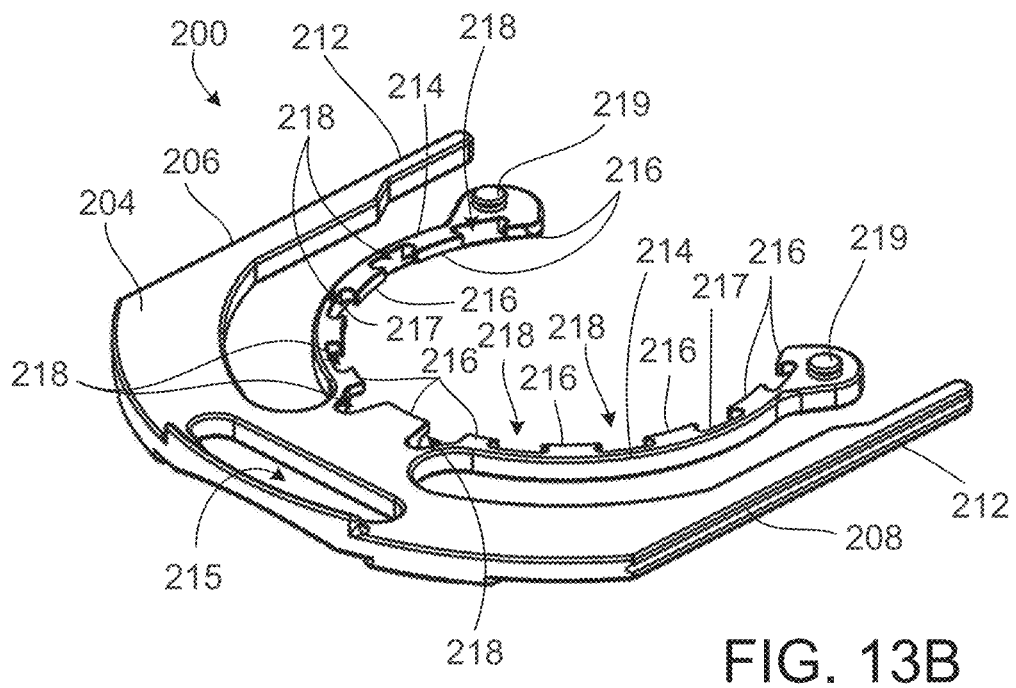
FIG. 13B is a perspective view illustrating the bottom of the clip.

Referring to FIGS. 13A and 13B, the clip 200 is used to secure the cuff 120 about the cannula 150. The clip 200 cooperates with features of the pump 250, described below, to limit travel of the cuff 120 relative to the cannula 150. The clip 200 includes a top side 202, a bottom side 204, and opposite lateral sides 206, 208. The clip 200 can be formed of, for example, a rigid plastic, such as PEEK, or metal, such as titanium.

The clip 200 includes guide rails 212 and arms 214, and defines a recess or opening 215 or opening. The guide rails 212 guide the clip 200 through a linear motion as the clip 200 is received by the pump 250. The opening 215 admits a tool or a finger of the clinician to facilitate disengagement of the clip 200 from its locked position relative to the cuff 120. The arms 214 are curved and resilient, and define an opening 220. As the clip 200 moves relative to the pump 250, the pump 250 forces the arms 214 laterally outward, expanding the opening 220 and allowing the arms 214 to extend about the linking member 124 of the cuff 120. In the locked position of the clip 200, the pump 250 forces the arms 214 laterally inward to engage the linking member 124 and to secure the cuff 120 to the pump 250.

The arms 214 include teeth 216 that extend from inner walls 217 of the arms 214 toward the opening 220. In the locked position of the clip 200, the teeth 216 are disposed over the flanged portions 146 of the attachment member 126, thus capturing the flanged portions 146 between the teeth 216 and the circumferential flange 162 of the cannula 150. Between the teeth 216 are gaps 218 that permit the arms 214 to flex laterally as the clip 200 is received by the pump 250. When the clip 200 is in a locked position about the cuff 120, the teeth 216 engage the linking member 124 of the cuff 120 to impede rotation of the cuff 120 relative to the clip 200 and the pump 250.

Each arm 214 includes a post 219 extending from the bottom side 204 that is received in one of the channels 254 (FIG. 14A) defined by the pump 250. As the pump 250 receives the clip 200, the posts 219 travel through the channels 254, directing the lateral flexion of the arms 214. The posts 219 each include angled walls 221, 222 (FIG. 13C) that engage angled walls 257, 258 (FIG. 16) of the pump 250 that define the channels 254, capturing the posts 219 in the channels 254.

Figure 14A:
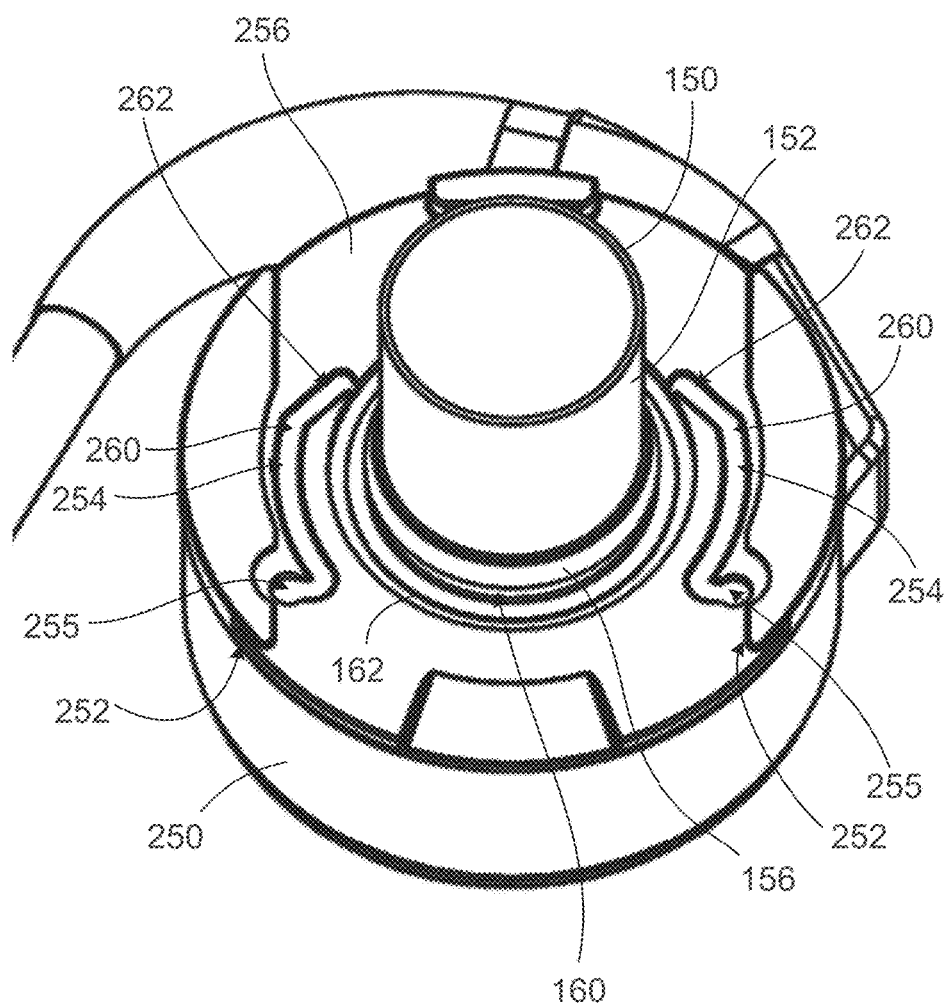
FIGS. 14A to 14C are perspective views illustrating the engagement of the clip with a pump.

Referring to FIG. 14A, the pump 250 is coupled to the cannula 150 and receives a clip 200. The pump 250 defines generally parallel slots 252 that receive the guide rails 212 of the clip 200. The pump 250, in a top side 256, also defines the channels 254 that receive the posts 219 between the angled walls 257, 258 (FIG. 16). The angled walls 257, 258 capture the posts 219, impeding the posts 219 from leaving the channels 254 and maintaining the arms 214 in a plane above the top side 256. The portion of the pump 250 that defines the channels 254 can be an integral component of, for example, a motor housing of the pump, or can be a separate component that attaches to the pump 250, for example, with welds, screws, or other fastening mechanisms.

The pump 250 defines an entry recess 255 at each channel 254 that admits the post 219. The distance between the entry recesses 255 is larger than the distance between the posts 219 when the arms 214 of the clip 200 are not flexed.

To insert the posts 219 into the channels 254, the clinician flexes the arms 214 outward, loading the resilient arms 214 and permitting the posts 219 to enter the channels 254 at the entry recesses 255. After the posts 219 are positioned in the entry recesses 255, the arms 214 flex inward to their natural resting condition, moving the posts 219 in the channels 254 away from the entry recesses 255. Because the posts 219 are captured in the channels 254, the clip 200 will not separate from the pump 250 until the clinician flexes the arms 214 outward and upward, permitting the posts 219 to leave the channels 254 at the entry recesses 255. The pump 250 can be provided with the clip 200 already positioned in the channels 254, and thus already captured by the pump 250, to streamline the implantation procedure.

A first portion 260 of the channels 254 curves outward about the cannula 150 to spread the arms 214, permitting the arms 214 to extend about the cannula 150 and the linking member 124 of the cuff 120. A second portion 262 of the channels 254 curves inward toward the cannula 150, moving the arms 214 inward about the cannula 150.

Figure 14B:
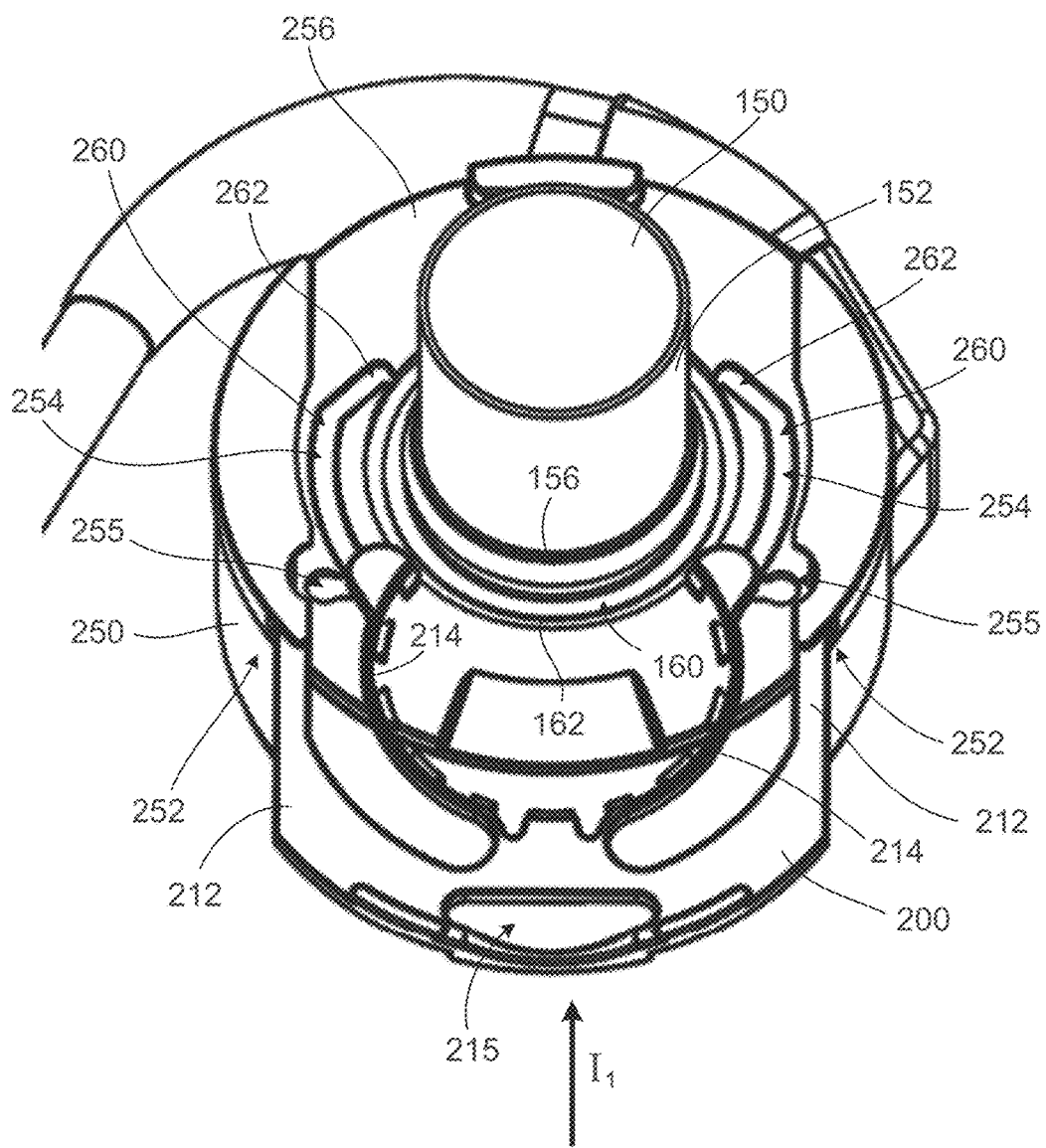
Figure 14C:
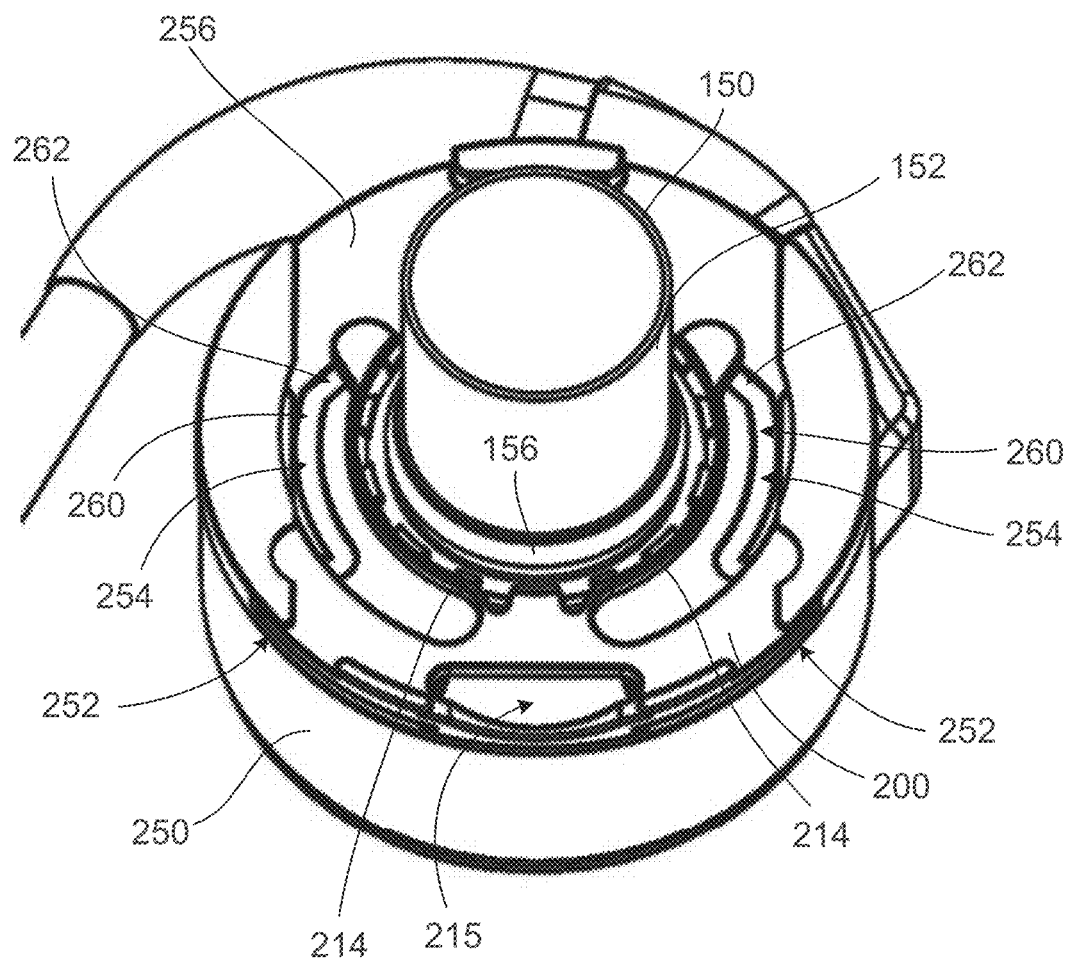

Referring to FIG. 14B, the guide rails 212 of the clip 200 enter the slots 252, and the posts 219 are captured in the channels 254. The clip 200 travels in a generally linear direction relative to the pump 250, in the direction of arrow I₁, until the clip 200 reaches the position of FIG. 14C. As the clip 200 is advanced into the pump 250, the force in the direction of arrow I₁ causes the posts 219 to deflect outward in the channels 254. Once the posts 219 have reached the peak distance between the channels 254, the insertion force required in the direction of arrow I₁ lessens as the inward deflection force of the arms 214 drive the clip 200 through the second portion 262 of the channels 254. The clip 200 travels linearly as the posts 219 travel through the channels 254, until the position of FIG. 14C is reached in which the arms 214 are in their relaxed position.

To move the clip 200 back to the unlocked position, the clip 200 is retracted in a direction opposite the arrow I₁, and the posts 219 travel in the opposite direction through the channels 254. During removal of the clip 200, the second portion 262 expands the arms 214 and the first portion 260 permits the arms 214 to become closer together. The angle of the first portion 260 is less steep than the angle of the second portion 262, which results in the force to remove the clip 200 being higher than the force to move the clip 200 into the locking position.

Figure 15A:
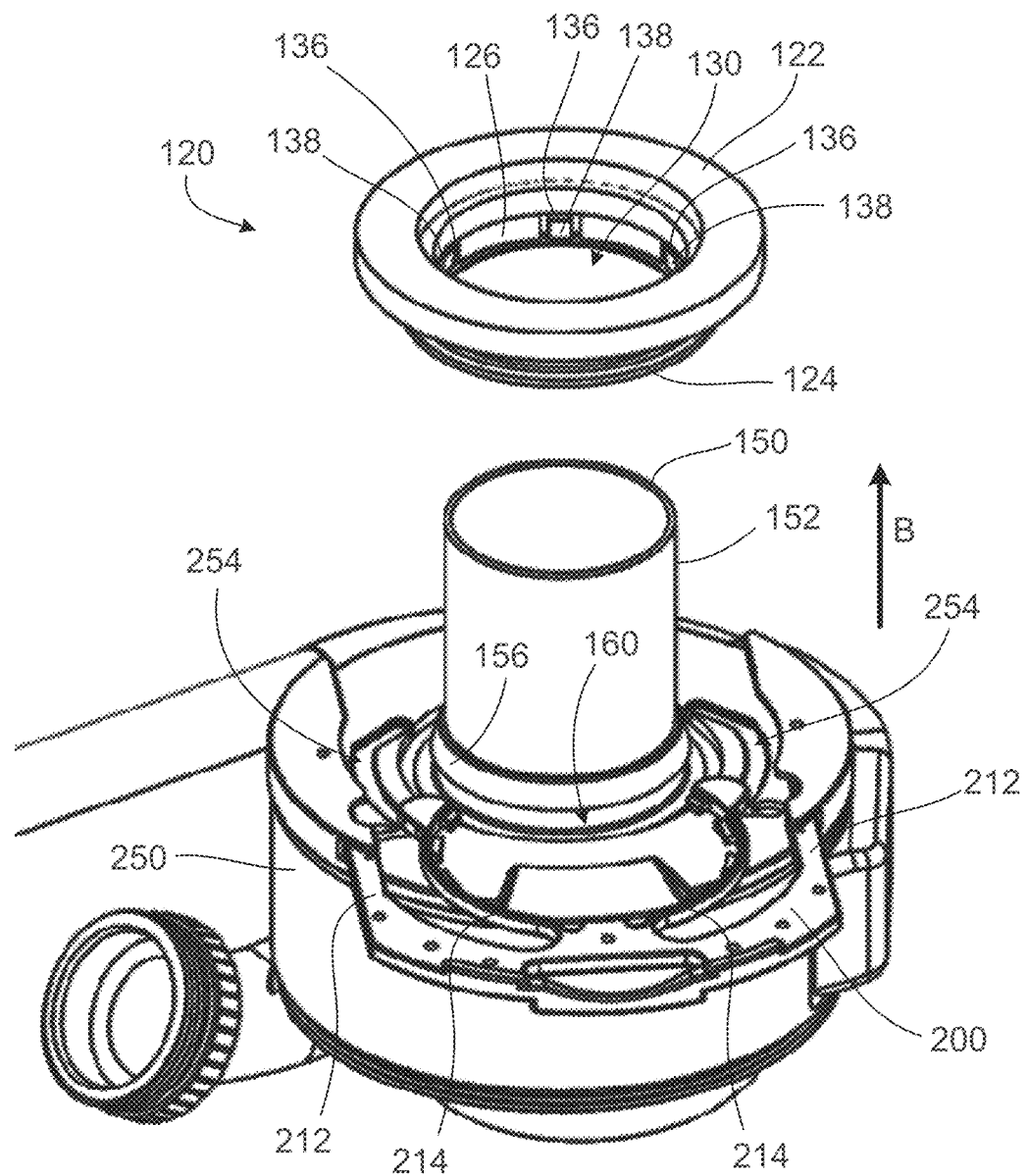
FIGS. 15A to 15C are perspective views illustrating the coupling of the pump of FIG. 14A to the ventricular cuff of FIG. 11A using the clip.

Referring to FIG. 15A, a clinician moves the pump 250 and the cannula 150 relative to the cuff 120, in the direction of arrow B, so that the proximal portion 152 enters the opening 130 of the cuff 120. As the cannula 150 advances, the first circumferential taper 156 deflects the extensions 136 away from the cannula 150. The first circumferential taper 156 and the second circumferential taper 158 advance past the tapered portions 138 of the extensions 136. As the first circumferential taper 156 advances past the tapered portions 138, the deflected extensions 136 straighten, forcing the tapered portions 138 into the circumferential groove 160. The clinician experiences tactile feedback, such as a snap-like sensation, that indicates that the cannula 150 is coupled to the cuff 120. The bottom surface 125 of the linking member 124 engages the circumferential flange 162 of the cannula 150. In some implementations, the bottom surface 125 engages a surface of the pump 250 as an alternative to, or in addition to, engaging a portion of the cannula 150.

Figure 15B:
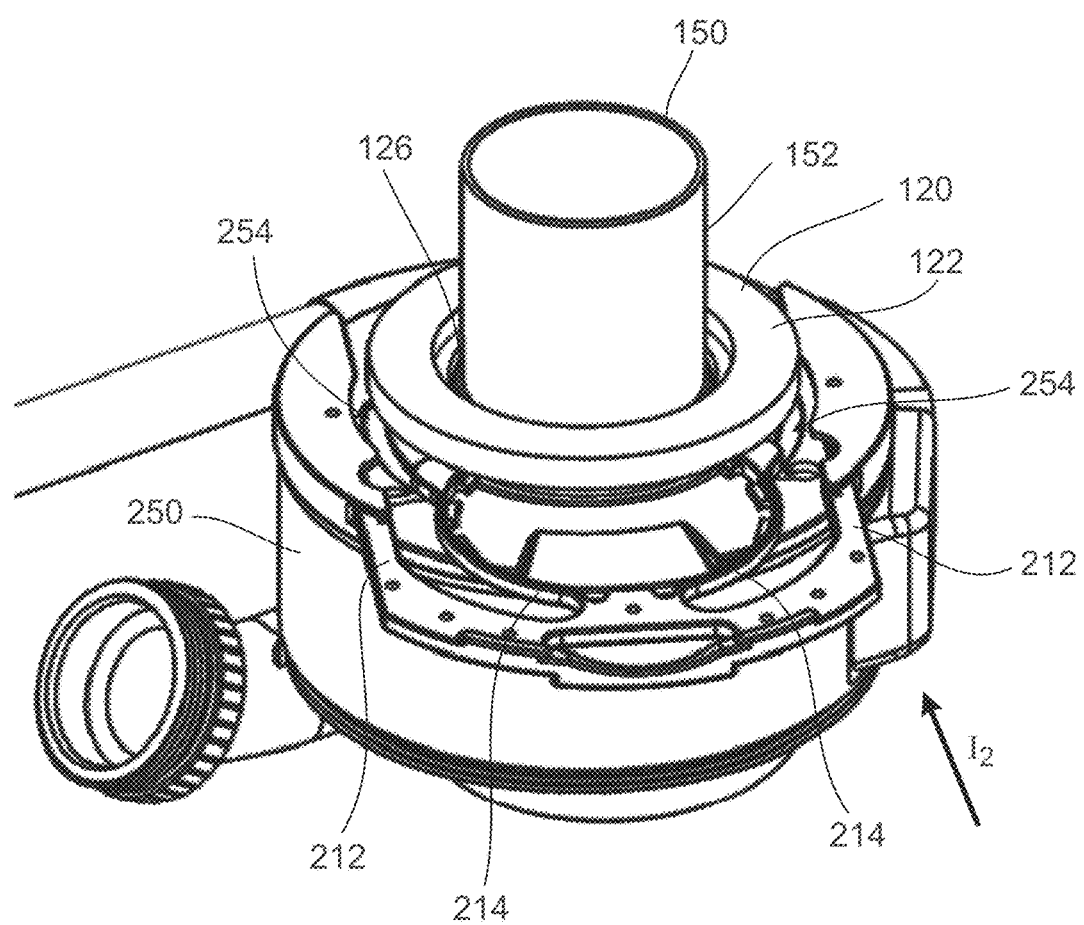

Referring to FIG. 15B, the clinician advances the clip 200 into the pump 250. The guide rails 212 of the clip 200 travel in the slots 252, guiding the clip 200 as it travels linearly in a plane above the top side 256, in the direction of arrow I₂. As the clip 200 travels relative to the pump 250, the arms 214 flex laterally due to engagement of the posts 219 with the angled walls 257, 258 defining the channels 254. The arms 214 move laterally outward to admit the linking member 124 and then laterally inward to engage the linking member 124.

Figure 15C:
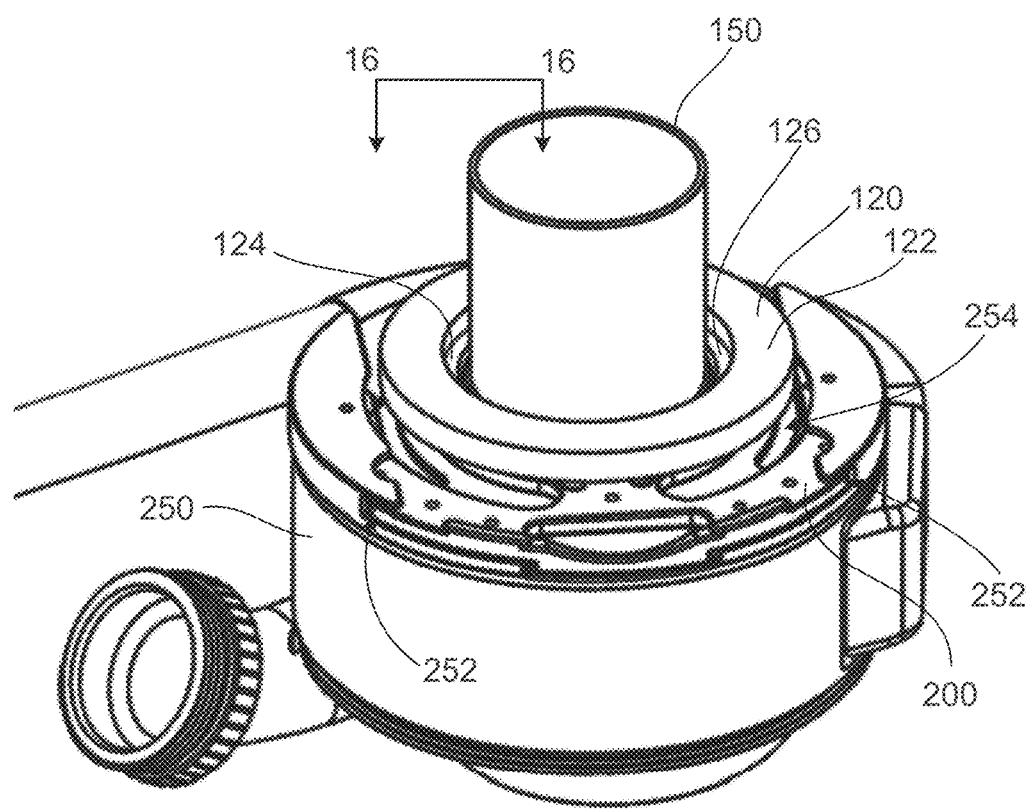

Referring to FIG. 15C, the clip 200, in its locked position, limits travel of the cuff 120 relative to the cannula 150. The engagement of the posts 219 with the angled walls 257, 258 that define the channels 254 forces the arms 214 inward such that the teeth 216 of the arms 214 are disposed over the flanged portions 146 of the attachment member 126. The flanged portions 146 are captured between the teeth 216 and the circumferential flange 162. The engagement of the teeth 216 to the linking member 124 presses the bottom surface 125 against the circumferential flange 162, forming a seal (FIG. 16).

In an implanted state, after the clip 200 is in its locked position, the pump 250 and the cannula 150 are in a position suitable for long-term stability relative to the cuff 120 and the heart. While the clip 200 is in its locked position, an extremely large force is required to remove the cuff 120 from the cannula 150. For example, the force required to forcibly separate the pump 250 or cannula 150 from the cuff 120 while the clip 200 is in its locked position can be as large as the force required to tear the cuff 120 from the heart.

The distance that the cannula 150 extends into a heart can be selected in a similar manner as described above. For example, a cannula 150 with a proximal portion 152 having a particular length can be selected, one or more spacers can be placed between the fastening member 122 and a heart, or the thickness of the fastening member 122 can be selected for a particular patient.

Figure 17A:
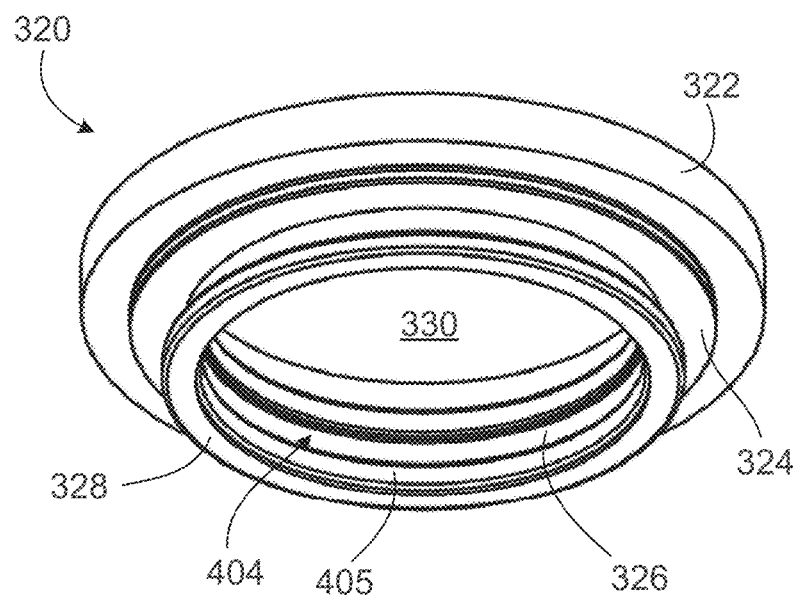
FIG. 17A is a perspective view of a ventricular cuff.
Figure 17B:
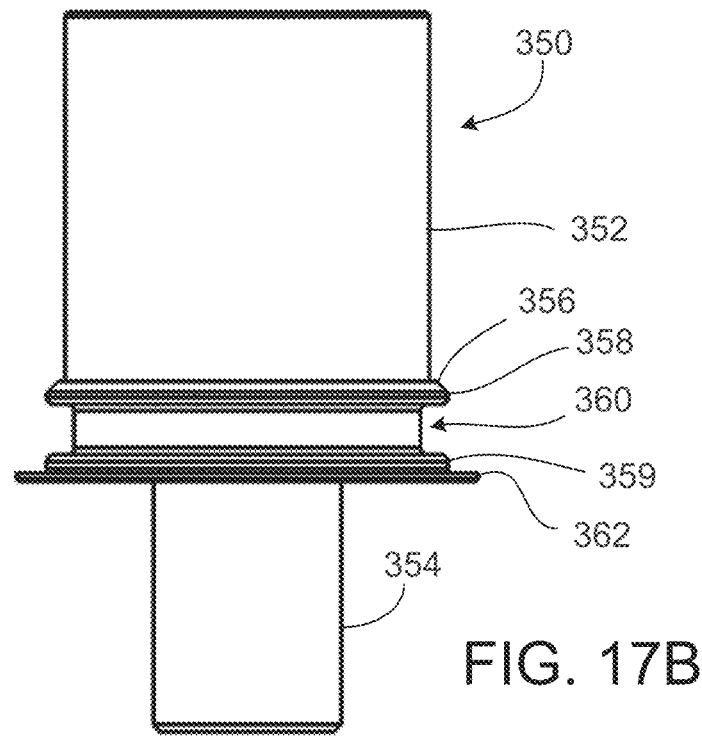
FIG. 17B is a side view of a cannula for coupling to the ventricular cuff of FIG. 17A.

Referring to FIGS. 17A and 17B, an alternate implementation includes a cuff 320 and a cannula 350 configured to cooperate with the pump 250 and the clip 200. The cuff 320 defines an opening 330 that admits a proximal portion 352 of the cannula 350. A coupling mechanism in the form of an attachment member 326 engages a sealing ring 502 (FIG. 19A), such as an o-ring, disposed about the cannula 350 to couple the cuff 320 to the cannula 350. The clip 200 (FIG. 13A) acts as a locking mechanism to impede the cuff 320 from becoming uncoupled from the cannula 350.

The cuff 320 includes an annular fastening member 322 that a clinician can fasten to heart tissue. For example, the fastening member 322 can be formed of a fabric such as PTFE felt. The cuff 320 includes a linking member 324 coupled to the fastening member 322, for example, by sutures or direct molding. The linking member 324 is formed of, for example, an elastomer such as silicone. The linking member 324 includes a reinforcement member 325 (FIG. 18B), such as a mesh ring. The linking member 324 couples the attachment member 326 to the fastening member 322, as described below.

The linking member 324 includes a bottom surface 328 that engages a circumferential flange 362 of the cannula 350. The primary sealing mechanism between the cuff 320 and the cannula 350 is the sealing ring 502, and as a result, the linking member 324 and the circumferential flange 362 are not required to form a seal. Nevertheless, in some implementations, the linking member 324 may form a secondary seal with the circumferential flange 362. In some implementations, the bottom surface 328 engages a surface of the pump 250 as an alternative to, or in addition to, engaging a portion of the cannula 350.

The cannula 350 includes the proximal portion 352, the circumferential flange 362, and a distal portion 354 housed within the pump 250. The cannula 350 includes a circumferential taper 356 that engages a circumferential taper 405 of the attachment member 326, guiding the cuff 320 into alignment with the cannula 350. The cannula 350 defines a circumferential groove 360 between a first circumferential ridge 358 and a second circumferential ridge 359. The circumferential groove 360 receives the sealing ring 502.

Figure 18A:
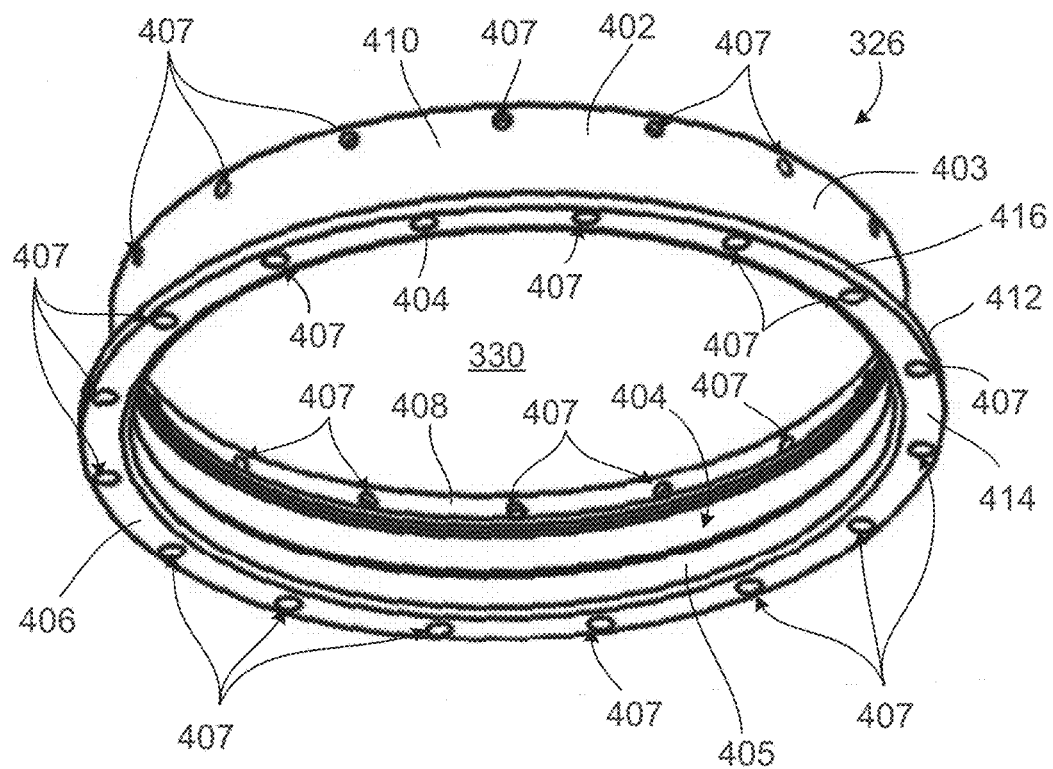
FIG. 18A is a perspective view of an attachment member of the ventricular cuff of FIG. 17A.
Figure 18B:
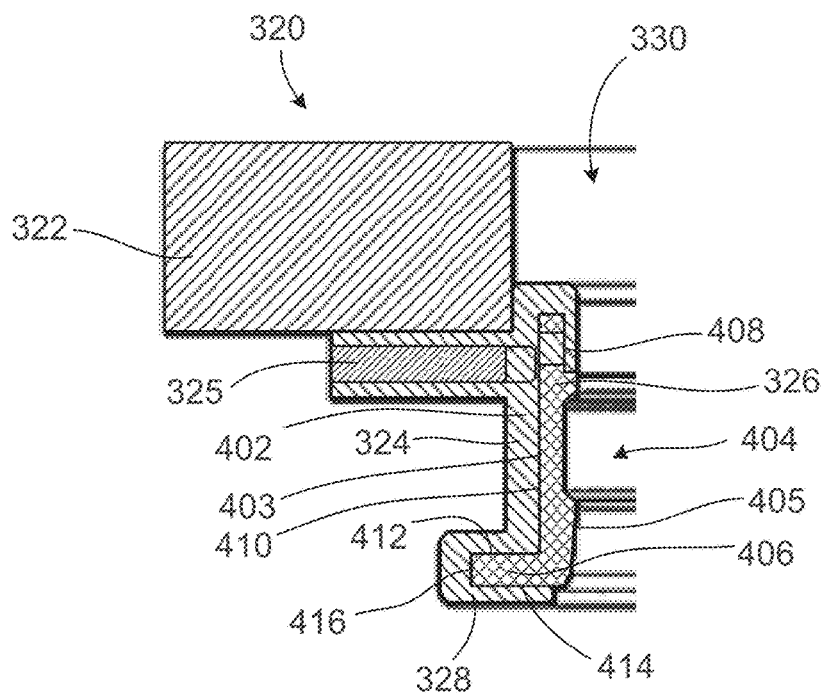
FIG. 18B is a cross-sectional view of a portion of the ventricular cuff of FIG. 17A.

Referring to FIGS. 18A and 18B, the attachment member 326 is formed of, for example, a rigid material such as metal or PEEK. The attachment member 326 includes a cylindrical portion 402, which defines an inner circumferential groove 404 that admits a portion of the sealing ring 502. The sealing ring 502 is formed of, for example, an elastomer such as silicone or implantable-grade ethylene propylene diene monomer (EPDM). In some implementations, the attachment member 326 does not define an inner circumferential groove 404 and instead has a substantially cylindrical inner surface.

The attachment member 326 includes a flanged portion 406, for example, a circumferential flange that extends in a plane generally perpendicular to an outer wall 403 of the cylindrical portion 402. The attachment member 326 includes the inner circumferential taper 405 that engages the sealing ring 502, compressing the sealing ring 502 and permitting the sealing ring 502 to enter the inner circumferential groove 404.

The linking member 324 is molded over the attachment member 326, and the flanged portion 406 and the cylindrical portion 402 define holes 407 that admit material of the linking member 324. The material of the linking member 324 that extends through the holes 407 forms mechanical locks that couple the linking member 324 to the attachment member 326. The linking member 324 is molded over an inner circumferential wall 408 and an outer circumferential surface 410 of the cylindrical portion 402, as well as a top surface 412, a bottom surface 414, and a circumferential side surface 416 of the flanged portion 406.

Figure 19A:
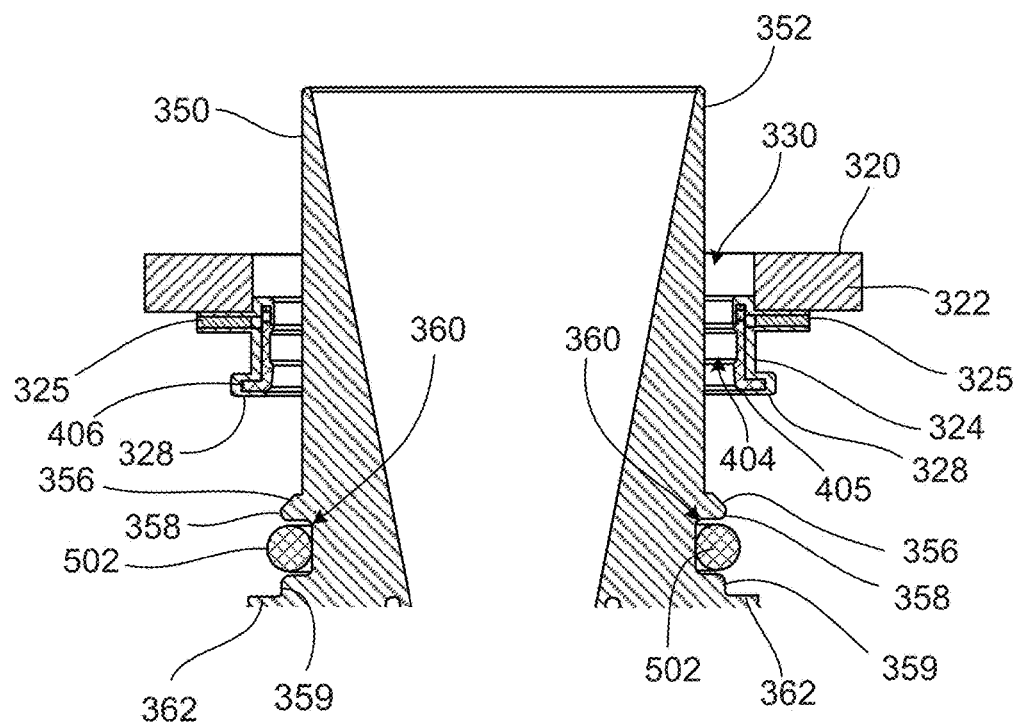
FIGS. 19A and 19B are cross-sectional views illustrating the engagement of the ventricular cuff of FIG. 17A with the cannula of FIG. 17B.
Figure 19B:
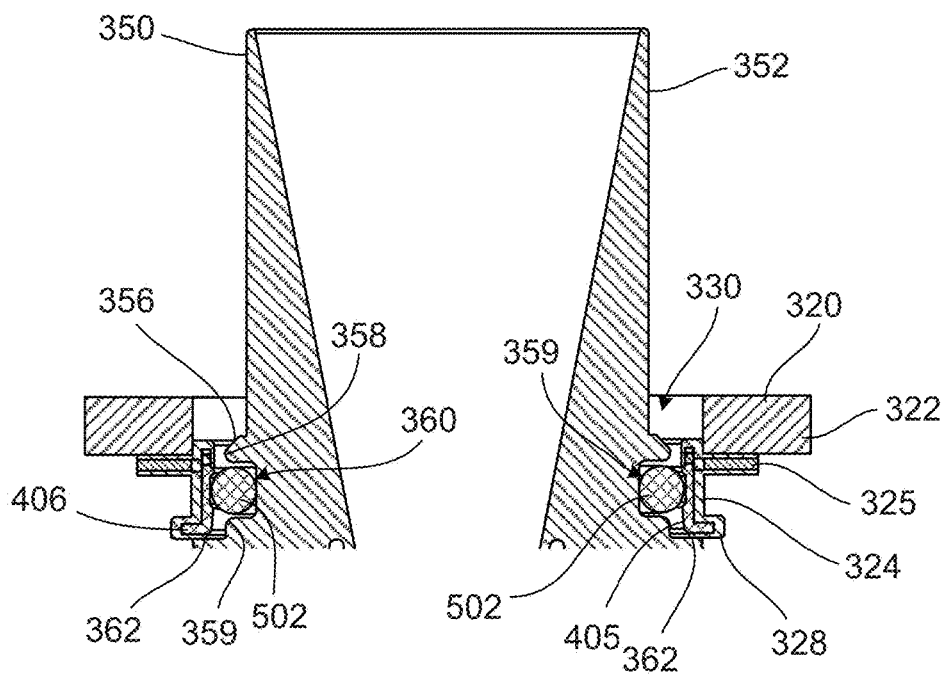

Referring to FIGS. 19A and 19B, the sealing ring 502 is disposed in the circumferential groove 360. To couple the cannula 350 to the cuff 320, the clinician moves the proximal portion 352 through the opening 330 of the cuff 320. The sealing ring 502 engages the circumferential taper 405 of the attachment member 326, compressing the sealing ring 502 into the circumferential groove 360.

As the cannula 350 advances through the opening 330, the sealing ring 502 advances past the circumferential taper 405 to the position of FIG. 19B. The sealing ring 502 expands into the circumferential groove 404 of the attachment member 326 and the bottom surface 328 of the linking member 324 engages the circumferential flange 362. The sealing ring 502 is partially disposed in the circumferential groove 404 and partially disposed in the circumferential groove 360 of the cannula 350. The engagement of the sealing ring 502 between the cuff 320 and the cannula 350 limits travel of the cannula 350 relative to the cuff 320, coupling the cannula 350 to the cuff 320. The expansion of the sealing ring 502 into the circumferential groove 404 provides snap-like tactile feedback to the clinician, indicating that the cannula 350 is coupled to the cuff 320. The sealing ring 502 also creates a hemostatic seal between the cannula 350 and the cuff 320.

Figure 20:
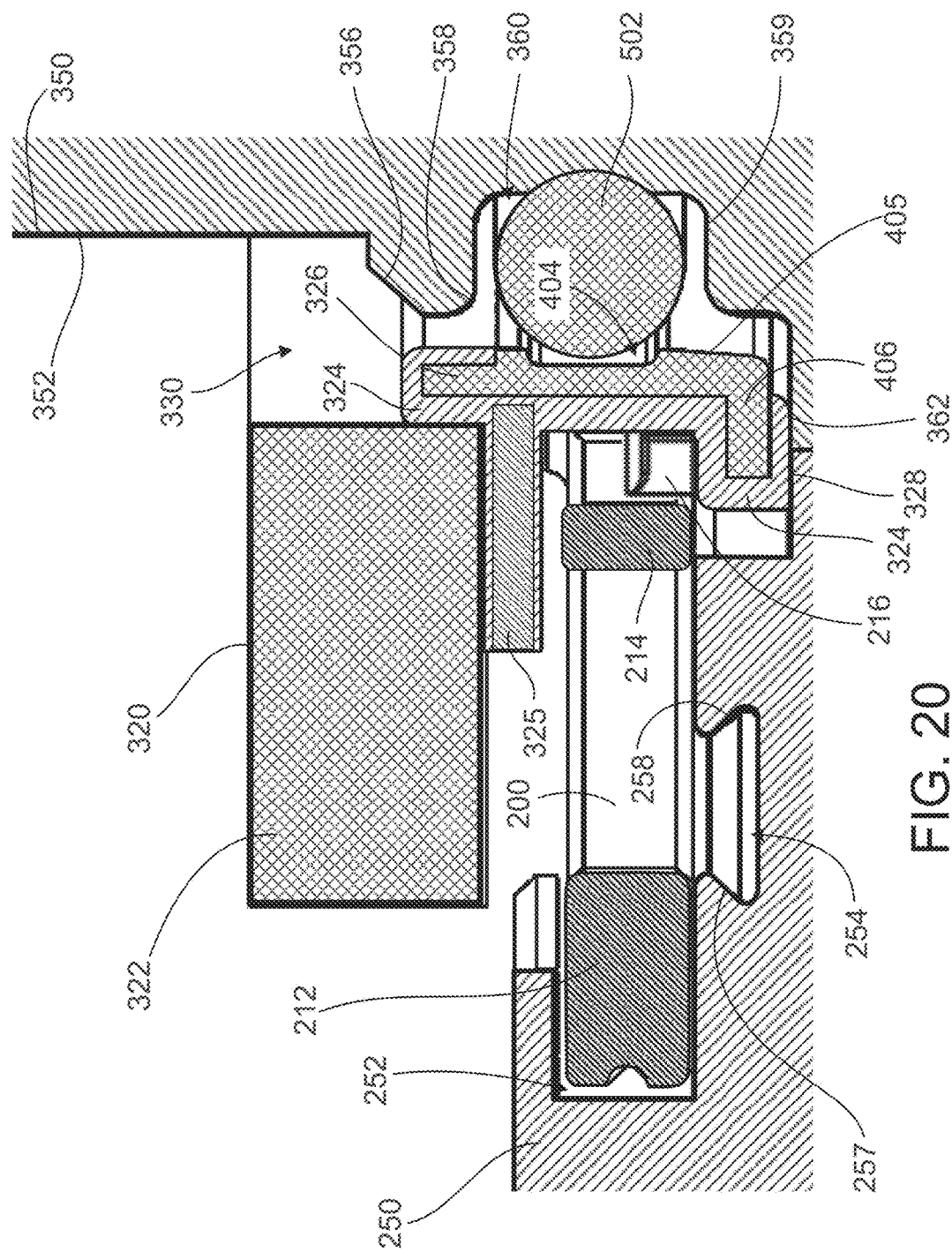
FIG. 20 is a side cross-sectional view of the ventricular cuff of FIG. 17A coupled to the cannula of FIG. 17B and secured to the pump of FIG. 14A using the clip.

From the position of FIG. 19B, the clinician can move the clip 200 into a locked position about the cuff 320 as described above with reference to FIGS. 14A to 14C. With the clip 200 in its locked position (FIG. 20), the flanged portion 406 is captured between the clip 200 and the circumferential flange 362, impeding the cuff 320 from becoming separated from the cannula 350.

The distance that the cannula 350 extends into a heart can be selected in a similar manner as described above. For example, a cannula 350 with a proximal portion 352 having a particular length can be selected, one or more spacers can be placed between the fastening member 322 and a heart, or the thickness of the fastening member 322 can be selected for a particular patient.

Figure 21:
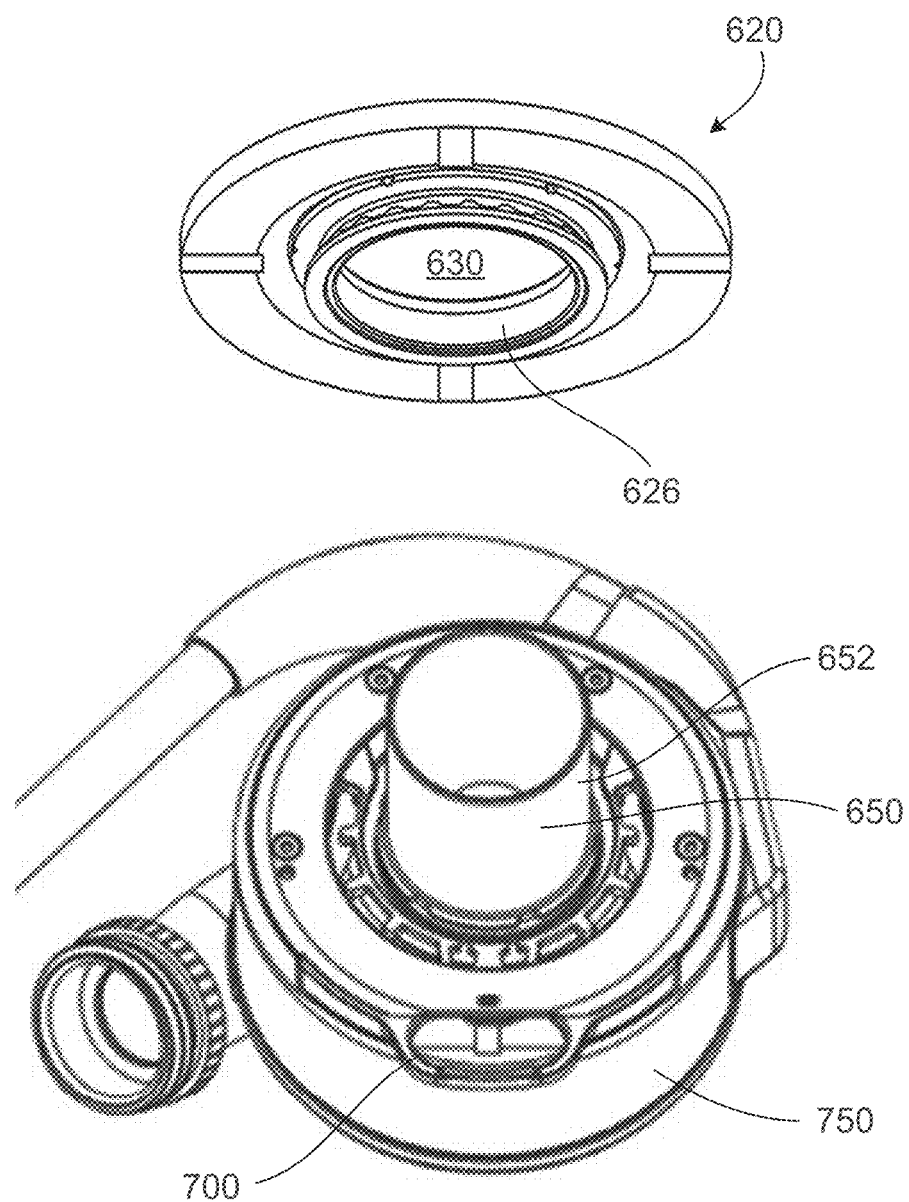
FIG. 21 is a perspective view of a pump, a cannula, and a ventricular cuff.

Referring to FIG. 21, an alternate implementation includes a cuff 620 that couples to a cannula 650 of a pump 750. The cuff 620 defines an opening 630 that admits a proximal portion 652 of the cannula 650. A coupling mechanism in the form of an attachment member 626 engages a sealing ring 802 (FIG. 23B), for example, an o-ring disposed about the cannula 650, to couple the cuff 620 to the cannula 650. A clip 700 (FIG. 25A) acts as a locking mechanism to impede the cuff 620 from becoming uncoupled from the cannula 650.

Like the implementations described above, the cuff 620 can be coupled to the pump 750 with a low profile, for example, in a distance from a heart that is approximately the height of the cuff 620 along the cannula 650. The cuff 620 is coupled to the pump 750 by moving the cannula 650 axially through the cuff 620. The locking mechanism, for example, the clip 700, can then be engaged to secure the position of the cuff 620 about the cannula 650. Similar to the cam 28 and the clip 200, the clip 700 moves into a locked position by moving in a plane perpendicular to a cannula, which facilitates attachment of the cuff 620 to the pump 750 in the low profile.

Figure 22A:
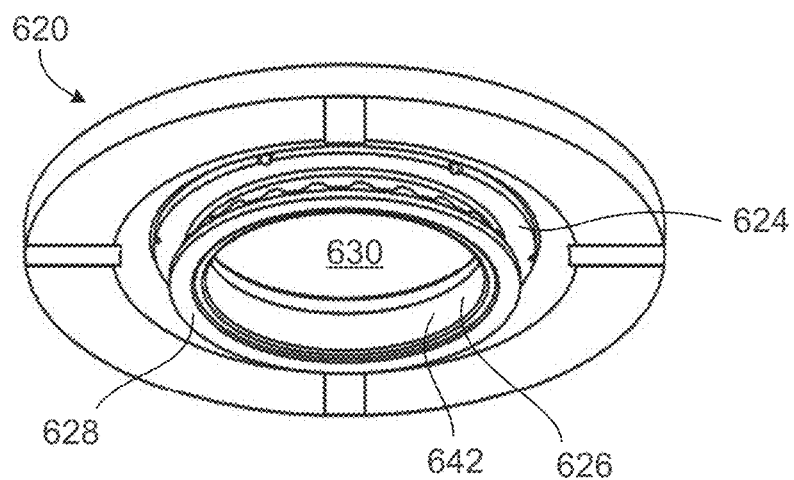
FIG. 22A is a perspective view of the cuff of FIG. 21.
Figure 22B:
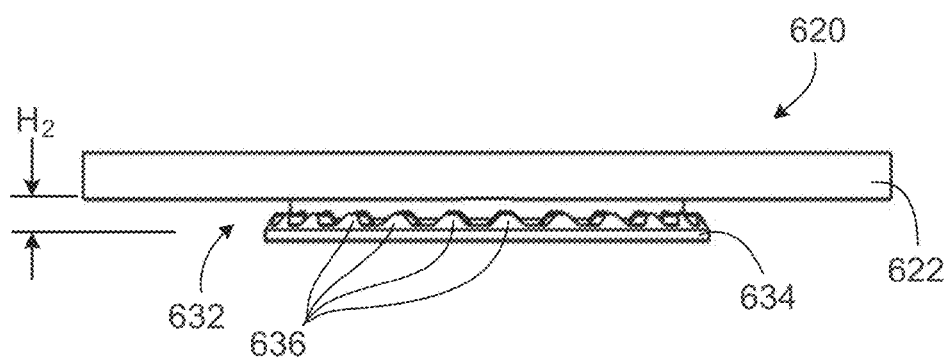
FIG. 22B is a side view of the ventricular cuff of FIG. 21.

Referring to FIGS. 22A and 22B, the cuff 620 includes an annular fastening member 622 that a clinician can fasten to heart tissue. For example, the fastening member 622 can be formed of a fabric such as PTFE felt. The cuff 620 includes a linking member 624 coupled to the fastening member 622, for example, by sutures or direct molding. The linking member 624 is formed of, for example, an elastomer such as silicone. The linking member 624 includes a reinforcement member 625 (FIG. 22D), such as a mesh ring. The linking member 624 couples the attachment member 626 to the fastening member 622, as described below.

The linking member 624 includes a bottom surface 628 that engages a circumferential flange 662 (FIG. 23B) of the cannula 650. The primary sealing mechanism between the cuff 620 and the cannula 650 is the sealing ring 802, and as a result, the linking member 624 need not form a seal about the cannula 650. Nevertheless, in some implementations, the linking member 624 may form a secondary seal through engagement with the circumferential flange 662. In some implementations, the bottom surface 628 engages a surface of the pump 750 as an alternative to, or in addition to, engaging a portion of the cannula 650.

The linking member 624 defines a circumferential groove 632 in the outer diameter of the cuff 620, located between the fastening member 622 and a flanged portion 634 of the linking member 624. The circumferential groove 632 receives a portion of the clip 700 to secure the cuff 620 to the pump 750, as described further below. The linking member 624 includes ridges 636 in the circumferential groove 632, for example, disposed on the flanged portion 634. The ridges 636 are spaced apart and extend approximately halfway along the height, $H_2$, of the circumferential groove 632. When the clip 700 is in a locked position about the cuff 620, the clip 700 engages the ridges 636 to limit rotation of the cuff 620 about the cannula 650.

Figure 22C:
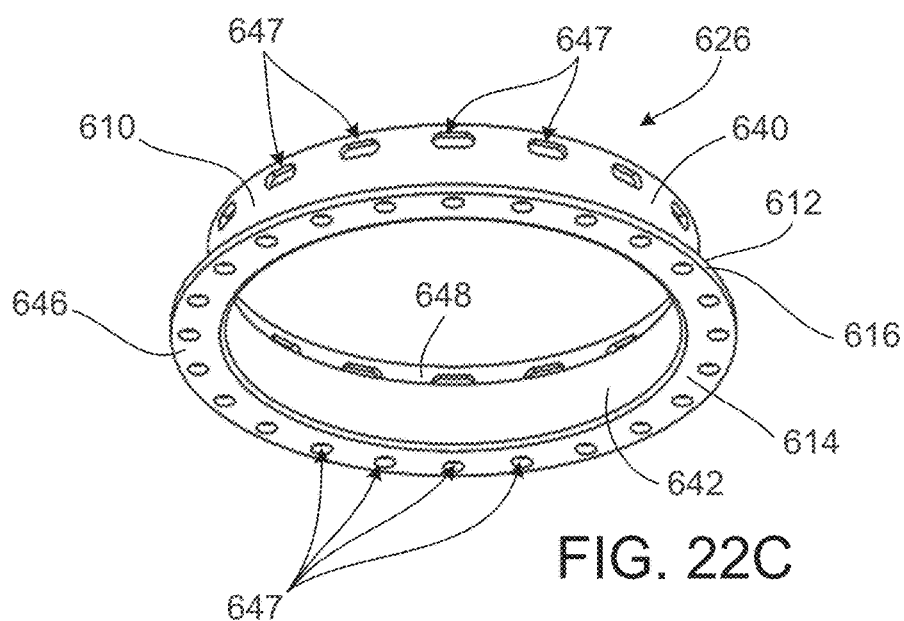
FIG. 22C is a perspective view of an attachment member of the ventricular cuff of FIG. 21.

Referring to FIG. 22C, the attachment member 626 is formed of, for example, a rigid material such as metal or PEEK. The attachment member 626 includes a cylindrical portion 640 that has an outer wall 644 and an inner surface 642 that engages the sealing ring 802. The attachment member 626 includes a flanged portion 646, for example, a circumferential flange that extends in a plane generally perpendicular to the outer wall 644.

Figure 22D:
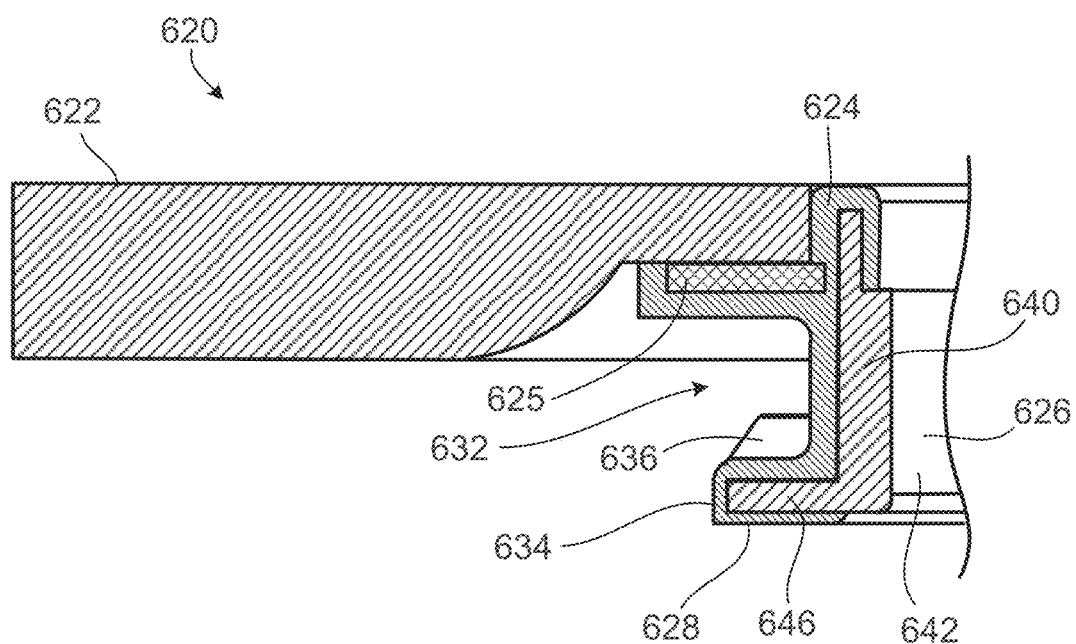
FIG. 22D is a side cutaway view of the ventricular cuff of FIG. 21.

Referring to FIG. 22D, the linking member 624 is molded over the attachment member 626. The flanged portion 646 and the cylindrical portion 640 define holes 647 that admit material of the linking member 624. The material of the linking member 624 that extends through the holes 647 forms mechanical locks that couple the linking member 624 to the attachment member 626. The linking member 624 is molded over an inner circumferential wall 648, which can have a larger inner diameter than the rest of the cylindrical portion 640. The linking member 624 is also molded over an outer circumferential surface 610 of the cylindrical portion 640, as well as a top surface 612, a bottom surface 614, and a circumferential side surface 616 of the flanged portion 646. The inner surface 642 of the attachment member 626 remains exposed.

Figures 23A, 23B:
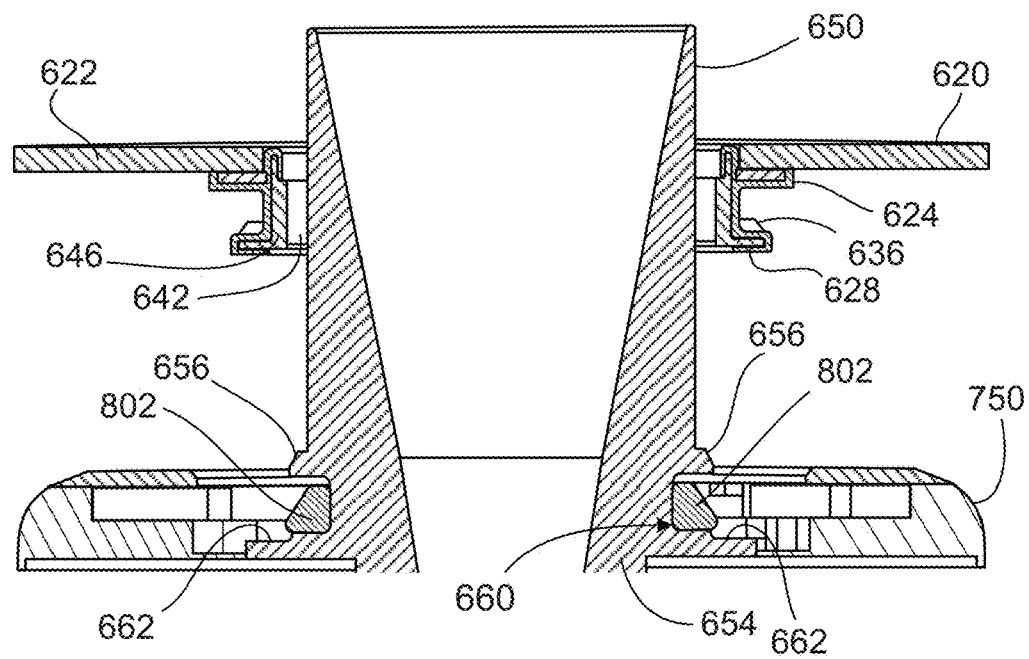
FIGS. 23A and 23B are side cutaway views of the cannula and ventricular cuff of FIG. 21.

Referring to FIGS. 23A and 23B, the cannula 650 includes the proximal portion 652, the circumferential flange 662, and a distal portion 654 housed within the pump 750. The cannula 650 includes a circumferential taper 656 that engages the attachment member 626, guiding the cuff 620 into alignment with the cannula 650. The cannula 650 defines a circumferential groove 660 between a first circumferential ridge 658 and a second circumferential ridge 659. The sealing ring 802 is disposed in the circumferential groove 660 and is formed of, for example, an elastomer such as silicone or implantable-grade EPDM.

To couple the cannula 650 to the cuff 620, the clinician moves the proximal portion 652 through the opening 630 of the cuff 620 (FIG. 23A). As the cannula 650 advances further, the sealing ring 802 engages the inner surface 642 of the attachment member 626, compressing the sealing ring 802 into the circumferential groove 660 (FIG. 23B). The engagement of the sealing ring 802 with the inner surface 642 and the engagement of the bottom surface 628 with the circumferential flange 662 provide tactile feedback to the clinician that the appropriate position has been achieved.

The engagement of the sealing ring 802 between the cuff 620 and the cannula 650 limits travel of the cannula 650 relative to the cuff 620, coupling the cannula 650 to the cuff 620. The compression of the sealing ring 802 between the cuff 620 and the cannula 650 also creates a hemostatic seal between the cannula 650 and the cuff 620. From the position shown in FIG. 23B, the clinician can move the clip 700 into a locked position about the cuff 620 to secure the cuff 620 about the cannula 650, as described further below.

Figure 24A:
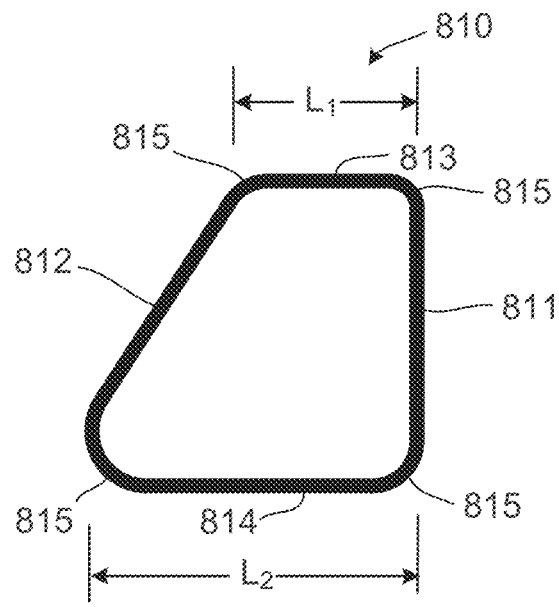
FIGS. 24A and 24B are cross-sectional view of sealing rings.

Referring to FIG. 24A, the sealing ring 802 has a cross-section 810 that is substantially trapezoidal. The force required to insert the cannula 650 into the cuff 620 using the sealing ring 802 is typically smaller than the force required to insert the cannula 650 using a sealing ring that has a round cross-section and a similar cross-sectional width. In some instances, a lower insertion force is desirable to facilitate installation of the cannula 650 relative to the implanted cuff 620.

The cross-section 810 has an inner side 811, and outer side 812, a top side 813, and a bottom side 814. Adjacent sides 811, 812, 813, 814 are connected by rounded corners 815. The inner side 811 faces toward the cannula 650 and is substantially flat. As a result, the inner surface of the sealing ring 810 is substantially cylindrical. The top side 813 faces away from the pump 750, and the bottom side 814 faces toward the pump 750. The top side 813 and the bottom side 814 are substantially parallel to each other, for example, both sides 813, 814 are substantially perpendicular to the inner side 811.

The top side 813 and the bottom side 814 have different lengths. The length, $L_1$, of the top side 813 can be, for example, between one-fourth and three-fourths of the length, $L_2$, of the bottom side 814. For example, the length, $L_1$, of the top side 813 can be approximately half or approximately two-thirds of the length, $L_2$, of the bottom side 814. The outer side 812 is angled, for example, forming substantially straight angled edge.

Figure 24B:
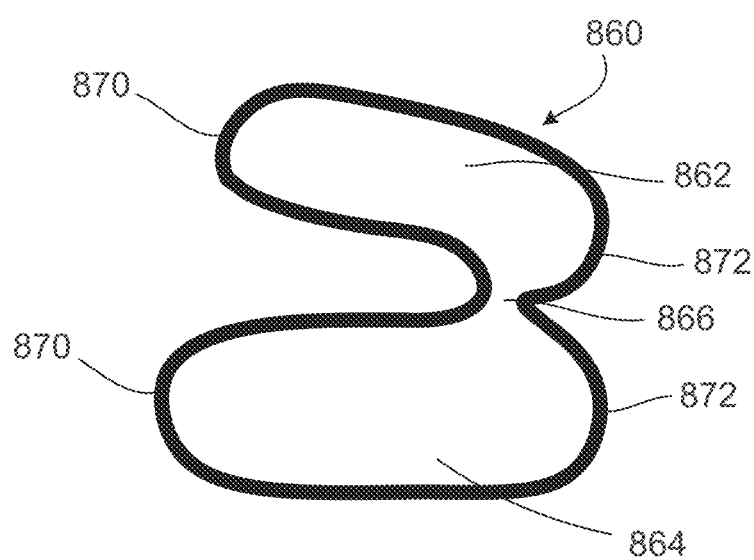

Referring to FIG. 24B an alternative sealing ring has a cross-section 860. The cross-section 860 includes an upper portion 862 and a lower portion 864, connected by a narrow neck 866. The sealing ring 850 thus includes two stacked discs, connected by an annular band. The cross-section 860 includes outer sides 870 engage the inner surface 642 of the cuff 620, and inner sides 872 that engage the cannula 650 in the circumferential groove 660.

Figure 25A:
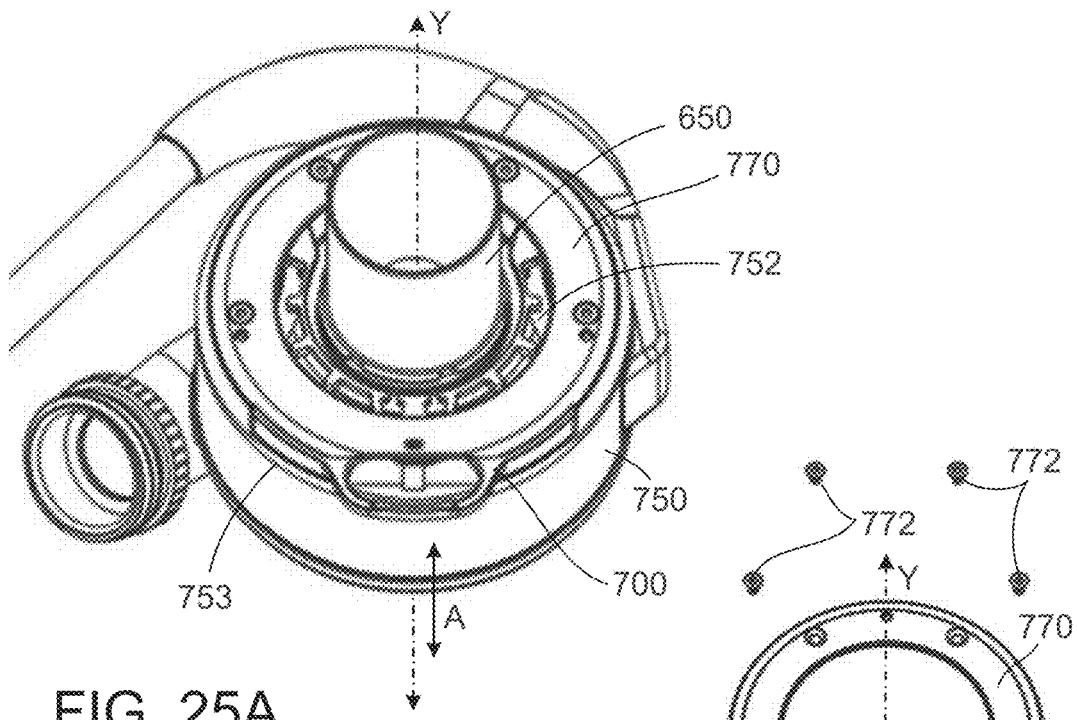
FIG. 25A is a perspective view of the pump of FIG. 21.
Figure 25B:
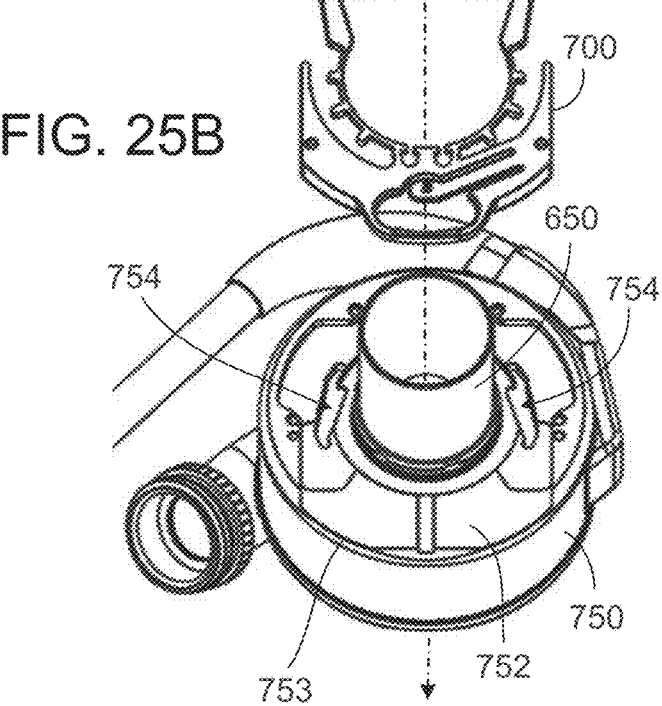
FIG. 25B is an exploded view of the pump of FIG. 21.

Referring to FIGS. 25A and 25B, the clip 700 cooperates with features of the pump 750, described below, to limit movement of the cuff 620 (not shown) relative to the cannula 650. The clip 700 has an unlocked position, in which the cuff 620 can be coupled about the cannula 650. The clip 700 also has a locked position, in which the clip 700 secures the cuff 620 relative to the cannula 650. A component, such as a motor housing 753 or an element attached to the motor housing 753, provides an upper surface 752 that defines channels 754. The clip 700 includes arms 714 that extend into the channels 754 and travel along the channels 754 as the clip 700 moves into its locked position.

The pump 750 captures the clip 700 between the upper surface 752 and a cover 770. The cover 770 is attached over the upper surface 752 by, for example, screws 772 or welds. The upper surface 752 and the cover 770 define a slot 740 for the clip 700 to travel within. The slot 740 permits the clip 700 to travel in a plane, for example, to travel in a linear direction, A, in a plane perpendicular to a longitudinal axis, Y, of the cannula 650.

Figure 26A:
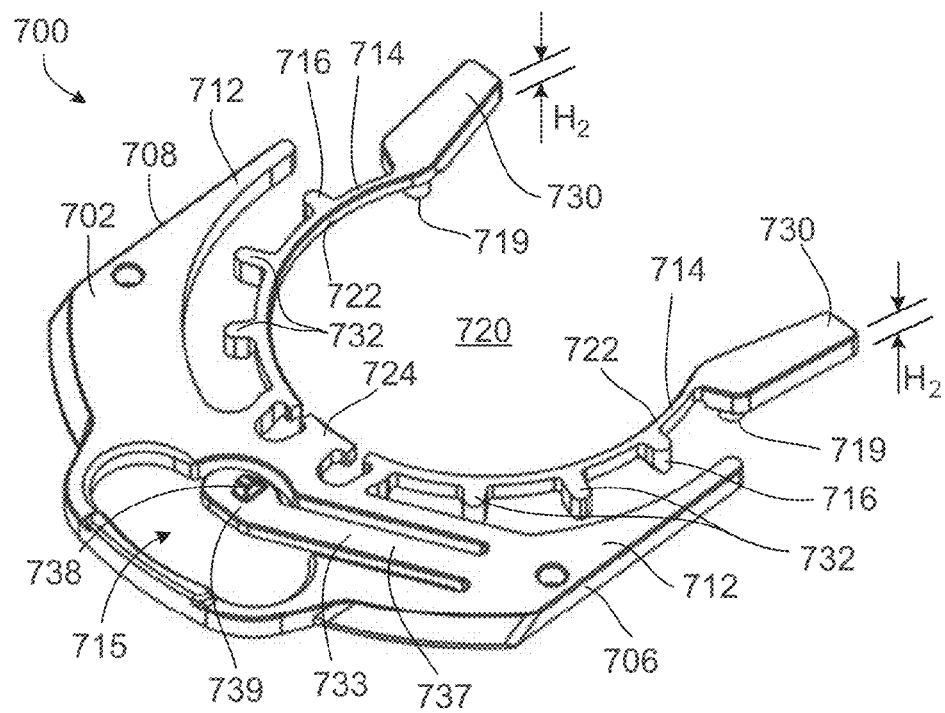
FIG. 26A is a top perspective view of a clip that cooperates with the pump and the ventricular cuff of FIG. 21.
Figure 26B:
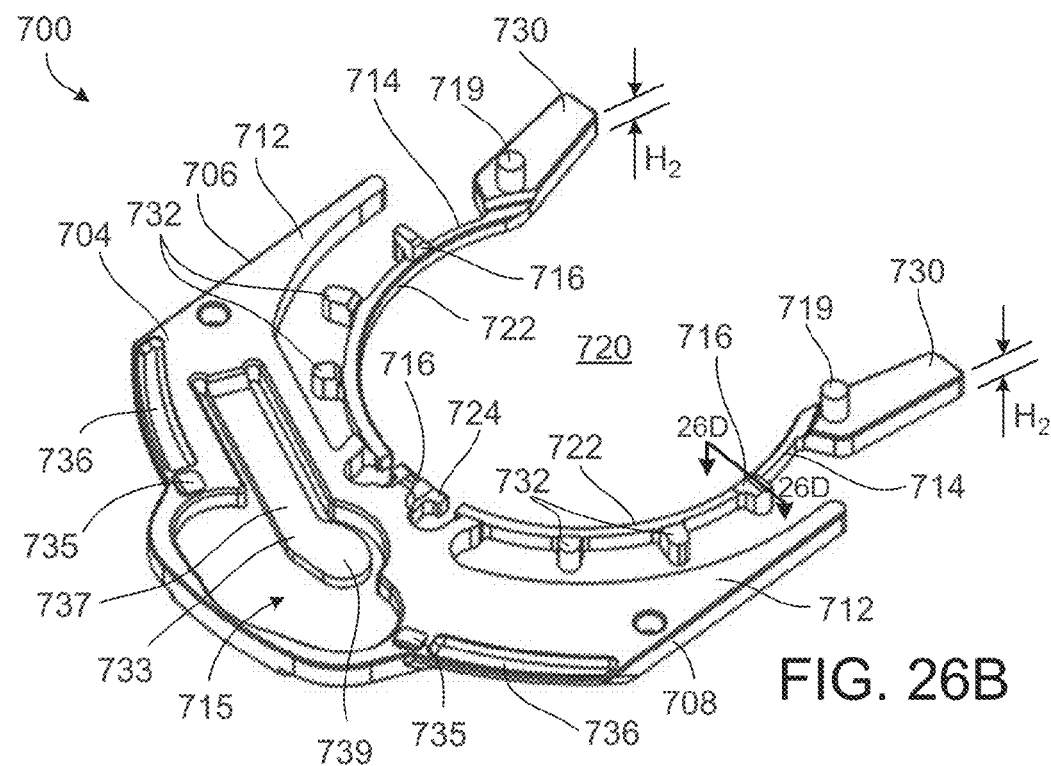
FIG. 26B is a bottom perspective view of the clip of FIG. 26A.
Figure 26C:
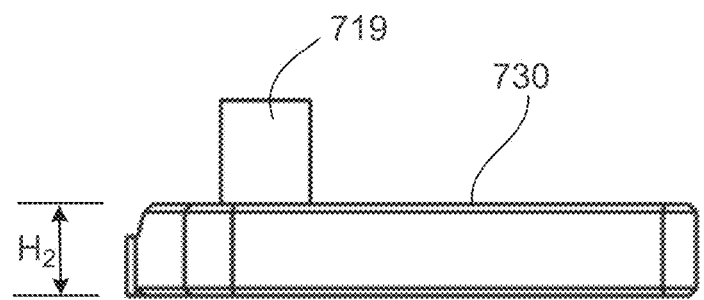
FIG. 26C is a side view of an end portion of an arm of the clip of FIG. 26A.

Referring to FIGS. 26A-26C, the clip 700 includes a top side 702 that faces the cover 770, a bottom side 704 that faces the upper surface 752, and opposite lateral sides 706, 708. The clip 700 can be formed of, for example, metal, such as titanium, or a rigid plastic, such as PEEK. The clip 700 includes guide rails 712 and defines a recess or opening 715. The guide rails 712 stabilize the clip 700 laterally and guide the clip 700 through a linear motion in the slot 740. The opening 715 admits a tool or a finger of the clinician to facilitate refraction of the clip 700.

The arms 714 of the clip 700 are curved and define an opening 720. The arms 714 are resilient and can deflect laterally to capture the cuff 620. Each arm 714 includes a post 719 that extends from the bottom side 704 of the clip 700. Each post 719 is received in one of the channels 754 (FIG. 25B) defined in the upper surface 752. The posts 719 are substantially cylindrical and extend perpendicular to, for example, a plane defined along the top side 702 of the clip 700. When the clip 700 is located in the slot 740, the posts 719 extend substantially parallel to the longitudinal axis, Y, of the cannula 650. As the clip 700 moves relative to the pump 750, the posts 719 travel through the channels 754.

In the locked position of the clip 700, the arms 714 extend about the cuff 620 and extend into the circumferential groove 632. The arms 714 have a substantially smooth inner surface 722 that engages the linking member 624 in the circumferential groove 632. The arms 714 also include teeth 716 (FIG. 26B) that fit between the ridges 636 to limit rotation of the cuff 620 relative to the clip 700. The teeth 716 can be disposed on the arms 714 and on a central extension 724 of the clip 700. Three teeth 716 are shown, positioned to press radially inward on the cuff 620 when the clip 700 is in its locked position. More teeth or fewer than three teeth can be used to promote rotational stability of the cuff 620.

Figure 26D:
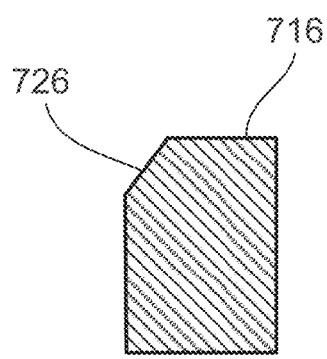
FIG. 26D is a side cross-sectional view of a tooth of the clip of FIG. 26A.

The teeth 716 have an angled or chamfered edge 726 (FIG. 26D), permitting the teeth 716 to engage the cuff 620 when the cuff 620 is not fully seated against the circumferential flange 662. As the clip 700 moves into its locked position, the teeth 716 move radially inward toward the circumferential groove 632. The chamfered edge 726 engages the flanged portion 634 of the cuff 620, forcing the cuff 620 toward the upper surface 752 into a fully seated position against the circumferential groove 662.

The clip 700 includes substantially flat end portions 730 that are captured between the upper surface 752 and the cover 770. The cover 770 impedes the end portions 730 from moving away from the surface 752, and thus holds the posts 719 in the channels 754. Engagement of the end portions 730 between the upper surface 752 and the cover 770 also limits twisting along the arms 714 in response to axial loads exerted along the arms 714. The end portions 730, the teeth 716, and stabilizing posts 732 on the arms 714 can each have a height, $H_2$, along the longitudinal axis, Y, that is substantially the same as a corresponding height of the slot 740, thereby limiting travel of the clip 700 along the longitudinal axis and limiting tilting of the clip 700 within the slot 740.

The clip 700 includes a latch 733 that engages the cover 770 to limit retraction of the clip 700 from the locked position. The latch 733 includes a deflection beam 737 and an extension 738 located on a free end 739 of the deflection beam 737. The extension 738 extends from the top side 702 of the clip 700. The deflection beam 737 provides a resilient force that holds the extension 738 in a mating receptacle of, for example, the cover 770, unless overcome by a sufficient force.

The clip 700 includes ramp features 735 that extend from the bottom side 704. The ramp features 735 wedge the clip 700 between the cover 770 and the upper surface 752, stabilizing the clip 700 along the longitudinal axis, Y, of the cannula 650 when the clip 700 is in the locked position. By forcing the top side 702 toward the cover 770, the ramp features 735 also force engagement of the latch 733 to the mating receptacle.

The clip 700 includes visual indicators 736 on the bottom side 704 that indicate when the clip 700 is out of the locked position. The visual indicators 736 are, for example, recesses containing a colored material that is easily noticeable by a clinician. The visual indicators 736 are exposed, and thus visible from the bottom of the pump 750, when the clip 700 is not in the locked position. The visual indicators 736 are obscured when the clip 700 is in the locked position.

Figure 27:
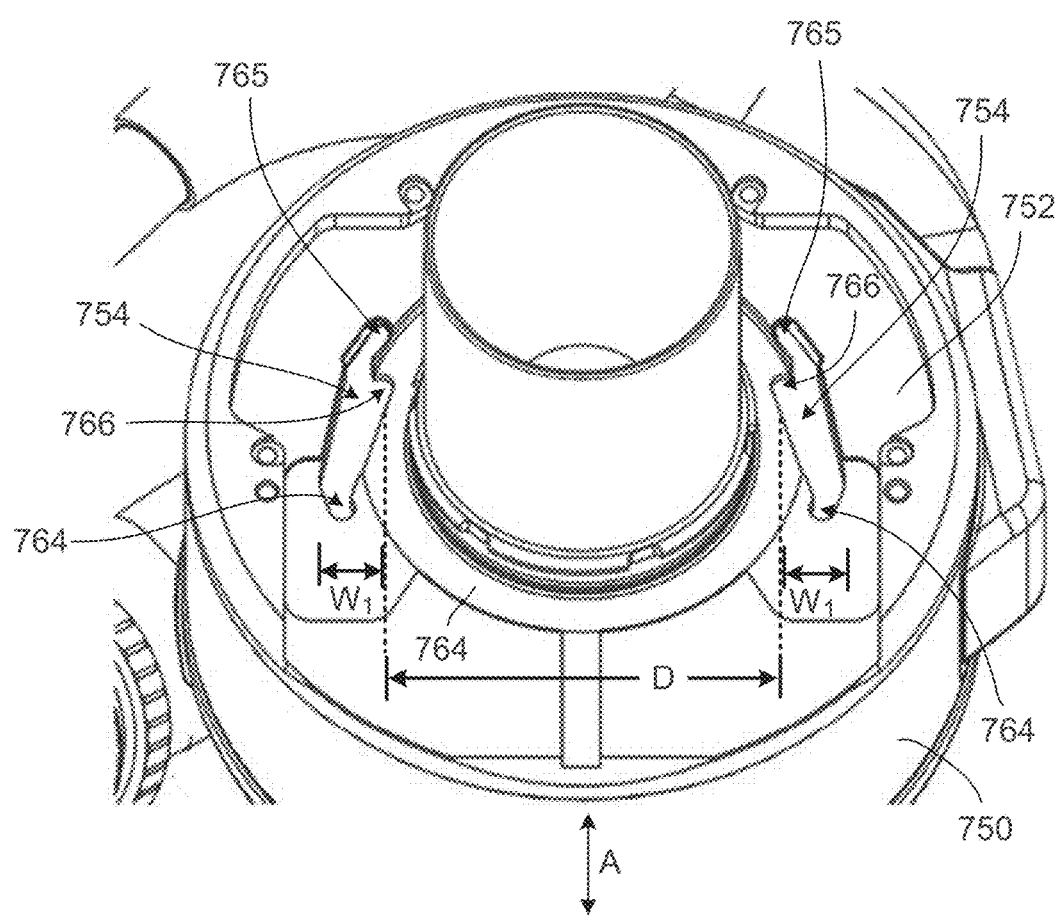
FIG. 27 is a perspective view of a surface of the pump of FIG. 21.

Referring to FIG. 27, the channels 754 in the surface 752 direct travel of the arms 714 as the clip 700 moves in the slot 740. As the clip 700 moves between an unlocked position to the locked position, the posts 719 move through the channels 754. The channels 754 have a width, $W_2$, that is larger than a diameter of the posts 719, which permits different lateral positions of the posts 719 in the channels 754. As described further below, the width, $W_2$, permits the posts 719 travel along different paths in the channels 754, rather than being constrained to travel along a single path.

The channels 754 are defined by inner walls 760 and outer walls 762. A lateral distance, D, between the inner walls 760 is greater than a distance between the posts 719 when the arms 714 are not flexed. As a result, positioning the posts 719 in the channels 754 flexes the arms 714 away from each other, causing the arms 714 to exert a resilient inward force against the inner walls 760. As the clip 700 travels in the slot 740, the posts 719 slide along the inner walls 760 unless displaced by, for example, the cuff 620.

The channels 754 define features that receive the posts 719. Each channel 754 defines, for example, a first end 764, a second end 765, and a detent 766, each of which can receive one of the posts 719. The posts 719 reside in the first ends 764 in an unlocked position of the clip 700, for example, when the clip 700 is fully retracted. At the first ends 764, the posts 719 engage the walls to impede the clip 700 from separating from the pump 750 by sliding out of the slot 740 along arrow A. The posts 719 reside in the second ends 765 when the clip 700 is in the locked position. The posts 719 reside in the detents 766 when the clip 700 is in a restrained position, for example, in which engagement of the posts 719 in the detents 766 impedes the clip 700 from travelling further toward the locked position. The unlocked position, the locked position, and the restrained position are stable positions of the clip 700 within the slot 740.

Figure 28A:
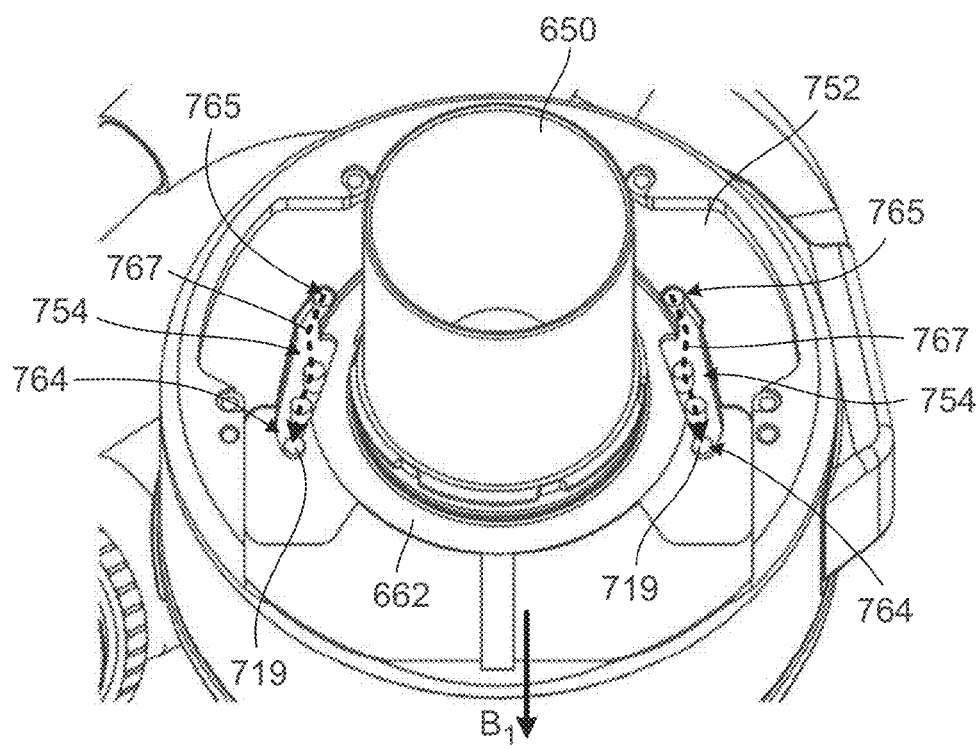
FIGS. 28A to 28C are perspective views illustrating different motions of the clip of FIG. 26A relative to the pump of FIG. 21.

Referring to FIG. 28A, the clip 700 is retracted in the direction of arrow $B_1$, and each post 719 travels along a path 767 between the second end 765 and the first end 764. Various positions of the posts 719 are shown, but other features of the clip 700 are not shown. The pump 750 can be provided to a clinician with the clip 700 in the locked position, with the posts 719 residing in the second ends 765. In some implementations, the arms 714 are in a relaxed state in the locked position. The clinician retracts the clip 700 to permit the cannula 650 to be coupled to the cuff 620.

Figure 28B:
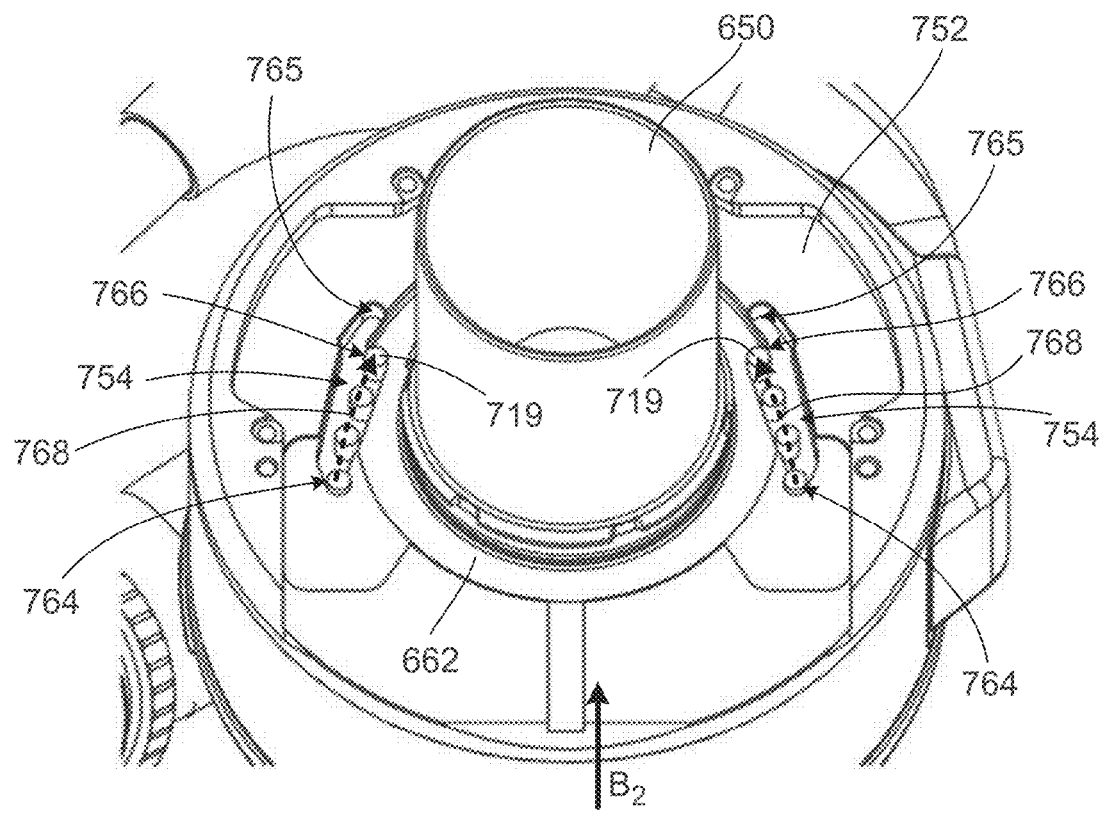

Referring to FIG. 28B, when the cuff 620 is not coupled about the cannula 650, advancing the clip 700 from the unlocked position toward the locked position places the clip 700 in the restrained position. As the clip 700 advances in the direction of arrow $B_2$, the arms 714 exert a lateral force inward toward the cannula 650, causing the posts 719 to travel in a path 768 along the inner walls 760. The posts 719 enter the detents 766 to impede the clip 700 from entering the locked position.

The clip 700 enters the restrained position when the cuff 620 is not properly coupled to the cannula 650, for example, when the cuff 620 is not located about the cannula 650 or the cuff 620 is improperly placed about the cannula 650. The placement of the clip 700 in the restrained position discourages premature locking of the clip 700 and indicates to the clinician that the cuff 620 is not properly placed about the cannula 650. Patient safety is enhanced because the clip 700 does not enter the locked position if doing so would not actually secure the cuff 620 to the pump 750.

In some implementations, the clip 700 can enter the restrained position when only one of the posts 719 engages one of the detents 766. Either post 719 can independently impede the clip 700 from entering the locked position. In some instances, the cuff 620 may be seated only partially against the circumferential flange 662. For example, the cuff 620 may be placed in a tilted orientation such that the cuff 620 is not aligned in a plane perpendicular to the cannula 650. With the cuff 620 partially seated, one of the posts 719 may avoid the detent 766. Engagement of the other post 719 with its corresponding detent 766, however, will place the clip 700 in the restrained position rather than permitting the clip 700 to enter the locked position.

Figure 28C:
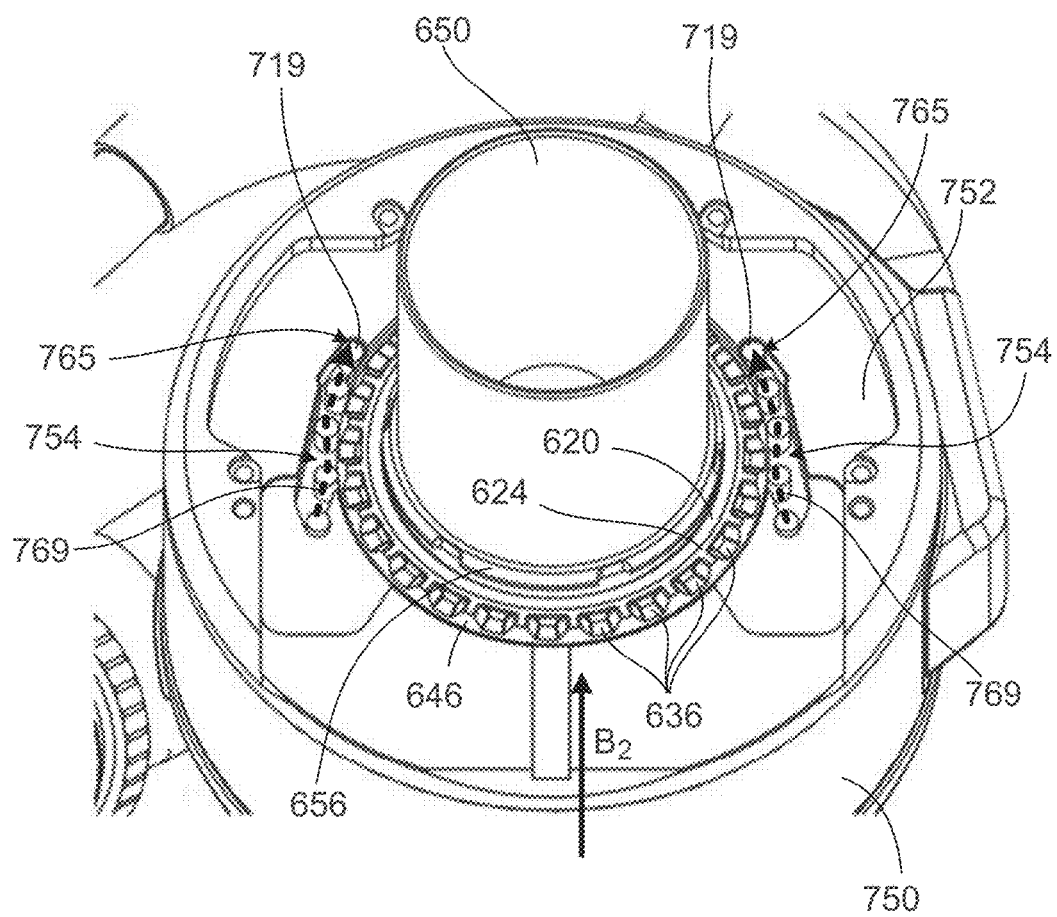

Referring to FIG. 28C, when the cuff 620 is properly coupled to the cannula 650, advancing the clip 700 in the direction of arrow $B_2$ moves the clip 700 into the locked position about the cuff 620. For clarity in illustration, the fastening member 622 and portions of the linking member 624 are not shown.

When the cuff 620 is coupled to the cannula 650, the flanged portions 634, 646 of the cuff 620 cover the detents 766. The cuff 620 blocks the posts 719 from entering the detents 766 and permits the posts 719 to enter the second ends 765. Between the unlocked position and the locked position, the posts 719 move along a path 769. The posts 719 slide along the outer circumference of the flanged portion 646, engaged to the cuff 620 by the resilient force of the arms 714, until the posts 719 reach the second ends 765. In the locked position, the arms 714 (not shown) extend into the circumferential groove 632, capturing the flanged portions 634, 646 between the arms 714 and the circumferential flange 662 of the cannula 650. The teeth 716 extend radially inward into the circumferential groove 632, becoming enmeshed between the ridges 636 to limit rotation of the cuff 620 relative to the cannula 650.

Figure 29A:
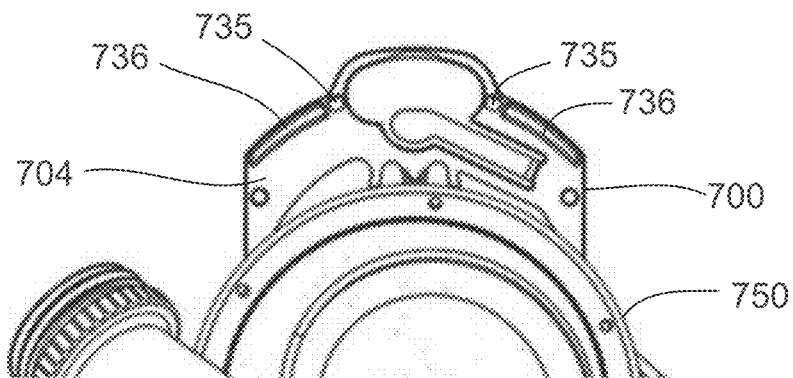
FIGS. 29A to 29C are bottom views of different positions of the clip of FIG. 26A relative to the pump of FIG. 21.
Figure 29B:
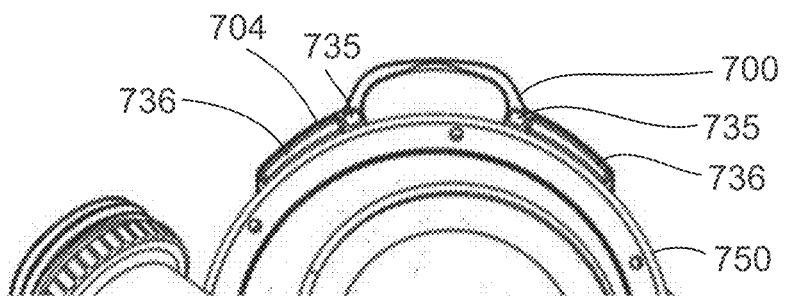

Referring to FIGS. 29A and 29B, when a clinician installs the pump 750, the visual indicators 736 on the clip 700 are exposed to the clinician's view. The visual indicators 736 indicate that the clip 700 is not securing the cuff 620, and thus that installation is incomplete. The visual indicators 736 are exposed in the unlocked position (FIG. 29A) and in the restrained position (FIG. 29B).

Figure 29C:
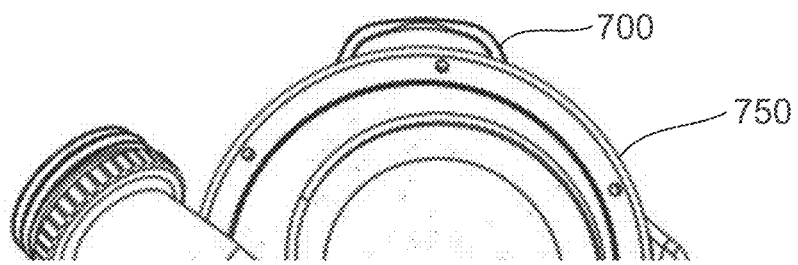

Referring to FIG. 29C, when the clip 700 enters the locked position, the pump 750 obscures the visual indicators 736, indicating to the clinician that the clip 700 has been properly locked about the cuff 620.

Figure 30A:
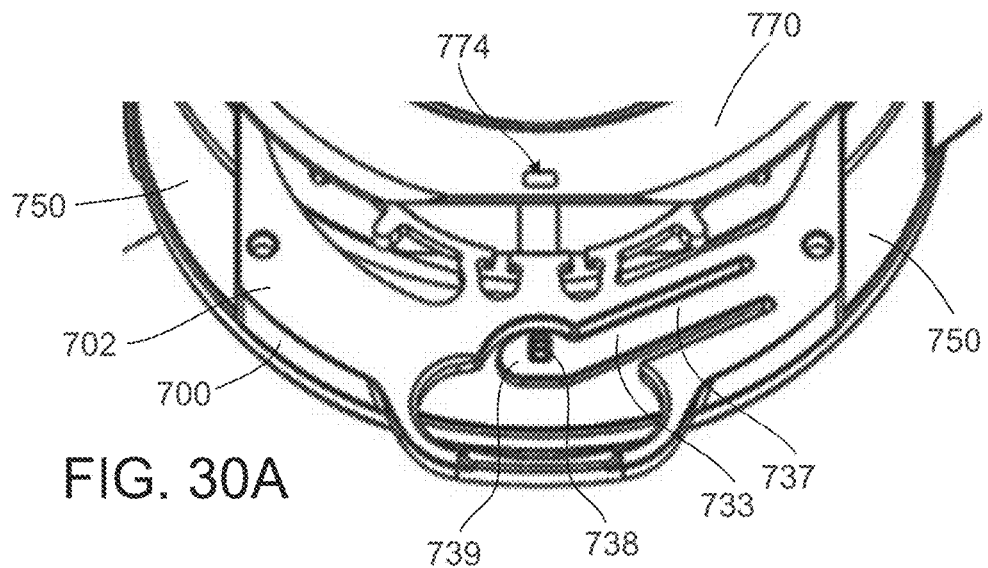
FIGS. 30A to 30C are top perspective views of different positions of the clip of FIG. 26A relative to the pump of FIG. 21.
Figure 30B:
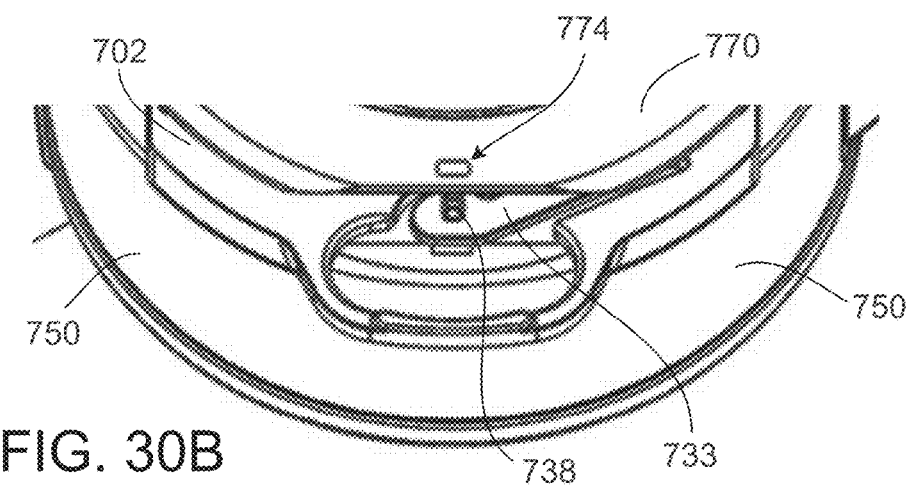
Figure 30C:
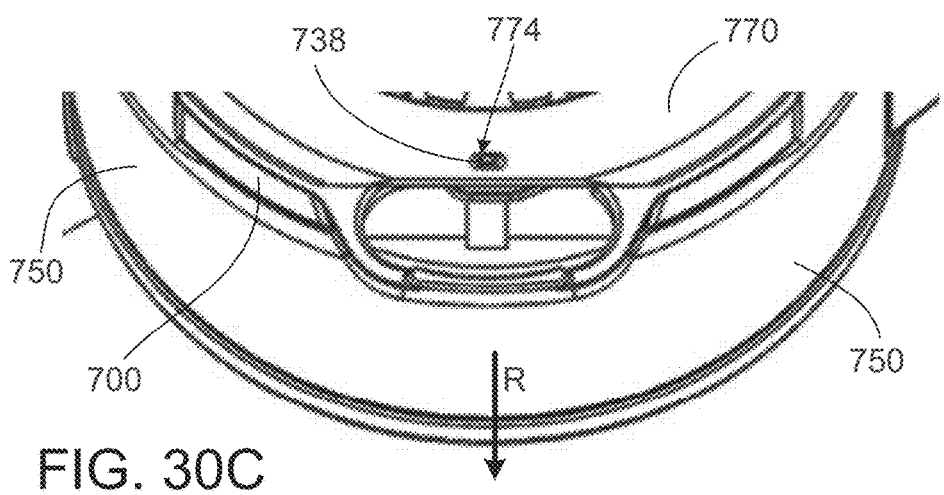

Referring to FIGS. 30A-30C, the cover 770 defines a mating receptacle 774, for example, a recess or an opening, that cooperates with the latch 733. The latch 733 does not secure the position of the clip 700 in the unlocked position (FIG. 30A) or the restrained position (FIG. 30B). In the locked position (FIG. 30C), the extension 738 extends into the mating receptacle 774 to impede retraction of the clip 700 in the direction of the arrow R.

Figure 31:
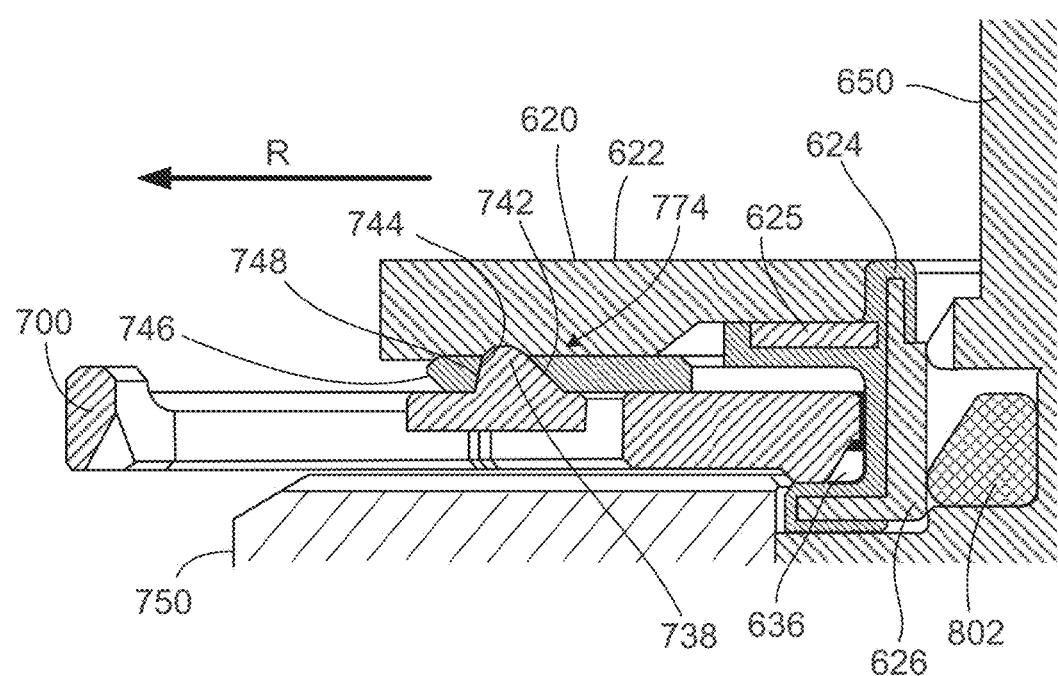
FIG. 31 is a side cutaway view of the pump, the cannula, and the ventricular cuff of FIG. 21.

Referring to FIG. 31, the extension 738 includes an angled leading edge 742 and an angled trailing edge 744 that engage the cover 770. The leading edge 742 engages an outer edge 746 of the cover 770 as the clip 700 travels into the locked position. The engagement of the leading edge 742 with the outer edge 746 deflects the deflection beam 737, permitting the extension 738 to slide under the outer edge 746 and into the mating receptacle 774. The trailing edge 744 engages an inner surface 748 of the mating receptacle 774 to limit removal of the clip 700.

The trailing edge 742 has a steeper slope than the leading edge 742. For example, the trailing edge 742 can have a slope of between approximately 70 degrees and approximately 85 degrees, and the leading edge can have a slope of between approximately 10 degrees to approximately 60 degrees. As a result, the amount of force required to dislodge the extension 738 from the mating receptacle 774 is greater than the force required to insert the extension into the mating receptacle 774. When removal of the clip 700 is desired, a clinician can engage a tool with the deflection beam 737 to move the extension 738 out of the mating receptacle 774, which permits the clip 700 to be refracted.

In some implementations, a plug can be fabricated for a cuff 20, 120, 320, 620. A plug can be placed in the opening 30, 130, 330, 630 of an implanted cuff 20, 120, 320, 620 after a pump 12, 250, 750 has been explanted. The plug can fill the opening 30, 130, 330, 630 to prevent blood from escaping through the cuff 20, 120, 320, 620 after the pump 12, 250, 750 is removed. Plugs can include features similar to those described for the cannulas 50, 150, 350, 650. As a result, a plug can be coupled to a corresponding cuff 20, 120, 320, 620 using one or more of the same mechanisms that couple a cuff 20, 120, 320, 620 to a cannula 50, 150, 350, 650. A plug can be further secured to a heart or to a cuff 20, 120, 320, 620 by sutures. A plug may further be configured to fill the opening through any of the further cuffs described below.

Figure 32:
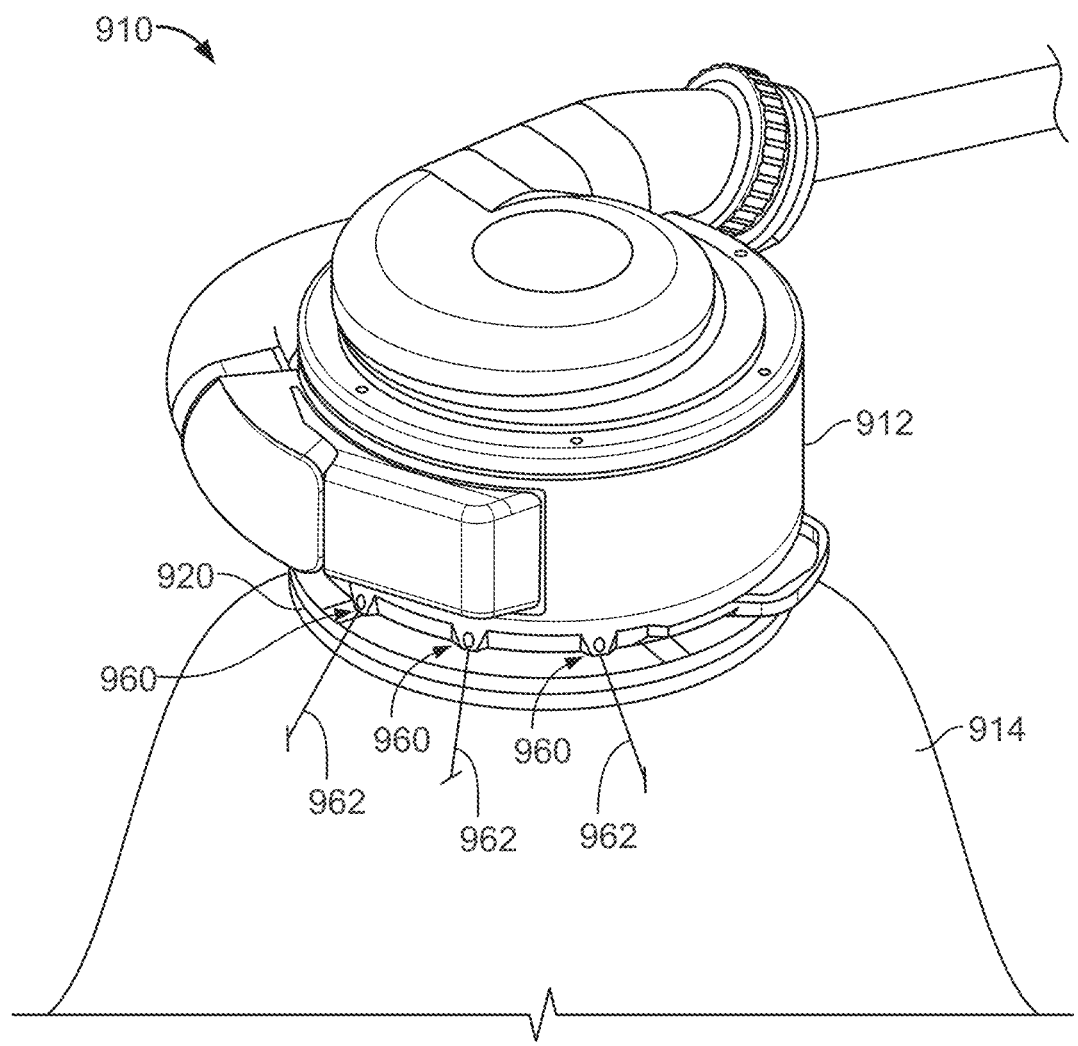
FIG. 32 is a perspective view of a pump installed at a heart.
Figure 33:
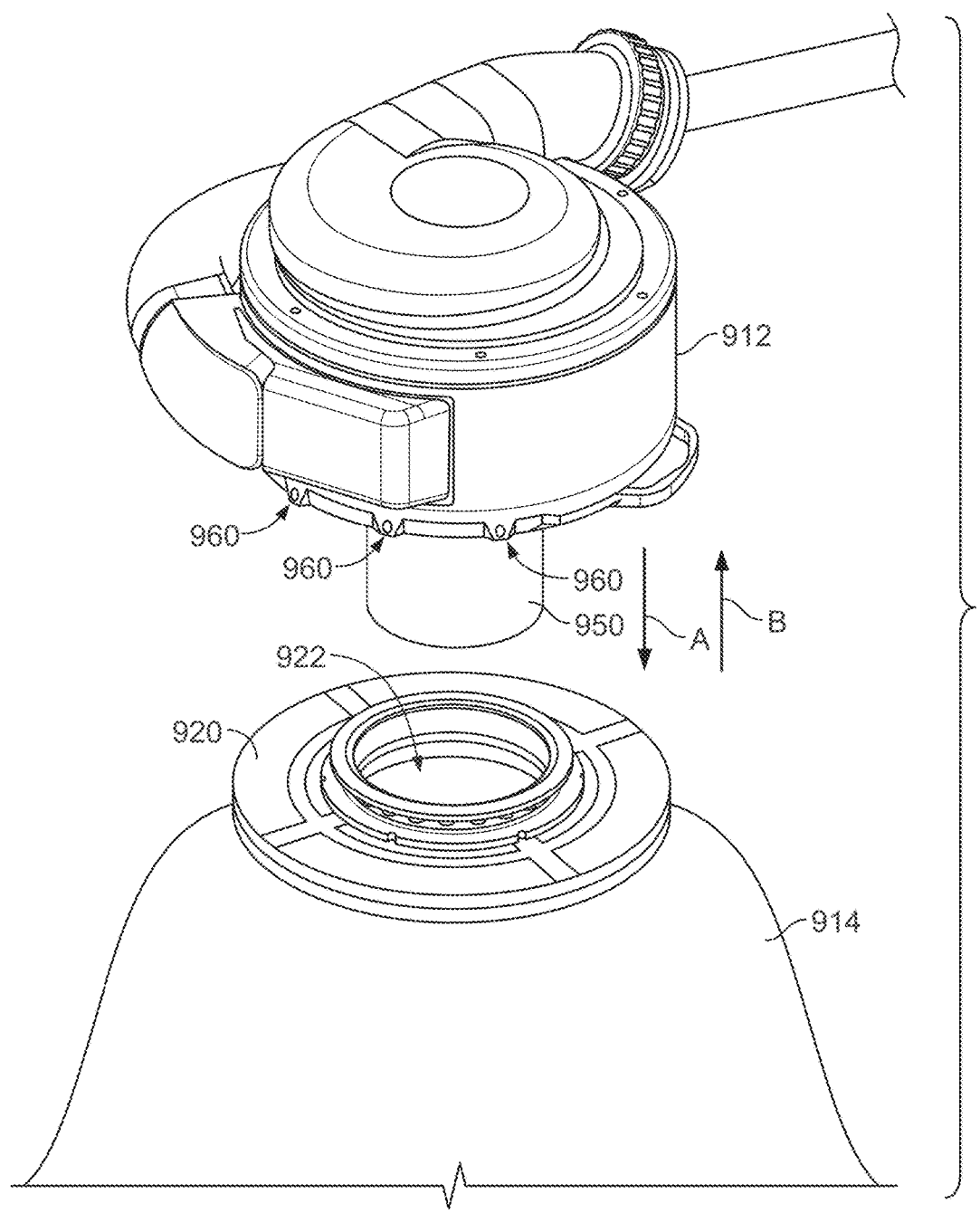
FIG. 33 is a perspective view of the pump of FIG. 32 and a cuff attached to the heart.

Referring to FIGS. 32 and 33, a ventricular assist system 910 for treating, for example, a patient with a weakened left ventricle, includes a blood pump 912 that receives blood from a patient's heart 914. The pump 912 is coupled to a cuff 920, which in turn is attached to the heart 914. The cuff 920 is attached to the heart 914 by, for example, sutures that attach a portion of the cuff 920 to the apex of the left ventricle of the heart 914. The pump 912 receives blood from the heart through an inflow cannula 950 (FIG. 33) of the pump 912 disposed through an opening 922 (FIG. 33) in the cuff 920.

The ventricular assist system 910 may be implanted in the thoracic cavity of a patient. After implantation, the cuff 920 limits the risk of inflow cannula malposition due to potential post-operative pump migration. Inflow cannula malposition is an adverse clinical event that may reduce pump performance and endanger the patient. The cuff 920 helps maintain a space around the inflow cannula 950 so that the inflow cannula 950 does not become partially or completely occluded by surfaces of the heart (e.g., by the septal wall of the heart). For example, the cuff 920 is sufficiently stiff to promote flattening of the myocardium when the sewing ring is attached to the heart 914. In other words, after installation of the cuff 920, the rigidity or resilience of the cuff 920 reshapes the myocardium in a manner that the geometry of the myocardium in the region of the cuff 920 is flatter than the natural or previous geometry of the myocardium. The cuff 920 can exert a resilient force that resists bending of the cuff 920 and flattens an area of the myocardium in contact with the cuff 920.

The cuff 920 also aids installation of the pump 912. Exemplary cuff 920 is relatively rigid and has a higher bending resistance to bending than conventional ventricular cuffs. The relatively increased stiffness of the cuff 920 permits a clinician to hold the cuff 920 (e.g., at outer edges of the cuff 920) and apply counter-pressure with the cuff 920 against the inflow cannula 950 during installation of the pump 912.

The pump 912 includes anchors 960, such as eyelets or other openings defined in the housing 964, where sutures 962 or other fasteners can attach to the pump 912. The sutures 962 secure the pump 912 to, for example, the cuff 920, the myocardium of the heart 914, ribs of the patient, or other structures. The sutures 962 limit rotation of the pump 912 relative to the heart 914 and other movement of the pump 912 relative to the heart 914. Securing the pump 912 using the anchors 960 and flattening the myocardium in the region of the pump 912 help limit the risk of inflow cannula malposition, as discussed further below.

Figure 34A:
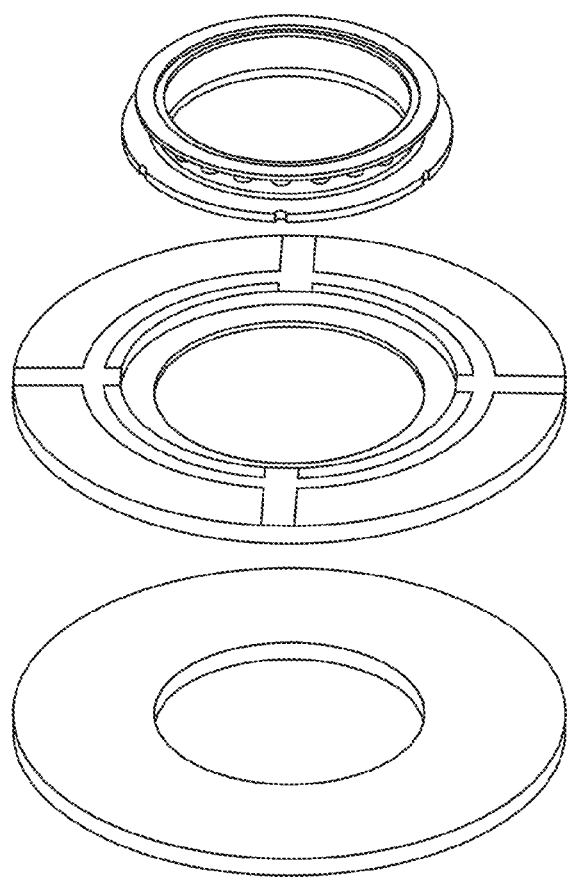
FIG. 34A is an exploded view of the cuff of FIG. 33.
Figure 34B:
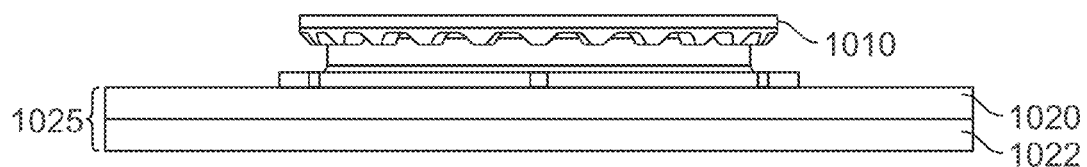
FIG. 34B is a side view of the cuff of FIG. 33.

Referring to FIGS. 34A and 34B, the cuff 920 includes an attachment component such as a ring 1010 that engages the inflow cannula 950 and/or other portions of the pump 912 to secure the cuff 920 and pump 912 together. In the example illustrated, the ring 1010 is formed by a patterned metal component (e.g. titanium) covered with, for example, silicone. The ring 1010 may include, for example, an attachment member (having one or more features of any of the attachment members 26, 126, 326, 626), and a linking member (having one or more features of any of the linking members 24, 124, 324, 624). The cuff 920 is secured to the pump 912 using the techniques described above. For example, the cuff 920 may be coupled to and locked to the pump 912 in the same manner that any of the cuffs 20, 120, 320, 620 are locked and coupled to the pumps 12, 250, 750. A clinician may lock the cuff 920 to the pump 912 using any of the locking mechanisms described above, such as using the clips 200, 700.

The cuff 920 includes two disc-shaped layers 1020, 1022, and together, the layers 1020, 1022 form a sewing ring 1025. To install the cuff 920, a clinician places sutures, staples, or other fasteners through the sewing ring 1025 and the heart 914. In some implementations, only one disc or more than two discs are included in the sewing ring 1025.

The layers 1020, 1022 are formed of, for example, a felt, a mesh, a woven material, or another fabric. The layers 1020, 1022 are formed of polytetrafluoroethylene (PTFE), polyethylene terephthalate (PET) (e.g., Dacron), polyester, or another material. In some implementations, the layers 1020, 1022 are each formed of PTFE felt. In some implementations, the layers 1020, 1022 are each formed of a woven polyester.

The layers 1020, 1022 are joined together by sutures, for example, sutures at the inner diameter and outer diameter of the layers 1020, 1022. In some implementations, the layers 1020, 1022 are additionally or alternatively joined by an adhesive, such as a silicone adhesive, or another fastener.

The layers 1020, 1022 have a stiffness that tends to flatten the myocardium of the heart 914 when the cuff 920 is installed. This flattening reduces the probability of inflow cannula malposition. As an additional advantage, in some implementations, the stiffness of the layers 1020, 1022 (and of the sewing ring 1025 as a whole) makes the cuff 920 easier for the clinician to hold. The relative stiffness of the cuff 920 may aid a clinician in pressing the cuff 920 against the pump 912 when attaching the pump 912 and the cuff 920. For example, the clinician may more easily apply a counterforce against the pump 912 when the inflow cannula 950 is inserted into the cuff 920, permitting the cuff 920 to be more easily seated against the pump 912.

In some implementations, the sewing ring 1025 has a flexural modulus of greater than 50 psi (pound-force per square inch). In some implementations, the flexural modulus of the sewing ring 1025 is at least 60 psi, at least 75 psi, at least 90 psi, at least 100 psi, at least 125 psi, or at least 150 psi. The sewing ring 1025 may have a flexural modulus in one of these ranges along a portion of, a majority of, or substantially all of the sewing ring 1025. In some implementations, the sewing ring 1025 has a flexural modulus in one of the ranges indicated above across the entire diameter of the sewing ring. In some implementations, the flexural modulus of the sewing ring 1025 is, for example, less than 1500 psi, less than 1000 psi, or less than 750 psi. A flexural modulus under one of these ranges can facilitate insertion of a needle through the sewing ring 1025 without requiring an excessive amount of insertion force.

The fabric of the layers 1020, 1022 can provide the rigidity that causes the sewing ring 1025 to have a flexural modulus in these ranges, without any additional component formed of, for example, metal or polymer. Because the sewing ring 1025 is fabric, in some implementations, a clinician is able to insert a needle through any exposed portion the sewing ring 1025 without the needle being impeded by structures of the sewing ring 1025. In some implementations, another component in the sewing ring 1025, such as the insert 1030 described below, can contribute to the rigidity of the sewing ring 1025, so that the sewing ring 1025 as a whole has a flexural modulus in one of the ranges indicated above.

In some implementations, one or more of the layers 1020, 1022 individually has a flexural modulus of greater than 50 psi, for example, a flexural modulus at least 60 psi, at least 75 psi, at least 90 psi, at least 100 psi, at least 125 psi, or at least 150 psi. In addition, the flexural modulus of each of the layers 1020, 1022 can be, for example, less than 1500 psi, less than 1000 psi, or less than 750 psi. In some implementations, the sewing ring 1025 includes only a single layer of fabric or other material that provides a flexural modulus in the ranges indicated above.

Referring to FIG. 33, to install the pump 912, the cuff 920 may be installed at the heart 914. A clinician or a tool holds the cuff 920 by the ring 1010 and/or the sewing ring 1025 as the pump 912 is subsequently positioned relative to the cuff 920. For example, a tool or the clinician's fingers may grasp the cuff 920 by pressing against the outer edges of the sewing ring 1025. The clinician moves the pump 912 toward the cuff 920 in the direction of arrow A. As the pump 912 moves relative to the cuff 920, a coupling mechanism attaches the cuff 920 to the pump 912. For example, features of the ring 1010 engage features of the inflow cannula 950. The cuff 920 may be required to provide a particular amount of counterforce for the pump 912 to become coupled to the cuff 920. The cuff 920, held by the clinician's fingers or a tool, provides counterforce in the direction of arrow B, to permitting the coupling mechanism to engage. The sewing ring 1025 may be sufficiently rigid that, while the cuff 920 is held through inward force from the outer edges of the sewing ring 1025, the sewing ring 1025 does not buckle or deform, and the cuff 920 exerts a sufficient amount of force against the pump 912 that a coupling mechanism the pump 912 and the cuff 920.

Referring again to FIGS. 34A and 34B, in some implementations, the layers 1020, 1022 each have a thickness of between approximately 1.3 mm and 2.3 mm, or approximately 1.8 mm, and may have a maximum water permeability of between approximately 450 ml/cm2/min and 650 ml/cm2/min, or approximately 550 ml/cm$^2$/min. Accordingly the use of two such layers 1020, 1022 together in the sewing ring 1025 provides a higher stiffness than a single layer of lower density, higher porosity PTFE felt, for example, a single layer having a thickness of approximately 2.9 mm and a maximum water permeability of approximately 750 ml/cm$^2$/min. A high-density, low-porosity felt material for the layers 1020, 1022 may be obtained by compressing a lower density felt material, (such as compressing the 2.9 mm thick felt with 750 ml/cm$^2$/min maximum water permeability to approximately half of its initial thickness).

Figure 34C:
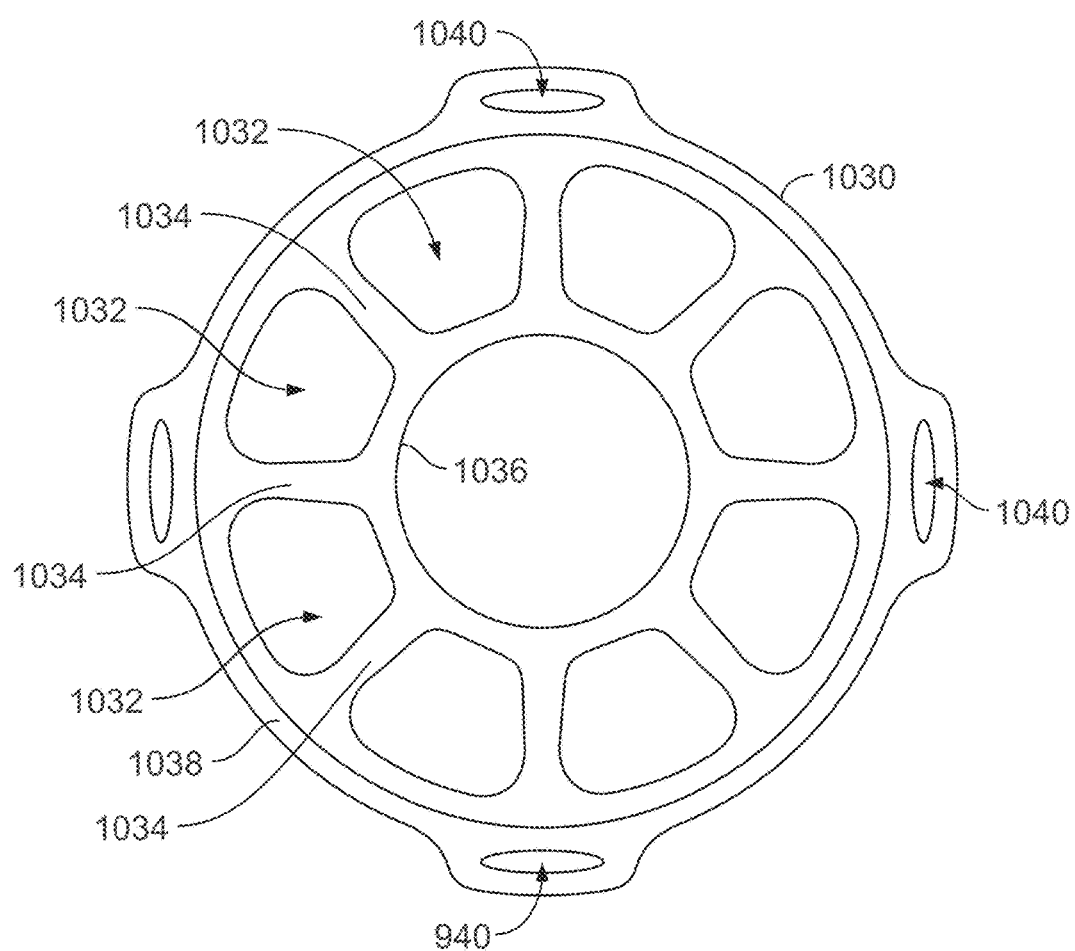
FIG. 34C is a top view of an insert that may be included in the cuff of FIG. 33.
Figure 34D:
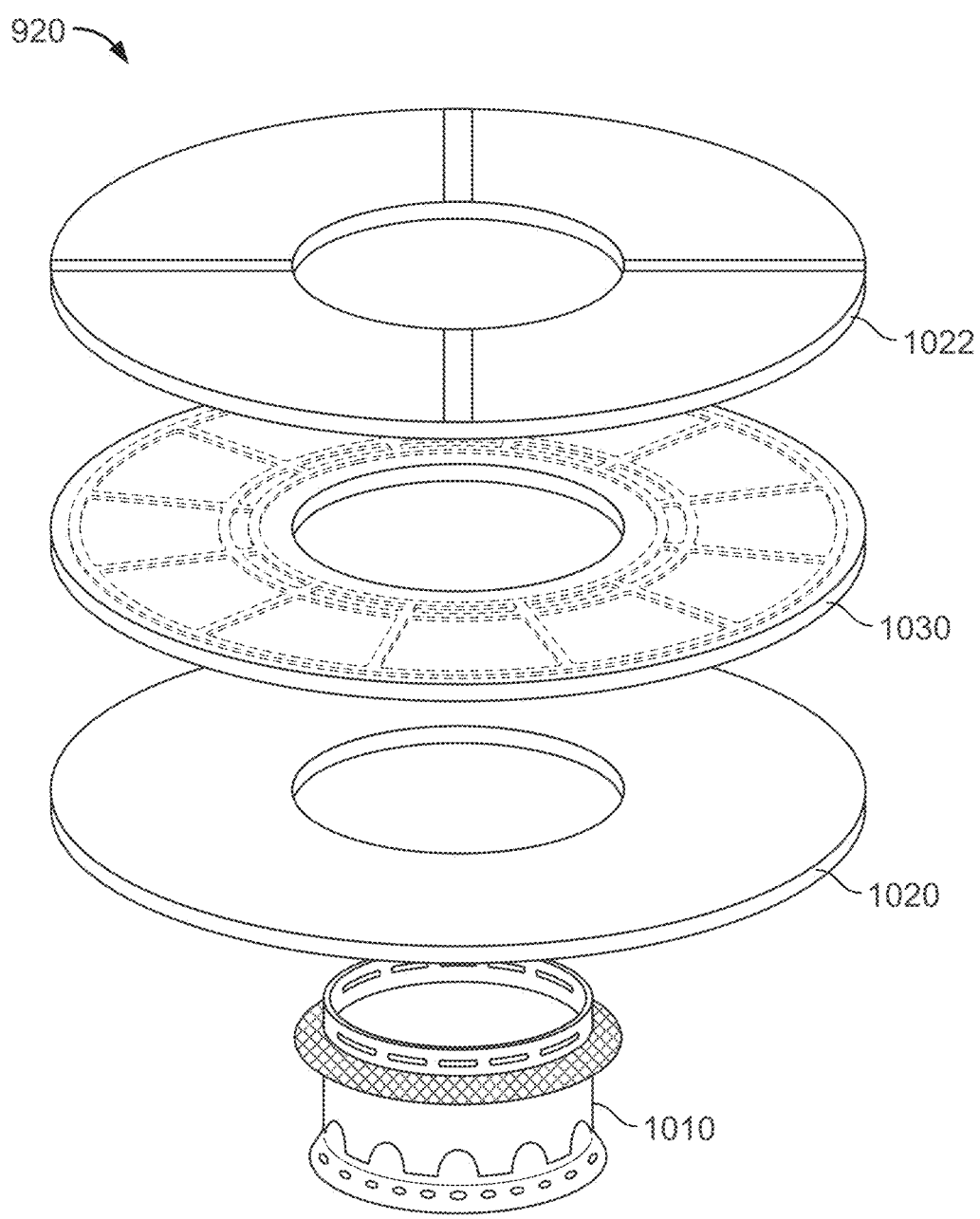
FIG. 34D is an exploded view of the cuff of FIG. 33 including the insert.

Referring to FIGS. 34C and 34D, in some implementations, an insert 1030, such as a lattice or web of a firm or resilient material, is included in the sewing ring 1025, forming a sewing ring 1025a (FIG. 34D). The insert 1030 is generally planar. The insert 1030 may be positioned between the layers 1020, 1022, and may be formed of a material stiffer than the material of the layers 1020, 1022. For example, the insert 1030 may be formed of polyether ether ketone (PEEK), titanium, a cobalt chromium alloy, a shape-memory polymer, or another material. The insert 1030 can be molded, machined, printed, stamped, formed of wire, laser cut from a metal sheet, or formed in another manner. In some implementations, the insert is formed of a super-elastic material such as titanium alloy (e.g. nickel-titanium alloy).

In some implementations, the insert 1030 retains its shape when bent, permitting a clinician to manually shape the sewing ring 1025a as desired for a particular implantation (e.g., shaping the sewing ring 1025a with one bent edge, in a conical shape, etc.). After implantation, the sewing ring 1025a shapes the myocardium to substantially conform to the shape of the sewing ring 1025a.

The insert 1030 defines windows or openings 1032 through the insert 1030. The openings 1032 define areas where sutures may be placed through the insert 1030 to achieve hemostasis. The insert 1030 may be formed as, for example, a web, lattice, or mesh that defines the openings 1032, thereby providing regions where needles can pass through unimpeded while providing strength and stiffness across substantially the entire sewing ring 1025. At the openings 1032, sutures can be inserted without interference from, for example, extensions or supports 1034 that extend radially, connecting an inner ring 1036 and an outer ring 1038 of the insert 1030. The insert 1030 may be covered in silicone or another material. For example, the insert 1030 may be embedded within in a sheet of silicone, with the silicone covering the openings 1032. An opening in the center of the insert 1030 is not covered with silicone, allowing the inflow cannula 950 to pass through the center of the insert 1030. In some implementations, the insert 1030 includes one or more anchors 1040 located at the outer edge of the insert 1030. The anchors 1040 are openings defined in the insert 1030 through which sutures may be placed to secure the cuff 920 to the myocardium.

In some implementations, the insert 1030 has a flexural modulus of greater than 50 psi, for example, a flexural modulus at least 60 psi, at least 75 psi, at least 90 psi, at least 100 psi, at least 125 psi, or at least 150 psi. In some implementations, the sewing ring 1025a as a whole has a flexural modulus in one of these ranges.

Figure 35:
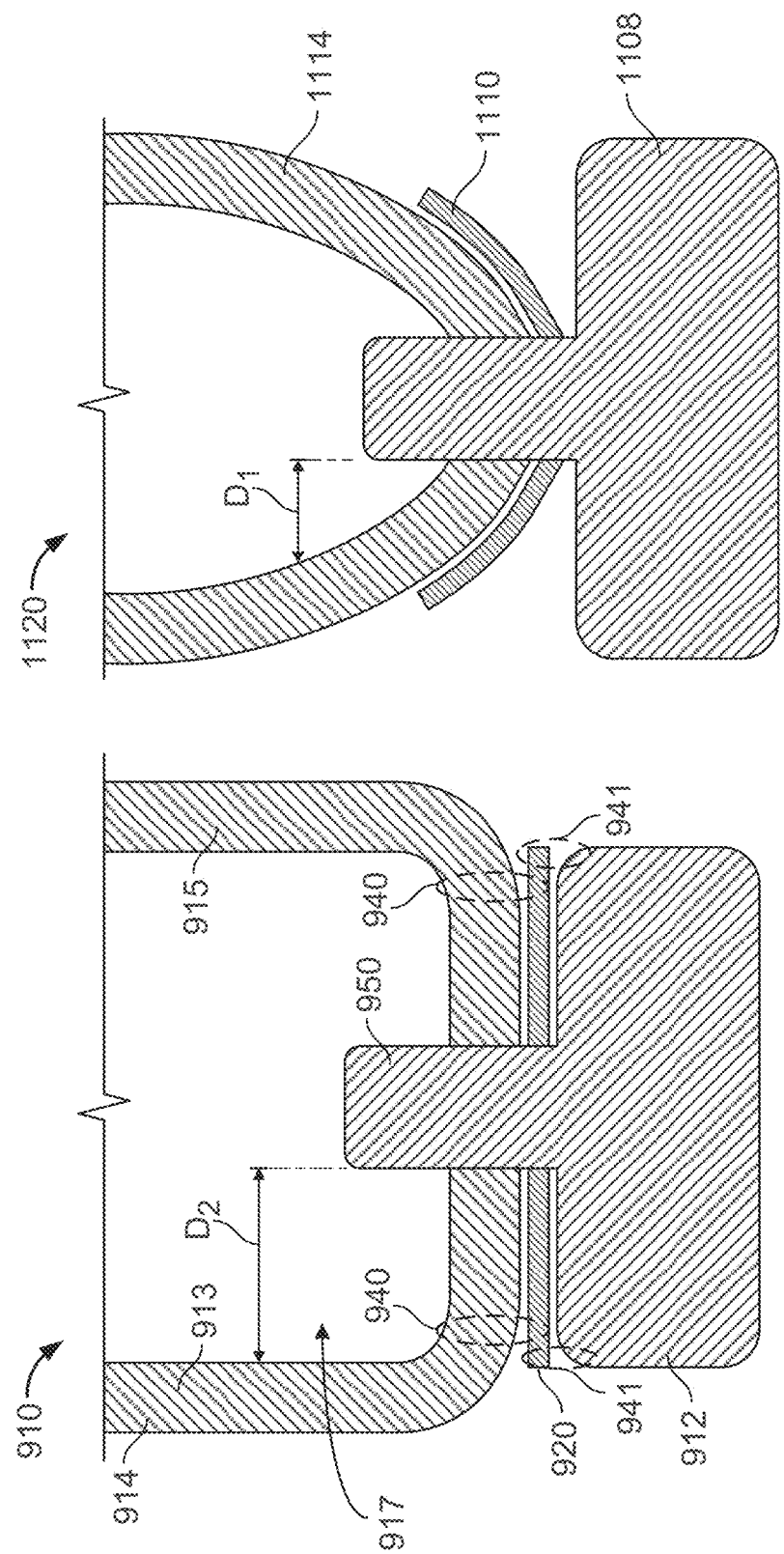
FIG. 35 is a side cutaway view of two different cuffs and associated pumps.

Referring to FIG. 35, some ventricular cuffs provide a flexible interface that allows myocardial tissue to be free from restriction after implantation. As an example, a pump 1108 is attached to a heart 1114 using a cuff 1110. The cuff 1110 is compliant and conforms to the shape of a heart 1114 to which the cuff 1110 is attached. The pump 1108 includes an inflow cannula 1130 that extends into a space 1120 within the heart 1114. The space 1120 in which the inflow cannula 1130 resides is primarily defined by the natural geometry of the heart 1114. In addition, a distance, $D_1$, between the inflow cannula 1130 may change as the patient moves (e.g., as the pump 1108 tilts, twists, or otherwise moves relative to the heart 1114.

By contrast with the cuff 1110, the stiffness of the cuff 920 substantially flattens the myocardium, which expands a space 917 around the inflow cannula 950 and helps maintain an appropriate distance, $D_2$, between the inflow cannula 950 and inner walls 913 of the ventricle. This, in turn, reduces the potential for inflow cannula malposition because of the expanded space 1000 within the ventricle created near the inflow cannula 950. Malpositioning is associated with several risks including decreased pump poor performance and adverse clinical events. If the cannula inflow gets close to or contacts internal structures (e.g. the septum or ventricular walls), the inflow may become partially or completely occluded. Moreover, malpositioning of the inflow near internal structures can alter flow patterns and even form regions of stasis. Accordingly, malpositioning may increase the risk of hemolysis and thrombosis. By making interface of the cuff 920 and pump 912 with the heart 914 (e.g., myocardium) stiffer, the myocardium can be flattened and clinical outcomes can be improved. In some implementations, a clinician attaches the cuff 920 to the heart 914 using sutures 940 placed at or near the outer edge of the sewing ring 1025, permitting the cuff 920 to substantially flatten the myocardium across substantially the entire region of the myocardium that engages the cuff 920. As noted above, flattening the myocardium may limit inflow cannula malposition or reduce the risk of occlusion of the inlet tip of the inflow cannula 950 in the event of malposition. The stiffness of the cuff 920, for example, the stiffness of the sewing ring 1025, may cause the flattening of the myocardium.

Sutures anchored to the pump 912 can also promote flattening of the myocardium. In some implementations, as discussed further below, sutures 941 may be placed through the sewing ring 1025 and a portion of the pump 912, such as the anchors 960. These sutures 941 can hold the sewing ring 1025 near or against the pump 912, further flattening the myocardium or maintaining the shape defined by the cuff 920. In some implementations, one or more sutures may be placed through an anchor 960 and the myocardium, as shown in FIG. 32, in addition to or instead of through the sewing ring 1025.

As shown in FIG. 35, the sewing ring 1025, when generally perpendicular to the inflow cannula 950, can extend along a majority of the diameter of the pump 912. For example, the sewing ring 1025 can have an outer diameter that is at least 50%, at least 75%, or at least 90% of the outer diameter of the pump 912. In some implementations, as shown in FIG. 35A, the sewing ring 1025 extends along substantially all of a proximal side of the pump 912, extending to an outer peripheral wall 982 of the pump 912.

Figure 36A:
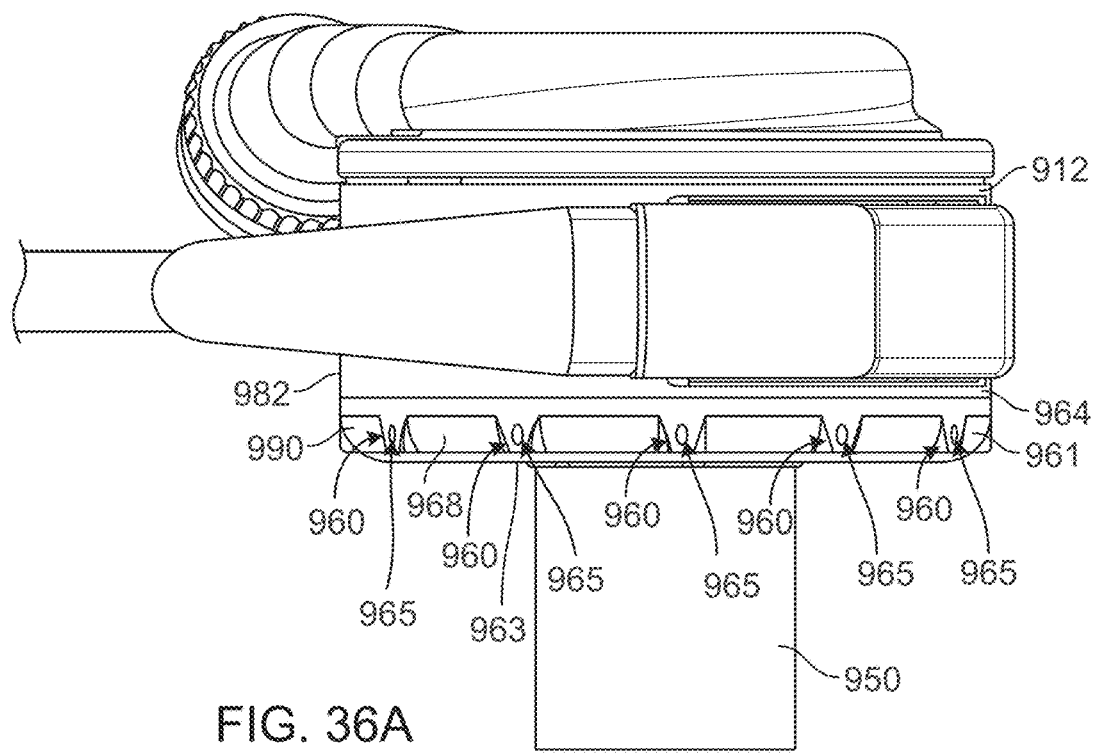
FIG. 36A is a side view of the pump of FIG. 32.
Figure 36B:
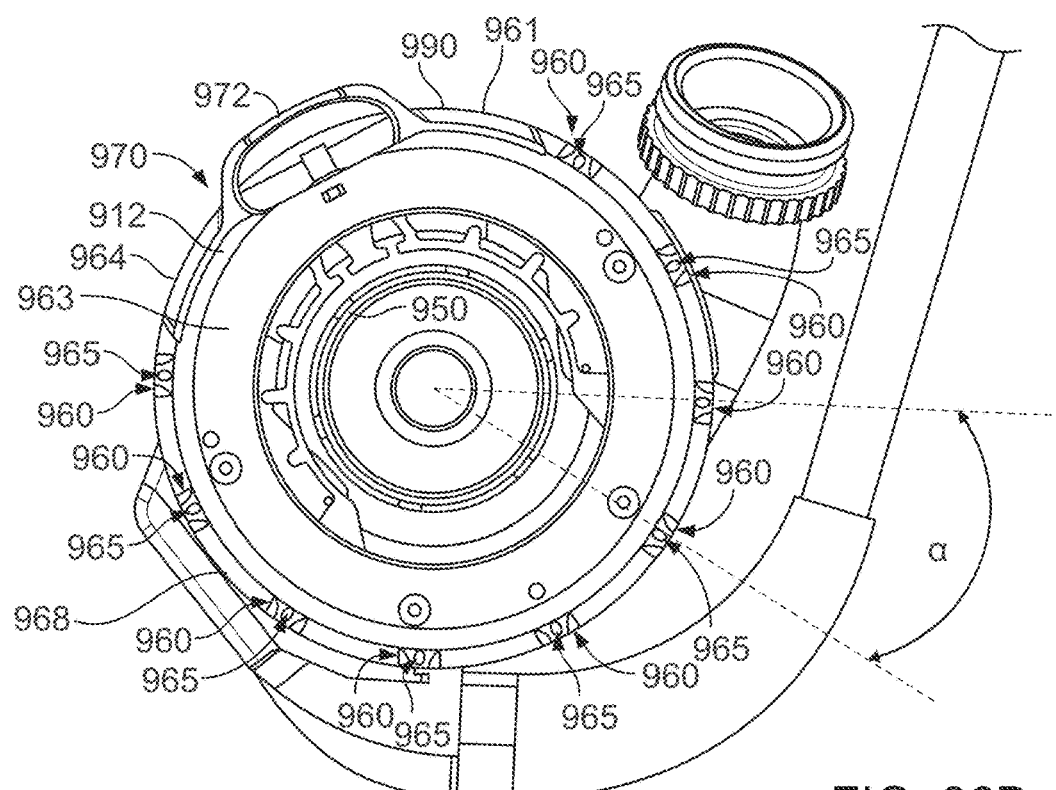
FIG. 36B is a top view of the pump of FIG. 32.

Referring to FIGS. 36A and 36B, the pump 912 can be secured relative to the heart 914 using one or more of the anchors 960. The pump 912 includes the anchors 960 at locations on the exterior of the pump 912, for example, spaced apart around an outer perimeter 961 of a housing 964 of the pump 912. The outer perimeter 961 is generally circular and represents the circumference of the housing 964. The anchors 960 are spaced apart along at least a portion of the circumference. The anchors 960 may be disposed around more than half of the circumference of the housing 964. In the example shown, the anchors 960 are located around the entire circumference of the pump 912 except in a region 970 where a cuff lock 972 is located. The anchors 960 are spaced apart around the pump 912 at an angle α, which may be, for example, between 10 degrees and 50 degrees, or approximately 30 degrees. The pump 912 includes eight anchors 960, but more or fewer anchors 960 may be included. In some implementations, at least three anchors 960 are included.

In some implementations, the anchors 960 include suture eyelets 965 located at an edge of the housing 964. The eyelets 965 are defined to be adjacent to the sewing ring 1025 of the cuff 920 when the pump 912 is implanted. For example, each eyelet 965 has an exit opening adjacent the cuff 920 when the cuff 920 is engaged to the proximal side 994 of the housing 964. During implantation, a clinician may pass sutures or other fasteners through the eyelets 965. At the site of each eyelet 965, the clinician may also pass the sutures through the cuff 920 and/or the myocardium. Passing the sutures through the cuff 920 and/or myocardium at locations adjacent the anchors 960 may help maintain the cuff 920 in a substantially flat against a proximal side 994 of the pump 912, thus flattening the cuff 920 and myocardium. For example, sutures may extend through sewing ring 1025 at or near the outer edge of the sewing ring 1025, pulling the outer edge of the sewing ring 1025 toward (e.g., close to or against) the pump 912.

The sutures may connect the anchors 960 to any of various structures located within the thoracic cavity, such as the patient's ribs, a portion of the myocardium (e.g., a portion spaced apart from the cuff), synthetic material such as Gore-Tex, or other structures. The clinician may secure the other end of each suture at a distance from the anchors 960 (e.g., approximately 0.5 cm, 1 cm, 3 cm, 5 cm, etc.), as selected by the clinician.

In some implementations, the anchors 960 do not increase the outer diameter of the pump 912. The features in which the eyelets 965 are defined occupy space in the region where the edge 968 of the pump housing 964 has been cut, e.g., with a radius. The housing 964 has a rounded, chamfered, or beveled edge where no anchors 960 are placed.

Figure 37A:
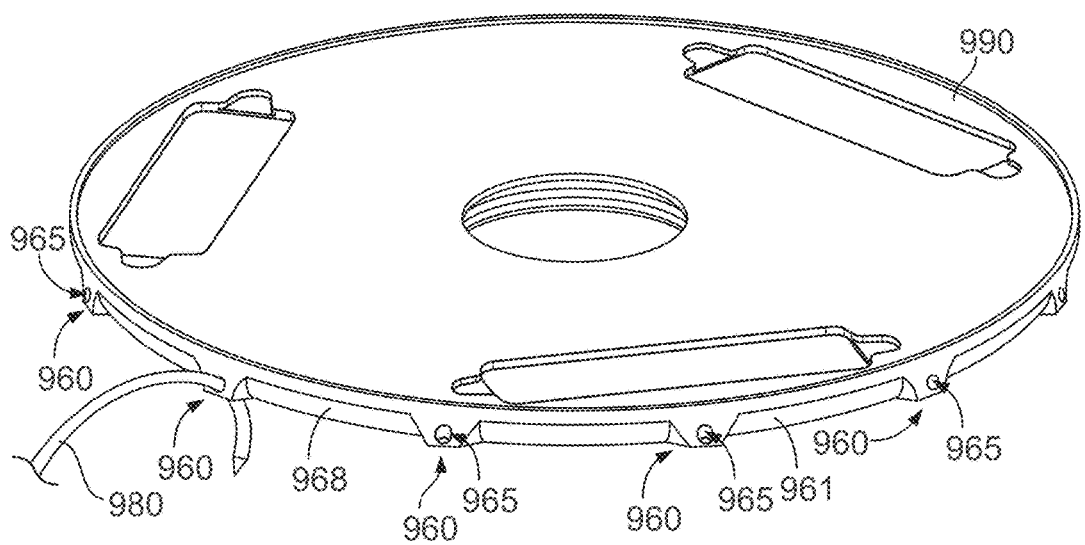
FIGS. 37A and 37B are perspective views of a portion of the pump of FIG. 32.
Figure 37B:
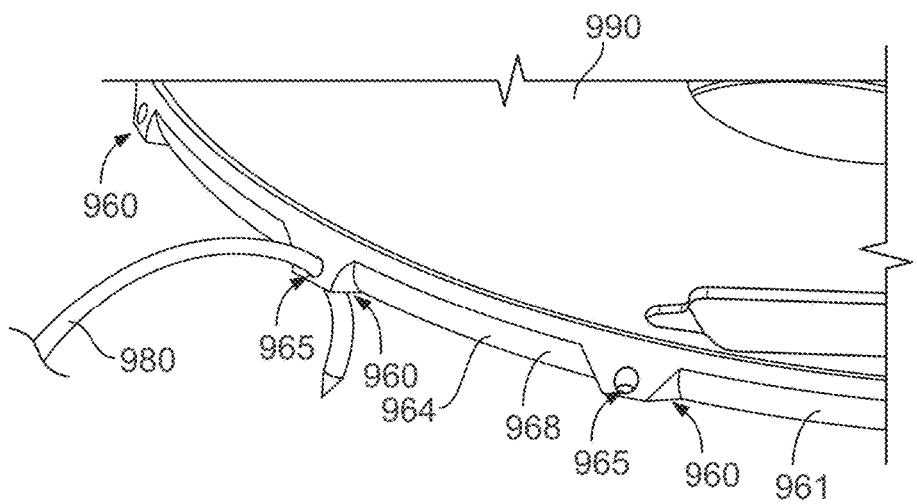
Figure 37C:
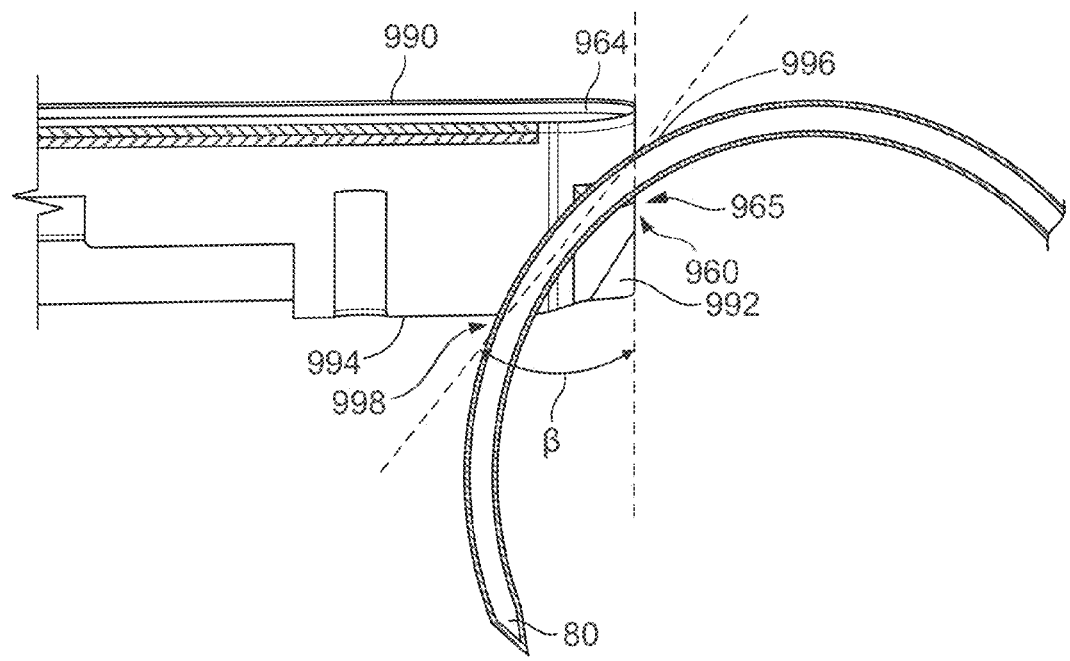
FIG. 37C is a side cutaway view of a portion of the pump of FIG. 32 and a needle.

Referring to FIGS. 37A to 37C, the eyelets 965 are defined in a motor cap 990, which is part of the housing 964 of the pump 912. The motor cap 990 has a side surface 992 and also has a proximal side 994 oriented perpendicular to the side surface 992. The inflow cannula 950 of the pump 912 extends from the proximal side 994, in a direction generally perpendicular to the proximal side 994 (See FIG. 36A). The proximal side 994 faces the cuff 920 when the pump 912 is implanted.

Each eyelet 965 defines a passage that angles inward from an outer wall of the pump 912. In some implementations, each eyelet 965 extends toward the inflow cannula 950 in the center of the proximal side 994. The passage extends between an entry opening 996 defined in the side surface 992 and an exit opening 998 defined in the proximal side 994. The passage defined by each eyelet 965 is oriented at an angle β (FIG. 37C) from the substantially cylindrical peripheral wall 982 (FIG. 36A) of the pump housing 964. In some implementations, the angle β is between approximately 20 degrees and 50 degrees, or is approximately 35 degrees. The angled trajectory of the eyelet 965 allows the clinician to place a suture through the eyelet 965 and capture the PTFE felt or other material of the sewing ring 1025 of the cuff 920 as well as the myocardium if desired. When the cuff 920 is positioned about the inflow cannula 950 and the sewing ring 1025 is positioned adjacent the proximal side 994 of the housing 964, each eyelet 965 is oriented to direct a needle travelling through the eyelet 965 into the sewing ring 1025.

The eyelets 965 may accommodate a curved needle 980 and may define a curved or linear path through the pump housing 964. The eyelets are designed to accommodate a #1-0 suture and needle. To accommodate the diameter and typical radius of curvature for these needles, the diameter of the eyelet 965 may be approximately 0.034 inches.

A clinician may selectively fasten the anchors 960 to portions of a patient's anatomy to limit potential for subsequent malposition of the inflow cannula 950. For example, the clinician may select the particular anchors 960 at which to attach sutures according to the needs of the patient. The clinician may attach sutures or other fasteners at fewer than all of the anchors 960, may attach secure different anchors 960 to different tissues or different regions of tissue, and may connect the anchors 960 to locations at different distances from the pump 912 and cuff 920. For example, while the pump 912 includes eight anchors 960, a clinician may select to secure the pump 912 using only three anchors 960 that are evenly spaced apart around the pump 912, or may select to secure the pump 912 using five of the anchors 960 that are adjacent to each other, or may use another set of the anchors 960.

In some implementations, anchors 960 are disposed at portions of the pump housing 964 other than the outer edge of the motor cap 990. For example, anchors 960 may additionally or alternatively be placed on the peripheral wall 982 or other surfaces of the housing 964.

Figure 38:
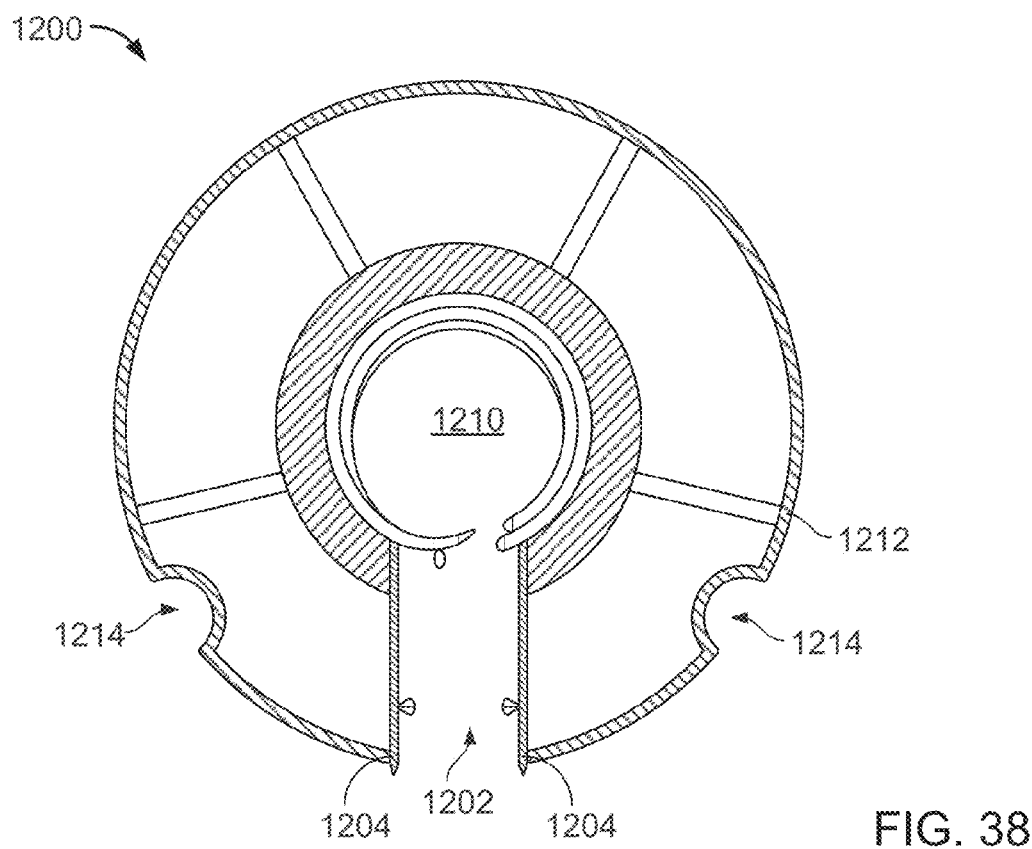
FIG. 38 is a top view of an alternative cuff.

Referring to FIG. 38, an alternative cuff 1200 defines a radial opening 1210. The cuff 1200 includes fasteners 1204 that permit a clinician to close the opening 1202 after the cuff 1200 is placed about the inflow cannula 950 of the pump 912. The fasteners 1204 may be snapped together to capture the inflow cannula 950 in a central opening 1210 defined in the cuff 1200. The cuff 1200 defines, in an outer edge 1212, indentations or recesses 1214 that a tool or clinician's finger may engage to force the fasteners 1204 against each other.

During implantation of the pump 912, a clinician may attach a portion of the cuff 1200 to the heart 914 (e.g., attach the cuff 1200 partially around the circumference of the cuff 1200). The clinician may then mate the pump 912 to the cuff 1200, close the cuff 1200 with the fasteners 1204, and attach the rest of the cuff 1200 to the heart to form a hemostatic seal.

Figure 39:
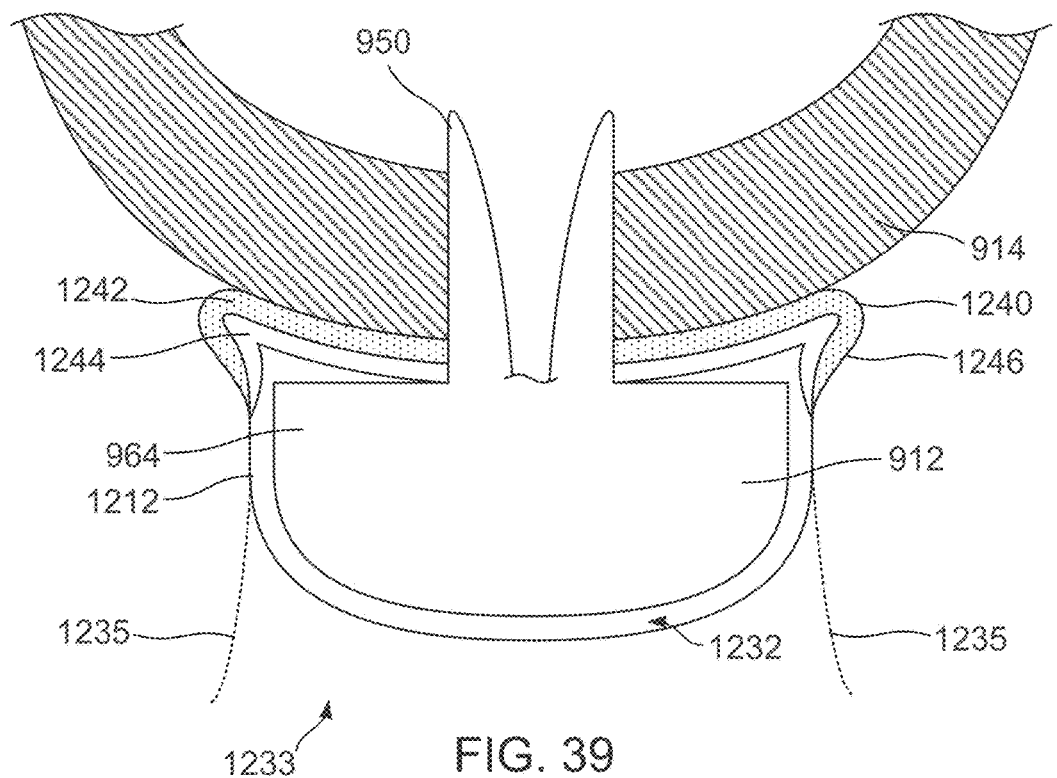
FIG. 39 is a cross-sectional view of the pump of FIG. 32 with a flexible cover.

Referring to FIG. 39, a cover 1230 may be placed around the pump 912 during implantation to facilitate later removal of the pump 912. After the pump 912 is implanted, various tissues may adhere to the pump 912 over time. Adhered tissues may make removal of the pump 912 from the patient's body difficult, since the clinician may need to scrape off or cut off tissues adhered to various surfaces of the pump 912. To limit tissue adhesion and tissue growth on the pump 912, a clinician may surround a portion of or all of the housing 964 of the pump 912 with the cover 1230. As a result, the cover 1230 forms a pouch or pocket around the pump 912 and acts as a barrier to block tissue adhesion to the pump 912. The cover 1230 remains implanted with the pump 912. Tissues may adhere to the exterior of the cover 1230, but do not contact the surface of the pump 912. The cover 1230, unlike the pump 912, may be easily dissected at the time the pump 912 is removed.

If removal of the pump 912 is later desired, the cover 1230 is opened and the pump 912 removed from the patient's body. In some implementations, a clinician cuts apart the cover 1230 to access the pump 912. The surgeon may then remove the pump 912, and may also remove the cover 1230.

The cover 1230 is formed of a flexible material, for example, one or more layers of a fabric. The cover 1230 may be formed of polyester, PET, PTFE, or another biocompatible material. In some implementations, the cover 1230 is part of a cuff 1240 that attaches to the heart 914. The cuff 1240 includes a sewing ring 1241 comprising a fabric layer 1242 formed of, for example, PTFE felt, and a silicone layer 1244. The cover 1230 is attached to the outer edge 1246 of the cuff 1240, for example, along some of or all of the outer circumference of the sewing ring 1241. The cover 1230 may be attached to the sewing ring 1241 with, for example, sutures, staples, adhesives or other means. For example, a portion of the cover 1230 may be disposed between the fabric layer 1242 and the silicone layer 1244, or between other layers of the sewing ring 1241.

In FIG. 39, the cover 1230 is shown closed around the pump 912. Before closing the cover 1230, the cover 1230 has an opening 1233 that admits the pump 912 into an interior space 1232 within the cover 1230 during implantation. Side walls 1235 of the cover 1230, representing the cover 1230 before being closed, are illustrated in dashed lines. The opening 1233 is located between the side walls 1235. After the pump 912 is positioned within the cover 1230 and is attached to the cuff 1240, the clinician closes the opening in the cover 1230 to enclose the pump 912. The cover 1230 may be closed using, for example, sutures, staples, adhesives, or other fasteners. Even when the cover 1230 is closed, the cover 1230 defines an opening to allow an outflow conduit and a driveline cable to exit the cover 1230.

In some implementations, a cover is separate from the cuff 1240. For example, after the pump 912 has been attached at the heart 914, a cover may be placed around the pump 912 and then be sutured to the sewing ring 1241 or otherwise secured around the pump 912.

In some implementations, the sewing ring 1241 extends radially outward from the inflow cannula 950 to or beyond the outer perimeter 961 of the pump 912. That is, the outer diameter of the sewing ring 1241 can be as large as or larger than the outer diameter of the pump 912 at the proximal side 994. As a result, after the pump 912 is seated against the cuff 1240, the outer edge of the sewing ring 1241 remains exposed and accessible to the clinician. The clinician may then place a cover over the pump 912, and may attach the edge of the cover to the fabric at the exposed regions of the sewing ring 1241 with sutures or another fastener.

In some implementations, a portion 1243 of the sewing ring 1241 extends distally, for example, past the proximal side 994 of the pump 912 when the cuff 1240 is seated against the pump 912. In some implementations, the portion 1243 extends around a majority of, or substantially all of, the circumference of the pump 912. The clinician may attach a cover around the pump 1242 by attaching a fabric or other material to the portion 1243.

Figure 40:
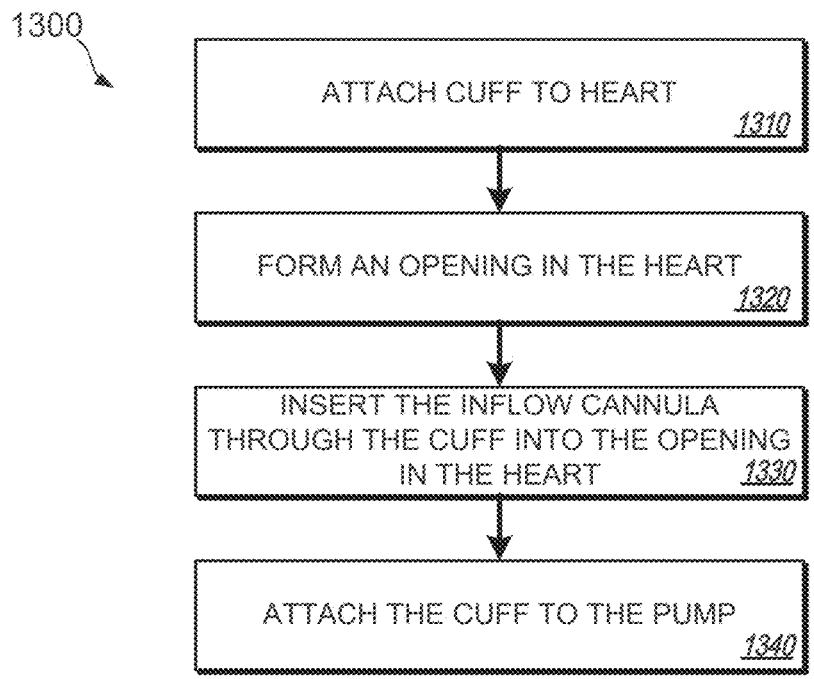
FIG. 40 is a flow chart illustrating a process for implanting a pump.

Referring to FIG. 40, an example of a process 1300 for implanting the pump 912 is illustrated. The process 1300 describes implantation with an apical approach, but other implantation locations and techniques may be used.

A clinician attaches the cuff 920 to a heart (1310). For example, for implantation in an LVAD configuration, the clinician locates the apex of the left ventricle, and sutures the sewing ring 1025 of the cuff 920 to the myocardium. As discussed above, the cuff 920 can be sufficiently rigid to flatten at least a portion of a myocardium of the heart (e.g., a portion adjacent the cuff) when the cuff 920 is attached to the heart 914. For example, the cuff 920 may include two or more layers of fabric, and may include a generally planar insert 1030 that is more rigid than the layers of fabric.

The clinician forms an opening in the myocardium (1320). For example, the clinician may use a coring tool to excise a cylindrical segment of the myocardium. In some implementations, when the cuff 920 is attached to the heart before cutting the opening in the myocardium, the clinician cuts the opening through a central opening in the cuff 920. In other implementations, the clinician cuts the opening in the myocardium and afterward attaches the cuff 920 to the heart 914, with the central opening of the cuff 920 located over the opening of the myocardium.

The clinician inserts the inflow cannula 950 of the pump 912 through the central opening in the cuff 920 and into the opening in the myocardium (1330).

The clinician then attaches the pump 912 to the cuff 920 (1340). For example, the clinician may engage a coupling mechanism that is configured to limit translation of the inflow cannula through the central opening of the cuff 920. To engage the coupling mechanism, the clinician holds the cuff 920 by pressing inward on the outer edge of the cuff 920. The clinician applies a counterforce against the inflow cannula 950 or the pump 912, in a direction along the central axis of the inflow cannula 950, to seat the cuff 920 on the inflow cannula 950 or another portion of the pump 912. In some implementations, the clinician engages a locking mechanism after engaging the coupling mechanism. For example, the clinician may slide a clip into position, by moving the clip in a plane generally perpendicular to the inflow cannula 950.

To attach the pump 912 to the cuff 920, the clinician optionally attaches one or more sutures to one or more suture anchors disposed on an exterior of the pump 912. For example, the clinician passes sutures through eyelets disposed along an outer perimeter of the pump 912 and through the sewing ring 1025 of the cuff 920. The clinician additionally or alternatively may pass the sutures through a portion of the myocardium. Sutures attached at various suture anchors around the pump maintain the position of the sewing ring 1025 extending generally along a plane perpendicular to the inflow cannula 950.

In some implementations, the process 1300 includes covering the pump 912 with the cover 1230. For example, the clinician wraps a fabric around the housing 964 of the pump 912, and closes the fabric to encase the pump 912, shielding the exterior of the pump 912 from tissue adhesion.

Referring to FIG. 41, an assembly 1400 includes a cuff 1410 and an inflow cannula 1430 that are connected together prior to implantation, and then implanted as a single unit. Pre-attaching the cuff 1410 and inflow cannula 1430 may reduce the number of components the clinician must install during implantation. In addition, using the assembly 1400 may reduce the complexity of the implantation procedure and may reduce the risk of bleeding after implantation.

The cuff 1410 includes a fabric ring 1412, for example, a ring of polyester velour or PTFE felt, that a clinician may suture to the heart 914. The fabric ring 1412 is attached to a body 1414 that extends around the inflow cannula 1430. A clamp or clip 1416 extends around the body 1414 and the inflow cannula 1430 to secure the cuff 1410 to the inflow cannula 1430. In some implementations, an adhesive or other fastener secures the cuff 1410 and inflow cannula 1430.

The inflow cannula 1430 has a distal end 1438 that includes one or more attachment features, such as screw threads or clips, to attach to the pump 912. The inflow cannula 1430 defines a central axis 1432 and defines an inlet 1434 at a proximal end 1436. The inflow cannula 1430 flares outward from the central axis 1432 at the proximal end 1436. When implanted, the flared proximal end 1436 contacts the endocardium, e.g., the inner surface of the heart 914. The flared proximal end 1436 separates the endocardium 915 from the inlet 1434, limiting the potential for occlusion of the inlet 1434 by the endocardium 915. As a result, the region of the heart 914 adjacent the inflow cannula 1430 is secured between the fabric ring 1412 on the exterior of the heart 914 and the flared proximal end 1436 on the interior of the heart 914.

To implant the assembly 1400, the clinician first cuts an opening in the myocardium. The clinician then inserts the proximal end 1436 into the opening, and sutures the fabric ring 1412 to the myocardium. With the assembly 1400 attached to the heart, the clinician attaches the distal end 1438 of the inflow cannula 1430 to the pump. For example, the distal end 1438 may be received into the housing of the pump, and may be secured by threads, a clip, or another fastening mechanism.

Referring to FIGS. 42A and 42B, a cuff and cannula assembly 1450 includes an inflow cannula 1460 having a fabric 1470 attached directly to the exterior of the inflow cannula 1460. The inflow cannula 1460 has a circumferential ridge 1462 that extends around the exterior of the inflow cannula 1460. The fabric 1470, for example, a ring of a polyester velour or PTFE felt, is positioned on the ridge 1462 and extends around the inflow cannula 1460.

As shown in FIG. 42B, holes 1464 are defined through the ridge 1462. Sutures 1472 extend through the holes 1464 and the fabric 1470 to secure the fabric 1470 to the inflow cannula 1460. The assembly 1450 may be provided to a clinician with the fabric 1470 already secured to the inflow cannula 1460. During implantation, after the clinician positions the assembly 1450 relative to the heart 914, for example, with the inflow conduit 1460 extending into the left ventricle, a clinician places sutures 1480 to secure the fabric 1470 to the myocardium.

Figure 43:
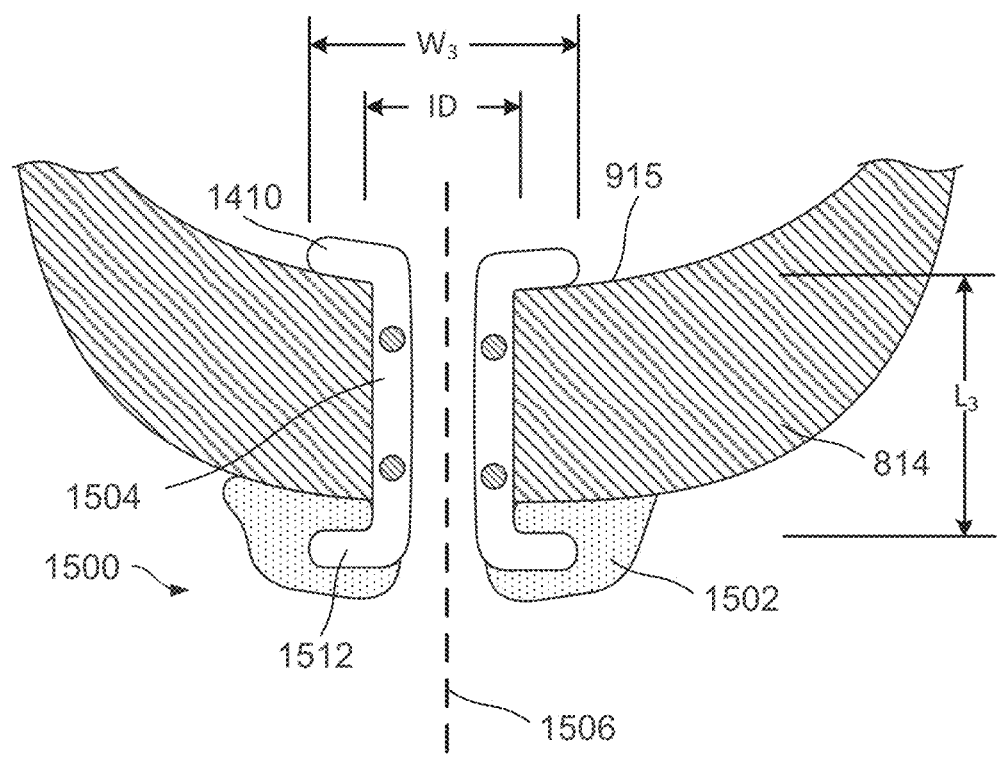
FIGS. 43 and 44 are cross-sectional views of alternative cuffs.

Referring to FIG. 43, a cuff 1500 includes a proximal portion 1510 that extends into the heart 914 and contacts the endocardium 915. In general, positioning a portion of an inflow cannula, cuff, or other component against the endocardium 915 can separate the endocardium 915 from the inlet of an inflow cannula, reducing the risk of occlusion of the inflow cannula.

As shown in FIG. 43, the cuff 1500, which is separate from the inflow cannula 950 of the pump 912, engages the interior of the heart 914 and the exterior of the heart 914. After a hole is cored in the heart 914, the cuff 1500 is deployed to capture a portion of the myocardium between the proximal portion 1510 and a distal portion 1512, which results in flattening of the myocardium. After the cuff 1500 is placed on the heart 914, the clinician may insert the inflow cannula 950 of the pump 912 through the center of the cuff 1500 and attach the cuff 1500 to the pump 912. The cuff 1500 remains in place on the heart 915, with the inflow cannula 950 extending through the cuff 1500, to limit the risk of pump malposition and occlusion of the inflow cannula 950.

To promote flattening of the myocardium, the proximal portion 1510 and/or the distal portion 1512 can have a flexural modulus of greater than 50 psi, for example, a flexural modulus at least 60 psi, at least 75 psi, at least 90 psi, at least 100 psi, at least 125 psi, or at least 150 psi.

In the example of FIG. 43, the cuff 1500 includes a fabric 1502, such as a ring of a polyester velour or PTFE felt, and a member 1504 formed of, for example, a flexible material such as silicone. The fabric 1502 may be attached to the distal portion 1512 of the member 1504. For example, the fabric 1502 may be captured in silicone of the member 1504. The clinician may attach the fabric 1502 to the heart 914, for example, with sutures. As discussed further below, some implementations of the cuff 1500 may be attached to the heart 915 without the fabric 1502 and without sutures or other fasteners.

The member 1504 defines a central axis 1506. The member 1504 includes the proximal portion 1510, which is formed as one or more extensions or tabs that extend outward from the central axis 1506. In some implementations, the proximal portion 1510 is a circumferential ring that extends radially outward from the central axis 1506 in a plane generally perpendicular to the central axis 1506. The proximal portion 1510 has a width, $W_3$, larger than the inner diameter, ID, of the opening in the heart 914. As a result, to pass through the opening, the proximal portion 1510 deflects inward toward the central axis 1506. Once the proximal portion 1510 has passed through the myocardium into, for example, a ventricle of the heart 914, the proximal portion 1510 expands outward, limiting the cuff 1500 from separating from the heart 914. The proximal portion 1510 rests on the endocardium 915, along the inner surface of the heart 914.

After the cuff 1500 is coupled to the heart 914, an inflow cannula may be placed through the member 1504 and secured within the member 1504. The presence of the proximal portion 1510 against the endocardium 915 can reduce the risk that heart tissue encroaches on the internal lumen of the inflow cannula. In the implanted configuration, the cuff 1500 remains around the inflow cannula 950 of the pump 912, securing the pump 912 to the heart 914.

In some implementations, the distal portion 1512 of the member 1504 extends generally radially outward from the central axis 1506, for example, as a circumferential flange. The proximal portion 1510 also extends generally radially outward from the central axis 1506, for example, as a circumferential flange. The length, $L_3$, of the member 1504 between the proximal portion 1510 and the distal portion 1512 can be configured to exert pressure on the portions of the myocardium captured between the proximal portion 1510 and the distal portion 1512.

In some implementations, the member 1504 is elastic, expandable, or otherwise adjustable to change the length, $L_3$. The length, $L_3$, may be adjusted to exert a desired amount of force on the myocardium to flatten the myocardium and secure the position of the cuff 1500 relative to the heart 914. The length, L, may also be adjusted to accommodate varying thicknesses of heart walls. For example, the member 1504 may have corrugated walls that may expand or compress to adjust the length, $L_3$. As another example, the member 1504 may include a resilient member, such as a spring, located between the proximal portion 1510 and the distal portion 1512 to exert a compressive force against tissue located between the proximal portion 1510 and the distal portion 1512. As another example, the member 1504 may include a frame 1540 (shown in dashed lines) or other component with a shape memory, for example, an internal frame formed of nickel-titanium alloy, a polymer, or other material. After placement of the cuff 1500 into the opening in the heart 914, the frame 1540 may contract to decrease the length, $L_3$, and compress the myocardium between the proximal portion 1510 and the distal portion 1512. For example, heat may activate the shape memory of the frame 1540 and cause the cuff member 1504 to contract.

In some implementations, the cuff 1500 is configured to maintain its position on the heart 914 without being sutured to the heart. The cuff 1500 may be secured to the heart 914 by the capture of the myocardium between the proximal portion 1510 and the distal portion 1512. Accordingly, the fabric 1502 or other material may be omitted. Engagement with the heart 915 can also flatten the myocardium as discussed above.

A cuff 1500 that can be secured to the heart without sutures includes the frame 1540, which may be formed of, for example, a super-elastic or shape memory material, such as nickel-titanium alloy or a polymer. The frame 1540 may be covered in, for example, fabric, PTFE felt, polyester, silicone, or another biocompatible material. In some implementations of the cuff 1500, the frame 1540 is exposed and does not have a covering. In preparation for placement on the heart 915, the proximal portion 1510 is deflected inward toward the axis 1506, which permits the proximal portion 1510 to enter a hole in the heart 915 having an inner diameter, ID, less than the width, $W_3$, or outer diameter of the proximal portion 1510. The clinician may use a tool to hold the proximal portion 1510 in the deflected position while inserting the proximal portion 1510 through the hole in the heart 915.

Once within the heart 915, the proximal portion 1510 expands outward, for example, due to the resiliency or shape memory of the frame 1540. For example, the frame 1540 may be configured to respond to body heat or other conditions to regain its natural form, in which the proximal portion 1510 extends radially outward. The shape memory or resiliency of the frame 1540 also causes the cuff 1500 to contract, exerting a force on the myocardium between the proximal portion 1510 and the distal portion 1512. In some implementations, a tool may be used to expand the proximal portion 1510 within the heart 914 and/or to adjust the length, $L_3$, in addition to or instead of the resiliency or shape memory of the frame 1540. With the cuff 1500 deployed in this manner, pressure on the region of the myocardium surrounding the hole in the heart 914 secures the cuff 1500 in position with respect to the heart 914, without the need for sutures or other fasteners. The pressure exerted by the cuff 1500 on the heart 914 maintains the position of the pump 914 and its inflow cannula 950 relative to the heart 914 after the pump 914 is secured to the cuff 1500.

Other techniques may also be used to capture portions of the myocardium. For example, the member 1504 may be divided into a proximal component that includes the proximal portion 1510 and a distal component that includes the distal portion 1512. In addition, the proximal and distal components may be rigid or have rigid inner frames, formed, for example, of metal or PEEK, rather than a flexible material. The proximal component and distal component may threadedly connect to each other. Rotation of the proximal and distal components relative to each other may adjust the length, $L_3$, between the proximal portion 1510 and distal portion 1512 to capture tissue disposed between. A clinician may use a clip or other tool to hold the proximal component while rotating the distal component to adjust the length, $L_3$.

Figure 44:
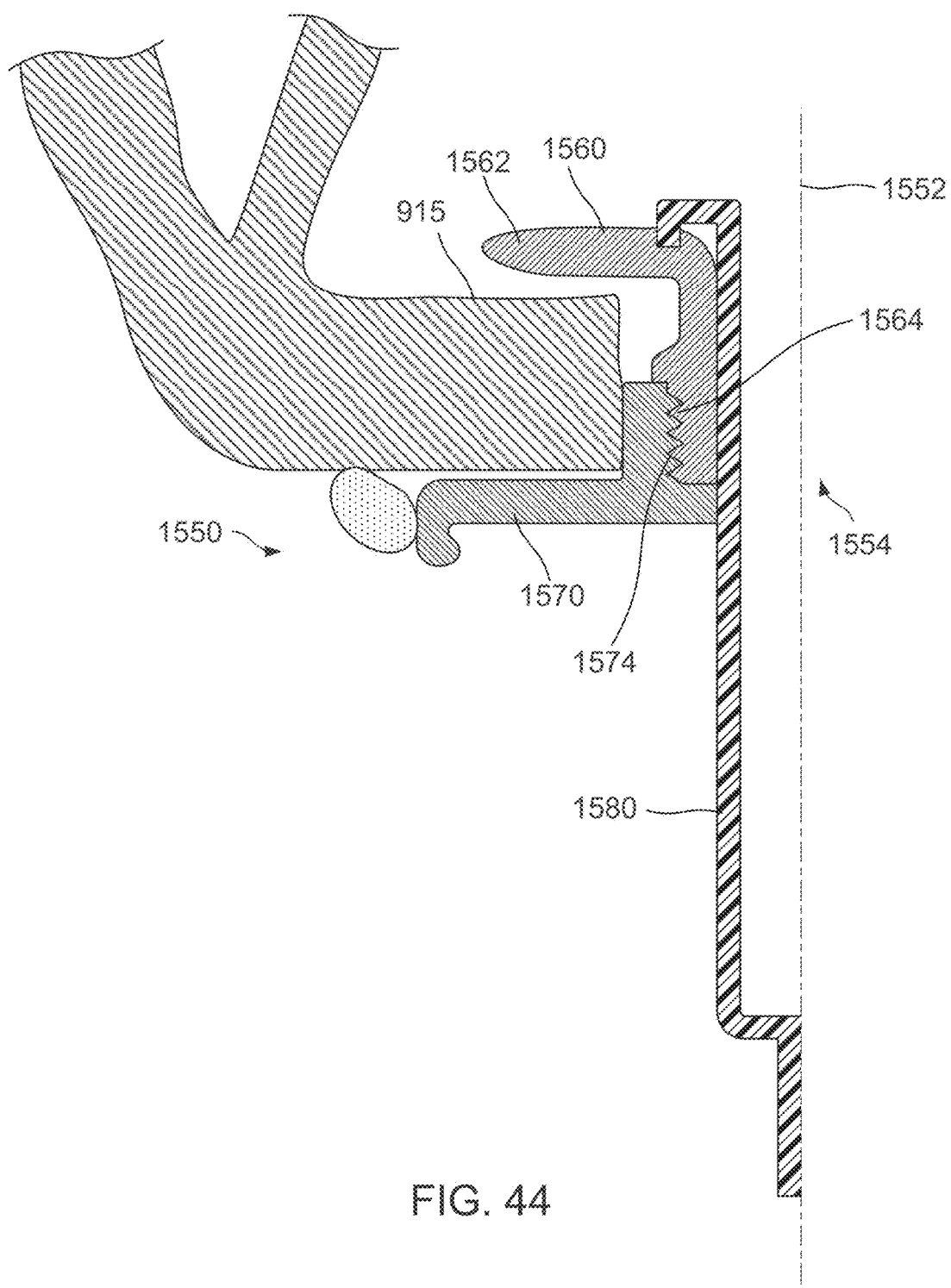

FIG. 44 shows an example of cuff 1550 that has a proximal component 1560 that can be adjusted relative to a distal component 1570. The proximal component 1560 has a portion 1562 that extends radially outward from an axis 1552 through a central opening 1554 in the cuff 1550. The proximal component 1560 also includes screw threads 1564 that mesh with screw threads 1574 of the distal component 1570. A clinician may use a tool 1580 to hold the proximal component 1560, while the proximal component 1560 and the distal component 1570 are rotated relative to each other to tighten the portion 1562 against the endocardium 915. This force may capture the myocardium between the proximal component 1560 and the distal component 1570. In some implementations, capture of the myocardium in this manner may be used to couple the cuff 1550 to the heart 914 without sutures or other fasteners.

Figure 45:
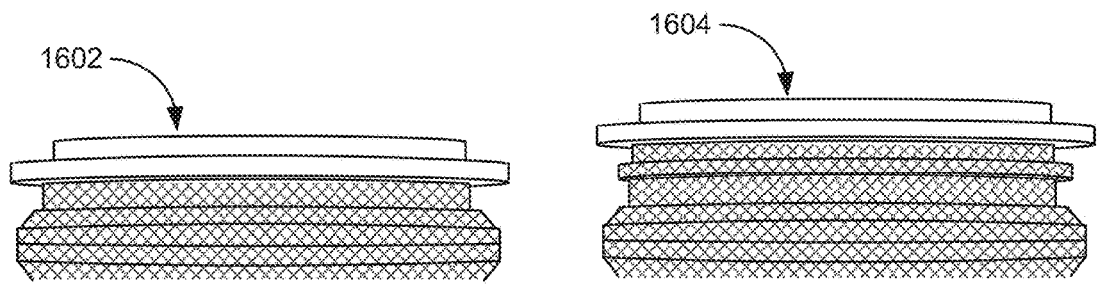
FIG. 45 shows a comparison between a 5.5 mm high apical cuff and a taller 8 mm high apical cuff according to embodiments of the present invention.
Figure 46:
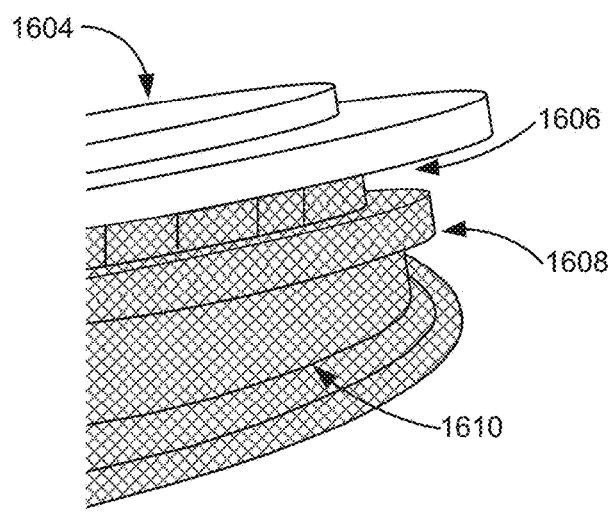
FIG. 46 shows an optional tool engagement feature for use with apical cuffs according to embodiments of the present invention.

FIG. 45 shows a comparison between a 5.5 mm high ring 1602 for a low profile apical cuff and a taller 8 mm high ring 1604 for a high profile apical cuff according to embodiments of the invention. While a lower profile apical cuff with ring 1602 (e.g., less than 6.5 mm or 5.5 mm high) may be desired in many situations, taller cuffs with a high ring 1604 (e.g., greater than 6.5 mm or 8.5 mm high) may be desirable in certain situations. The rings 1602, 1604 may include, for example, an attachment member (having one or more features of any of the attachment members 26, 126, 326, 626), and a linking member (having one or more features of any of the linking members 24, 124, 324, 624). In some situations, the added height from ring 1604 may facilitate the use of a tool to hold a cuff in place while inserting the inflow cannula through the cuff and cored hole in the heart. For example, as shown in FIG. 46, a tool engagement feature 1606 may be provided in ring 1604. The engagement feature 1606 may comprise a circumferential slot for receiving a clamp mechanism of a corresponding tool. The engagement feature 1606 may be separated from the cuff lock by a tab 1608. Tab 1608 may keep a clamp tool from contacting the cuff lock 1610 during actuation of the lock. While illustrated as a groove/slot, it should be understood that engagement feature 1606 may take other forms as described throughout the application and/or as is apparent to one of skill in the art. For example, in some embodiments, engagement features 1606 may comprise a lip for cooperation with a grooved surface of a corresponding tool.

Figure 47:
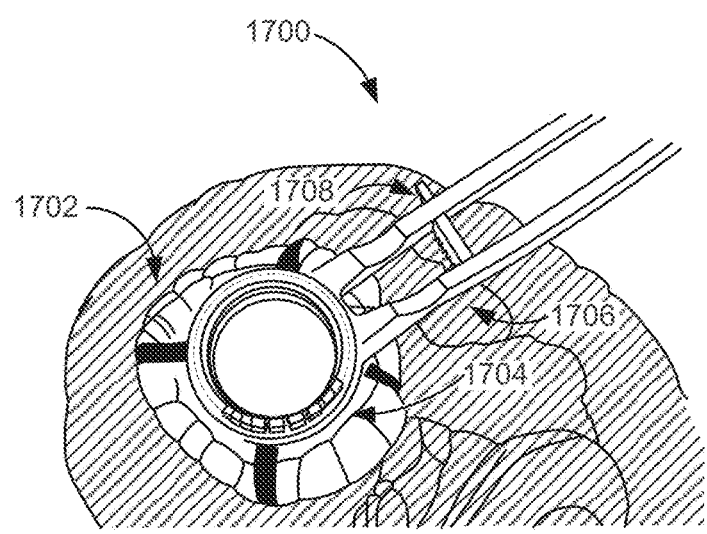
FIG. 47 shows an exemplary tool for coupling with an apical cuff according to embodiments of the present invention.

FIG. 47 shows an exemplary tool 1700 for coupling with an apical cuff 1702 according to some embodiments. Tool 1700 may be used by an operator to hold the cuff 1702 at a distance so as keep the operator's hands out of the way and to allow the operator to maintain visibility of the operating field while suturing the cuff 1702 onto the heart. Additionally, tool 1700 may allow the operator to clamp and manipulate the cuff 1702 during alignment and coupling with a corresponding pump. Tool 1700 includes a clamp 1704 for coupling with and holding an apical cuff 1702. Clamp 1704 may be closed to a clamped configuration by manipulation of handle 1706. Handles 1706 may include a locking feature 1708 for locking tool 1700 in the clamped position.

Apical cuff 1702 may be any one of the apical cuffs described in this application or variations thereof. While clamp 1704 is illustrated as a ring clamp, it should be understood that other clamp configurations are possible, such as opposing clamp jaws. Handles 1706 may have a length in a range of about 3 cm to about 10 cm for example. Locking feature 1708 may comprise one or more engagement features extending between handles 1706. In the illustrated embodiment, engagement feature 1708 comprises an protrusion extending laterally from handle 1706. The protrusion includes a number of teeth configured to cooperate with engagement features in the opposing handle 1706. As the handles 1706 are moved into a clamped configuration, locking feature 1708 engages and maintains the handles 1706 in the clamped position until user actuation of the locking feature 1708 (e.g., disengagement of the teeth with the corresponding engagement feature) release handles 1706 from the clamped position. In some embodiments, it may be advantageous to use tool 1700 with an apical cuff that includes the taller ring 1604 with a tool engagement feature 1606, as described above. This may allow a clinician to clamp apical cuff 1702 without interfering with a cuff lock during coupling with a pump.

Figure 48A:
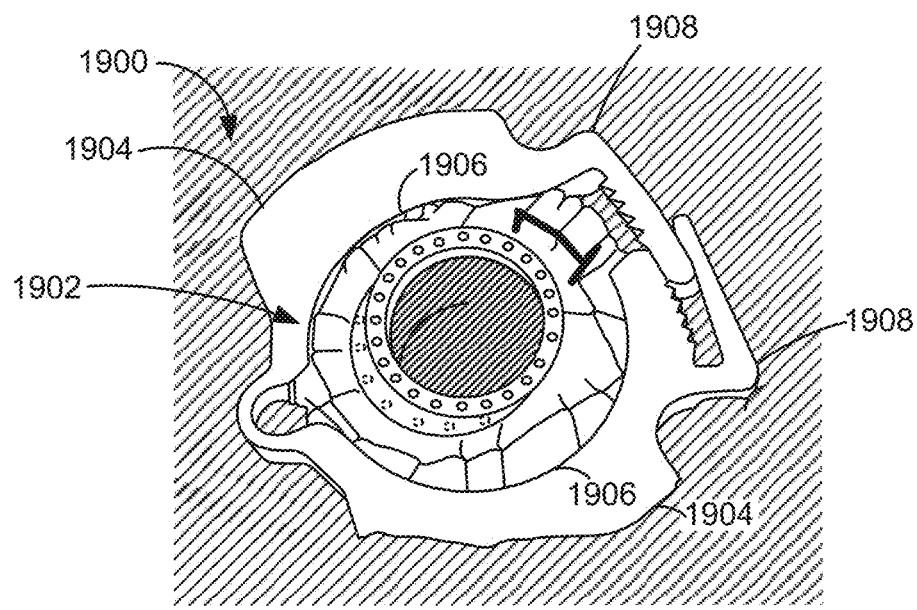
FIGS. 48A and 48B show another exemplary tool for coupling with an apical cuff according to embodiments of the present invention.
Figure 48B:
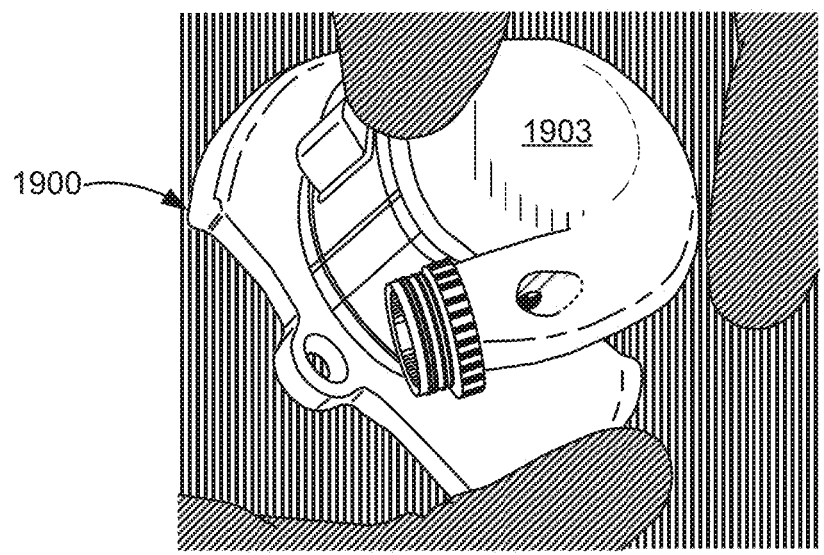

FIGS. 48A-48B show another exemplary tool 1800 for coupling with an apical cuff 1802 according to some embodiments. Tool 1800 may be similarly used by an operator to hold a cuff 1802 from a distance so as keep the operator's hands out of the way and to allow the operator to maintain visibility of the operating field while suturing the cuff 1802 onto the heart. Additionally, tool 1800 may allow the operator to clamp and manipulate the cuff 1802 during alignment and coupling with a corresponding pump 1803, as shown in FIG. 48B. Tool 1800 may rest on a clinician's hand with a plurality of contact points 1804. A clamp 1806 may extend from the one or more contact points 1804 and may be configured to engage the apical cuff 1802. In the illustrated embodiment, tool 1800 includes three contact points 1804. The contact points 1804 have a concave engagement surface for cooperating with the clinician's fingers and hand and allow the clinician to apply a clamping force with the clamps 1806 using the clinicians forefinger and thumb. In some embodiments, tool 1800 may be used with a cuff including a ring 1604 with a corresponding engagement feature 1606. The taller cuff may be advantageous for engagement of a tool 1800 without contacting a cuff lock. Further, while illustrated as including three contact points 1804, some embodiments may comprise one, two, four, or more contact points, etc.

Figure 49A:
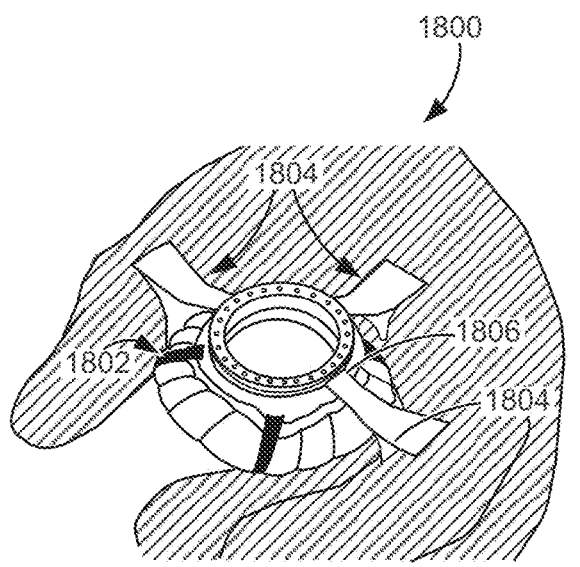
FIGS. 49A and 49B show yet another exemplary tool for coupling with an apical cuff according to embodiments of the present invention.
Figure 49B:
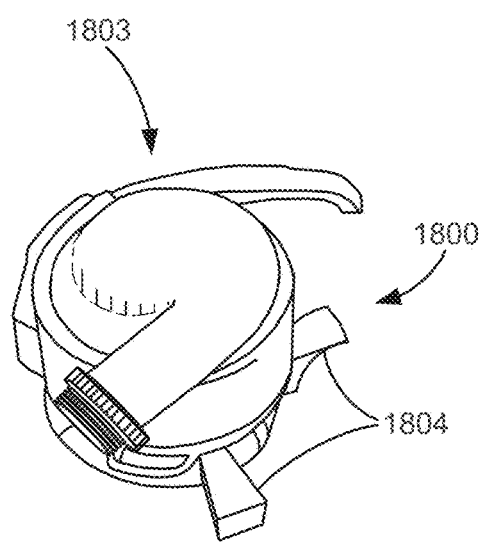

FIGS. 49A-49B show yet another exemplary tool 1900 for coupling with an apical cuff 1902 according to some embodiments. Tool 1900 may be similarly used by an operator to hold a cuff 1902 from a distance so as keep the operator's hands out of the way and to allow the operator to maintain visibility of the operating field while suturing the cuff 1902 onto the heart. Additionally, tool 1900 may allow the operator to clamp and manipulate the cuff 1902 during alignment and coupling with a corresponding pump 1903, as shown in FIG. 49B. Tool 1900 may seat and/or clamp the outer diameter of cuff 1902. In some embodiments, the tool 1900 may seat and/or clamp an outer perimeter of a metal ring of a cuff 1902. In some embodiments, tool 1900 may seat and/or clamp an outer perimeter of a felt sewing ring of a cuff 1902. This clamp 1900 may be used with both low profile apical cuffs with ring 1602 or taller cuffs with ring 1604, described above. Tool 1900 includes opposing jaws 1904. Jaws 1904 may include a groove 1906 for seating portions of the felt of a cuff 1902, for example. Jaws 1904 may further include engagement features 1908 at an end of each jaw 1904 for locking the jaws 1904 into a clamped position. In the illustrated embodiment, engagement features 1908 comprise locking teeth. While illustrated as locking teeth, other engagement features may be used such as snap-fit engagement features or the like.

Figure 50A:
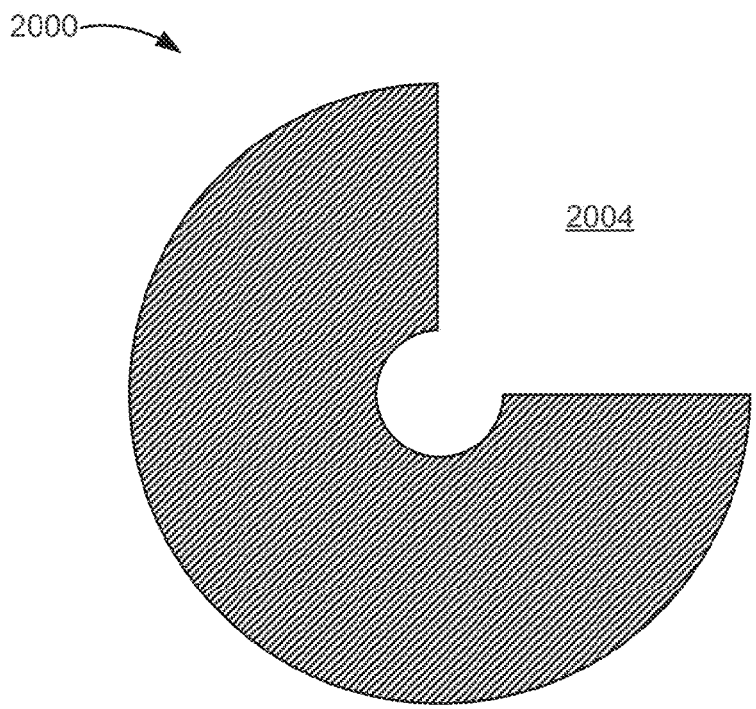
FIGS. 50A and 50B show exemplary sewing rings which may be configured to avoid abutment or overlap of the right ventricle of the heart according to embodiments of the present invention.
Figure 50B:
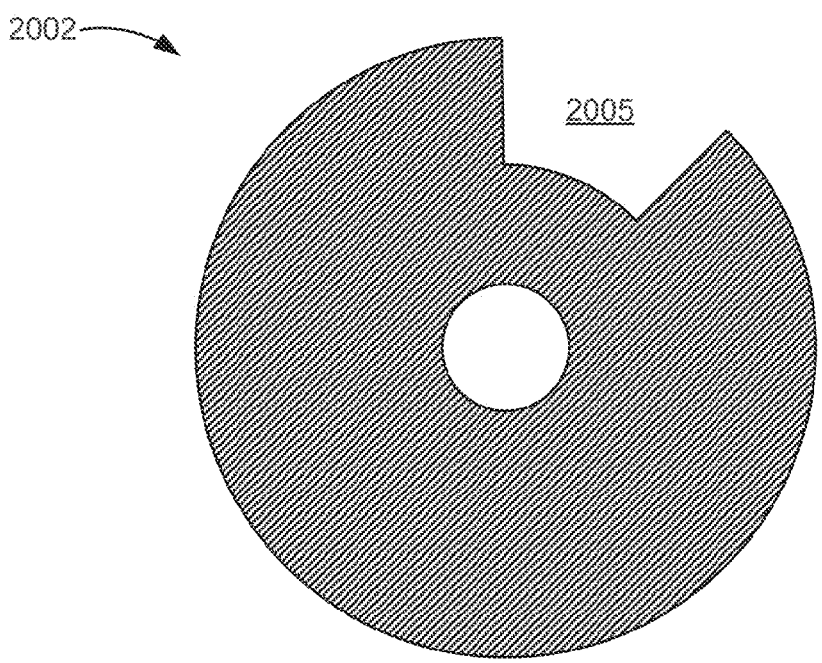

Additionally, while sewing rings/cuffs in some of the figures are illustrated as having a diameter that corresponds to a diameter of an attached pump, it should be understood that sewing ring/cuff diameters may be larger than a diameter of the attached pump. In some embodiments, a larger diameter, perimeter, size, and/or shape sewing ring/cuff may beneficially provide additional flattening of the apex of the heart and improve the positioning of the inflow cannula of an attached pump. Accordingly, in some embodiments, a sewing ring/cuff may have a diameter of 3 cm or more, such as 4 cm, 5 cm, 6 cm, or larger. Further, while sewing rings/cuffs are generally shown as having an annular, circular, or round configuration, some sewing rings/cuffs may be partial annular configuration or annular configurations with various sized openings to allow for differently sized inflow cannulas. For example, some sewing rings/cuffs may have an annular segment configuration or the like. In some situations, a sewing ring/cuff with a large diameter/perimeter may abut or overlap with the right ventricle (RV) of the heart. It may be preferable in most cases to avoid suturing the RV of the heart and/or flattening the RV of the heart. Accordingly, a sewing ring/cuff may be configured with openings for accommodating the RV of the heart and to avoid suturing and/or flattening the RV of the heart. FIGS. 50A-50B show exemplary sewing rings 2000, 2002 with such openings for accommodating the RV of a heart. Sewing ring 2000, 2002 may include a wedge shaped opening 2004, 2005. The wedge shaped opening 2004, 2005 may be beneficial when sewing ring 2000, 2002 has a larger diameter and may overlap or abut the right ventricle (RV) of the heart. A wedge shaped opening 2004, 2005 of a sewing ring 2000 may be oriented to avoid contact/overlap with the RV and may thereby avoid inadvertent flattening and suturing of the RV when suturing a cuff to the apex of the heart. Some embodiments of cuffs may have similar configurations.

Figure 51:
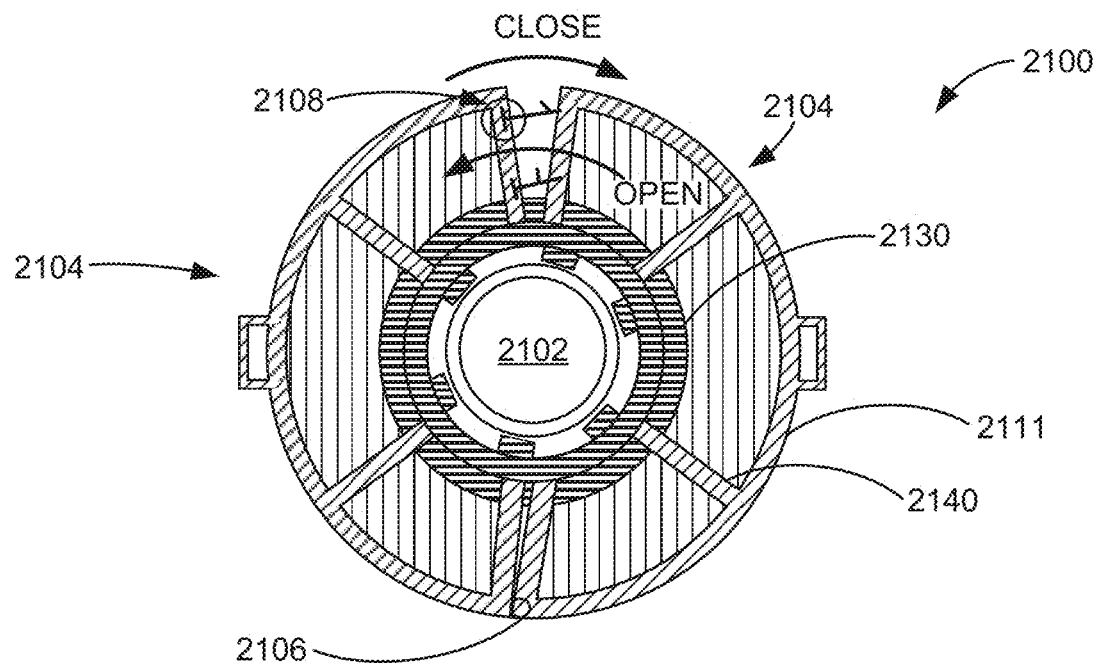
FIGS. 51 to 53 show various exemplary embodiments of a cuff according to embodiments of the present invention.

FIG. 51 shows another exemplary embodiment 2100 of a cuff similar to the cuff illustrated in FIG. 38. Cuff 2100 may have an open configuration for receiving an inflow cannula of a pump and a closed configuration for securing the cuff 2100 to the pump. The cuff 2100 may define an opening 2102 for receiving an inflow cannula of a pump. Cuff 2100 further includes a sewing ring 2130. While the sewing ring is illustrated as not extending to the outer perimeter 2111 of the cuff 2100, other embodiments may include larger diameter sewing rings 2130 that extend to the outer perimeter 2111 of cuff 2100 or beyond the cuff 2100. For example, similar to the embodiment illustrated in FIG. 34D, the web 2140 may be disposed or sandwiched between two felt layers 1010, 1020. The cuff 2100 comprises two half circle segments 2104 with a first end and a second end. The segments 2104 may be coupled at a pivot or hinge joint 2106 at one end and may include engagement features 2108 coupled to one another at the second end of each segment 2104. The cuff 2100 permits a clinician to close opening 2102 by moving the engagement features toward one another after the cuff 2100 is placed about the inflow cannula of a pump. The engagement features 2108 may lock with one another to capture the inflow cannula in the opening 2102. In the illustrated embodiments, even when cuff 2100 is in an open configuration, the engagement features 2108 may still couple the segments 2104 to one another. Accordingly, segments 2104 may still move relative to one another but the engagement features 2108 may prevent the cuff 2100 from fully opening. When in the closed position, engagement features 2108 engage with one another to lock segments 2104 together and to close opening 2102.

Figure 52:
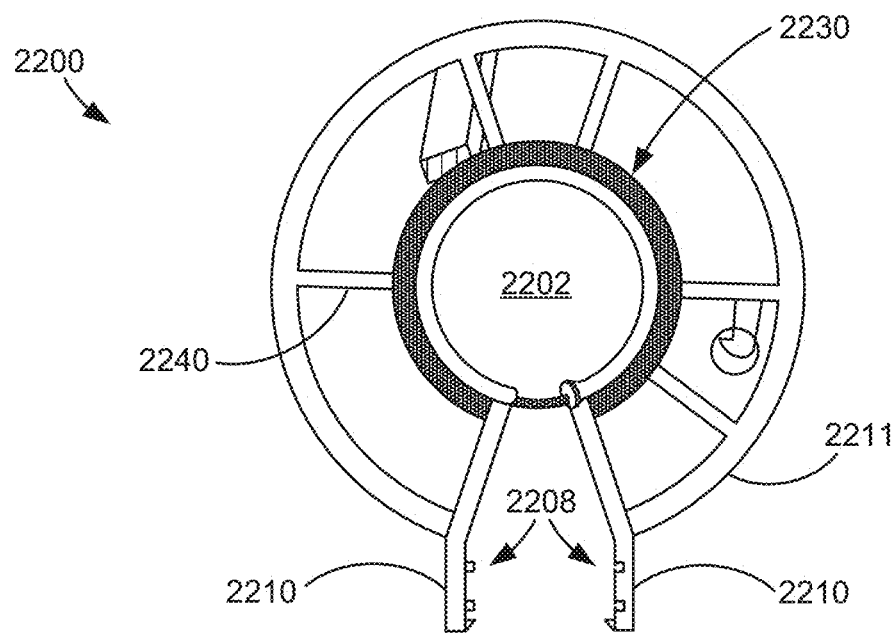

FIG. 52 shows another exemplary embodiment 2200 of a cuff similar to the cuff illustrated in FIG. 38. Cuff 2200 may have an open configuration for receiving an inflow cannula of a pump and a closed configuration for securing the cuff 2200 to the pump. Cuff 2200 may define an opening 2202 for receiving an inflow cannula of a pump. Cuff 2200 further includes a sewing ring 2230. While the sewing ring is illustrated as not extending to the outer perimeter 2211 of the cuff 2200, other embodiments may include larger diameter sewing rings 2230 that extend to the outer perimeter 2211 of cuff 2200. For example, similar to the embodiment illustrated in FIG. 34D, the web 2240 may be disposed or sandwiched between two felt layers 1010, 1020. The cuff 2200 permits a clinician to close opening 2202 after the cuff 2200 is placed about the inflow cannula of a pump. The engagement features 2208 may lock with one another to capture the inflow cannula in the opening 2202. Cuff 2200 further includes arms 2210 which extend from the outer perimeter 2211 of cuff 2200. Arms 2210 may provide a clinician an easily accessible feature that may be manually pressed together in order to couple engagement features 2208 together and to close opening 2202 around an inflow cannula. Engagement features 2208 may be snap-fit engagement features or the like.

Figure 53:
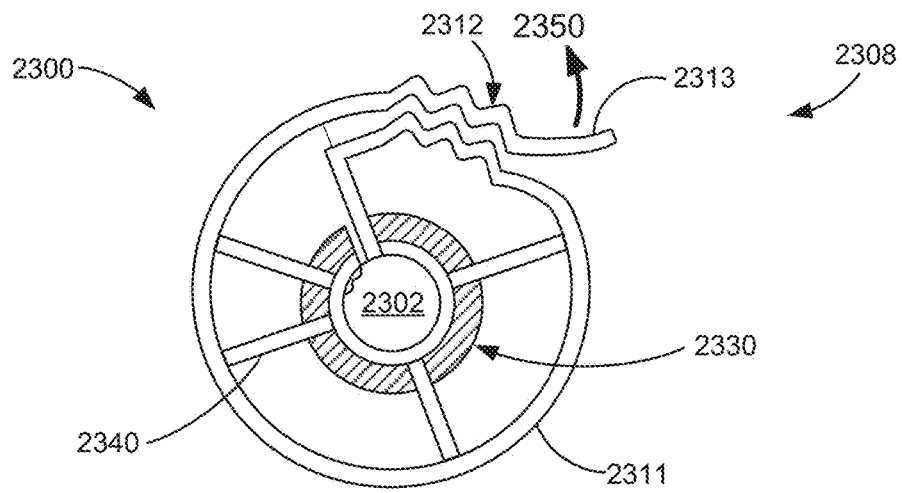

FIG. 53 shows another exemplary embodiment 2300 of a cuff. Cuff 2300 may define an opening 2302 for receiving an inflow cannula of a pump. Cuff 2300 may have an open configuration for receiving an inflow cannula of a pump and a closed configuration for securing the cuff 2300 to the pump. Cuff 2300 further includes a sewing ring 2330. While the sewing ring 2330 is illustrated as not extending to the outer perimeter 2311 of the cuff 2300, other embodiments may include larger diameter sewing rings 2330 that extend to the outer perimeter 2311 of cuff 2300. For example, similar to the embodiment illustrated in FIG. 34D, the web 2340 may be disposed or sandwiched between two felt layers 1010, 1020. The cuff 2300 permits a clinician to close opening 2302 after the cuff 2300 is placed about the inflow cannula of a pump. The free ends of outer perimeter 2311 of cuff 2300 may include engagement features 2308. The engagement features 2308 may comprise an ear clamp with overlapping ends and corresponding teeth. As the ends of outer perimeter 2311 are pushed together, the teeth of the engagement features 2308 may cooperate and lock with one another to capture the inflow cannula in the opening 2302. The outer end 2312 may include a pull tab 2313 which may be pulled away in the direction of arrow 2350 to release the clamp 2308.

Figure 54:
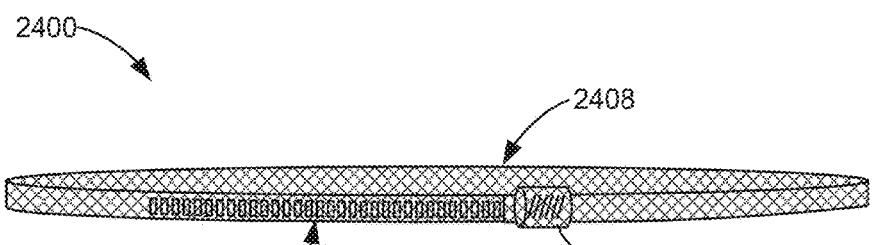
FIG. 54 illustrates another exemplary embodiment of a cuff that may be secured to a pump using a screw/band ("worm gear") clamp according to embodiments of the present invention.
Figure 55A:
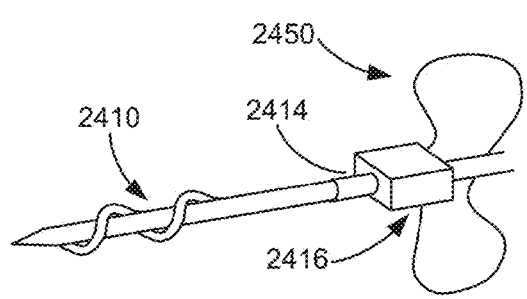
FIGS. 55A and 55B illustrate an exemplary key for use with the exemplary cuff shown in FIG. 54 according to embodiments of the present invention.
Figure 55B:
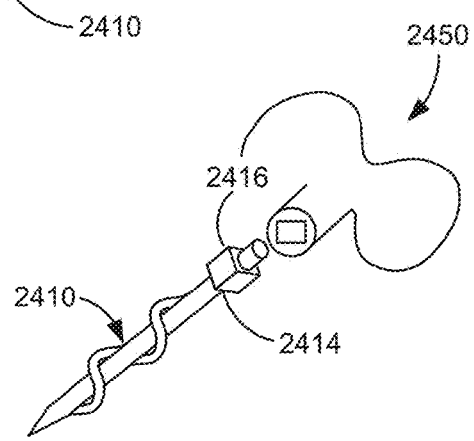

FIG. 54 illustrates a cuff 2400 that may include a screw/band ("worm gear") clamp 2408 for securing cuff 2400 to a pump. Cuff 2400 may have an open configuration for receiving an inflow cannula of a pump and a closed configuration for securing the cuff 2400 to the pump. Clamp 2408 includes a screw or worm gear 2410 that cooperates with grooves 2412 to tighten and loosen clamp 2408. In some embodiments, it may be preferable to require a special key for turning screw 2410 to prevent inadvertent turning of the screw 2410. FIG. 55A-55B illustrate an exemplary key 2450. Screw 2410 may have an actuation end 2414 that couples with a lockout feature 2416. When key 2450 couples with lockout feature 2416, as shown in FIG. 55A, the key 2450 may be used turn screw 2410 to tighten or loosen clamp 2408. When key 2450 is removed from the lockout feature 2416, as shown in FIG. 55B, lockout feature 2416 may prevent inadvertent turning of screw 2410 without the key 2450. Cuffs 2100, 2200, 2300, 2400, have an open configuration for receiving an inflow cannula of a pump and a closed configuration for securing the cuff around the inflow cannula to thereby attach the pump to the cuff. A cuff with the open configuration and closed configuration may be advantageous as a separate locking clip or like component is not required.

Figures 56, 57, 58:
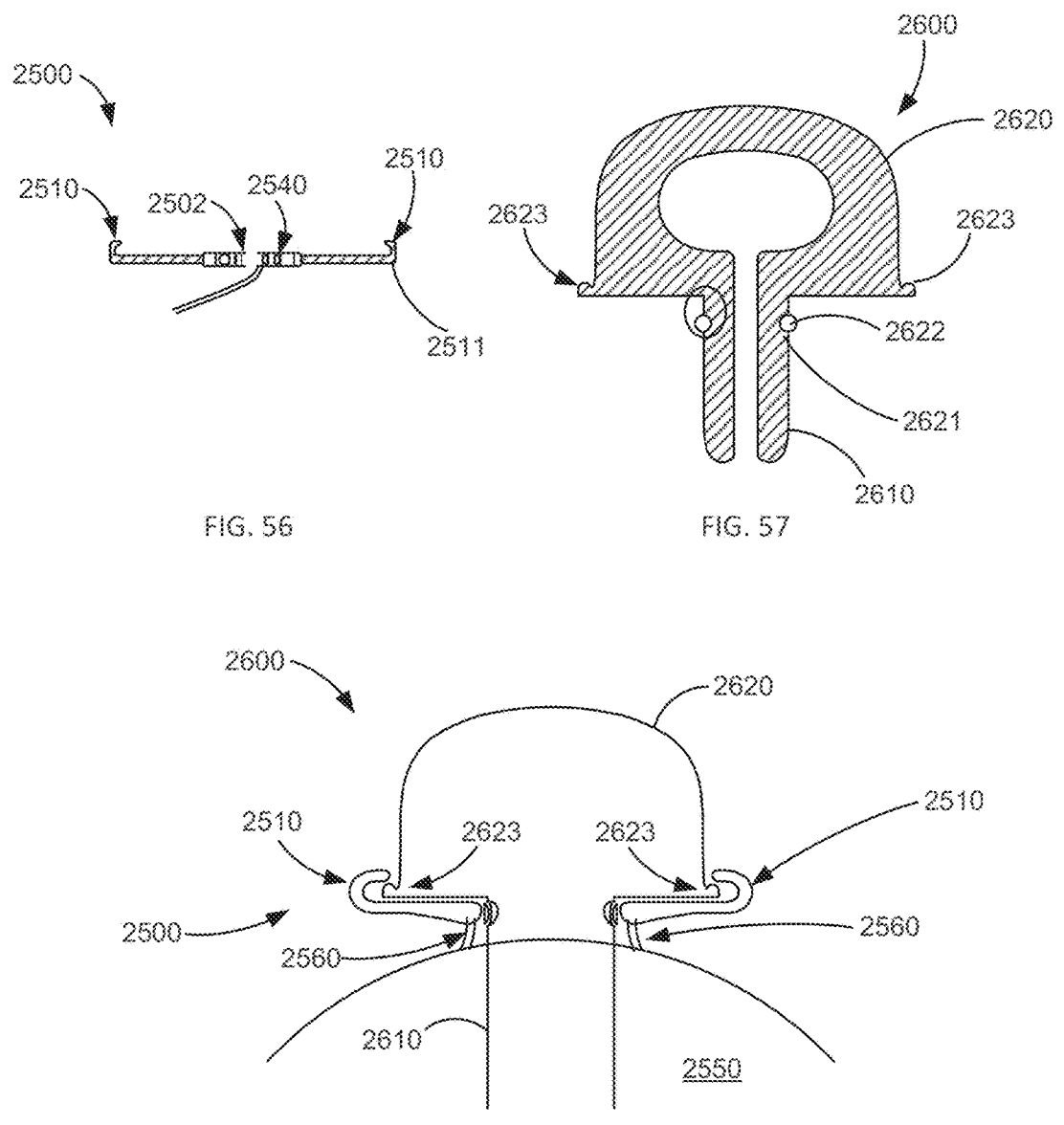

FIG. 56 shows an exemplary cross-sectional view of a cuff 2500. Cuff 2500 may be any of the cuffs described herein (e.g., cuff 20, 1200, 2100, 2200, 2300, 2400, etc. or variations thereof). Cuff 2500 includes a sewing ring 2540 around opening 2502. Cuff 2500 includes a hook feature 2510 or teeth that extend axially from at least some portions of the outer perimeter 2511. The hook feature 2510 may be configured to couple with a lip, outer ridge, notch or groove on an outer perimeter and/or top portion of a pump. While illustrated as extending from the outer perimeter 2511, some embodiments may have feet (e.g., two feet, three feet, or more, etc.) that extend from the cuff 2500 to capture a lip or groove of an attached pump.

FIG. 57 shows an exemplary pump 2600 for coupling with the hook features 2510 of cuff 2500. Pump 2600 includes inflow cannula 2610 extending from a housing 2620. The inflow cannula 2610 may extend through an opening of cuff 2500. Pump 2600 may include an o-ring groove 2621 for housing an o-ring 2622 along the base of the inflow cannula 2610 where the inflow cannula 2610 couples with housing 2620. O-ring 2622 may help prevent leakage between the coupling of the pump 2600 to the heart. Housing 2620 may include a lip 2623 that protrudes out from a perimeter of the housing 2620. Lip 2623 may cooperate with hook features 2510 of cuff 2500 as illustrated in FIG. 58.

FIG. 58 shows a cross-sectional view of an exemplary coupling between a pump, a cuff, and a heart. As illustrated, a cuff 2500 may be coupled with a heart 2550 via sutures 2560. Inflow cannula 2610 extends through cuff 2500 and into heart 2550. Further, hook features 2510 of cuff 2500 may be closed around and engage lip 2623 of pump housing 2620 so as to further secure pump 2600 to cuff 2500. While illustrated as a lip 2623, other pumps may include grooves for cooperating with hook features 2510 of a cuff 2500. The engagement between hook features 2510 of a cuff 2500 and a corresponding lip 2623 or groove of pump 2600 may help transfer some loads from the cuff 2500 to the pump 2600 to provide less stress on the cuff 2500. This integrated coupling/locking cuff design is further advantageous as a separate/independent locking clip or like component is not required for secure coupling of the heart pump to the ventricular cuff.

FIG. 59A-59C illustrated an exemplary method of attaching a cuff 2700 to the apex of the heart. In the method illustrated in FIG. 59A-59B, the apex may first be located and the cuff 2700 may be positioned. Sutures 2750 may then be placed evenly on the perimeter of the sewing ring of cuff 2700 to secure it onto the heart. Optionally, two, three, four or more sutures may be used to secure cuff 2700 to the heart. In such a method, sewing ring of cuff 2700 may act as a pledget or anchor for sutures 2750. In some embodiments eight sutures 2750 or more may be used. In some embodiments, the heart may be cored before suturing the cuff 2700 onto the apex of the heart. In other embodiments, the heart may be cored after suturing the cuff 2700 onto the apex of the heart.

FIG. 60A-60C illustrate an alternative method of attaching a cuff 2700 to the apex of the heart. In the method illustrated in FIG. 60A-60B, the apex may first be located and sutures 2750 may be secured at pledgets or anchors around the apex of the heart. The sutures 2750 may be secured at locations under cuff 2700 when the cuff 2700 is placed against the apex. The secured sutures 2750 may then be fed through the sewing ring of cuff 2700. Cuff 2700 may then be pushed towards the apex of the heart to overlap with the pledgets or anchors of the sutures 2750. Once positioned adjacent the heart, cuff 2700 may be adjusted to a desired position. The sutures 2750 may then be tightened and fastened to the sewing ring of cuff 2700. Advantageously, with the illustrated method, the operator's field of view is not obstructed nor interferes with the securing of the cuff 2700.

FIG. 61A-61C illustrates yet another method of attaching a cuff 2700 to the apex of the heart. In the method illustrated in FIG. 61A-61B, the apex may first be located and sutures 2750 may be secured at pledgets or anchors around the apex of the heart. The secured sutures 2750 may be secured at locations that are spaced apart from an outer perimeter 2711 of the cuff 2700 when the cuff 2700 placed against the apex. For example, in some embodiments, the sutures may be secured at locations that are spaced between 0.5-2.0 cm away from the outer perimeter 2711 of the cuff 2700. The sutures 2750 may then be fed through sewing ring of cuff 2700. Cuff 2700 may then be pushed against the surface of the heart. The sutures 2750 may then be tightened and fastened to the sewing ring of cuff 2700. In some embodiments, the method may provide additional flattening of the apex of the heart due to the sutures 2750 being secured at positions spaced apart from the outer perimeter of cuff 2700 and fastened to cuff 2700. For example, when the sutures 2750 are secured approximately 1 cm spaced apart from an outer perimeter of cuff 2700 and tightened to cuff 2700, the fastening and tightening of the sutures may provide an additional 1 cm of flattening around the outer perimeter of the cuff 2700. Accordingly, the method may allow a clinician to adjust the flattening of the apex depending on the tightening of the sutures 2750.

Figures 62A, 62B:
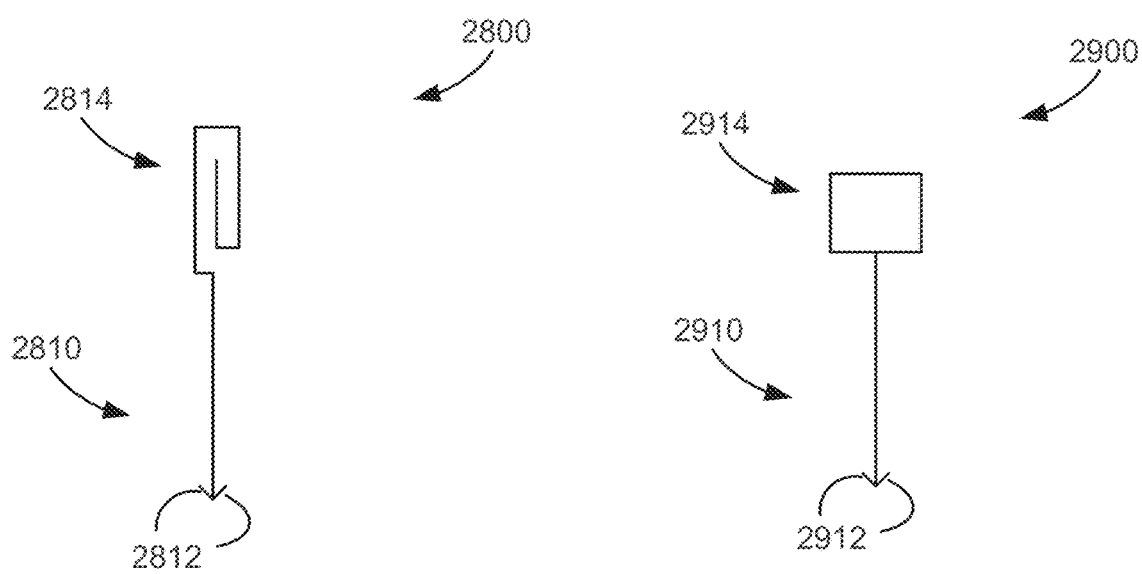
FIGS. 62A and 62B illustrate exemplary anchors that may be used to secure a suture to heart tissue according to embodiments of the present invention.

While illustrated as generally using pledgets to secure a suture to the heart tissue, other embodiments may use tissue penetrating anchors for securing a suture to heart tissue. FIGS. 62A-62B illustrate exemplary anchors 2800, 2900 that may be used to secure a suture to heart tissue. Anchors 2800, 2900 include a tissue penetrating end 2810, 2910. The tissue penetrating end 2810, 2910 may include one or more barbs 2812, 2912 for securing the anchor 2800, 2900 in the tissue. An end of anchors 2800, 2900 opposite of tissue engagement end may include a suture engagement feature 2814, 2914. Suture engagement feature 2814 of anchor 2800 may comprise a hook feature that permits a clinician to slide a suture into the engagement feature 2814. Suture engagement feature 2914 of anchor 2900 may comprise an eyelet that may require a clinician to thread a suture through the eyelet of the anchor 2900. While illustrated and described with two barbs 2812, 2912, it should be understood that embodiments may include three, four, five, or more barbs 2812, 2912 for securing an anchor 2800, 2900 to tissue once inserted therein.

FIGS. 63A-63B illustrate another ventricular cuff 3000 according to some embodiments of the invention. FIG. 63A illustrates a cross-sectional view of the cuff 3000 and FIG. 63B illustrates the side view of the cuff 3000. The cuff 3000 may be configured to attach to the heart of a patient along attachment direction 3001. The cuff 3000 may include a sewing ring 3020. The sewing ring 3020 may be coupled with an insert ring 3030. The sewing ring 3020 may be backed with a rigid frame 3040. An apical ring 3050 may be configured to couple with insert ring 3030. The rigid frame 3040 may be pressed against the sewing ring 3020 and captured between the apical ring 3050 and insert ring 3030 by the engagement of the apical ring 3050 with the insert ring 3030.

Figure 63C:
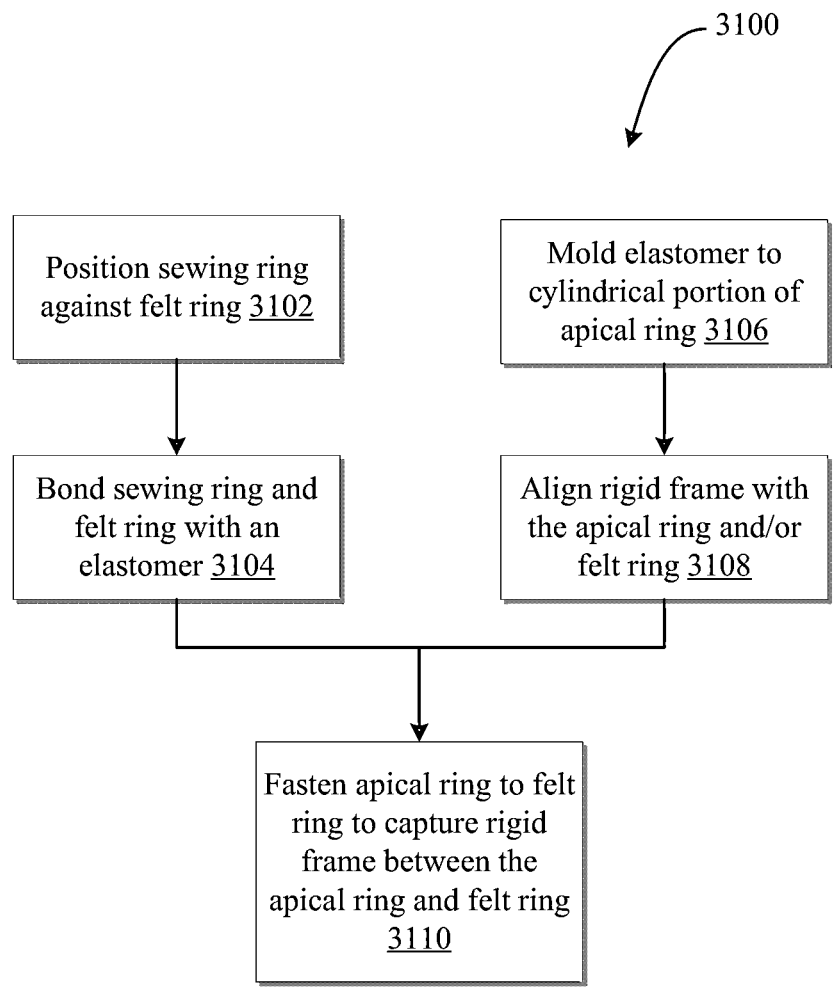

FIG. 63C illustrates an exemplary method 3100 of manufacturing a cuff (e.g., cuff 3000). Method 3100 may include positioning a sewing ring against an insert ring 3102. The sewing ring and insert ring may be bonded together with an elastomer 3104. Elastomer may be molded onto a cylindrical portion of an apical ring 3106. A rigid frame may be aligned with the apical ring 3108. The rigid frame may be captured by fastening the apical ring to the insert ring 3110.

Figure 64A:
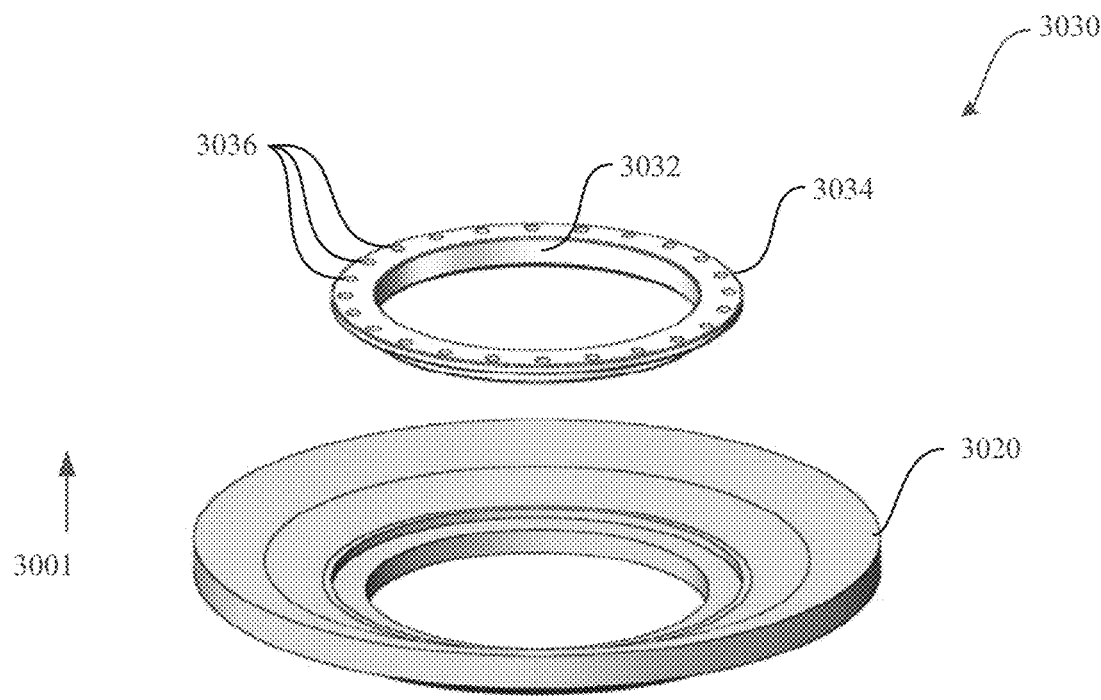
FIGS. 64A to 64C illustrate the aligning and bonding between an exemplary sewing ring and insert ring according to embodiments of the invention.
Figure 64B:
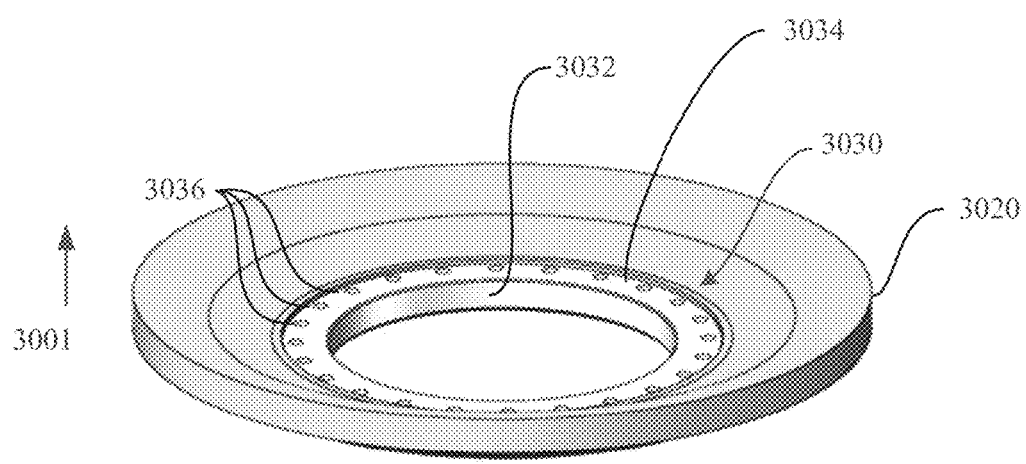
Figure 64C:
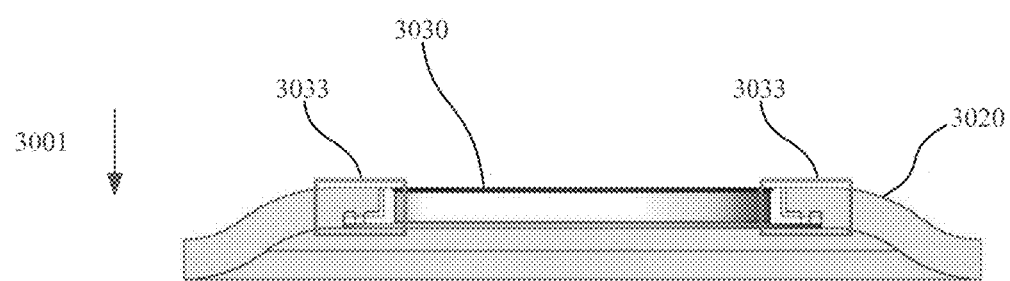

FIGS. 64A-64C illustrate the aligning 3102 and bonding 3104 between the sewing ring 3020 and the insert ring 3030. The sewing ring 3020 may comprise a single layer of felt that defines a central opening for receiving an inlet cannula of a heart pump (e.g., cannula 50, 150, 350, 650, 950, 1430, or the like etc.). A sewing ring 3020 with only a single layer of felt or other form of soft, permeable fabric may be advantageous for facilitating the passing a needle through the sewing ring 3020 during fastening of the sewing ring 3020 to the heart of a patient. The sewing ring 3020 may have a porosity of 550-4000 ml/cm$^2$/min in water, preferably between 700-1800 ml/cm$^2$/min in water, and even more preferably between 750-1000 ml/cm$^2$/min in water. In addition to facilitating the passing of a needle through the sewing ring 3020, the higher porosity material may improve a mechanical attachment of the sewing ring 3020 to the insert ring 3030, as will be discussed below. Further, the higher porosity felt may provide additional flexibility of the sewing ring 3020. The additional flexibility of sewing ring 3020 may increase tissue apposition during attachment which is associated with better hemostasis. The more compliant felt may also provide better recovery of the felt after needle passage such that bleeding is minimized at suture holes. The sewing ring 3020 may also include a thin layer of elastomeric material that can provide additional tactile feedback to the surgeon during attachment while preventing the passage of fluids such as blood after the attachment is complete. The sewing ring 3020 may have an outer diameter as large as 2.5 inches, (e.g., approximately 2 inches) with an internal opening appropriately sized for receiving an inlet cannula of a heart pump (e.g., cannula 50, 150, 350, 650, 950, 1430, or the like etc.). The sewing ring 3020 may have a thickness of 0.5 to 4.0 mm with a preferred range of 1.0 to 2.0 mm. While a single layer of PTFE felt is shown, additional embodiments can include polyester knit or woven fabric, or other textile configurations that meet the criteria above and may include a layer of silicone or other elastomer to be captured on both sides by a layer of fabric.

In many embodiments, the insert ring 3030 may be made of a rigid material, such as metal. In a preferred embodiment, the insert ring 3030 may comprise of titanium. The insert ring 3030 may define an opening with an axis for receiving an inlet cannula of a pump. The insert ring 3030 may include a cylindrical portion 3032 with a lip 3034 extending laterally from the axis of the opening of the insert ring 3030. The lip 3032 may extend generally perpendicular from an outer surface of the cylindrical portion 3032 and may include a plurality of holes 3036 therethrough for receiving an elastomer. In some embodiments, the insert ring 3030 may engage with an apical ring (e.g., apical ring 3050). The insert ring 3030 may engage with an apical ring in a friction fit manner. For example, the inner surface of the cylindrical portion 3032 may be configured to receive the apical ring and to engage with an outer surface of the apical ring as will be described further below. In some embodiments, the insert ring 3030 has a height less than 5 mm and in some embodiments less than 2 mm. The insert ring 3030 may be configured with an inner diameter that accommodates the attachment with the apical ring as discussed below. In some embodiments, the insert ring 3030 may have an outer diameter that accommodates the attachment with the sewing ring 3020 as described below. In some embodiments, the outer diameter of insert ring 3030 does not exceed 1.5 inches.

Once aligned 3102, the insert ring 3030 and the sewing ring 3020 may be coupled together by an elastomer (e.g., silicone rubber or the like) 3104. In some embodiments, a primer (e.g., NUSIL MED 6-161) may be applied to the outer surface of the insert ring 3030 to increase the chemical attachment of the elastomer to the insert ring 3030. Additionally, the plurality of holes of the lip 3032 may also provide for the elastomer to flow therethrough and cure to provide a mechanical link attachment of the insert ring 3030 with the elastomer. The sewing ring 3020 may be placed about the insert ring 3030 such that the openings of each component are aligned and such that the lip 3032 of the insert ring 3030 overlaps with a surface of the sewing ring 3020 (also illustrated in FIG. 63A). Thereafter, press molding with the elastomer (e.g., liquid silicone rubber (NUSIL MED 4870)) may bond 3104 the sewing ring 3020 to the insert ring 3030 by elastomer impregnation of the voids in the felt of sewing ring 3020, through chemical attachment of the elastomer to the insert ring 3030, and by allowing the elastomer to flow through the holes 3036 in the lip 3034 of the insert ring 3030 and cure to form a mechanical linkage. FIG. 64C illustrates an exemplary location 3033 where an elastomer may be applied or injected to bond the sewing ring 3020 with insert ring 3030. This construction may provide a liquid tight seal at the interface of the sewing ring 3020 and the insert ring 3030. The liquid tight seal may reduce the occurrence of bleeding through the cuff 3000 at this interface once attached to the heart. The lower density felt may also allow for better impregnation of the elastomer (e.g., silicone) to provide the liquid tight seal at the interface between the sewing ring 3020 and the insert ring 3030. In some embodiments, the felt of sewing ring 3020 is coupled to the insert ring 3030 by molding and/or press-fit operation alone. In some embodiments, the sewing ring 3020 may be coupled to the insert ring 3030 without the need for sutures between the two components, thus simplifying manufacturing.

Figure 65A:
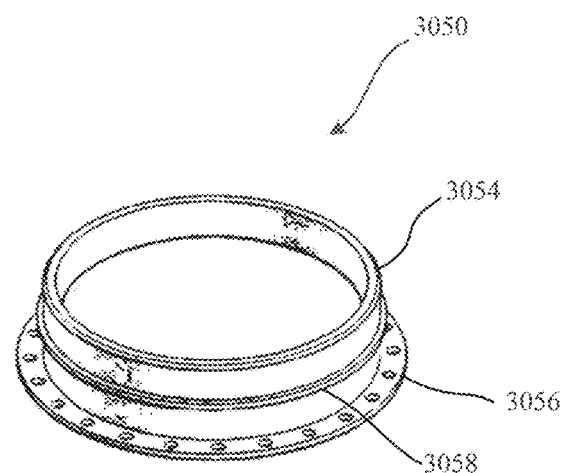
FIGS. 65A to 65C illustrate an exemplary apical ring according to embodiments of the invention.
Figure 65B:
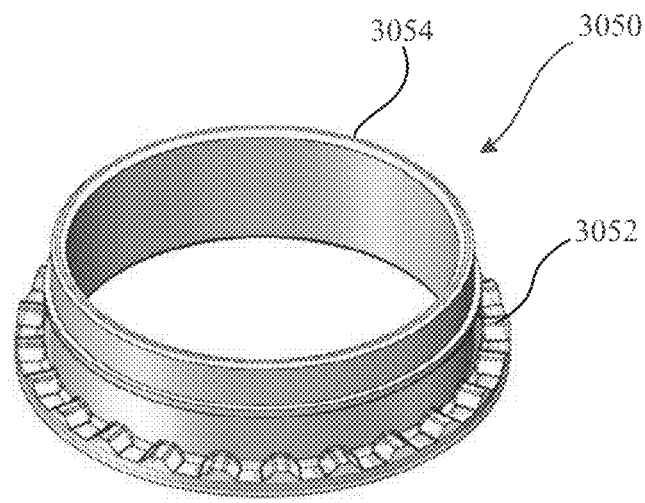
Figure 65C:
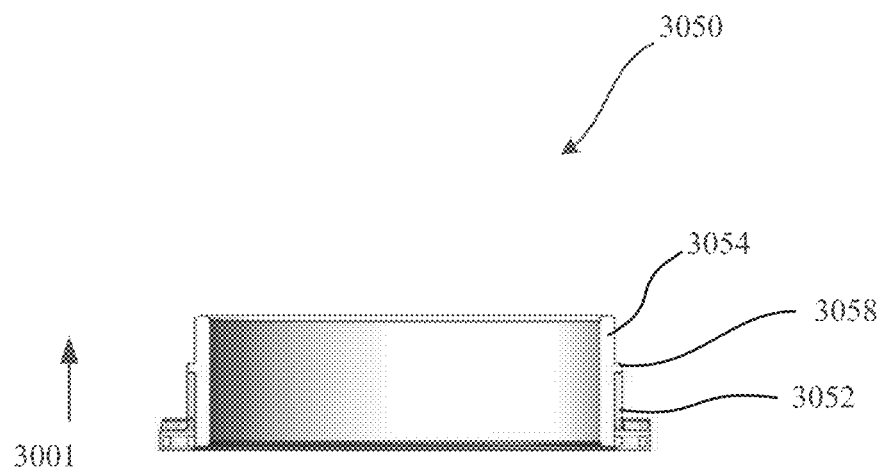

FIG. 65A-65C illustrate an exemplary apical ring 3050. Apical ring 3050 may include an elastomer 3052 molded over a cylindrical portion 3054. FIG. 65A illustrates the apical ring 3050 prior to the elastomer 3052 being molded over the cylindrical portion 3054. FIG. 65B illustrates the apical ring 3050 after an elastomer 3052 is molded over a portion of the cylindrical portion 3054. FIG. 65C illustrates a cross section of apical ring 3050. In many embodiments, the cylindrical portion 3054 may be made of a rigid material, such as metal. In a preferred embodiment, the cylindrical portion 3054 may comprise of titanium. Cylindrical portion 3054 may include a lip or flange 3056 extending outwardly from a heart pump attachment end of the cylindrical portion 3054. The flange 3056 may include a plurality of holes therethrough for forming elastomeric links that mechanically fasten the elastomer 3052 to the cylindrical portion 3054 of the apical ring 3050. The cylindrical portion 3054 may further include a central lip 3058 extending from a central portion of the cylindrical portion 3054. The central lip 3058 may be configured to engage with a portion of the rigid frame 3040 to align the rigid frame 3040 with the apical ring 3050 during cuff assembly, as will be described further below. The sewing ring engaging end of the cylindrical portion 3054 may have an outer portion which mates with the inner surface of the opening defined by an insert ring. In some embodiments, the apical ring 3050 may be 3-8 mm in height, preferably 3-5 mm. The apical ring 3050 diameters may be configured to permit attachment to the insert ring 3030 during manufacturing. This might include a small radial gap, 0.001" to 0.025" on the radius, preferably 0.005"-0.015" on the radius to allow adhesive bonding between the components. The diameters might also be sized to provide minimal gaps for laser welding as a joining method. The diameters might also be sized to interfere in a manner that creates a press-fit assembly when the parts are pressed together. The inside diameter of the insert ring 3030 and outside diameter of the apical ring 3050 may also be threaded so that they might be threaded together during manufacturing. While metal is described as a preferred material, any rigid material, such as plastic or ceramic materials, might be used to create the apical ring 3050.

In some embodiments, the apical ring 3050 may be insert molded 3106. The cylindrical portion 3054 may be primed (e.g., NUSIL MED6-161) to increase a chemical adhesion of the elastomer 3052 to the outer surface of the cylindrical portion 3054. In some embodiments, liquid silicone rubber may be injected 3106 to cover the flange 3056 cylindrical portion 3054 to form the elastomeric mechanical links and to cover the outer surface of cylindrical portion 3054 up to the central lip or protrusion 3058. In some embodiments the thickness of the elastomer coating 3052 may be about equal to a distance which lip 3058 projects from the outer surface of the cylindrical portion 3054. In some embodiments, the elastomer may be molded into shapes that facilitate a secondary feature of the cuff, such as anti-rotation or general rotational stiffness. Features might also be molded into the elastomer for alignment with the pump locking mechanism as described below.

Figure 66:
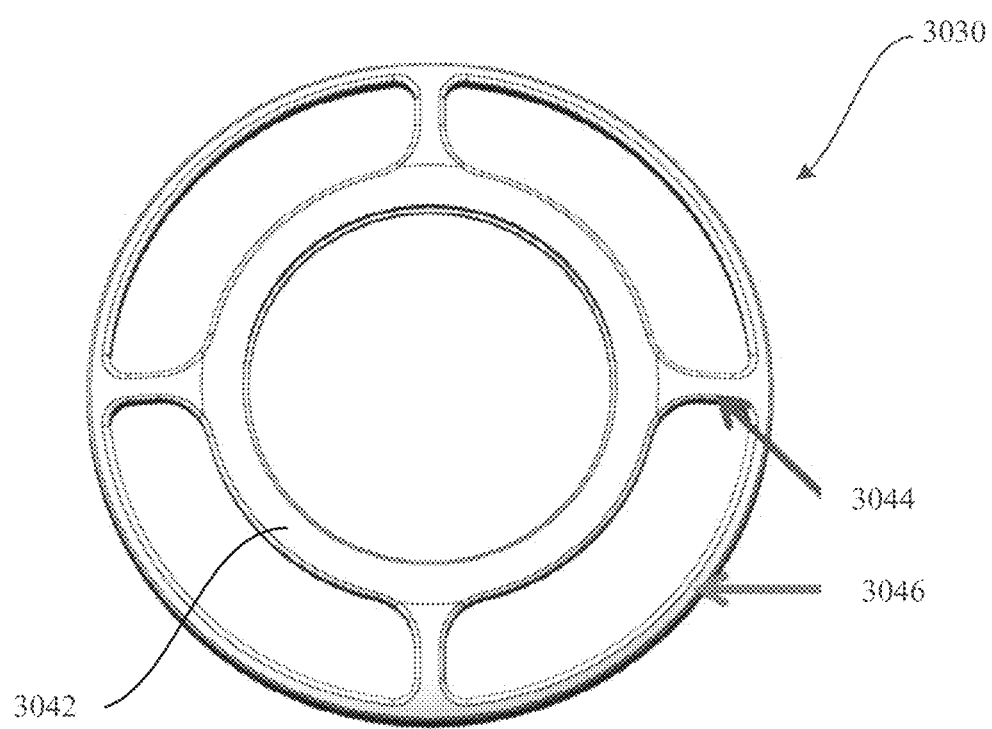
FIG. 66 illustrates a top view of an exemplary rigid frame according to embodiments of the invention.

FIG. 66 illustrates a top view of an exemplary rigid frame 3040. In many embodiments, rigid frame 3040 may provide the cuff 3000 a rigidity sufficient for resisting the forces created by the myocardium or remodeling or forcing the tissue to take a shape (e.g. flattening). In some embodiments, the frame has sufficient rigidity to re-shape the heart wall. The re-shaping of the wall may be in a localized section adjacent the frame or a larger region. The re-shaping may be for a period of time or generally permanent as long as the frame is attached to the heart. In some embodiments, the frame has sufficient rigidity to maintain the heart wall in a remodeled shape. As used herein, "heart wall" generally refers to the entire wall of the heart chamber including the epicardium (outer layer), the myocardium (middle layer), and the endocardium (inner layer). In some respects, "heart wall" is used somewhat interchangeably with "myocardial wall" or "myocardium." In many embodiments the rigid frame 3040 may be made of a metal material. In some embodiments the rigid frame 3040 comprises a titanium metal. In some embodiments the rigid frame 3040 may be made of a rigid plastic or ceramic material. As discussed above, flattening of the myocardium during cuff and pump attachment may reduce the probability of inflow cannula malpositioning by expanding a space around the inflow cannula of the pump. A rigid cuff may also help maintain the space about the inflow cannula throughout implantation of the pump within a patient.

Rigid frame 3040 may have an inner ring 3042 defining an opening. One or more struts 3044 may extend outwardly from the inner ring 3042. In some embodiments 2-8 struts 3044 may extend outwardly from the inner ring 3042, and in one embodiment between 4-6 struts 3044 extend outwardly. The one or more struts 3044 may support an outer ring 3046 against the sewing ring 3020 when the cuff 3000 is assembled. The one or more struts 3044 extending from the inner ring 3042 to the outer ring 3046 define one or more holes through the rigid frame 3040 and between the struts 3044 where a surgeon may pass a needle for suturing the sewing ring 3020 to the surface of a heart of the patient. The struts 3044 and frame 3040 may be designed to withstand the forces created during surgical attachment to the tissue or handling during implantation. In some embodiments, the struts 3044 may have a width of 0.5-2.0 mm, preferably 0.75-1.25 mm. In some embodiments, the struts 3044 may have a thickness of 0.2-2.0 mm, preferably 0.2 to 0.7 mm. In some embodiments, the outer ring 3046 may have a width and thickness of 0.2 to 2.0 mm, preferably 0.2 to 0.7 mm.

In some embodiments the rigid frame 3040 may be flat (e.g., similar to insert 1030). In other embodiments the rigid frame 3040 has a non-planar shape. In one embodiment, the frame has a frustoconical, or dome configuration where the inner surface 3047 (surface positioned towards the heart) is concave and the outer surface 3048 (opposite the inner surface) is convex as illustrated in FIGS. 63A-63B. One will appreciate that the entire frame does not need to be of an entirely uniform shape. The frame may have a generally conical shape or only a portion may be conical. In some embodiments at least a portion of the frame defines a non-degenerate shape. In some embodiments the frame has a shape with a generally decreasing diameter moving in a direction away from the heart wall. In some embodiments the convex surface of the rigid frame 3040 has a rise between 0.02 inches and 0.25 inches, a rise between 0.05 inches and 0.2 inches, a rise between 0.065 inches and 0.1 inches (e.g., 0.07-0.08 inches), or the like. In some embodiments the struts may extend in the attachment direction 3001 as the struts extend outwardly from the opening. While illustrated as gradually extending in the attachment direction 3001, it should be understood that embodiments of the struts may extend at a constant rate.

In some embodiments, the inner perimeter of the inner ring 3042 may include an alignment feature 3048 for aligning 3108 the rigid frame 3040 with an apical ring 3050. As illustrated in FIG. 63A, the alignment feature 3048 may be a recessed surface along the inner perimeter of the inner ring 3042 that receives the projection 3058 from the apical ring 3050, as described above. It should be understood that other alignment features may be provided for engaging with corresponding alignment features of the apical ring 3050.

After alignment 3108, the apical ring 3050 may be engaged with insert ring 3030 to assemble the cuff 3000. As illustrated in FIG. 63A, the outer diameter of cylindrical portion 3054 of apical ring 3050 mates with the inner surface of cylindrical portion 3032 of insert ring 3030 in a press-fit connection. In some embodiments, it may be preferable if the interference between the apical ring 3050 and the insert ring 3030 resists separation with an axial pull force of at least 8 lb-f. In some embodiments, it may be preferable if the interference between the apical ring 3050 and the insert ring 3030 resists separation with an axial pull force of 20-50 lb-f (e.g., at least 20 lb-f). In some embodiments it may be preferable to have at least of 0.0005" interference (e.g., a 0.001-0.003" interference) for the press-fit assembly of the apical ring 3050 to the insert ring 3030. Additionally, in some embodiments, it may be preferable if the apical ring 3050 and the insert ring 3030 are made of the same material or otherwise have a similar coefficient of thermal expansion and have an equivalent wall thickness. Such a configuration may limit the effect of thermal stresses on the press-fit connection.

As illustrated, the inner diameter of frame 3040 is less than an outer diameter of lip 3058, thus the frame 3040 is captured between the press fit engagement of the apical ring 3050 and the insert ring 3030. Preferably, the engagement of the apical ring 3050 to the insert ring 3030 urges the frame 3040 against the sewing ring 3020 to provide sufficient support to prevent the sewing ring 3020 from significant deformation or concavity during implantation.

Figure 67A:
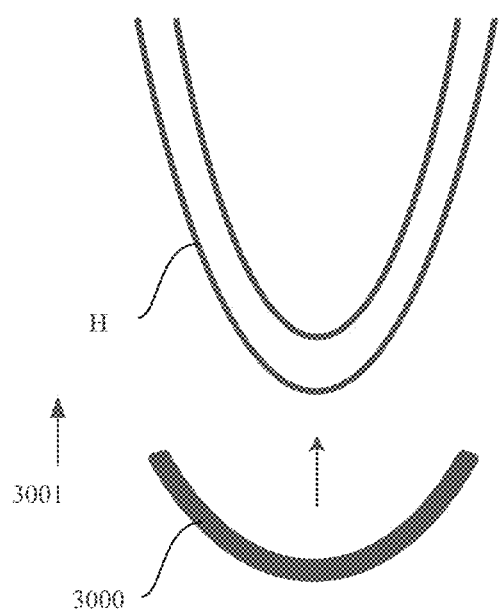
FIGS. 67A to 67C illustrate simplified drawings showing the attachment of an exemplary cuff and pump to the heart of a patient according to embodiments of the invention.
Figure 67B:
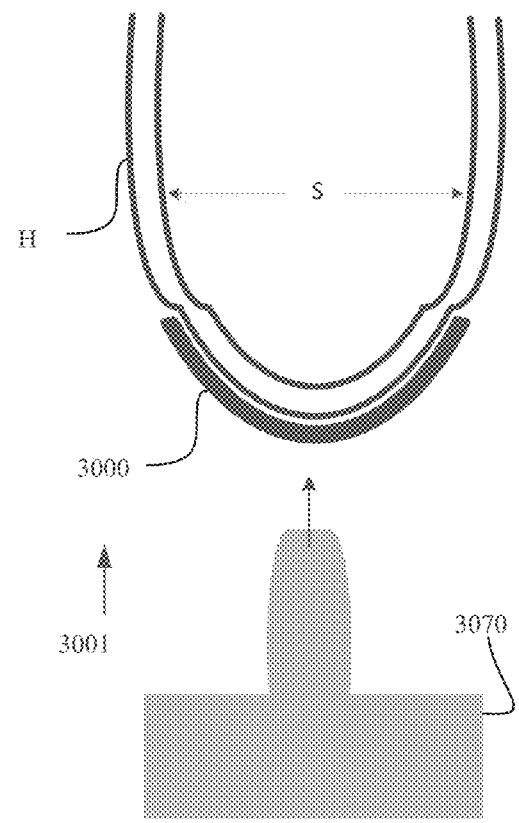
Figure 67C:
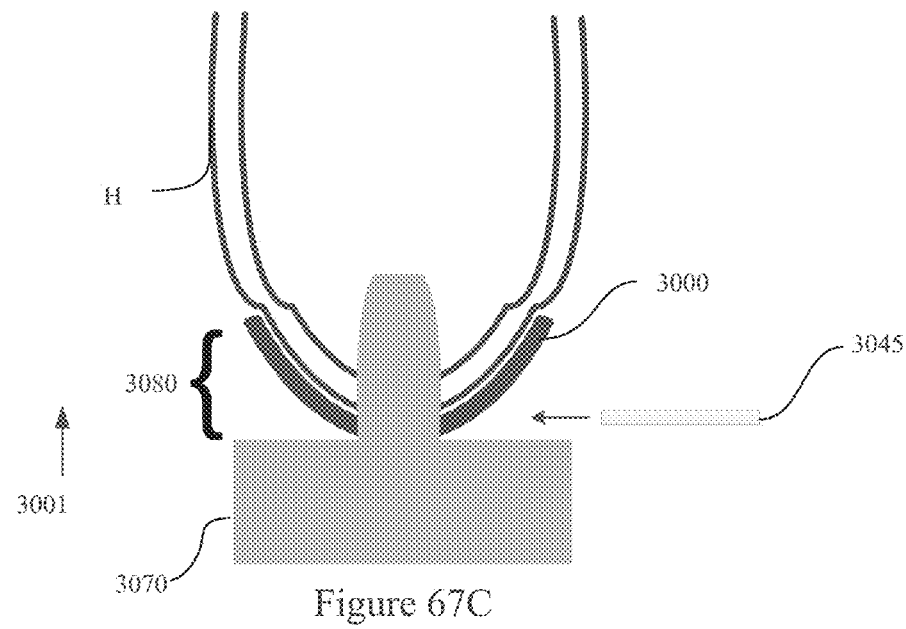

The dome or cupped configuration of the rigid frame 3040 may be advantageous for increasing the consistency of surgical attachment methods. FIGS. 67A-67C illustrate simplified drawings (not to scale) showing the attachment of the cuff 3000 and pump 3070 to the heart H of a patient. FIG. 67A illustrates the attachment of the cuff 3000 to the surface of the heart H. Although the cuff is shown attached to apex of the left ventricle (LV), one will appreciate that the cuff may be configured and attached to other portions of the heart. For example, the cuff may be attached along the anterior wall or posterior wall. The cuff may also be shaped and configured for attached to the RV. For example, the cuff may have a less pronounced concave shape. The attachment of the cuff 3000 flattens a portion of the myocardium and may expand a space S in the heart H as illustrated in FIG. 67B. The dome configuration of rigid frame 3040 may minimize deformation of the sewing ring 3020 along an outer perimeter of the sewing ring 3020 during flattening of the myocardium as the one or more struts 3044 and/or outer ring 3046 support the sewing ring 3020 against the tissue and may be configured to oppose deformation in the attachment direction 3001. In many embodiments, the dome configuration of the rigid frame 3040 provides a structural component between the sewing ring 3020 and the pump 3040 that prevents deformation and/or concavity of the sewing ring 3020 during attachment. Such deformation or concavity of the sewing ring 3020 may interfere with the attachment of the pump 3070 to the cuff 3000 by limiting the space for a surgeon to insert a slide lock (e.g., clip 200, clip 700, or the like, etc.) or by limiting the surgeon's view the interface between the cuff 3000 and the pump 3070. Thus, reducing deformation/concavity of the sewing ring 3020 may allow a surgeon to more readily couple the pump 3070 to the cuff 3000 by increasing clearance between the pump 3070 and the sewing ring 3020 for insertion of a slide lock 3045 and may also increase a surgeon's view of the cuff/pump interface. For example, as illustrated in FIG. 67C, the dome configuration of the rigid frame 3040 may increase a spacing 3080 between the cuff 3000 and the pump 3070. The increased spacing 3080 may facilitate advancing slide lock 3045 (e.g., clip 200, clip 700, or the like) between the pump 3070 and the cuff 3000 to secure the pump 3070 to the cuff 3000. The spacing afforded by the frame and struts may be sufficient to allow visual inspection by the physician (or access with an instrument).

In some embodiments the outer ring 3046 of the rigid frame 3040 has a diameter about 2-6 mm less than a diameter of the sewing ring 3020. Accordingly, the sewing ring 3020 may have an outer diameter the protrudes outwardly past the outer ring 3046 of the rigid frame 3040. This portion of the sewing ring 3020 preferably protrudes at least 1.5 mm (e.g., 2-3 mm) outwardly past the outer ring 3046 of the rigid frame 3040 such that it may provide a location where a surgeon can accomplish a running stitch about the perimeter of the sewing ring 3020.

While rigid frame 3040 is illustrated with the outer ring 3046, other embodiments may forgo the use of outer ring 3046. In some embodiments, a plurality of struts 3044 extending outwardly from the inner ring 3042 may be sufficient to maintain the desired shape of the sewing ring 3020 (e.g. flat or convex) during attachment of the cuff 3000 to the heart of the patient.

In many embodiments, the rigid frame 3040 backs the sewing ring 3020 and is not covered by a felt layer. Such a configuration may be advantageous as it allows the surgeon to see the openings of the rigid frame 3040 and thus where to pass the needle to suture the sewing ring 3020 to the heart of the patient.

In general, flattening of the myocardium may be achieved using one or more of the techniques described above. For example, the myocardium may be flattened using (i) sutures connected to the housing of a pump, (ii) a cuff having an appropriate flexural modulus, (iii) a member that extends into the heart to engage the endocardium, or (iv) capture of the myocardium from within and from outside the heart, or any combination or sub-combination thereof. Other structures and techniques may also be applied as will be understood by one of skill from the description herein.

A number of exemplary implementations have been described. Nevertheless, it will be understood that various modifications may be made without departing from the spirit and scope of the disclosure. Implementations can include any appropriate combination or subcombination of features described above. For example, some of or all of the features described for the pumps 50, 250, 750, 912 cuffs 20, 120, 320, 620, 1240, 1500, 1550 cannulas 50, 150, 350, 650, 950, 1430, 1460 and clips 200, 700 can be combined or implemented individually. Accordingly, other implementations are within the scope of the following claims.

Figure 68A:
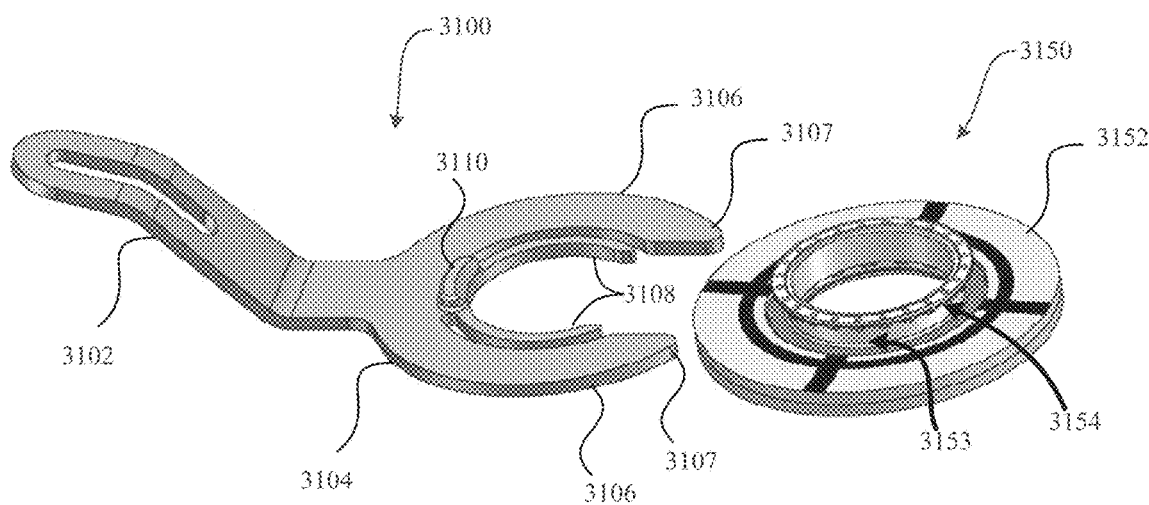
FIGS. 68A and 68B illustrate a stabilization tool that may be used to stabilize a cuff during attachment of a heart pump to the cuff according to some embodiments of the invention.
Figure 68B:
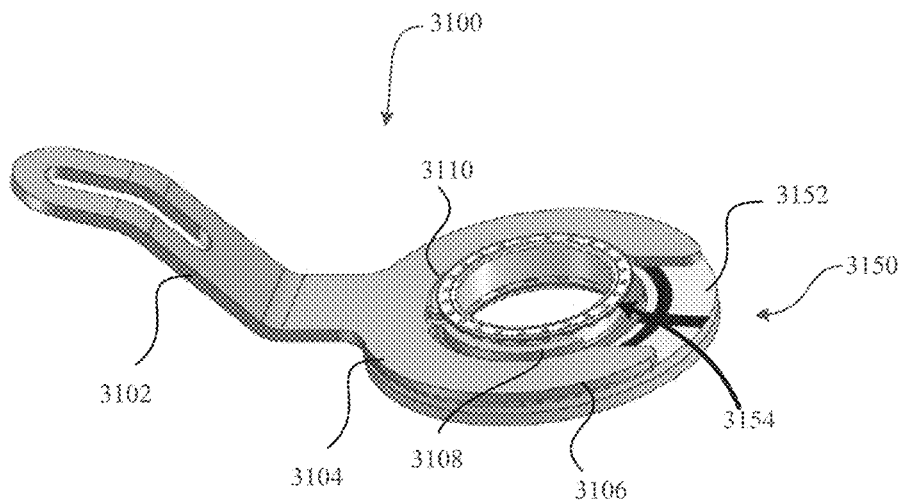

FIGS. 68A-68B illustrate a stabilization tool 3100 that may be used to stabilize a cuff during attachment of a heart pump to the cuff. The stabilization tool 3100 includes a handle 3102 for grasping by a hand of a surgeon. The handle 3102 is coupled with a tool head 3104 that is configured to engage with and stabilize a cuff 3150 during attachment of a heart pump to the cuff 3150. The tool head 3104 may include two prongs 3106 that generally define a U-shape opening between the two prongs 3106 for receiving the apical ring 3153 of cuff 3150. The tool head 3104 may further include clips 3108 that are configured to engage with an outer surface of the apical ring 3153 of the cuff 3150. Tool head 3104 may further include a stand-off feature 3110 that is positioned about a portion of the clips 3108 and is configured to engage with a lip 3154 of apical ring 3153.

In addition to increased stabilization of a cuff/port, embodiments of stabilization tool 3100 may minimize manual manipulation of the heart during pump attachment/removal as the tool may be used to apply a counter force during pump attachment/removal. Additionally, use of embodiments of the stabilization tool 3100 may provide an increased field of view as the surgeon's hands may be positioned a distance from the cuff or port.

The prongs 3106 may have ends 3107 spaced apart a distance approximately equal to or slightly larger than a diameter of the apical ring 3153 of the cuff 3150 so that the tool 3100 may slide over the apical ring 3153 in a direction transverse to an axis of the opening defined apical ring 3153. Further a bottom surface of the prongs 3106 may define a generally flat or concave surface. The bottom surface of the prongs 3106 may also be configured to cover a majority of the top surface of sewing ring 3152 of cuff 3150. For example, as illustrated in FIG. 68B, an outer perimeter defined by prongs 3106 may be coextensive with an outer perimeter of sewing ring 3152. With such a configuration, the bottom surface of prongs 3106 may urge the sewing ring 3152 in a flat or concave configuration when the tool 3100 is coupled with the cuff 3150. As described above, maintaining the sewing ring 3152 in a preferred configuration (e.g., flat, concave, domed, cupped, frustoconical, or the like) may facilitate coupling of a heart pump to the cuff 3150 by reducing obstructions or interference with the coupling of a heart pump to the cuff 3150. Additionally, the prongs 3106 may be configured to cover sutures placed through the sewing ring 3152 and to ensure that the sutures or portions thereof do not interfere with heart pump attachment to the cuff 3150. In some embodiments, the prongs 3106 may have a width greater than the sewing ring 3152 such that a portion of the prongs 3106 overhangs the sewing ring 3152. Such a configuration may be advantageous for covering tissue or other protrusions/obstructions along the perimeter of the sewing ring 3152 that may interfere with the attachment of a heart pump to cuff 3150.

The clips 3108 may be disposed interiorly from the prongs 3106. The clips 3108 may be configured to snap to or otherwise fasten to an outer surface of apical ring 3153. Snapping to clips 3108 to apical ring 3153 may provide haptic or audio feedback to the surgeon to indicate that the tool 3100 is fully engaged with cuff 3150. Accordingly, in some embodiments, the opening defined by clips 3108 corresponds with an outer dimension of apical ring 3153. The ends of clips 3108 may be spaced apart a distance slightly smaller than an outer diameter of apical ring 3153. Clips 3108 may be configured to flex open during engagement of the apical ring 3153 and may be configured to snap toward the resting position or otherwise be urged toward one another to engage with apical ring 3153.

The stand-off feature 3110 may be a raised surface about a portion of the clips 3180. The stand-off feature 3110 may engage with a bottom surface of lip 3154 of apical ring 3153 to urge the prongs 3106 against the sewing ring 3152 of the cuff 3150. The engagement of stand-off feature 3110 with lip 3154 may maintain a desired spacing or otherwise increase a spacing between the sewing ring 3152 and the heart pump during attachment of the heart pump.

Figure 69A:
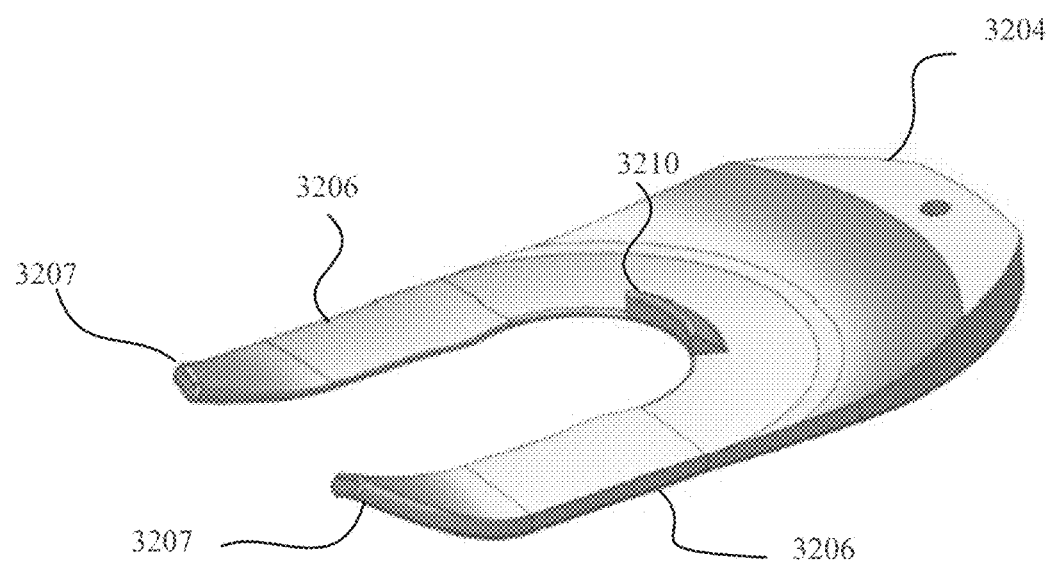
FIG. 69A illustrates another tool head according to some embodiments of the invention.

While the above tool 3100 is illustrated with use with cuff 3150, it should be understood that the tool 3100 is applicable with other cuffs disclosed herein or embodiments thereof. Further, tool head 3104 may have other configurations. For example some exemplary tool heads may not include clips 3108, as illustrated in FIG. 69A. Tool head 3204 may include prongs 3206 which define a U-shaped opening to receive an apical ring of a cuff. Prongs 3206 may define an opening that closely approximates an outer dimension of the apical ring. The close approximation of the U-shaped opening of prongs 3206 may be sufficient to serve the functionality of clip 3108. As illustrated, ends 3207 of prongs 3206 may be slightly raised or curved upward to facilitate engagement of the tool head 3204 with the apical ring at various angles. Tool 3204 may also include a stand-off feature 3210 positioned about a portion of the U-shaped opening to engage with a lip of a cuff to urge the prongs 3206 against a sewing ring of the cuff and/or tissue of the patient or other obstructions.

Figure 69B:
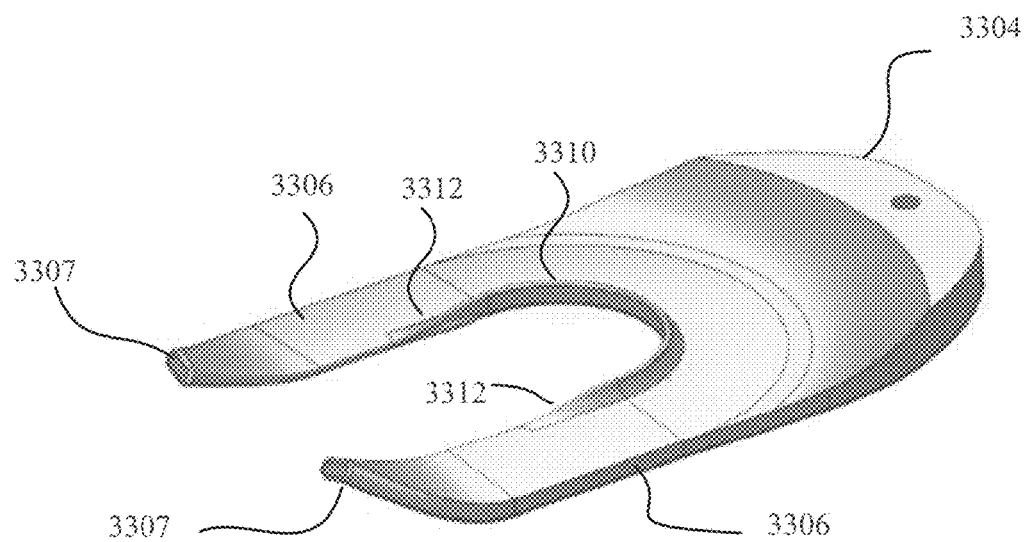
FIG. 69B illustrates another tool head according to some embodiments of the invention.

FIG. 69B illustrates yet another tool head 3304 according to some embodiments of the invention. Tool head 3304 may similar features as tool head 3204. For example, tool head 3304 may include similar prongs 3306 with angled ends 3307 that provide similar functionality as prongs 3206 and ends 3207. The stand-off feature 3310 may be disposed about the U-shaped open defined by prongs 3306. Further, stand-off feature 3310 may similarly include a U-shaped configuration with the ends of the stand-off feature defining ramps 3312 for gradually increasing a spacing between the sewing ring and the top of the apical ring with the engagement of the tool head 3304 with the cuff.

Figure 70A:
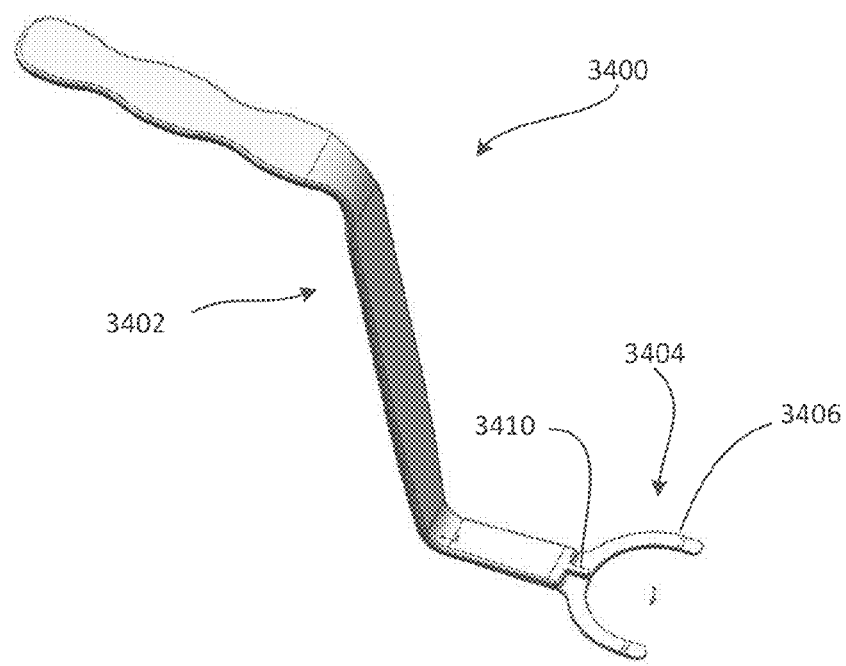
FIGS. 70A and 70B illustrates another tool coupling with and stabilizing a cuff during attachment of a heart pump to the cuff according to some embodiments of the invention.
Figure 70B:
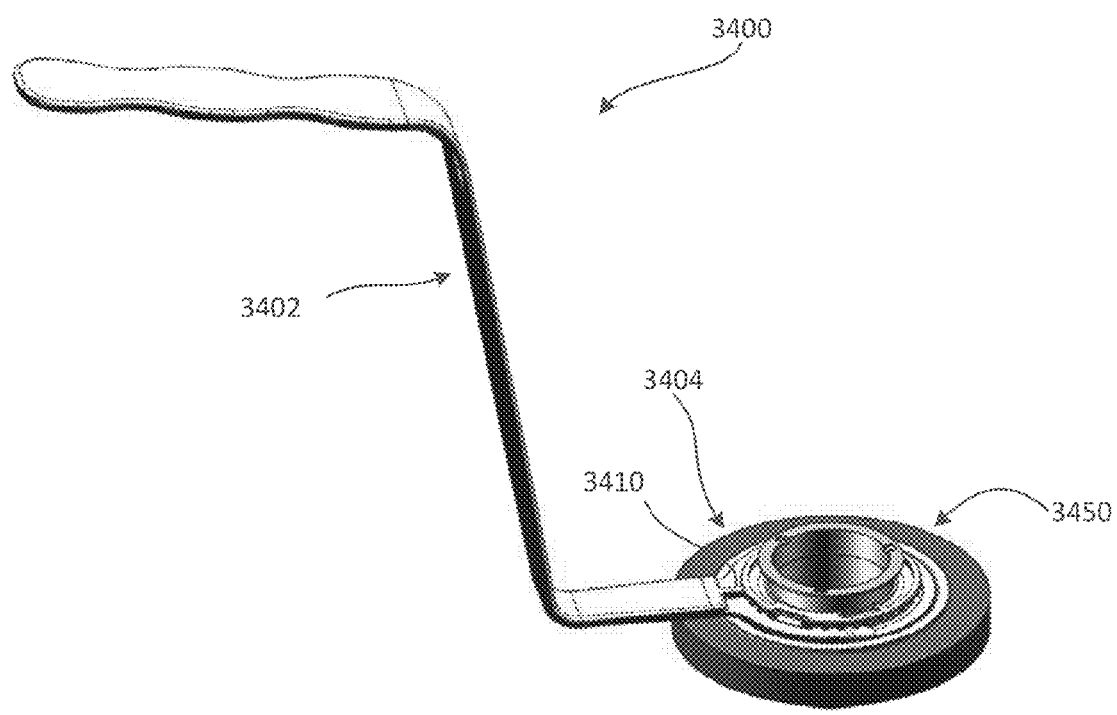

FIGS. 70A and 70B illustrate yet another tool 3400 coupling with and stabilizing a cuff during attachment of a heart pump to the cuff. The tool 3400 may include a handle 3402. The handle 3402 may couple with tool head 3404. Tool head 3404 may generally have prongs 3406 with a C-shape configuration defining a U-shaped opening for receiving and engaging with a cuff 3450. Additionally, tool head 3404 may include a stand-off feature 3410 that cooperates with a portion of the cuff 3450 to provide additional clearance between the cuff 3450 and a corresponding heart pump. The additional clearance may be for inserting locking mechanisms or the like. In some embodiments the stand-off feature 3410 may be inserted into a corresponding engagement feature on the cuff 3450. The insertion of stand-off feature 3410 into the corresponding engagement feature of the cuff 3450 may provide the clearance desired for heart pump engagement. Additionally, the engagement of the stand-off feature 3410 with a corresponding engagement feature of the cuff 3450 may also provide for rotational stabilization of the cuff 3450 relative to the stabilization tool 3400 thereby providing additional control and stabilization and also potentially reducing loads applied to the patient's heart during cuff and/or pump attachment. In some embodiments, the tool 3400 may be moldable or pliable such that portions of the tool 3400 may be shaped during the procedure. For example, in some embodiments, the prongs 3406 may be manually reshaped or reconfigured as needed to better access a cuff attached to a heart of the patient. Additionally, the handle 3402 may also be reshaped (such as the bends in the handle 3402) depending on the size, orientation, and amount of clearance in the surgical field.

Figure 70C:
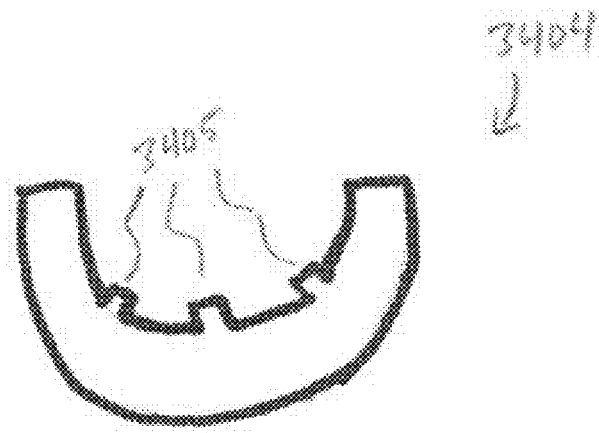
FIG. 70C illustrates another tool head according to some embodiments of the invention.

As illustrated in FIG. 70C, an exemplary tool head 3404 may be configured to include one or more engagement features 3405 that project inwardly from the tool head 3404. The one or more engagement feature 3405 may engage with corresponding engagement features on the cuff to provide rotational stabilization of the cuff 3450 relative to the tool 3400. The cuff 3450 may be a cuff described in related international application PCT/US2014/028346 (the '346 application), the disclosure of which is incorporated herein by reference.

It should be understood that the tools (e.g., 3100, 3204, 3304, 3400) described above may be used with many embodiments of the cuff to stabilize the cuff during heart pump implantation and/or removal. For example, the stabilization tools may be used with the cuffs described above (e.g., FIGS. 63A and 63B, FIGS. 67A to 67C, FIGS. 68A and 68B, FIG. 70B, FIGS. 72A and 72B, FIG. 73 or the like) or the cuffs/cannulas described in the '346 application.

Figure 71:
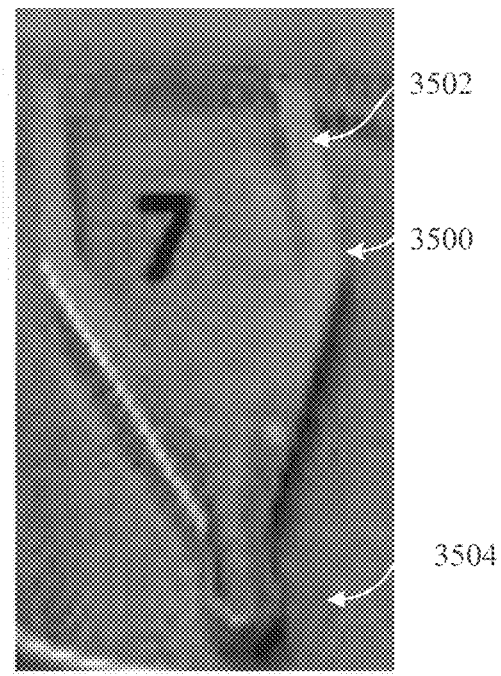
FIG. 71 illustrates a cannula release tool according to some embodiments of the invention.

FIG. 71 illustrates a cannula release tool 3500. The tool 3500 may be used to release the cannula from a cuff. The tool includes two prongs 3502. The prongs 3502 are coupled to one another about elbow 3504. The prongs 3502 may be flexed toward one another about elbow 3504. The prongs 3502 may be positioned about the interface between a cannula and a cuff (e.g., anchoring coil of '346 application). Thereafter, the prongs 3502 may be urged toward one another to engage the interface between the cannula and cuff to separate the two components from one another. The tool 3500 may be used with embodiments of the anchoring coil described in the '346 application.

Figure 72A:
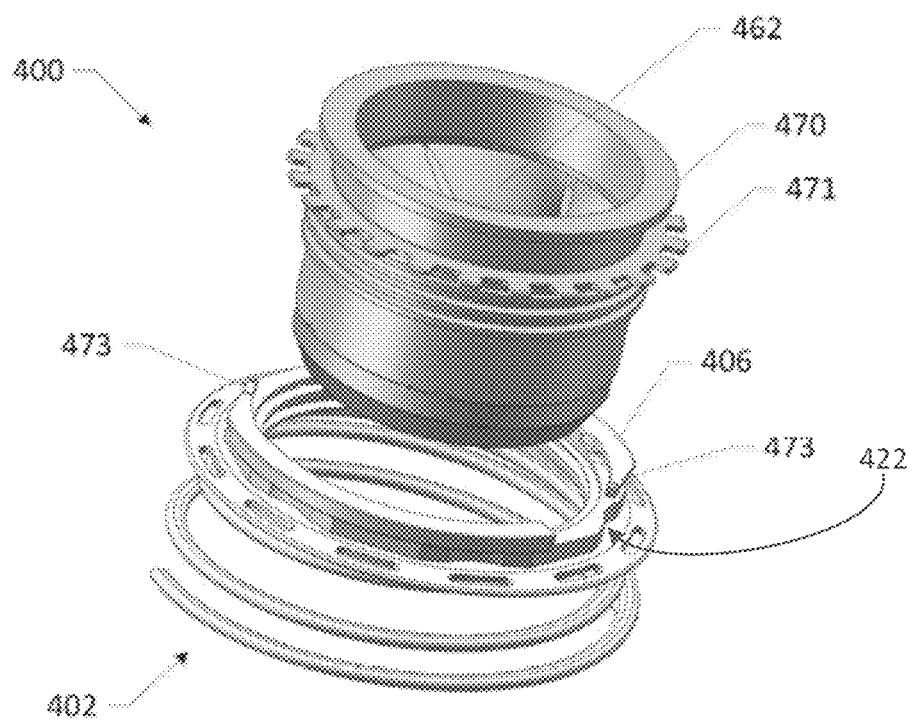
FIGS. 72A and 72B illustrate an embodiment of a portion of a heart connector.
Figure 72B:
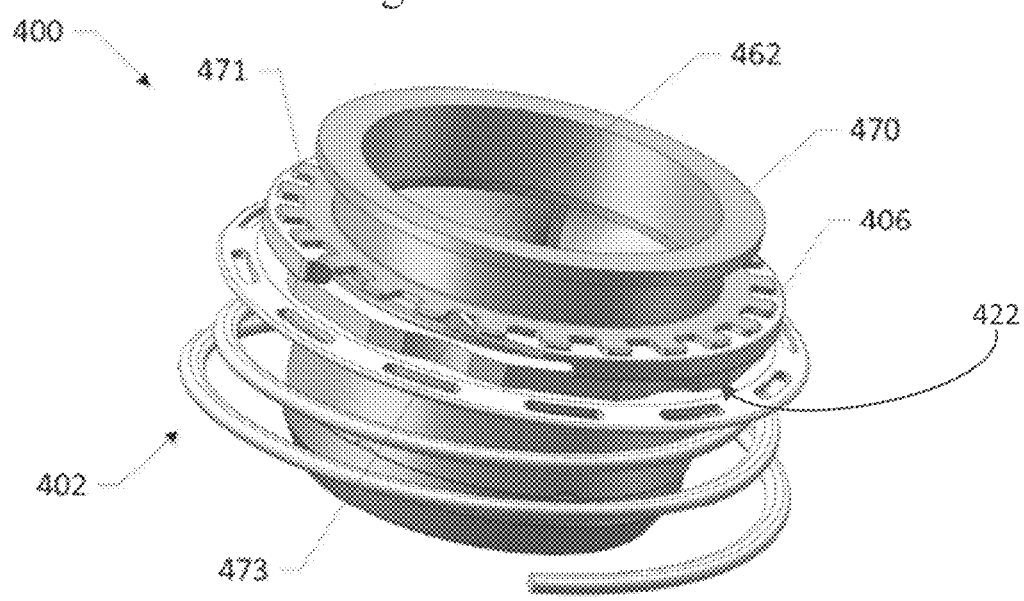

FIGS. 72A and 72B illustrate an embodiment of a portion of an apical connector 400 where embodiments of the stabilization tool may be utilized during cuff attachment to the heart or during heart pump attachment to the cuff. The apical connector 400 may be configured for securing in a heart wall to facilitate in vivo implantation of a VAD and its attachment to the heart. The connector 400 may include an anchoring device 402, a port 406, and a cannula 470 having a hemostasis valve 462. It will be appreciated that the connector 400 also may include other features, such as a coupler device, configured in a manner similar to those described with respect to the various embodiments of the '346 application.

The cannula 470 may include a plurality of tabs 471 positioned at or near the proximal end of the cannula 470 and extending radially outward. In particular, the tabs 471 may be arranged in a circumferential array extending from the outer surface of the cannula 470, as shown in FIGS. 72A and 72B. The port 406 may include one or more pawls 473 positioned at or near the proximal end of the port 406 and extending along the circumference thereof. The pawls 473 may be resilient or spring-like and configured to deflect away from a natural position when a biasing force is applied thereto via the tabs 471 as the cannula 470 threadably engages the port 406. In this manner, the tabs 471 of the cannula 470 and the one or more pawls 473 of the port 406 may form a ratchet mechanism as the one or more pawls 473 selectively engage the tabs 471. The ratchet mechanism may prevent the cannula 470 from being unthreaded from the port 406 unless the pawls 473 are biased by a user to disengage the tabs 471.

As compared to some other connector embodiments, the ratchet mechanism of the connector 400 provides a means for locking the cannula 470 to the port 406, which may improve the structural integrity of connector as well as the hemostasis achieved upon implantation of the connector 400. Moreover, the ratchet mechanism provides tactile feedback as the cannula 470 is attached to the port 406.

Figure 73:
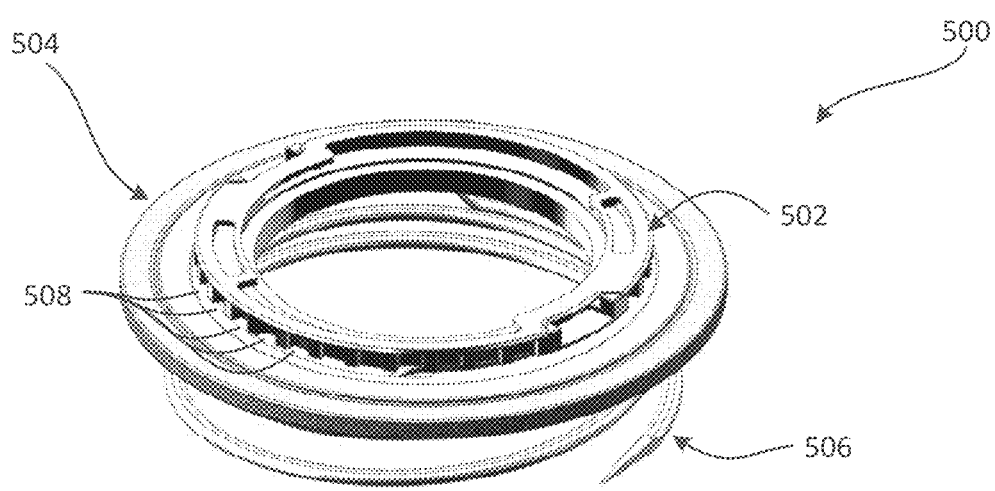
FIG. 73 illustrates yet another embodiment of a heart connector portion.

Port 406 may also include engagement features 422 about an outer perimeter of port 406. The engagement features 422 may be configured to engage with corresponding engagement features of a stabilization tool (e.g., engagement features 3405 or the like). Engagement of the features 422 with a stabilization tool may provide rotational stabilization when the stabilization tool is attached to the port 406. While port 406 is illustrated with rotational stabilization engagement features, it should be understood that cannula 470 may also be configured to include such features such that the stabilization tool couples with cannula 470. Further, the particular rotational engagement features 422 are provided for illustrative purposes only and are non-limiting. For example, FIG. 73 illustrates another heart connector portion 500.

The heart connector portion 500 includes a port 502 defining an opening for receiving a cannula of a heart pump system. The port 502 may include a sewing ring 504 extending outwardly from the port 502. The sewing ring 504 may extend about the perimeter of port 502 and allow for suturing of the heart connector portion 500 onto a heart tissue surface of a patient. The sewing ring 504 may be made of a porous material such as PTFE felt. The heart connector portion 500 may further include a tissue penetrating coil 506 extending from a heart engaging surface of the heart connector portion 500. The coil 506 may have a distal tissue penetrating end that provides an improved interface between the heart connector portion 500 and a heart tissue surface of a patient. In some embodiments port 502 may further include one or more engagement features 508 for engaging with a corresponding engagement feature of a stabilization tool. Optionally, the port 502 may include a plurality of engagement features 508 as illustrated in FIG. 73. The plurality of engagement features 508 may be spaced about the outer surface or perimeter of port 502. As illustrated in the exemplary embodiment 500 of FIG. 73, the engagement features 508 may be notches along an outer surface of port 502 and may be configured to receive a corresponding engagement feature of a stabilization tool. The plurality of engagement features 508 may be configured to allow a stabilization tool to engage with the heart connector portion 500 from a plurality of directions relative to the opening of the heart connector portion 500. In some embodiments, the plurality of engagement features 508 may provide discrete engagement positions every 5-90 degrees, preferably at least every 15 to 30 degrees, at least every 10 degrees. Heart connector portion 500 may be a portion of cuff 3450 illustrated in FIG. 70B.

What is claimed is:

1. A ventricular cuff for coupling to a heart of a patient in an attachment direction and facilitating engagement of a heart pump to the heart, the ventricular cuff comprising:
   an apical ring defining an opening for receiving an inlet cannula of the heart pump, the apical ring having a heart pump engaging perimeter and a sewing ring engaging perimeter opposite the heart pump engaging perimeter;
   a sewing ring coupled with the sewing ring engaging perimeter of the apical ring, the sewing ring including a heart tissue engaging surface and a top surface opposite the heart tissue engaging surface; and
   a rigid frame backing the sewing ring along the top surface of the sewing ring, the rigid frame comprising a plurality of struts extending outwardly from the opening defined by the apical ring and toward an outer perimeter of the sewing ring;
   wherein the plurality of struts of the rigid frame are configured to maintain a space between the top surface of the sewing ring and the heart pump engaging perimeter of the apical ring during implantation of the ventricular cuff and the heart pump to the heart of the patient;
   wherein the plurality of struts extend outwardly and in the attachment direction towards the heart from the opening defined by the apical ring; and
   wherein a top surface of the rigid frame defines a convex surface and a sewing ring engaging surface opposite the top surface of the rigid frame defines a concave surface.

2. The ventricular cuff of claim 1, wherein the top surface of the rigid frame defines a frustoconical shape.

3. The ventricular cuff of claim 1, wherein the rigid frame comprises an outer ring and wherein peripheral ends of the plurality of struts are coupled with the outer ring.

4. The ventricular cuff of claim 3, wherein the rigid frame comprises an inner ring, wherein the plurality of struts extend from the inner ring toward the outer ring, and wherein the plurality of struts are visible to a physician during implantation.

5. The ventricular cuff of claim 3, wherein the outer ring has a diameter less than a diameter of the sewing ring.

6. The ventricular cuff of claim 5, wherein the outer ring diameter is at least 2 mm less than the sewing ring diameter.

7. The ventricular cuff of claim 6, wherein the outer ring diameter is at least 4 mm less than the sewing ring diameter.

8. The ventricular cuff of claim 1, further comprising an insert ring coupling the sewing ring to the apical ring.

9. The ventricular cuff of claim 8, wherein the insert ring defines an opening for receiving and engaging with the apical ring, an outer surface of the apical ring configured to engage with an inner surface of the insert ring in a friction fit engagement.

10. The ventricular cuff of claim 9, wherein the rigid frame is configured to be clamped between a central lip of the apical ring and the insert ring during engagement of the apical cuff and the insert ring to secure the rigid frame against the sewing ring, wherein the central lip extends from the outer surface of the apical ring.

11. The ventricular cuff of claim 10, wherein the apical ring includes an alignment feature for engaging with a corresponding alignment feature of the rigid frame, wherein engagement of the alignment feature of the apical ring with the corresponding alignment feature of the rigid frame aligns the rigid frame about the opening defined by the apical ring.

12. The ventricular cuff of claim 8, wherein the insert ring comprises a metal material, wherein the sewing ring comprises a fabric material, and wherein the insert ring and sewing ring are coupled together to provide a fluid tight seal between the insert ring and the sewing ring.

13. The ventricular cuff of claim 12, wherein the insert ring includes a lip that overlaps with the heart tissue engaging surface of the sewing ring, the lip having a plurality of holes therethrough, wherein the insert ring and sewing ring are coupled together at the overlap by an elastomer, wherein the elastomer impregnates the fabric material of the sewing ring and forms mechanical links through the holes in the lip of the insert ring.

14. The ventricular cuff of claim 13, wherein an adhesion of the elastomer to the metal material of the insert ring is increased by application of an adhesion promoter to the metal of the insert ring.

15. The ventricular cuff of claim 1, wherein the rigid frame is configured for urging the top surface of the sewing ring to a convex configuration.

16. The ventricular cuff of claim 1, wherein the rigid frame is configured to maintain the sewing ring in a frustoconical configuration.

17. The ventricular cuff of claim 1, wherein the rigid frame is configured for urging the heart tissue engaging surface of the sewing ring to a concave configuration.

18. A ventricular cuff for coupling with a heart of a patient in an attachment direction, the ventricular cuff comprising:
an insert ring comprising metal material having a cylindrical portion defining a central opening;
a single sewing ring comprising a felt material disposed about the insert ring, the sewing ring including a heart tissue engaging surface and a top surface opposite the heart tissue engaging surface;
an elastomer coupling the sewing ring to the insert ring at an interface between the insert ring and the sewing ring and forming a fluid tight engagement between the sewing ring and the insert ring; and
a rigid frame secured to the insert ring and including a plurality of struts extending outwardly from the central opening, the rigid frame secured to the insert ring such that the plurality of struts of the rigid frame are urged against the sewing ring and extend toward an outer perimeter of the sewing ring, the plurality of struts supporting the sewing ring so as to resist deformation of the sewing ring in the attachment direction during attachment of the ventricular cuff to a heart of a patient, wherein:
the plurality of struts extend outwardly and in the attachment direction towards the heart from the opening defined by the apical ring; and
a top surface of the rigid frame defines a convex surface and a sewing ring engaging surface opposite the top surface of the rigid frame defines a concave surface.

19. The ventricular cuff of claim 18, wherein the insert ring includes a lip extending outwardly of the central opening of the insert ring from an end of the cylindrical portion, the lip including a plurality of holes therethrough; and wherein the lip of the insert ring overlaps with sewing ring so as to form the interface between the insert ring and the sewing ring.

20. The ventricular cuff of claim 19, wherein the elastomer impregnates the felt material of the sewing ring so as to form a mechanical engagement with the sewing ring and forms mechanical links through the holes of the lip of the insert ring so as to form a mechanical engagement with the insert ring.

21. The ventricular cuff of claim 20, wherein the elastomer chemically adheres to the insert ring through an adhesion promoter.

22. The ventricular cuff of claim 18, wherein the plurality of struts of the rigid frame are visible to a surgeon during attachment of the cuff to the heart.

23. The ventricular cuff of claim 18, wherein the plurality of struts extend in the attachment direction at least 0.05 inches as the plurality of struts extend outwardly.

24. The ventricular cuff of claim 18, wherein the rigid frame urges the sewing ring into a domed configuration where the top surface of the sewing ring is convex and the heart tissue engaging surface of the sewing ring is concave.

25. The ventricular cuff of claim 24, wherein the rigid frame includes an outer ring, and wherein the plurality of struts of the rigid frame extend outwardly and couple to the outer ring to support the outer ring against the perimeter of the sewing ring.

26. The ventricular cuff of claim 18, further comprising an apical ring, the apical ring including a heart pump engaging end and a sewing ring engaging end, and wherein the sewing ring engaging end is configured to engage with the insert ring.

27. The ventricular cuff of claim 26, wherein the sewing ring engaging end of the apical ring engages with the insert ring in a press-fit engagement.

28. The ventricular cuff of claim 26, wherein the apical ring includes an alignment feature for engaging a corresponding alignment feature on the rigid frame so as to align the apical ring with the rigid frame.

29. The ventricular cuff of claim 26, wherein the rigid frame is urged against the sewing ring by the engagement of the apical ring to the insert ring.

* * * * *

UNITED STATES PATENT AND TRADEMARK OFFICE
CERTIFICATE OF CORRECTION

PATENT NO. : 9,981,076 B2
APPLICATION NO. : 14/641164
DATED : May 29, 2018
INVENTOR(S) : Justin Aron Callaway et al.

It is certified that error appears in the above-identified patent and that said Letters Patent is hereby corrected as shown below:

In the Claims

In Column 64, Line 17, Claim 19: after "with" please insert --the--.

Signed and Sealed this
Fourth Day of December, 2018

Andrei Iancu
*Director of the United States Patent and Trademark Office*